US010078085B2

(12) United States Patent
Lim et al.

(10) Patent No.: US 10,078,085 B2
(45) Date of Patent: Sep. 18, 2018

(54) SCREENING AND ENGINEERING METHOD OF SUPER-STABLE IMMUNOGLOBULIN VARIABLE DOMAINS AND THEIR USES

(75) Inventors: Hyung-Kwon Lim, Yongin-si (KR); Sung Geun Kim, Yongin-si (KR); Young Seoub Park, Yongin-si (KR); Hyo Jung Nam, Yongin-si (KR); Dong-Sik Kim, Yongin-si (KR); Jae Chan Park, Yongin-si (KR); Yeup Yoon, Yongin-si (KR)

(73) Assignee: Mogam Biotechnology Institute, Yongin-si, Gyeonggi-do (KR)

( * ) Notice: Subject to any disclaimer, the term of this patent is extended or adjusted under 35 U.S.C. 154(b) by 356 days.

(21) Appl. No.: 14/422,912

(22) PCT Filed: Aug. 22, 2012

(86) PCT No.: PCT/KR2012/006680
§ 371 (c)(1),
(2), (4) Date: Mar. 17, 2015

(87) PCT Pub. No.: WO2014/030780
PCT Pub. Date: Feb. 27, 2014

(65) Prior Publication Data
US 2016/0003844 A1     Jan. 7, 2016

(51) Int. Cl.
*C40B 40/10* (2006.01)
*G01N 33/68* (2006.01)
(Continued)

(52) U.S. Cl.
CPC ......... *G01N 33/6857* (2013.01); *C07K 16/00* (2013.01); *C07K 16/18* (2013.01);
(Continued)

(58) Field of Classification Search
None
See application file for complete search history.

(56) References Cited

U.S. PATENT DOCUMENTS

| 2002/0012909 A1 | 1/2002 | Plaksin |
| 2005/0054001 A1 | 3/2005 | Muyldermans |

(Continued)

FOREIGN PATENT DOCUMENTS

| JP | 2006-518188 A | 8/2006 |
| JP | 2009-523460 A | 6/2009 |

(Continued)

OTHER PUBLICATIONS

Auf Der Maur A., et al., "Antigen-independent selection of intracellular stable antibody frameworks", Methods, vol. 34, No. 2, Oct. 1, 2004, pp. 215-224, XP004526807.

(Continued)

*Primary Examiner* — Christian C Boesen
(74) *Attorney, Agent, or Firm* — Knobbe Martens Olson & Bear LLP

(57) ABSTRACT

There are provided a method named Tat-associated protein engineering (TAPE), of screening a target protein having higher solubility and excellent thermostability, in particular, an immunoglobulin variable domain (VH or VL) derived from human germ cells, by preparing a gene construct where the target protein and an antibiotic-resistant protein are linked to a Tat signal sequence, and then expressing this within *E. coli*, and human or engineered VH and VL domain antibodies and human or engineered VH and VL domain antibody scaffolds having solubility and excellent thermostability, which are screened by the TAPE method. There are also provided a library including random CDR sequences in the human or engineered VH or VL domain antibody scaffold screened by the TAPE method, and a preparing method thereof. There are also provided a VH or VL domain antibody having binding ability to the target protein (Continued)

screened by using the library, and a pharmaceutical composition including the domain antibody.

14 Claims, 16 Drawing Sheets

Specification includes a Sequence Listing.

(51) Int. Cl.
  *C07K 16/00* (2006.01)
  *C07K 16/18* (2006.01)
  *C07K 16/32* (2006.01)

(52) U.S. Cl.
  CPC .......... *C07K 16/32* (2013.01); *C07K 2317/21* (2013.01); *C07K 2317/56* (2013.01); *C07K 2317/565* (2013.01); *C07K 2317/569* (2013.01); *C07K 2317/94* (2013.01); *C07K 2319/00* (2013.01); *C07K 2319/10* (2013.01); *C40B 40/10* (2013.01); *G01N 2500/00* (2013.01)

(56) References Cited

U.S. PATENT DOCUMENTS

| | | | |
|---|---|---|---|
| 2005/0215770 A1* | 9/2005 | Bell | C07K 16/28 530/388.22 |
| 2007/0026012 A1* | 2/2007 | DeLisa | C12N 15/1086 424/190.1 |
| 2009/0011995 A1 | 1/2009 | Lee et al. | |
| 2010/0285567 A1 | 11/2010 | Bao et al. | |

FOREIGN PATENT DOCUMENTS

| | | |
|---|---|---|
| JP | 2009-536527 A | 10/2009 |
| KR | 10-1996-007784 A | 3/1996 |
| WO | 00/34308 A2 | 6/2000 |
| WO | 01/18058 A2 | 3/2001 |
| WO | 02/051870 A2 | 7/2002 |
| WO | 2005/005604 A2 | 1/2005 |
| WO | 2005/032460 A2 | 4/2005 |
| WO | 2006/026759 A2 | 3/2006 |
| WO | 2007/016591 A2 | 2/2007 |
| WO | 2007/024877 A2 | 3/2007 |
| WO | 2007/085815 A2 | 8/2007 |
| WO | 2009/089295 A2 | 7/2009 |
| WO | 2012/100343 A1 | 8/2012 |

OTHER PUBLICATIONS

Worn A., et al., "Stability engineering of antibody single-chain Fv fragments", Journal of Molecular Biology, vol. 305, No. 5, Feb. 2, 2001, pp. 989-1010, XP004465987.
European Search Report dated Mar. 11, 2016 of corresponding European Patent Application No. 12883278—9 pages.
Baneyx et al., "Recombinant protein folding and misfolding in *Escherichia coli*", Nature Biotechnology, Nov. 2004, vol. 22, No. 11, pp. 1399-1408.
Cabantous et al., "Protein tagging and detection with engineered self-assembling fragments of green fluorescent protein", Nature Biotechnology, Jan. 2005, vol. 23, No. 1, pp. 102-107.
Davies et al., "'Camelising' human antibody fragments: NMR studies on VH domains", Federation of European Biochemical Societies, 1994, vol. 339, pp. 285-290.
Delisa et al., "Folding quality control in the export of proteins by the bacterial twin-arginine translocation pathway", PNAS, May 2003, vol. 100, No. 10, pp. 6115-6120.
Fisher et al., "Genetic selection for protein solubility enabled by the folding quality control feature of the twin-arginine translocation pathway", Protein Science, 2006, vol. 15, pp. 449-458.
Hendershot et al., "Assembly and Secretion of Heavy Chains that Do Not Associate Posttranslationally with Immunoglobulin Heavy Chain-binding Protein", The Journal of Cell Biology, Mar. 1987, vol. 104, pp. 761-767.
Wesolowski et al., "Single domain antibodies: promising experimental and therapeutic tools in infection and immunity", Med Microbial Immunol, 2009, vol. 198, pp. 157-174.
Huston et al., "Protein engineering of antibody binding sites: Recovery of specific activity in an anti-digoxin single-chain Fv analogue produced in *Escherichia coli*", Proc. Natl. Acad. Sci. USA, Aug. 1988, vol. 85, pp. 5879-5883.
Iliades et al., "Triabodies: single chain Fv fragments without a linker form trivalent trimers", Federation of European Biochemical Societies (FEBS) Letters, 1997, vol. 409, pp. 437-441.
Kristensen et al., "Proteolytic selection for protein folding using filamentous bacteriophages", Folding & Design, 1998, vol. 3, No. 5, pp. 321-328.
Lim et al., "Mining mammalian genomes for folding competent proteins using Tat-dependent genetic selection in *Escherichia coli*", Protein Science, 2009, vol. 18, pp. 2537-2549.
Maids et al., "The Tat system proofreads FeS protein substrates and directly initiates the disposal of rejected molecules", The EMBO Journal, 2008, vol. 27, pp. 2055-2063.
Maxwell et al., "A simple in vivo assay for increased protein solubility", Protein Science, 1999, vol. 8, pp. 1908-1911.
Pedelacq et al., "Engineering soluble proteins for structural genomics", Nature Biotechnology, Sep. 2002, vol. 20, pp. 927-932.
Pei et al., "The 2.0-A resolution crystal structure of a trimeric antibody fragment with noncognate VH—VL domain pairs shows a rearrangement of VH CDR3", Proc. Natl. Acad. Sci. USA, Sep. 1997, vol. 94, pp. 9637-9642.
Sanders et al., "Transport of cytochrome c derivatives by the bacterial Tat protein translocation system", Molecular Microbiology, 2001, vol. 41, No. 1, pp. 241-246.
Sieber et al., "Selecting proteins with improved stability by a phage-based method", Nature Biotechnology, Oct. 1998, vol. 16, pp. 955-960.
Tomlinson et al., "The structural repertoire of the human VK domain", The EMBO Journal, 1995, vol. 14, No. 18, pp. 4628-4638.
Yang et al., "Directed evolution approach to a structural genomics project: Rv2002 from Mycobacterium tuberculosis", PNAS, Jan. 2003, vol. 100, No. 2, pp. 455-460.
Zhao et al., "Targeting CD37-positive lymphoid malignancies with a novel engineered small modular immunopharmaceutical", Blood, Oct. 2007, vol. 110, No. 7, pp. 2569-2577.
Barthelemy et al., "Comprehensive Analysis of the Factors Contributing to the Stability and Solubility of Autonomous Human VH Domains", The Journal of Biological Chemistry, Feb. 2008, vol. 283, No. 6, pp. 3639-3654.
Coppieters et al., "Formatted Anti—Tumor Necrosis Factor & VHH Proteins Derived From Camelids Show Superior Potency and Targeting to Inflamed Joints in a Murine Model of Collagen-Induced Arthritis", Arthritis & Rheumatism, Jun. 2006, vol. 54, No. 6, pp. 1856-1866.
Ward et al., "Binding activities of a repertoire of single immunoglobulin variable domains secreted from *Escherichia coli*", Nature, Oct. 1989, vol. 341, pp. 544-546.
Conrath et al., "Camel Single-domain Antibodies as Modular Building Units in Bispecific and Bivalent Antibody Constructs", The Journal of Biological Chemistry, Mar. 2001, vol. 276, No. 10, pp. 7346-7350.
Enever et al., "Next generation immunotherapeutics—honing the magic bullet", Current Opinion in Biotechnology, 2009, vol. 20, pp. 405-411.
Ewert et al., "Biophysical Properties of Camelid VHH Domains Compared to Those of Human VH3 Domains", Biochemistry, 2002, vol. 41, pp. 3628-3636.
Ewert et al., "Stability improvement of antibodies for extracellular and intracellular applications: CDR grafting to stable frameworks and structure-based framework engineering", Methods, 2004, vol. 34, pp. 184-199.
Fisher et al., "Efficient Isolation of Soluble Intracellular Single-chain Antibodies using the Twin-arginine Translocation Machinery", J. Mol. Biol., 2009, vol. 385, pp. 299-311.

(56) References Cited

OTHER PUBLICATIONS

Waldo, "Genetic screens and directed evolution for protein solubility", Current Opinion in Chemical Biology, 2003, vol. 7, pp. 33-38.
Holliger et al., "Engineered antibody fragments and the rise of single domains", Nature Biotechnology, Sep. 2005, vol. 23, No. 9, pp. 1126-1136.
Jespers et al., "Aggregation-resistant domain antibodies selected on phage by heat denaturation", Nature Biotechnology, Sep. 2004, vol. 22, No. 9, pp. 1161-1165.
Kolkman et al., "Nanobodies—from llamas to therapeutic proteins", Drug Discovery Today: Technologies, 2010, vol. 7, No. 2, pp. 139-146.
Worn et al., "Stability Engineering of Antibody Single-chain Fv Fragments", J. Mol. Biol., 2001, vol. 305, pp. 989-1010.
Martin et al., "Affinity selection of a camelized VH domain antibody inhibitor of hepatitis C virus NS3 protease", Protein Engineering, 1997, vol. 10, No. 5, pp. 607-614.
De Wildt et al., "Analysis of Heavy and Light Chain Pairings Indicates that Receptor Editing Shapes the Human Antibody Repertoire", J. Mol. Biol., 1999, vol. 285, pp. 895-901.
Tijink et al., "Improved tumor targeting of anti—epidermal growth factor receptor Nanobodies through albumin binding: taking advantage of modular Nanobody technology", Molecular Cancer Therapeutics, 2008, vol. 7, No. 8, pp. 2288-2297.
To et al., "Isolation of Monomeric Human VHS by a Phage Selection", The Journal of Biological Chemistry, Dec. 2005, vol. 280, No. 50, pp. 41395-41403.
Japanese Office Action dated Mar. 8, 2016 of corresponding Japanese Patent Application No. 2015-528372—4 pages.
Chinese Office Action dated May 26, 2016 of corresponding Chinese Patent Application No. 201280076586.9—12 pages.
Extended European Search Report dated Mar. 28, 2017 of corresponding European Patent Application No. 16202979.7—9 pages.
Ewert et al., "Biophysical Properties of Human Antibody Variable Domains", Journal of Molecular Biology, 2003, vol. 325, pp. 531-553.
International Search Report dated Mar. 28, 2013 of PCT/KR2012/006680 which is the parent application—6 pages.
Aries Da Silva et al., "Camelized Rabbit-derived VH Single-domain Intrabodies Against Vif Strongly Neutralize HIV-1 Infectivity", Journal of Molecular Biology, 2004, vol. 340, pp. 525-542.
Bargou et al., "Tumor Regression in Cancer Patients by Very Low Doses of a T Cell-Engaging Antibody", Science, Aug. 15, 2008, vol. 321, No. 5891, pp. 974-977.
Better et al., "*Escherichia coli* Secretion of an Active Chimeric Antibody Fragment", Science, May 20, 1988, vol. 240, No. 4855, pp. 1041-1043.
Bird et al., "Single-Chain Antigen-Binding Proteins", Science, Oct. 21, 1988, vol. 242, No. 4877, pp. 423-426.
Dolk et al., "Induced Refolding of a Temperature Denatured Llama Heavy-chain Antibody Fragment by its Antigen", PROTEINS: Structure, Function, and Bioinformatics, 2005, vol. 59, pp. 555-564.
Chao et al., "Isolating and Engineering Human Antibodies using Yeast Surface Display", Nature Protocols, 2006, vol. 1, No. 2, pp. 755-769.
Skerra, "Engineered Protein Scaffolds for Molecular Recognition", Journal of Molecular Recognition, 2000, vol. 13, pp. 167-187.
Jung et al., "Selection for Improved Protein Stability by Phage Display", Journal of Molecular Biology, 1999, vol. 294, pp. 163-180.
He et al., "Eukaryotic Ribosome Display with in situ DNA Recovery", Nature Methods, Mar. 2007, vol. 4, No. 3, pp. 281-288.
Riechmann, Rearrangement of the Former VL Interface in the Solution Structure of a Camelised, Single Antibody VH Domain, Journal of Molecular Biology, 1996, vol. 259, pp. 957-969.
Williams et al., "Sequence and Evolution of the Human Germline VλRepertoire", Journal of Molecular Biology, 1996, vol. 264, pp. 220-232.

\* cited by examiner

[FIG. 7]
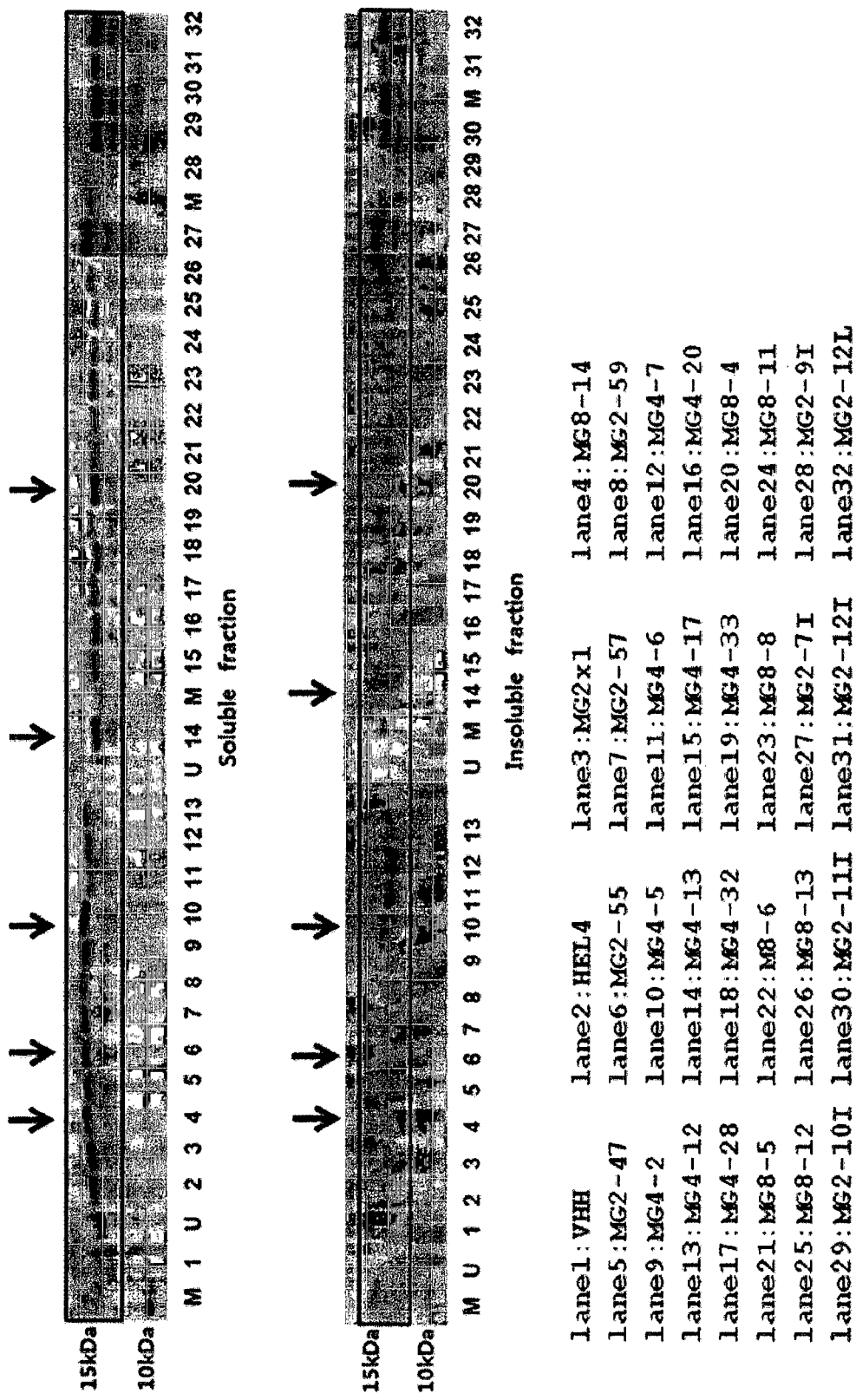

[FIG. 8]
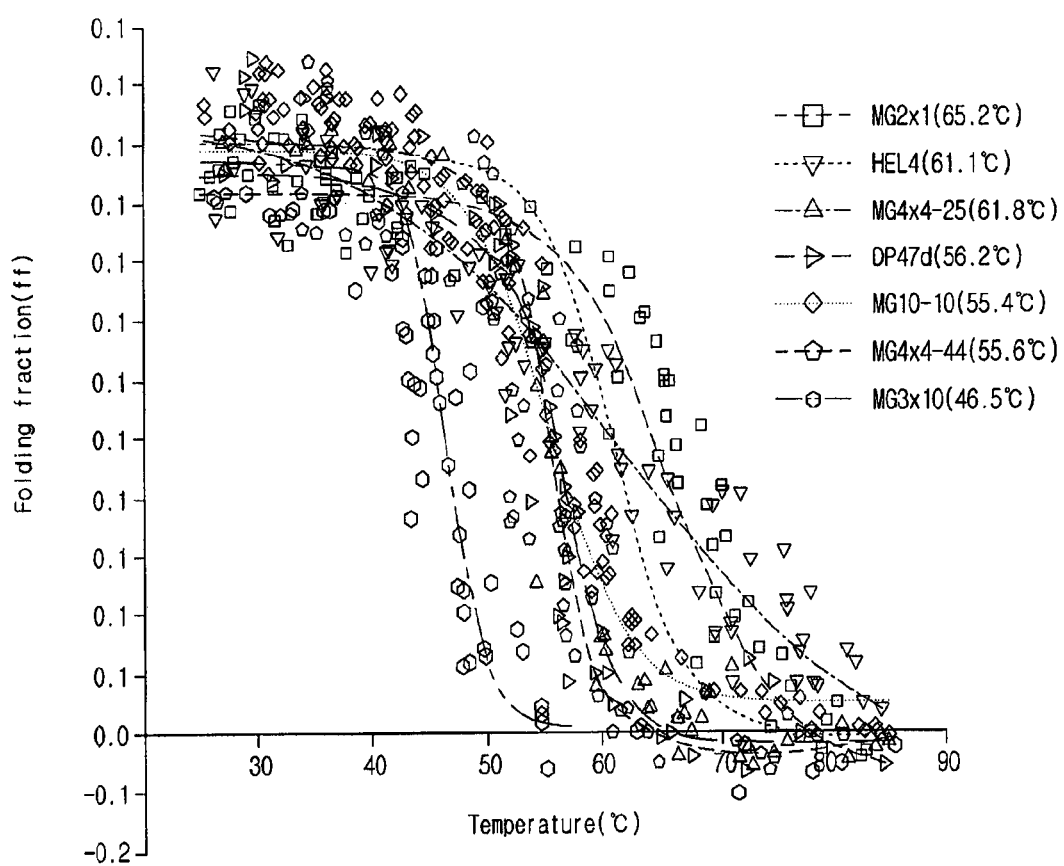

[FIG. 9]
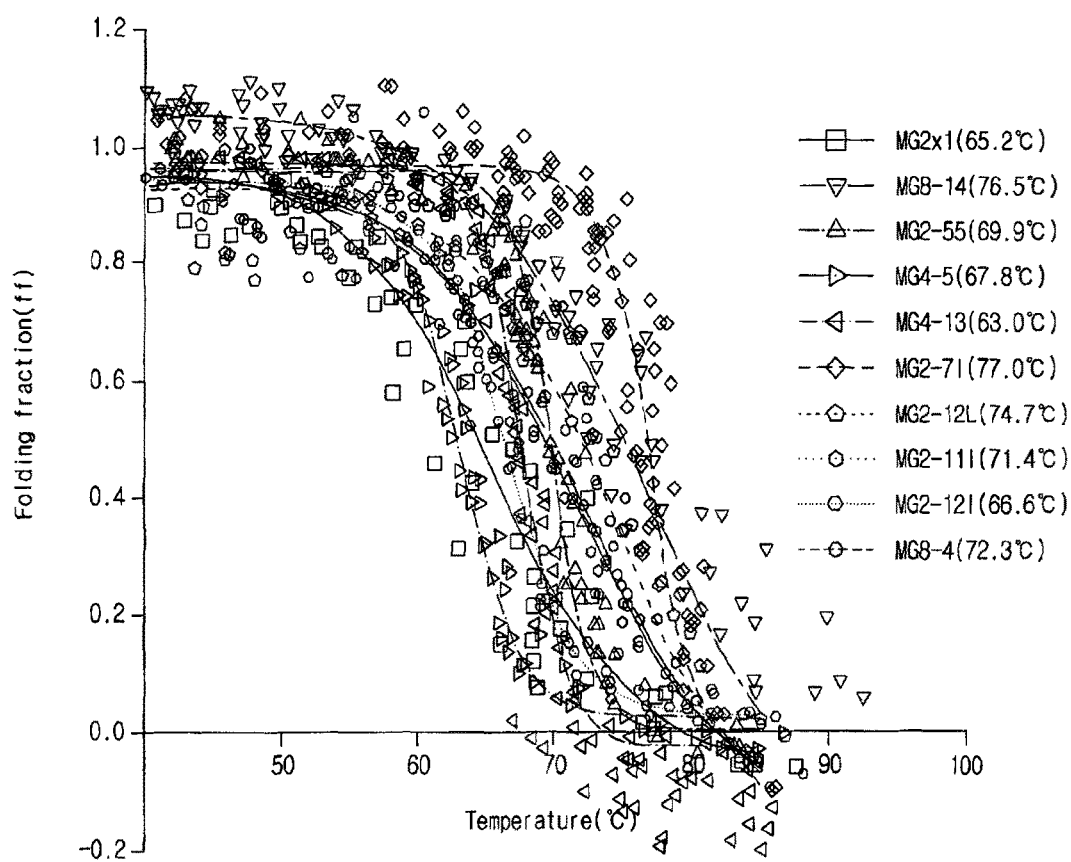

[FIG. 10]
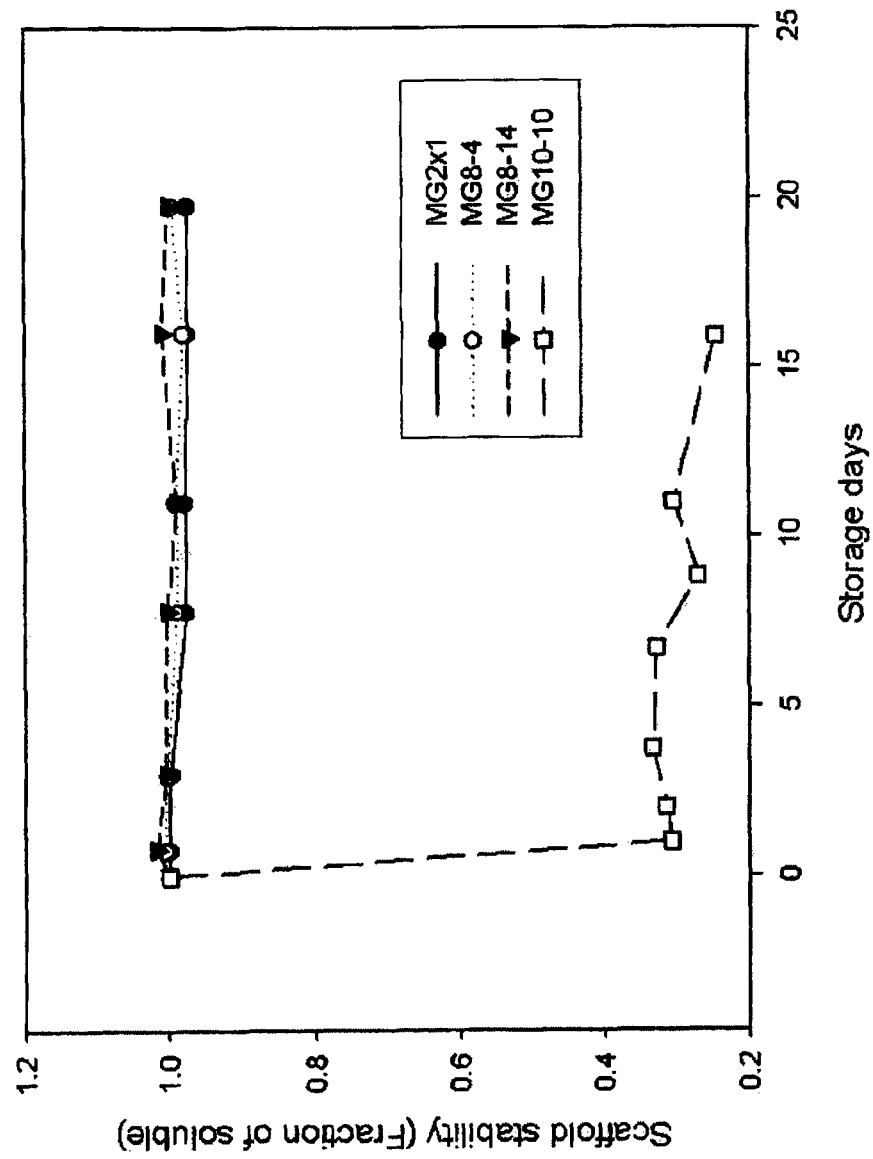

[FIG. 11]
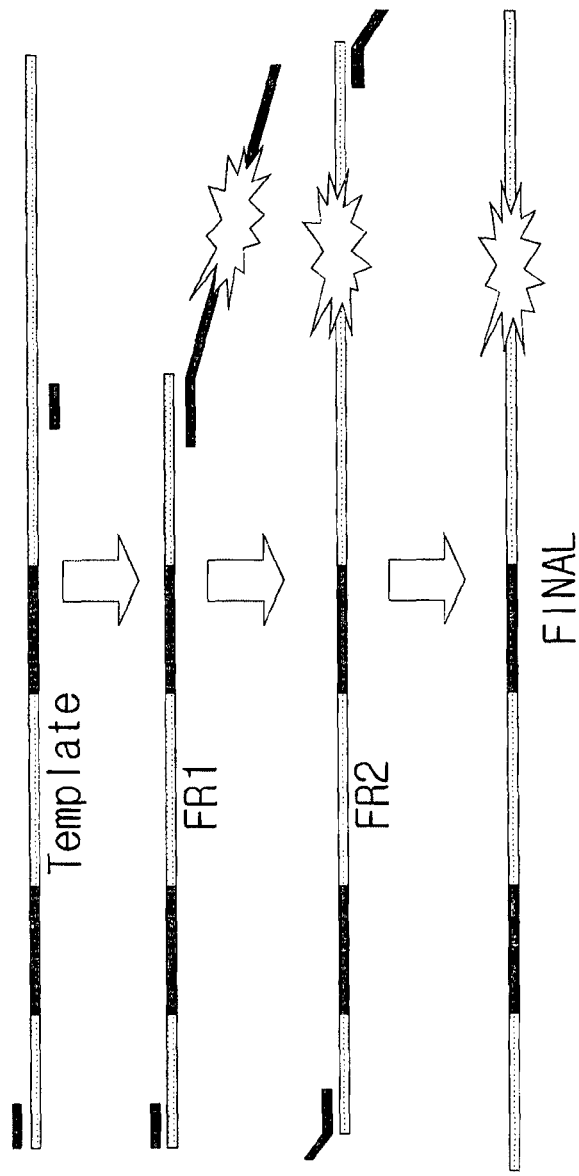

Fig. 12

| No. | FR1 | CDR H1 | FR2 | CDR H2 | FR3 | CDR H3 | FR4 |
|-----|-----|--------|-----|--------|-----|--------|-----|
| Kabat | 1  2  3  4  5  6  7  8  9 10 11 12 13 14 15 16 17 18 19 20 21 22 23 24 25 | 26 27 28 29 30 31 32 33 34 35 35a 35b | 36 37 38 39 40 41 42 43 44 45 46 47 48 49 | 50 51 52 52a 52b 52c 53 54 55 56 57 58 59 60 61 62 63 64 65 | 66 67 68 69 70 71 72 73 74 75 76 77 78 79 80 81 82 82a 82b 82c 83 84 85 86 87 88 89 90 91 92 93 94 | 95 96 97 98 99 100 100a 100b 100c 100d 100e 100f 100g 100h 100i 101 102 | 103 104 105 106 107 108 109 110 111 112 113 |
| M2x1  | E V Q L V E S . G G G L V Q P G G S L R L S C A A S G | . F T F S S . S Y A M S | W V R Q A P G K G L E W V S | A I S G . . . S G G S T Y Y A D S V K G | R F T I S R D N S K N T L Y L Q M N S L R A E D T A V Y Y C A R | H A P S T E A P . . . . . . . . . | D Y W G Q G T L V T V S S |
| M8-4  | E V Q L V E S . G G G L V Q P G G S L R L S C A A S G | . F T F S S . S Y A M G | W V R Q A P G K G P E V V S | L I S G . . . S G G S T W Y D D S V K G | R F T I S R D N S K N T L Y L Q M N S L R A E D T A V Y Y C A R | H A P S T E A P . . . . . . . . . | D Y W G Q G T L V T V S S |
| M8-14 | E V Q L V E S . G G G L V Q P G G S L R L S C A A S G | . F T F S S . S Y A M G | W V R Q A P G K G P E W V S | L I S G . . . S G G S T W Y D D S V K G | R F T I S R D N S K N T L Y L Q M N S L R A E D T A V Y Y C A R | H A P S T E A P . . . . . . . . . | D Y W G Q G T L V T V S S |

[FIG. 13]
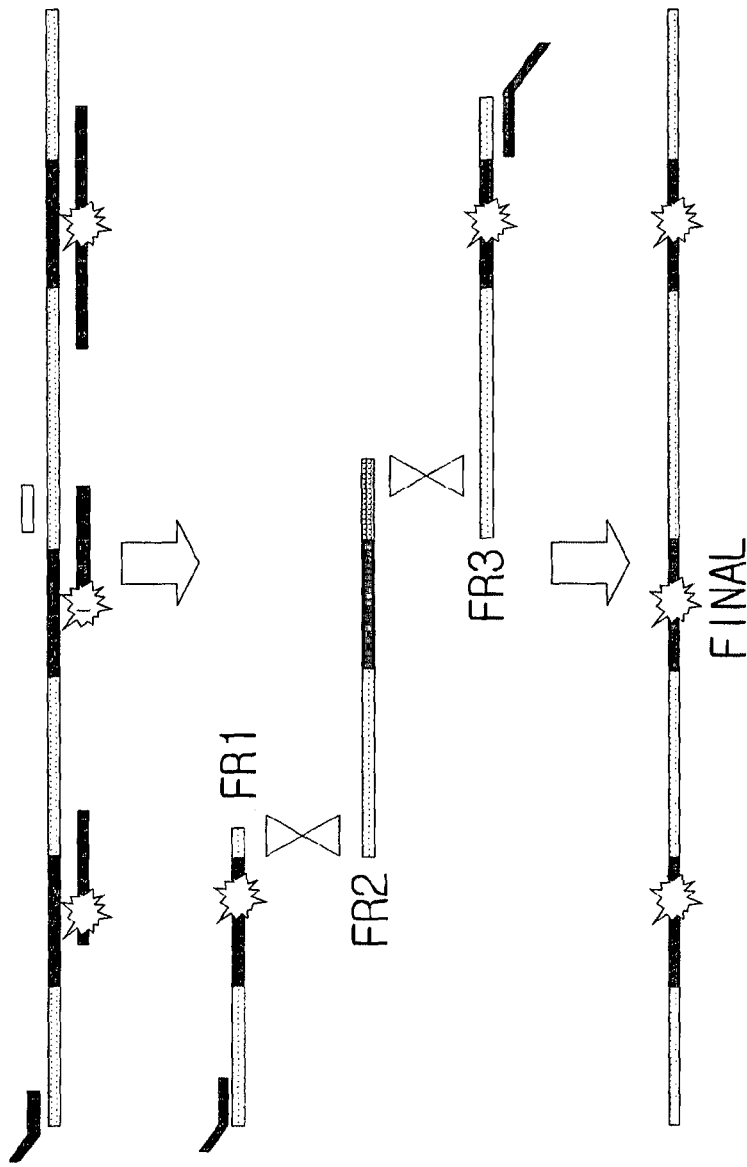

SEQUENCE LISTING

<160> NUMBER OF SEQ ID NOS: 637

<210> SEQ ID NO 1
<211> LENGTH: 38
<212> TYPE: DNA
<213> ORGANISM: Artificial Sequence
<220> FEATURE:
<223> OTHER INFORMATION: primer

<400> SEQUENCE: 1
gccatatgaa caataacgat ctctttcagg catcacgt                    38

<210> SEQ ID NO 2
<211> LENGTH: 59
<212> TYPE: DNA
<213> ORGANISM: Artificial Sequence
<220> FEATURE:
<223> OTHER INFORMATION: primer

<400> SEQUENCE: 2
gcggatccat ggtggtgatg gtggtgtgcg gccgctgaag agacggtcac caacgtgcc    59

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
gcgcggccgc acacccagaa acgctggtg                              29

```
<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
gcggatcctt accaatgctt aatcagtgag gc                                    32

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
gcgctagcca ggtkcagctg gtgcag                                           26

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
gcgctagcca ggtccagctt gtgcag                                           26

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gcgctagcsa ggtccagctg gtacag                                           26

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
gcgctagcca ratgcagctg gtgcag                                           26

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
gcgctagcca gatcaccttg aaggag                                           26

<210> SEQ ID NO 10
<211> LENGTH: 26
<212> TYPE: DNA
<213> ORGANISM: Artificial Sequence
<220> FEATURE:
<223> OTHER INFORMATION: primer
```

```
<400> SEQUENCE: 10
gcgctagcca ggtcaccttg arggag                                           26

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
gcgctagcga rgtgcagctg gtggag                                           26

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
gcgctagcca ggtgcagctg gtggag                                           26

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
gcgctagcga ggtgcagctg ttggag                                           26

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
gcgcggccgc tgaggagacg gtgac                                            25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
gcgcggccgc tgaagagacg gtgac                                            25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
gcgcggccgc tgaggagaca gtgac                                            25

<210> SEQ ID NO 17
<211> LENGTH: 44
```

```
<212> TYPE: DNA
<213> ORGANISM: Artificial Sequence
<220> FEATURE:
<223> OTHER INFORMATION: primer

<400> SEQUENCE: 17
gcccatggga agtccaactg gttgaatctg gtggcggttt agtt            44

<210> SEQ ID NO 18
<211> LENGTH: 114
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 18
agttgaaccg ccagagccgg aaatmnntga gacmnnttcm nnacctttgc ctggcgcmnn    60
acgcacccag cccatagcat aagaagaaaa ggtaaagcca cttgcagcac agct         114

<210> SEQ ID NO 19
<211> LENGTH: 63
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 19
atttccggct ctggcggttc aactnnktac nnkgatagcg ttaaaggtcg tttcacaatc    60
tcc                                                                 63

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20
gcgcggccgc actgctcaca gtaaccaggg taccctg                             37

<210> SEQ ID NO 21
<211> LENGTH: 35
<212> TYPE: DNA
<213> ORGANISM: Artificial Sequence
<220> FEATURE:
```

<223> OTHER INFORMATION: primer

<400> SEQUENCE: 21
gcccatggga agtccaactg gttgaatctg gtggc    35

<210> SEQ ID NO 22
<211> LENGTH: 34
<212> TYPE: DNA
<213> ORGANISM: Artificial Sequence
<220> FEATURE:
<223> OTHER INFORMATION: primer

<400> SEQUENCE: 22
gcctcgagac tgctcacagt aaccagggta ccct    34

<210> SEQ ID NO 23
<211> LENGTH: 35
<212> TYPE: DNA
<213> ORGANISM: Artificial Sequence
<220> FEATURE:
<223> OTHER INFORMATION: primer

<400> SEQUENCE: 23
gcgctagcga agtccaactg gttgaatctg gtggc    35

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
actggcgcag taatacactg cggtatc    27

<210> SEQ ID NO 25
<211> LENGTH: 101
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 25

```
gcagatcttg aggagacagt gaccagggtt ccctggcccc amnmnmnnmn mnnmnnmnnm      60
nntctggcgc agtaatacac tgcggtatct tcagcacgca g                         101
```

<210> SEQ ID NO 26
<211> LENGTH: 104
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 26

```
gcagatcttg aggagacagt gaccagggtt ccctggcccc amnmnmnnmn mnnmnnmnnm      60
nnmnntctgg cgcagtaata cactgcggta tcttcagcac gcag                      104
```

<210> SEQ ID NO 27
<211> LENGTH: 107
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:

<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t

<400> SEQUENCE: 27
gcagatcttg aggagacagt gaccagggtt ccctggcccc amnnmnnmnn mnnmnnmnnm    60
nnmnnmnntc tggcgcagta atacactgcg gtatcttcag cacgcag                  107

<210> SEQ ID NO 28
<211> LENGTH: 110
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t

<400> SEQUENCE: 28
gcagatcttg aggagacagt gaccagggtt ccctggcccc amnnmnnmnn mnnmnnmnnm    60
nnmnnmnnmn ntctggcgca gtaatacact gcggtatctt cagcacgcag              110

<210> SEQ ID NO 29
<211> LENGTH: 113

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t

<400> SEQUENCE: 29
gcagatcttg aggagacagt gaccagggtt ccctggcccc amnnmnnmnn mnnmnnmnnm      60
nnmnnmnnmn nmnntctggc gcagtaatac actgcggtat cttcagcacg cag            113

<210> SEQ ID NO 30
<211> LENGTH: 116
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:

<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t

<400> SEQUENCE: 30
gcagatcttg aggagacagt gaccagggtt ccctggcccc amnnmnnmn mnnmnnmnnm    60 nnmnnmnnmn nmnnmnntct ggcgcagtaa tacactgcgg tatcttcagc acgcag      116

<210> SEQ ID NO 31
<211> LENGTH: 119
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature

```
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t

<400> SEQUENCE: 31
gcagatcttg aggagacagt gaccagggtt ccctggcccc amnnmnnmn mnnmnnmnnm      60 nnmnnmnnmn nmnnmnnmnn tctggcgcag taatacactg cggtatcttc agcacgcag     119

<210> SEQ ID NO 32
<211> LENGTH: 101
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 32
gcagatcttg aggagacagt gaccagggtt ccctggcccc amnnmnnmn mnnmnnmnnm      60 nnggaggcgc agtaatacac tgcggtatct tcagcacgca g                       101

<210> SEQ ID NO 33
<211> LENGTH: 104
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
```

```
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 33
gcagatcttg aggagacagt gaccagggtt ccctggcccc amnnmnnmnn mnnmnnmnnm        60
nnmnnggagg cgcagtaata cactgcggta tcttcagcac gcag                       104

<210> SEQ ID NO 34
<211> LENGTH: 107
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t

<400> SEQUENCE: 34
```

```
gcagatcttg aggagacagt gaccagggtt ccctggcccc amnnmnnmnn mnnmnnmnnm      60
nnmnnmnngg aggcgcagta atacactgcg gtatcttcag cacgcag                  107
```

<210> SEQ ID NO 35
<211> LENGTH: 110
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t

<400> SEQUENCE: 35

```
gcagatcttg aggagacagt gaccagggtt ccctggcccc amnnmnnmnn mnnmnnmnnm      60
nnmnnmnnmn nggaggcgca gtaatacact gcggtatctt cagcacgcag               110
```

<210> SEQ ID NO 36
<211> LENGTH: 113
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:

<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t

<400> SEQUENCE: 36
gcagatcttg aggagacagt gaccagggtt ccctggcccc amnmnmnmn mnnmnmnnm    60 nnmnnmnnmn nmnnggaggc gcagtaatac actgcggtat cttcagcacg cag          113

<210> SEQ ID NO 37
<211> LENGTH: 116
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t

<400> SEQUENCE: 37
gcagatcttg aggagacagt gaccagggtt ccctggcccc amnnmnnmnn mnnmnnmnnm    60
nnmnnmnnmn nmnnmnngga ggcgcagtaa tacactgcgg tatcttcagc acgcag        116

<210> SEQ ID NO 38
<211> LENGTH: 119
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: misc_feature
<222> LOCATION: (79)..(80)

<223> OTHER INFORMATION: n is a, c, g, or t

<400> SEQUENCE: 38
gcagatcttg aggagacagt gaccagggtt ccctggcccc amnnmnnmnn mnnmnnmnnm    60
nnmnnmnnmn nmnnmnnmnn ggaggcgcag taatacactg cggtatcttc agcacgcag   119

<210> SEQ ID NO 39
<211> LENGTH: 63
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(30)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t

<400> SEQUENCE: 39
ctgacgcacc cagcccatag catannnnnn aaannnaaag ccacttgcag cacagcttaa    60
gcg    63

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
tatgctatgg gctgggtgcg t    21

<210> SEQ ID NO 41
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(30)
<223> OTHER INFORMATION: n is a, c, g, or t

<400> SEQUENCE: 41
gctatcatcg taccaagttg aaccgccnnn gccggaaatc aatgagac    48

<210> SEQ ID NO 42
<211> LENGTH: 27
<212> TYPE: DNA
<213> ORGANISM: Artificial Sequence
<220> FEATURE:
<223> OTHER INFORMATION: primer

<400> SEQUENCE: 42
ggcggttcaa cttggtacga tgatagc    27

<210> SEQ ID NO 43
<211> LENGTH: 69
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (25)..(27)
<223> OTHER INFORMATION: n is a, c, g, or t
<220> FEATURE:
<221> NAME/KEY: misc_feature
<222> LOCATION: (31)..(33)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t

<400> SEQUENCE: 43
tccctggccc cagtagtcag gagcnnnagt nnncggnnna tgtctggcgc agtaatacac     60
tgcggtatc                                                             69

<210> SEQ ID NO 44
<211> LENGTH: 53
<212> TYPE: DNA
<213> ORGANISM: Artificial Sequence
<220> FEATURE:
<223> OTHER INFORMATION: primer

<400> SEQUENCE: 44
gcggatcctg aggagacagt gaccagggtt ccctggcccc agtagtcagg agc            53

<210> SEQ ID NO 45
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(27)
<223> OTHER INFORMATION: n is a, c, g, or t
<220> FEATURE:
<221> NAME/KEY: misc_feature
<222> LOCATION: (31)..(33)
<223> OTHER INFORMATION: n is a, c, g, or t

<400> SEQUENCE: 45
acgcacccaa gacatagcat annnnnnaaa nnnaaagcca cttgcagcac agcttaagcg     60

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
tatgctatgt cttgggtgcg t                                               21

<210> SEQ ID NO 47
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (31)..(33)
<223> OTHER INFORMATION: n is a, c, g, or t

<400> SEQUENCE: 47
aacgctatca gcgtaataag ttgaaccgcc nnngccggaa atagctgaga c              51

<210> SEQ ID NO 48
```

```
<211> LENGTH: 30
<212> TYPE: DNA
<213> ORGANISM: Artificial Sequence
<220> FEATURE:
<223> OTHER INFORMATION: primer

<400> SEQUENCE: 48
ggcggttcaa cttattacgc tgatagcgtt                                      30

<210> SEQ ID NO 49
<211> LENGTH: 89
<212> TYPE: PRT
<213> ORGANISM: Artificial Sequence
<220> FEATURE:
<223> OTHER INFORMATION: MG1X8; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 49

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Val Trp Val Ser Xaa Arg Phe Thr
        35                  40                  45

Ile Ser Arg Asp Asn Ala Lys Asn Thr Leu Phe Leu Gln Met Asn Ser
    50                  55                  60

Leu Arg Asp Glu Asp Thr Ser Val Tyr Tyr Cys Ala Arg Xaa Trp Gly
65                  70                  75                  80

Gln Gly Ala Leu Val Thr Val Ser Ser
                85

<210> SEQ ID NO 50
<211> LENGTH: 89
<212> TYPE: PRT
<213> ORGANISM: Artificial Sequence
<220> FEATURE:
<223> OTHER INFORMATION: MG2X1; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ser Xaa Arg Phe Thr
```

```
                35                  40                  45

Ile Ser Arg Asp Asn Ser Lys Asn Thr Leu Tyr Leu Gln Met Asn Ser
         50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85

<210> SEQ ID NO 51
<211> LENGTH: 89
<212> TYPE: PRT
<213> ORGANISM: Artificial Sequence
<220> FEATURE:
<223> OTHER INFORMATION: MG2X1-34; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 51

Gln Val Gln Leu Val Glu Ser Gly Gly Asn Val Val Gln Pro Gly Thr
 1               5                  10                  15

Ser Leu Arg Leu Ser Cys Ala Ala Ser Gly Phe Thr Phe Xaa Trp Val
                 20                  25                  30

Arg Gln Ala Pro Gly Lys Gly Leu Glu Trp Val Ala Xaa Arg Phe Thr
             35                  40                  45

Ile Ser Arg Asp Asn Ser Arg Asn Thr Val Phe Leu Gln Met Thr Ser
         50                  55                  60

Leu Arg Ala Glu Asp Thr Ala Val Tyr Tyr Cys Gly Arg Xaa Trp Gly
 65                  70                  75                  80

Gln Gly Ile Leu Val Thr Val Ser Ser
                 85

<210> SEQ ID NO 52
<211> LENGTH: 89
<212> TYPE: PRT
<213> ORGANISM: Artificial Sequence
<220> FEATURE:
<223> OTHER INFORMATION: MG2X2-12; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 52

Gln Val Gln Leu Val Gln Ser Gly Ala Glu Val Lys Lys Pro Gly Ala
 1               5                  10                  15

Ser Val Lys Ile Ser Cys Glu Ala Ser Gly Tyr Ala Phe Xaa Trp Val
                 20                  25                  30
```

```
Arg Gln Ala Pro Gly Gln Gly Leu Glu Trp Met Gly Xaa Arg Val Thr
            35                  40                  45

Leu Thr Arg Asp Thr Ser Thr Arg Thr Val Tyr Met Glu Leu Lys Asn
 50                  55                  60

Leu Arg Ser Ala Asp Thr Gly Val Tyr Tyr Cys Ala Arg Xaa Trp Gly
 65                  70                  75                  80

Gln Gly Thr Leu Val Thr Val Ser Ser
                85

<210> SEQ ID NO 53
<211> LENGTH: 89
<212> TYPE: PRT
<213> ORGANISM: Artificial Sequence
<220> FEATURE:
<223> OTHER INFORMATION: MG2X2-13; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 53

Glu Val Gln Leu Leu Glu Ser Gly Gly Gly Val Val Gln Pro Gly Lys
 1               5                  10                  15

Ser Leu Arg Leu Ser Cys Val Gly Ser Gly Phe Ser Phe Xaa Trp Val
                20                  25                  30

Arg Gln Ala Pro Gly Lys Gly Leu Glu Trp Leu Ala Xaa Arg Phe Thr
            35                  40                  45

Ile Ser Arg Asp Asn Ser Lys Thr Met Val Asn Leu Gln Met Asn Ser
 50                  55                  60

Leu Arg Pro Asp Asp Thr Ala Val Tyr Phe Cys Ala Arg Xaa Trp Gly
 65                  70                  75                  80

Gln Gly Thr Leu Val Thr Val Ser Ser
                85

<210> SEQ ID NO 54
<211> LENGTH: 89
<212> TYPE: PRT
<213> ORGANISM: Artificial Sequence
<220> FEATURE:
<223> OTHER INFORMATION: MG3X1; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 54

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Asn Phe Xaa Trp Leu
                20                  25                  30
```

```
Arg Gln Ala Pro Gly Lys Gly Leu Glu Trp Val Ala Xaa Arg Phe Thr
            35                  40                  45

Ile Ser Arg Asp Asn Ser Lys Asn Thr Leu Tyr Leu Glu Met Asn Ser
        50                  55                  60

Leu Arg Pro Glu Asp Thr Ala Val Tyr Tyr Cys Ala Lys Xaa Cys Gly
 65                  70                  75                  80

Gln Gly Thr Leu Val Thr Val Ser Ser
                85

<210> SEQ ID NO 55
<211> LENGTH: 89
<212> TYPE: PRT
<213> ORGANISM: Artificial Sequence
<220> FEATURE:
<223> OTHER INFORMATION: MG3X10; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 55

Glu Val Gln Leu Val Glu Ser Gly Gly Gly Leu Val Lys Pro Gly Gly
 1               5                  10                  15

Ser Leu Arg Val Ser Cys Ala Ala Ser Gly Phe Thr Phe Xaa Trp Val
            20                  25                  30

Arg Gln Ala Pro Gly Lys Gly Leu Glu Trp Val Gly Xaa Arg Phe Thr
            35                  40                  45

Ile Ser Arg Asp Asp Ser Lys Asn Met Val Tyr Leu Gln Met Asn Ser
        50                  55                  60

Leu Lys Thr Glu Asp Thr Ala Val Tyr Tyr Cys Thr Thr Xaa Tyr Gly
 65                  70                  75                  80

Gln Gly Thr Leu Val Thr Val Ser Ser
                85

<210> SEQ ID NO 56
<211> LENGTH: 89
<212> TYPE: PRT
<213> ORGANISM: Artificial Sequence
<220> FEATURE:
<223> OTHER INFORMATION: MG4X1-8; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 56

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Xaa Trp Val
```

```
                    20                  25                  30

Arg Gln Gly Pro Gly Glu Gly Leu Val Trp Leu Ser Xaa Arg Phe Thr
            35                  40                  45

Ile Ser Arg Asp Asn Ala Lys Asn Thr Val Tyr Leu Glu Met Asn Ser
        50                  55                  60

Val Arg Val Asp Asp Thr Ala Val Tyr Tyr Cys Val Ser Xaa Trp Gly
65                  70                  75                  80

Gln Gly Ala Leu Val Thr Val Ser Ser
                85

<210> SEQ ID NO 57
<211> LENGTH: 89
<212> TYPE: PRT
<213> ORGANISM: Artificial Sequence
<220> FEATURE:
<223> OTHER INFORMATION: MG4X1-33; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 57

Glu Val Gln Leu Leu Glu Ser Gly Gly Gly Leu Val Lys Pro Gly Gly
1               5                   10                  15

Ser Leu Arg Leu Ser Cys Val Gly Ser Glu Arg Ser Phe Xaa Trp Val
            20                  25                  30

Arg Gln Ala Pro Gly Lys Gly Leu Glu Trp Val Ala Xaa Arg Phe Thr
        35                  40                  45

Val Ser Arg Asp Asn Val Gln Lys Ser Leu Asp Leu Gln Met Asp Ser
    50                  55                  60

Leu Arg Ala Glu Asp Thr Ala Val Tyr Phe Cys Ala Arg Xaa Trp Gly
65                  70                  75                  80

Gln Gly Thr Thr Val Thr Val Ser Ser
                85

<210> SEQ ID NO 58
<211> LENGTH: 89
<212> TYPE: PRT
<213> ORGANISM: Artificial Sequence
<220> FEATURE:
<223> OTHER INFORMATION: MG4X1-35; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 58

Glu Val Gln Leu Leu Glu Ser Gly Gly Gly Leu Val Lys Pro Gly Gly
1               5                   10                  15
```

Ser Leu Arg Leu Ser Cys Val Gly Ser Glu Arg Ser Phe Xaa Trp Val
            20                  25                  30

Arg Gln Ala Pro Gly Lys Gly Leu Glu Trp Val Ala Xaa Arg Phe Thr
        35                  40                  45

Val Ser Arg Asp Asn Val Gln Lys Ser Leu Asp Leu Gln Met Asp Ser
    50                  55                  60

Leu Arg Ala Glu Asp Thr Ala Val Tyr Phe Cys Ala Arg Xaa Trp Gly
65                  70                  75                  80

Gln Gly Thr Thr Val Thr Val Ser Ser
                85

<210> SEQ ID NO 59
<211> LENGTH: 89
<212> TYPE: PRT
<213> ORGANISM: Artificial Sequence
<220> FEATURE:
<223> OTHER INFORMATION: MG4X3-27; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 59

Glu Val Gln Leu Leu Glu Ser Gly Gly Gly Leu Ala Gln Ser Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Ile Ser Xaa Arg Phe Thr
        35                  40                  45

Ile Ser Arg Asp Ile Ala Lys Asn Ser Leu Tyr Leu Gln Met Asn Ser
    50                  55                  60

Leu Arg Asp Glu Asp Thr Ala Val Tyr Tyr Cys Ala Lys Xaa Trp Gly
65                  70                  75                  80

Gln Gly Ala Leu Val Thr Val Ser Ser
                85

<210> SEQ ID NO 60
<211> LENGTH: 89
<212> TYPE: PRT
<213> ORGANISM: Artificial Sequence
<220> FEATURE:
<223> OTHER INFORMATION: MG4X4-2; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 60

Glu Val Gln Leu Val Gln Ser Gly Ala Glu Val Lys Lys Pro Gly Glu
1               5                   10                  15

Ser Leu Arg Ile Ser Cys Arg Gly Ser Gly Tyr Arg Phe Xaa Trp Ala
            20                  25                  30

Arg Asp Lys Pro Gly Lys Gly Leu Glu Trp Ile Gly Xaa His Val Thr
        35                  40                  45

Ile Ser Ser Asp Arg Ser Val Ser Val Ala Tyr Leu Gln Trp Asp Ser
 50                  55                  60

Leu Lys Ala Ser Asp Asn Gly Ile Tyr Tyr Cys Ala Leu Xaa Trp Gly
 65                  70                  75                  80

Gln Gly Thr Leu Val Thr Val Ser Ser
                85

<210> SEQ ID NO 61
<211> LENGTH: 89
<212> TYPE: PRT
<213> ORGANISM: Artificial Sequence
<220> FEATURE:
<223> OTHER INFORMATION: MG4X4-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Val Pro Ser Gly Phe Thr Phe Xaa Trp Val
            20                  25                  30

Arg Gln Ala Pro Gly Lys Gly Leu Val Trp Val Ser Xaa Arg Phe Thr
        35                  40                  45

Ile Ser Arg Asp Asn Ala Glu Asp Thr Leu Phe Leu Gln Met Asn Ser
 50                  55                  60

Leu Arg Val Asp Asp Thr Ala Val Tyr Tyr Cys Val Arg Xaa Trp Gly
 65                  70                  75                  80

Gln Gly Val Leu Val Thr Val Ser Ser
                85

<210> SEQ ID NO 62
<211> LENGTH: 89
<212> TYPE: PRT
<213> ORGANISM: Artificial Sequence
<220> FEATURE:
<223> OTHER INFORMATION: MG4X4-25; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 62

Gln Val Gln Leu Val Glu Ser Gly Gly Gly Leu Val Gln Pro Gly Gly

```
    1               5                  10                 15
Ser Leu Arg Leu Ser Cys Ile Ala Ser Gly Phe Ser Leu Xaa Trp Val
                 20                  25                 30

Arg Arg Ser Pro Gly Lys Gly Leu Glu Trp Val Ala Xaa Arg Phe Thr
                 35                  40                 45

Val Ser Arg Asp Asn Ala Lys Asn Ser Leu Phe Leu Gln Met Asn Asn
                 50                  55                 60

Val Arg Pro Glu Asp Thr Ala Leu Tyr Phe Cys Ala Arg Xaa Trp Gly
 65                  70                  75                 80

Gln Gly Thr Met Val Thr Val Ser Ser
                 85
```

```
<210> SEQ ID NO 63
<211> LENGTH: 89
<212> TYPE: PRT
<213> ORGANISM: Artificial Sequence
<220> FEATURE:
<223> OTHER INFORMATION: MG4X4-44; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 63
```

```
Glu Val Gln Leu Val Glu Ser Gly Gly Gly Leu Val Gln Pro Gly Gly
  1               5                  10                 15

Ser Leu Arg Leu Ser Cys Ala Ala Ser Gly Phe Thr Phe Xaa Trp Val
                 20                  25                 30

Arg Gln Ala Pro Gly Lys Gly Leu Glu Trp Val Ala Xaa Arg Phe Thr
                 35                  40                 45

Ile Ser Arg Asp Asn Ala Lys Asn Ser Leu Tyr Leu Gln Met Asn Ser
                 50                  55                 60

Leu Arg Ala Glu Asp Thr Ala Leu Tyr Tyr Cys Ala Arg Xaa Trp Gly
 65                  70                  75                 80

Gln Gly Thr Leu Val Thr Val Ser Ser
                 85
```

```
<210> SEQ ID NO 64
<211> LENGTH: 89
<212> TYPE: PRT
<213> ORGANISM: Artificial Sequence
<220> FEATURE:
<223> OTHER INFORMATION: MG4X5-30; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 64
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Leu Ser Xaa Arg Phe Thr
            35                  40                  45

Ile Ser Arg Asn Asn Ala Lys Asn Ser Leu Tyr Leu Gln Met Asn Ser
    50                  55                  60

Leu Arg Val Asp Asp Thr Ala Val Tyr Tyr Cys Ala Arg Xaa Trp Gly
65                  70                  75                  80

Gln Gly Thr Leu Val Thr Val Ser Ser
                85

<210> SEQ ID NO 65
<211> LENGTH: 89
<212> TYPE: PRT
<213> ORGANISM: Artificial Sequence
<220> FEATURE:
<223> OTHER INFORMATION: MG4X6-27; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Gly Pro Gly Lys Gly Leu Glu Trp Val Ala Xaa Arg Phe Thr
            35                  40                  45

Ile Ser Arg Asp Asn Ala Glu Asn Ser Leu Tyr Leu Gln Val Asn Ser
    50                  55                  60

Leu Arg Ala Glu Asp Thr Ala Ile Tyr Tyr Cys Ala Lys Xaa Trp Gly
65                  70                  75                  80

Gln Gly Ala Leu Val Thr Val Ser Ser
                85

<210> SEQ ID NO 66
<211> LENGTH: 89
<212> TYPE: PRT
<213> ORGANISM: Artificial Sequence
<220> FEATURE:
<223> OTHER INFORMATION: MG4X6-48; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 66

```
Glu Val Gln Leu Leu Glu Ser Gly Gly Gly Val Val Gln Pro Gly Arg
1               5                   10                  15

Ser Leu Arg Leu Ser Cys Glu Val Phe Gly Phe Thr Leu Xaa Trp Val
            20                  25                  30

Arg Gln Ala Pro Gly Arg Arg Leu Glu Trp Val Ala Xaa Arg Phe Thr
            35                  40                  45

Ile Ser Arg Asp Ile Ala Thr Asn Arg Leu Tyr Leu Gln Met Arg Ser
50                      55                  60

Leu Arg Ala Glu Asp Thr Ala Leu Tyr Tyr Cys Ala Arg Xaa Trp Gly
65                  70                  75                  80

Gln Gly Thr Leu Val Thr Val Ser Ser
                85

<210> SEQ ID NO 67
<211> LENGTH: 89
<212> TYPE: PRT
<213> ORGANISM: Artificial Sequence
<220> FEATURE:
<223> OTHER INFORMATION: MG4X7-15; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Xaa Trp Val
            20                  25                  30

Arg Gln Ala Pro Gly Lys Gly Leu Glu Trp Val Ser Xaa Arg Phe Thr
            35                  40                  45

Ile Ser Arg Asp Asn Ser Lys Asn Thr Leu Tyr Leu Gln Met Asn Ser
50                      55                  60

Leu Arg Val Glu Asp Thr Ala Val Tyr Tyr Cys Ala Val Xaa Trp Gly
65                  70                  75                  80

Gln Gly Thr Thr Val Thr Val Ser Ser
                85

<210> SEQ ID NO 68
<211> LENGTH: 89
<212> TYPE: PRT
<213> ORGANISM: Artificial Sequence
<220> FEATURE:
<223> OTHER INFORMATION: MG4X8-24; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
```

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Asn Ser Asn Asn Thr Leu Tyr Leu Gln Met Asn Ser
    50                  55                  60

Leu Arg Ala Asp Asp Thr Ala Val Tyr Phe Cys Ala Lys Xaa Trp Gly
65                  70                  75                  80

Gln Gly Thr Leu Val Thr Val Ser Ser
                85

<210> SEQ ID NO 69
<211> LENGTH: 89
<212> TYPE: PRT
<213> ORGANISM: Artificial Sequence
<220> FEATURE:
<223> OTHER INFORMATION: MG0.5X-1; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Val Pro Gly Lys Gly Leu Glu Trp Val Ala Xaa Arg Phe Thr
        35                  40                  45

Ile Ser Arg Asp Asn Ala Lys Asn Ser Leu Tyr Leu Gln Met Asn Ser
    50                  55                  60

Leu Arg Ala Glu Asp Thr Ala Val Tyr Tyr Cys Ala Asn Xaa Trp Gly
65                  70                  75                  80

Gln Gly Thr Leu Val Thr Val Ser Ser
                85

<210> SEQ ID NO 70
<211> LENGTH: 89
<212> TYPE: PRT
<213> ORGANISM: Artificial Sequence
<220> FEATURE:
<223> OTHER INFORMATION: MG0.5X-3; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

```
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 70
```

Gln Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Xaa Trp Val
            20                  25                  30

Arg Gln Ala Pro Gly Thr Gly Leu Leu Trp Leu Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Arg Xaa Trp Gly
65                  70                  75                  80

Xaa Gly Thr Met Val Thr Val Ser Xaa
                85

```
<210> SEQ ID NO 71
<211> LENGTH: 89
<212> TYPE: PRT
<213> ORGANISM: Artificial Sequence
<220> FEATURE:
<223> OTHER INFORMATION: MG0.5X-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 71
```

Glu Val Gln Leu Leu Glu Ser Gly Gly Met Leu Val Lys Pro Gly Glu
1               5                   10                  15

Ser Leu Arg Leu Ser Cys Val Gly Ser Gly Leu Ile Phe Xaa Trp Val
            20                  25                  30

Arg His Ala Pro Gly Lys Gly Leu Glu Trp Val Gly Xaa Arg Leu Ser
        35                  40                  45

Ile Ser Arg Asp Asp Ser Met Asn Thr Val Tyr Leu Asp Ile Tyr Asn
    50                  55                  60

Leu Lys Ile Asp Asp Thr Gly Val Tyr Tyr Cys Thr Phe Xaa Trp Gly
65                  70                  75                  80

Gln Gly Thr Pro Val Thr Val Ser Ser
                85

```
<210> SEQ ID NO 72
<211> LENGTH: 89
<212> TYPE: PRT
<213> ORGANISM: Artificial Sequence
<220> FEATURE:
<223> OTHER INFORMATION: MG0.5X-14; Synthetic
<220> FEATURE:
<221> NAME/KEY: misc_feature
<222> LOCATION: (30)..(30)
```

```
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 72

Glu Val Gln Leu Leu Glu Ser Gly Gly Gly Leu Val His Ala Gly Gly
 1               5                  10                  15

Ser Val Arg Leu Ser Cys Ala Ala Ser Gly Phe Thr Phe Xaa Trp Val
            20                  25                  30

Arg Gln Ala Pro Gly Lys Gly Leu Glu Trp Val Ala Xaa Arg Phe Thr
        35                  40                  45

Ile Ser Arg Asp Asn Ser Lys Asn Ser Met Tyr Leu Gln Met Asn Ser
    50                  55                  60

Leu Arg Val Glu Asp Thr Ala Val Tyr Tyr Cys Ala Arg Xaa Trp Gly
65                  70                  75                  80

Gln Gly Thr Val Val Thr Val Ser Ser
                85

<210> SEQ ID NO 73
<211> LENGTH: 89
<212> TYPE: PRT
<213> ORGANISM: Artificial Sequence
<220> FEATURE:
<223> OTHER INFORMATION: MG0.75X-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 73

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Xaa Trp Leu
            20                  25                  30

Arg Gln Ala Pro Gly Lys Gly Pro Glu Tyr Val Ala Xaa Arg Phe Ile
        35                  40                  45

Ile Ser Arg Asp Asp Ser Asn Asp Met Leu Tyr Leu Glu Met Ile Ser
    50                  55                  60

Leu Lys Ser Glu Asp Thr Ala Val Tyr Tyr Cys Ser Asp Xaa Gly Ser
65                  70                  75                  80

Gln Gly Thr Leu Val Thr Val Ser Ser
                85

<210> SEQ ID NO 74
<211> LENGTH: 89
<212> TYPE: PRT
<213> ORGANISM: Artificial Sequence
<220> FEATURE:
<223> OTHER INFORMATION: MG2X-5; Synthetic
<220> FEATURE:
<221> NAME/KEY: misc_feature
```

-continued

```
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Asn Ser Lys Asn Thr Leu Tyr Leu His Met Asn Ser
    50                  55                  60

Leu Arg Ala Glu Asp Thr Ala Val Tyr Tyr Cys Val Lys Xaa Trp Gly
65                  70                  75                  80

Gln Gly Thr Leu Val Thr Val Ser Ser
                85

<210> SEQ ID NO 75
<211> LENGTH: 89
<212> TYPE: PRT
<213> ORGANISM: Artificial Sequence
<220> FEATURE:
<223> OTHER INFORMATION: MG2X-15; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Lys Xaa Trp Gly
65                  70                  75                  80

Gln Gly Thr Leu Val Thr Val Ser Ser
                85

<210> SEQ ID NO 76
<211> LENGTH: 89
<212> TYPE: PRT
<213> ORGANISM: Artificial Sequence
<220> FEATURE:
<223> OTHER INFORMATION: MG4X-5; Synthetic
<220> FEATURE:
```

<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 76

Gln Val Gln Leu Val Glu Ser Gly Gly Gly Leu Val Gln Pro Gly Gly
1               5                   10                  15

Ser Leu Arg Leu Ser Cys Glu Ala Ser Gly Leu His Phe Xaa Trp Val
            20                  25                  30

Arg Gln Ala Pro Gly Lys Gly Leu Glu Trp Val Ala Xaa Arg Phe Thr
        35                  40                  45

Val Ser Arg Asp Asn Ser Arg Asn Thr Leu Tyr Leu Gln Met Lys Ser
    50                  55                  60

Leu Ser Ala Glu Asp Thr Ala Val Tyr Tyr Cys Ala Lys Xaa Trp Gly
65                  70                  75                  80

Gln Gly Thr Met Val Thr Val Ser Ser
                85

<210> SEQ ID NO 77
<211> LENGTH: 89
<212> TYPE: PRT
<213> ORGANISM: Artificial Sequence
<220> FEATURE:
<223> OTHER INFORMATION: MG1-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 77

Gln Val Gln Leu Val Glu Ala Gly Gly Gly Leu Val Gln Pro Gly Gly
1               5                   10                  15

Ser Leu Arg Leu Ala Cys Ala Ala Ser Gly Phe Thr Phe Xaa Trp Val
            20                  25                  30

Arg Gln Ala Pro Gly Lys Gly Leu Glu Trp Ile Ser Xaa Arg Phe Thr
        35                  40                  45

Ile Ser Arg Asp Asn Ser Gln Asn Ser Leu Phe Leu Gln Met Asn Ser
    50                  55                  60

Leu Arg Ala Glu Asp Thr Ala Val Tyr Tyr Cys Ala Thr Xaa Trp Gly
65                  70                  75                  80

Gln Gly Thr Met Val Thr Val Ser Ser
                85

<210> SEQ ID NO 78
<211> LENGTH: 88
<212> TYPE: PRT
<213> ORGANISM: Artificial Sequence
<220> FEATURE:
<223> OTHER INFORMATION: MG1-6; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 78

Glu Val Gln Leu Val Gln Ser Gly Ala Glu Val Lys Lys Pro Gly Glu
1               5                   10                  15

Ser Leu Arg Lys Ser Cys Lys Gly Ser Gly Tyr Ser Phe Xaa Trp Val
            20                  25                  30

Arg Gln Met Pro Gly Lys Gly Leu Glu Trp Met Gly Xaa His Val Thr
        35                  40                  45

Ile Ser Val Asp Lys Ser Ile Ser Thr Ala Tyr Leu Gln Trp Ser Ser
    50                  55                  60

Leu Lys Ala Ser Asp Ser Ala Met Tyr Tyr Phe Leu Xaa Trp Gly Gln
65                  70                  75                  80

Gly Thr Leu Val Thr Val Ser Ser
                85

<210> SEQ ID NO 79
<211> LENGTH: 89
<212> TYPE: PRT
<213> ORGANISM: Artificial Sequence
<220> FEATURE:
<223> OTHER INFORMATION: MG1-7; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 79

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ala Xaa Arg Phe Thr
        35                  40                  45

Ile Ser Arg Asp Asn Ala Lys Asn Ser Leu Tyr Leu Gln Met Asn Ser
    50                  55                  60

Leu Arg Asp Glu Asp Thr Ala Val Tyr Tyr Cys Ala Arg Xaa Trp Gly
65                  70                  75                  80

Gln Gly Thr Leu Val Thr Val Ser Ser
                85

<210> SEQ ID NO 80
<211> LENGTH: 89
<212> TYPE: PRT
<213> ORGANISM: Artificial Sequence
<220> FEATURE:

```
<223> OTHER INFORMATION: MG1-8; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Trp Val
            20                  25                  30

Arg Gln Ala Pro Gly Gln Gly Leu Glu Trp Met Gly Xaa Arg Val Thr
        35                  40                  45

Met Thr Arg Asp Thr Ser Ser Thr Ala Tyr Met Glu Leu Asn Arg
    50                  55                  60

Leu Thr Ser Asp Asp Thr Ala Val Tyr Phe Cys Ala Arg Xaa Trp Gly
65                  70                  75                  80

Gln Gly Thr Leu Val Thr Val Ser Ser
                85

<210> SEQ ID NO 81
<211> LENGTH: 89
<212> TYPE: PRT
<213> ORGANISM: Artificial Sequence
<220> FEATURE:
<223> OTHER INFORMATION: MG1-9; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 81

Glu Val Gln Leu Val Glu Ala Gly Gly Gly Leu Val Gln Pro Gly Gly
1               5                   10                  15

Ser Leu Arg Leu Ala Cys Ala Ala Ser Gly Phe Thr Phe Xaa Trp Val
            20                  25                  30

Arg Gln Ala Pro Gly Lys Gly Leu Glu Trp Ile Ser Xaa Arg Phe Thr
        35                  40                  45

Ile Ser Arg Asp Asn Ala Gln Asn Ser Leu Phe Leu Gln Met Asn Ser
    50                  55                  60

Leu Arg Ala Glu Asp Thr Ala Val Tyr Tyr Cys Ala Thr Xaa Trp Gly
65                  70                  75                  80

Gln Gly Thr Met Val Thr Val Ser Ser
                85

<210> SEQ ID NO 82
<211> LENGTH: 89
<212> TYPE: PRT
<213> ORGANISM: Artificial Sequence
```

```
<220> FEATURE:
<223> OTHER INFORMATION: MG1-10; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 82

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Xaa Trp Val
            20                  25                  30

Arg Gln Met Pro Gly Arg Gly Leu Glu Trp Leu Gly Xaa Gln Val Thr
        35                  40                  45

Met Ser Ala Asn Arg Ser Ile Ser Thr Ala Tyr Leu Gln Trp Ser Ser
    50                  55                  60

Leu Lys Ala Ser Asp Thr Gly Ile Tyr Tyr Cys Ala Thr Xaa Trp Gly
65                  70                  75                  80

Gln Gly Thr Thr Val Thr Val Ser Ser
                85

<210> SEQ ID NO 83
<211> LENGTH: 89
<212> TYPE: PRT
<213> ORGANISM: Artificial Sequence
<220> FEATURE:
<223> OTHER INFORMATION: MG5-1; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 83

Gln Val Gln Leu Val Glu Ser Gly Gly Gly Leu Ile Gln Pro Gly Glu
1               5                   10                  15

Ser Leu Arg Leu Ser Cys Glu Ala Phe Gly Phe Thr Val Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Ser Thr Gln Asn Thr Val His Leu Gln Met Asn Ser
    50                  55                  60

Leu Thr Ala Glu Asp Thr Ala Val Tyr Tyr Cys Ala Arg Xaa Trp Gly
65                  70                  75                  80

Gln Gly Thr Leu Val Thr Val Ser Ser
                85

<210> SEQ ID NO 84
<211> LENGTH: 89
<212> TYPE: PRT
```

<213> ORGANISM: Artificial Sequence
<220> FEATURE:
<223> OTHER INFORMATION: MG5-2; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 84

Glu Val Gln Leu Val Gln Ser Gly Ala Glu Leu Lys Lys Pro Gly Ser
1               5                   10                  15

Ser Val Lys Val Ser Cys Thr Ser Ser Gly Ser Phe Xaa Trp Val
                20                  25                  30

Arg Gln Ala Pro Gly Gln Gly Leu Glu Trp Met Gly Xaa Arg Leu Ile
            35                  40                  45

Leu Ser Val Asp Glu Pro Thr Arg Thr Val Tyr Met Glu Leu Thr Ser
50                  55                  60

Leu Arg Ser Asp Asp Thr Ala Met Tyr Tyr Cys Ala Arg Xaa Trp Gly
65                  70                  75                  80

Gln Gly Thr Thr Val Thr Val Ser Ser
                85

<210> SEQ ID NO 85
<211> LENGTH: 89
<212> TYPE: PRT
<213> ORGANISM: Artificial Sequence
<220> FEATURE:
<223> OTHER INFORMATION: MG5-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 85

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Xaa Trp Val
                20                  25                  30

Arg Gln Ala Pro Gly Lys Gly Leu Glu Trp Val Ser Xaa Arg Phe Thr
            35                  40                  45

Ile Ser Arg Asp Asn Ala Lys Asp Ser Leu Tyr Leu Gln Met Asn Ser
            50                  55                  60

Leu Arg Pro Glu Asp Thr Ala Leu Tyr Tyr Cys Ala Arg Xaa Trp Gly
65                  70                  75                  80

Gln Gly Thr Met Val Thr Val Ser Ser
                85

<210> SEQ ID NO 86
<211> LENGTH: 89

```
<212> TYPE: PRT
<213> ORGANISM: Artificial Sequence
<220> FEATURE:
<223> OTHER INFORMATION: MG5-5; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 86

Glu Val Gln Leu Leu Glu Ser Gly Gly Gly Val Val Gln Pro Gly Arg
1               5                   10                  15

Ser Leu Arg Leu Ser Cys Val Ala Ser Gly Phe Thr Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Tyr Ser Asn Lys Ile Val His Leu Glu Met Asp Ser
    50                  55                  60

Leu Arg Ala Glu Asp Thr Ala Val Tyr Phe Cys Val Arg Xaa Trp Gly
65                  70                  75                  80

Gln Gly Thr Leu Val Thr Val Ser Ser
                85

<210> SEQ ID NO 87
<211> LENGTH: 89
<212> TYPE: PRT
<213> ORGANISM: Artificial Sequence
<220> FEATURE:
<223> OTHER INFORMATION: MG5-6; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 87

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Cys Val Ala Xaa Arg Phe Thr
        35                  40                  45

Ile Ser Arg Asp Asp Ser Arg Asp Met Leu Tyr Leu Gln Met Asn Asn
    50                  55                  60

Leu Lys Thr Glu Asp Thr Ala Val Tyr Tyr Cys Ser Asp Xaa Ser Ser
65                  70                  75                  80

Gln Gly Thr Leu Val Thr Val Ser Ser
                85

<210> SEQ ID NO 88
```

```
<211> LENGTH: 89
<212> TYPE: PRT
<213> ORGANISM: Artificial Sequence
<220> FEATURE:
<223> OTHER INFORMATION: MG5-7; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 88

Glu Val Gln Leu Val Glu Ser Gly Gly Gly Leu Val Gln Pro Gly Arg
1               5                   10                  15

Ser Leu Arg Leu Ser Cys Thr Thr Ser Gly Phe Ser Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Asp Ser Lys Ser Ile Val Tyr Leu Gln Met Ser Ser
50                  55                  60

Leu Gln Thr Glu Asp Thr Ala Val Tyr Tyr Cys Ser Arg Xaa Trp Gly
65                  70                  75                  80

Arg Gly Thr Leu Val Thr Val Ser Ser
                85

<210> SEQ ID NO 89
<211> LENGTH: 87
<212> TYPE: PRT
<213> ORGANISM: Artificial Sequence
<220> FEATURE:
<223> OTHER INFORMATION: MG5-9; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid

<400> SEQUENCE: 89

Glu Val Gln Leu Leu Glu Ser Gly Gly Gly Leu Val Arg Pro Gly Gly
1               5                   10                  15

Ser Leu Arg Leu Ser Cys Ser Ala Ser Gly Phe Ala Phe Xaa Trp Val
            20                  25                  30

Arg Gln Ala Pro Gly Lys Gly Leu Glu Trp Val Ser Xaa Thr Ile Ser
        35                  40                  45

Arg Asp Asn Ala Lys Asn Ser Val Tyr Leu Gln Met Asn Ser Leu Arg
50                  55                  60

Ala Glu Asp Ser Ala Val Tyr Phe Cys Ala Arg Xaa Trp Gly Gln Gly
65                  70                  75                  80

Thr Leu Val Thr Val Ser Ser
                85
```

```
<210> SEQ ID NO 90
<211> LENGTH: 89
<212> TYPE: PRT
<213> ORGANISM: Artificial Sequence
<220> FEATURE:
<223> OTHER INFORMATION: MG10-1; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 90

Gln Val Gln Leu Val Glu Ser Gly Gly Asn Val Val Gln Pro Gly Thr
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ala Xaa Arg Phe Thr
        35                  40                  45

Ile Ser Arg Asp Asn Ser Arg Asn Thr Val Phe Leu Gln Met Thr Ser
50                  55                  60

Leu Arg Ala Glu Asp Thr Ala Val Tyr Tyr Cys Gly Arg Xaa Trp Gly
65                  70                  75                  80

Gln Gly Ile Leu Val Thr Val Ser Ser
                85

<210> SEQ ID NO 91
<211> LENGTH: 89
<212> TYPE: PRT
<213> ORGANISM: Artificial Sequence
<220> FEATURE:
<223> OTHER INFORMATION: MG10-2; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 91

Glu Val Gln Leu Leu Glu Ser Gly Gly Gly Leu Val Gln Pro Gly Gly
1               5                   10                  15

Ser Leu Arg Leu Thr Cys Val Gly Tyr Gly Phe Thr Phe Xaa Trp Val
            20                  25                  30

Arg Gln Ala Pro Gly Lys Gly Pro Glu Trp Val Ala Xaa Arg Phe Thr
        35                  40                  45

Ile Ser Arg Asp Asn Ala Lys Asp Ser Leu Tyr Leu Gln Met Asp Ser
50                  55                  60

Leu Arg Pro Glu Asp Thr Ala Val Tyr Tyr Cys Ala Arg Xaa Ala Pro
65                  70                  75                  80

Gln Gly Thr Leu Val Thr Val Ser Ser
                85
```

```
<210> SEQ ID NO 92
<211> LENGTH: 89
<212> TYPE: PRT
<213> ORGANISM: Artificial Sequence
<220> FEATURE:
<223> OTHER INFORMATION: MG10-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Leu Xaa Trp Val
            20                  25                  30

Arg Gln Ala Pro Gly Lys Gly Leu Val Trp Val Ser Xaa Gln Phe Thr
        35                  40                  45

Ile Ser Arg Asp Asn Ala Lys Asn Thr Leu Tyr Leu Gln Met Asn Ser
    50                  55                  60

Leu Arg Val Glu Asp Thr Ala Val Tyr Tyr Cys Ala Arg Xaa Trp Gly
65                  70                  75                  80

Gln Gly Thr Met Val Thr Val Ser Ser
                85

<210> SEQ ID NO 93
<211> LENGTH: 89
<212> TYPE: PRT
<213> ORGANISM: Artificial Sequence
<220> FEATURE:
<223> OTHER INFORMATION: MG10-5; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 93

Glu Val Gln Leu Leu Glu Ser Gly Gly Gly Val Val His Pro Gly Arg
1               5                   10                  15

Ser Leu Arg Leu Ser Cys Ala Val Ser Gly Phe Ser Leu Xaa Trp Val
            20                  25                  30

Arg Gln Ala Pro Asp Lys Gly Leu Glu Trp Val Ala Xaa Arg Phe Thr
        35                  40                  45

Val Ser Arg Asp Ile Ser Lys Asn Thr Val Tyr Leu Gln Met Asn Ser
    50                  55                  60

Leu Arg Ala Glu Asp Thr Ala Leu Tyr Tyr Cys Ala Arg Xaa Trp Gly
65                  70                  75                  80

Gln Gly Thr Met Val Thr Val Ser Ser
                85
```

```
<210> SEQ ID NO 94
<211> LENGTH: 89
<212> TYPE: PRT
<213> ORGANISM: Artificial Sequence
<220> FEATURE:
<223> OTHER INFORMATION: MG10-6; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 94

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Xaa Trp Phe
            20                  25                  30

Arg Gln Gly Pro Gly Lys Gly Leu Glu Trp Val Ala Xaa Arg Phe Thr
        35                  40                  45

Ile Ser Arg Asp Asp Ser Lys Asn Ser Leu Ser Leu Gln Met Asp Ser
    50                  55                  60

Leu Arg Thr Glu Asp Thr Ala Val Tyr Tyr Cys Val Arg Xaa Trp Gly
65                  70                  75                  80

Gln Gly Thr Val Val Thr Val Ser Ser
                85

<210> SEQ ID NO 95
<211> LENGTH: 89
<212> TYPE: PRT
<213> ORGANISM: Artificial Sequence
<220> FEATURE:
<223> OTHER INFORMATION: MG10-8; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 95

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ala Phe Xaa Trp Val
            20                  25                  30

Arg Gln Thr Pro Gly Arg Gly Leu Glu Trp Leu Ala Xaa Arg Phe Thr
        35                  40                  45

Ile Ser Arg Asp Asn Ser Asn Asn Thr Val Tyr Leu Glu Met Asn Ser
    50                  55                  60

Leu Arg Pro Glu Asp Ser Ala Ile Tyr Tyr Cys Ala Lys Xaa Trp Gly
65                  70                  75                  80

Leu Gly Thr Val Val Thr Val Ser Ser
```

-continued

```
                85

<210> SEQ ID NO 96
<211> LENGTH: 88
<212> TYPE: PRT
<213> ORGANISM: Artificial Sequence
<220> FEATURE:
<223> OTHER INFORMATION: MG10-10; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 96

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Asn Ser Lys Asn Ser Leu Tyr Leu Gln Met Asn Ser
    50                  55                  60

Leu Arg Thr Asp Glu Thr Ala Leu Tyr Tyr Cys Val Xaa Trp Gly Gln
65                  70                  75                  80

Gly Thr Leu Val Thr Val Ser Ser
                85

<210> SEQ ID NO 97
<211> LENGTH: 89
<212> TYPE: PRT
<213> ORGANISM: Artificial Sequence
<220> FEATURE:
<223> OTHER INFORMATION: MG2; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ser Xaa Arg Phe Thr
        35                  40                  45

Ile Ser Arg Asp Asn Ala Lys Asn Ser Leu Tyr Leu Gln Met Asn Ser
    50                  55                  60

Leu Arg Thr Asp Glu Thr Ala Val Tyr Tyr Cys Ala Arg Xaa Trp Gly
65                  70                  75                  80
```

Gln Gly Thr Thr Val Thr Val Ser Ser
            85

<210> SEQ ID NO 98
<211> LENGTH: 89
<212> TYPE: PRT
<213> ORGANISM: Artificial Sequence
<220> FEATURE:
<223> OTHER INFORMATION: MG5; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 98

Glu Val Gln Leu Leu Gln Ser Gly Gly Gly Trp Val Lys Pro Gly Gly
1               5                   10                  15

Ser Leu Arg Leu Ser Cys Ala Ala Ser Gly Phe Ile Cys Xaa Trp Val
            20                  25                  30

Arg Gln Ala Pro Gly Lys Gly Leu Glu Trp Val Gly Xaa Arg Phe Thr
        35                  40                  45

Ile Ser Ile Asp Glu Ser Arg Asn Ala Leu Phe Leu His Met Asn Ser
    50                  55                  60

Leu Thr Thr Asp Asp Thr Ala Val Tyr Tyr Cys Ser Thr Xaa Trp Gly
65                  70                  75                  80

Gln Gly Thr Leu Val Thr Val Ser Ser
            85

<210> SEQ ID NO 99
<211> LENGTH: 89
<212> TYPE: PRT
<213> ORGANISM: Artificial Sequence
<220> FEATURE:
<223> OTHER INFORMATION: MG6; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 99

Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Leu Glu Trp Val Ala Xaa Arg Phe Thr
        35                  40                  45

Val Ser Arg Asp Thr Ser Thr Asn Thr Leu Tyr Leu Gln Met Asn Ser
    50                  55                  60

Leu Arg Val Glu Asp Thr Ala Val Tyr Tyr Cys Ala Arg Xaa Trp Gly
65                  70                  75                  80

```
Gln Gly Thr Leu Val Thr Val Ser Ser
                85

<210> SEQ ID NO 100
<211> LENGTH: 89
<212> TYPE: PRT
<213> ORGANISM: Artificial Sequence
<220> FEATURE:
<223> OTHER INFORMATION: MG7; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 100

Gln Met Gln Leu Val Gln Ser Glu Ala Glu Val Lys Lys Pro Gly Ala
1               5                   10                  15

Ser Met Lys Val Ser Cys Lys Ala Ser Gly Tyr Thr Phe Xaa Trp Val
                20                  25                  30

Arg Gln Ala Thr Gly Gln Gly Leu Glu Trp Met Gly Xaa Arg Val Thr
            35                  40                  45

Met Thr Arg Asn Thr Ser Ile Ser Thr Ala Tyr Met Glu Leu Ser Ser
        50                  55                  60

Leu Thr Ser Ala Asp Thr Ala Val Tyr Tyr Cys Ala Arg Xaa Trp Gly
65                  70                  75                  80

Gln Gly Thr Leu Val Thr Val Ser Ser
                85

<210> SEQ ID NO 101
<211> LENGTH: 89
<212> TYPE: PRT
<213> ORGANISM: Artificial Sequence
<220> FEATURE:
<223> OTHER INFORMATION: MG10; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 101

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Xaa Trp Val
                20                  25                  30

Arg Gln Met Pro Gly Lys Gly Leu Glu Trp Met Gly Xaa Gln Val Thr
            35                  40                  45

Ile Ser Ala Asp Lys Ser Ile Ser Thr Ala Phe Leu Gln Trp Asn Ser
        50                  55                  60

Leu Lys Ala Ser Asp Thr Ala Met Tyr Tyr Cys Ala Arg Xaa Trp Gly
```

```
65                  70                  75                  80

Leu Gly Thr Leu Val Thr Val Ser Ser
                85

<210> SEQ ID NO 102
<211> LENGTH: 89
<212> TYPE: PRT
<213> ORGANISM: Artificial Sequence
<220> FEATURE:
<223> OTHER INFORMATION: MG8-21; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Asn Ala Pro Gly Lys Gly Asn Glu Ile Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 103
<211> LENGTH: 89
<212> TYPE: PRT
<213> ORGANISM: Artificial Sequence
<220> FEATURE:
<223> OTHER INFORMATION: MG2-12L; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Arg Ala Pro Gly Lys Gly Ile Glu Val Val Ser Xaa Arg Phe Thr
        35                  40                  45

Ile Ser Arg Asp Asn Ser Lys Asn Thr Leu Tyr Leu Gln Met Asn Ser
    50                  55                  60
```

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 104
<211> LENGTH: 89
<212> TYPE: PRT
<213> ORGANISM: Artificial Sequence
<220> FEATURE:
<223> OTHER INFORMATION: MG2-7I; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Ile Ala Pro Gly Lys Gly Pro Glu Pro Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 105
<211> LENGTH: 89
<212> TYPE: PRT
<213> ORGANISM: Artificial Sequence
<220> FEATURE:
<223> OTHER INFORMATION: MG2-9I; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Lys Ala Pro Gly Lys Gly Tyr Glu Pro Val Ser Xaa Arg Phe Thr
        35                  40                  45

Ile Ser Arg Asp Asn Ser Lys Asn Thr Leu Tyr Leu Gln Met Asn Ser
50                  55                  60

```
Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85
```

<210> SEQ ID NO 106
<211> LENGTH: 89
<212> TYPE: PRT
<213> ORGANISM: Artificial Sequence
<220> FEATURE:
<223> OTHER INFORMATION: MG2-10I; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 106

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Asn Ala Pro Gly Lys Gly Tyr Glu Ile Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85
```

<210> SEQ ID NO 107
<211> LENGTH: 89
<212> TYPE: PRT
<213> ORGANISM: Artificial Sequence
<220> FEATURE:
<223> OTHER INFORMATION: MG2-11I; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Tyr Ala Pro Gly Lys Gly Tyr Glu Phe Val Ser Xaa Arg Phe Thr
        35                  40                  45

Ile Ser Arg Asp Asn Ser Lys Asn Thr Leu Tyr Leu Gln Met Asn Ser
```

```
                50                  55                  60
Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85
```

<210> SEQ ID NO 108
<211> LENGTH: 89
<212> TYPE: PRT
<213> ORGANISM: Artificial Sequence
<220> FEATURE:
<223> OTHER INFORMATION: MG2-12I; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 108

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Xaa Trp Val
                 20                  25                  30

Arg Val Ala Pro Gly Lys Gly Ile Glu Pro Val Ser Xaa Arg Phe Thr
             35                  40                  45

Ile Ser Arg Asp Asn Ser Lys Asn Thr Leu Tyr Leu Gln Met Asn Ser
 50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85
```

<210> SEQ ID NO 109
<211> LENGTH: 89
<212> TYPE: PRT
<213> ORGANISM: Artificial Sequence
<220> FEATURE:
<223> OTHER INFORMATION: MG2-32; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 109

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Xaa Trp Val
                 20                  25                  30

Arg Met Ala Pro Gly Lys Gly Pro Glu His Val Ser Xaa Arg Phe Thr
             35                  40                  45
```

```
Ile Ser Arg Asp Asn Ser Lys Asn Thr Leu Tyr Leu Gln Met Asn Ser
 50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85

<210> SEQ ID NO 110
<211> LENGTH: 89
<212> TYPE: PRT
<213> ORGANISM: Artificial Sequence
<220> FEATURE:
<223> OTHER INFORMATION: MG2-34; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 110

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Xaa Trp Val
                 20                  25                  30

Arg Ser Ala Pro Gly Lys Gly Val Glu Met Val Ser Xaa Arg Phe Thr
             35                  40                  45

Ile Ser Arg Asp Asn Ser Lys Asn Thr Leu Tyr Leu Gln Met Asn Ser
 50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85

<210> SEQ ID NO 111
<211> LENGTH: 89
<212> TYPE: PRT
<213> ORGANISM: Artificial Sequence
<220> FEATURE:
<223> OTHER INFORMATION: MG2-40; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 111

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Xaa Trp Val
                 20                  25                  30

Arg Thr Ala Pro Gly Lys Gly Thr Glu Met Val Ser Xaa Arg Phe Thr
             35                  40                  45
```

```
Ile Ser Arg Asp Asn Ser Lys Asn Thr Leu Tyr Leu Gln Met Asn Ser
         50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85

<210> SEQ ID NO 112
<211> LENGTH: 89
<212> TYPE: PRT
<213> ORGANISM: Artificial Sequence
<220> FEATURE:
<223> OTHER INFORMATION: MG2-46; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 112

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Xaa Trp Val
             20                  25                  30

Arg Cys Ala Pro Gly Lys Gly Tyr Glu Phe Val Ser Xaa Arg Phe Thr
         35                  40                  45

Ile Ser Arg Asp Asn Ser Lys Asn Thr Leu Tyr Leu Gln Met Asn Ser
         50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85

<210> SEQ ID NO 113
<211> LENGTH: 89
<212> TYPE: PRT
<213> ORGANISM: Artificial Sequence
<220> FEATURE:
<223> OTHER INFORMATION: MG2-47; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 113

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Xaa Trp Val
             20                  25                  30

Arg Ile Ala Pro Gly Lys Gly Leu Glu Met Val Ser Xaa Arg Phe Thr
```

```
                    35                  40                  45

Ile Ser Arg Asp Asn Ser Lys Asn Thr Leu Tyr Leu Gln Met Asn Ser
        50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 114
<211> LENGTH: 89
<212> TYPE: PRT
<213> ORGANISM: Artificial Sequence
<220> FEATURE:
<223> OTHER INFORMATION: MG2-48; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Met Ala Pro Gly Lys Gly Leu Glu Tyr Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 115
<211> LENGTH: 89
<212> TYPE: PRT
<213> ORGANISM: Artificial Sequence
<220> FEATURE:
<223> OTHER INFORMATION: MG2-51; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30
```

```
Arg Tyr Ala Pro Gly Lys Gly Thr Glu Phe Val Ser Xaa Arg Phe Thr
         35                  40                  45

Ile Ser Arg Asp Asn Ser Lys Asn Thr Leu Tyr Leu Gln Met Asn Ser
 50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85
```

<210> SEQ ID NO 116
<211> LENGTH: 89
<212> TYPE: PRT
<213> ORGANISM: Artificial Sequence
<220> FEATURE:
<223> OTHER INFORMATION: MG2-53; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 116

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Xaa Trp Val
         20                  25                  30

Arg Gln Ala Pro Gly Lys Gly Val Glu Trp Val Ser Xaa Arg Phe Thr
         35                  40                  45

Ile Ser Arg Asp Asn Ser Lys Asn Thr Leu Tyr Leu Gln Met Asn Ser
 50                  55                  60

Leu Arg Ala Glu Asp Thr Ala Val Tyr Tyr Cys Ala Ser Xaa Trp Gly
 65                  70                  75                  80

Gln Gly Thr Leu Val Thr Val Ser Ser
                 85
```

<210> SEQ ID NO 117
<211> LENGTH: 89
<212> TYPE: PRT
<213> ORGANISM: Artificial Sequence
<220> FEATURE:
<223> OTHER INFORMATION: MG2-55; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 117

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Xaa Trp Val
         20                  25                  30
```

Arg Trp Ala Pro Gly Lys Gly Pro Glu Phe Val Ser Xaa Arg Phe Thr
                35                  40                  45

Ile Ser Arg Asp Asn Ser Lys Asn Thr Leu Tyr Leu Gln Met Asn Ser
        50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 118
<211> LENGTH: 89
<212> TYPE: PRT
<213> ORGANISM: Artificial Sequence
<220> FEATURE:
<223> OTHER INFORMATION: MG2-57; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Phe Ala Pro Gly Lys Gly Arg Glu Trp Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 119
<211> LENGTH: 89
<212> TYPE: PRT
<213> ORGANISM: Artificial Sequence
<220> FEATURE:
<223> OTHER INFORMATION: MG2-58; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val

```
                    20                  25                  30
Arg Phe Ala Pro Gly Lys Gly Cys Glu Leu Val Ser Xaa Arg Phe Thr
                35                  40                  45

Ile Ser Arg Asp Asn Ser Lys Asn Thr Leu Tyr Leu Gln Met Asn Ser
            50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 120
<211> LENGTH: 89
<212> TYPE: PRT
<213> ORGANISM: Artificial Sequence
<220> FEATURE:
<223> OTHER INFORMATION: MG2-59; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
                20                  25                  30

Arg Lys Ala Pro Gly Lys Gly Leu Glu Thr Val Ser Xaa Arg Phe Thr
                35                  40                  45

Ile Ser Arg Asp Asn Ser Lys Asn Thr Leu Tyr Leu Gln Met Asn Ser
            50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 121
<211> LENGTH: 89
<212> TYPE: PRT
<213> ORGANISM: Artificial Sequence
<220> FEATURE:
<223> OTHER INFORMATION: MG2-60; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 121

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Xaa Trp Val
            20                  25                  30

Arg Asn Ala Pro Gly Lys Gly Leu Glu Cys Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 122
<211> LENGTH: 89
<212> TYPE: PRT
<213> ORGANISM: Artificial Sequence
<220> FEATURE:
<223> OTHER INFORMATION: MG2-64; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Lys Ala Pro Gly Lys Gly Leu Glu Thr Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 123
<211> LENGTH: 89
<212> TYPE: PRT
<213> ORGANISM: Artificial Sequence
<220> FEATURE:
<223> OTHER INFORMATION: MG4-12; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 123

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Xaa Trp Val
            20                  25                  30

Arg Leu Ala Pro Gly Lys Gly Val Glu Leu Val Ser Xaa Arg Phe Thr
            35                  40                  45

Ile Ser Arg Asp Asn Ser Lys Asn Thr Leu Tyr Leu Gln Met Asn Ser
        50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 124
<211> LENGTH: 89
<212> TYPE: PRT
<213> ORGANISM: Artificial Sequence
<220> FEATURE:
<223> OTHER INFORMATION: MG4-13; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Phe Ala Pro Gly Lys Gly Ala Glu Trp Val Ser Xaa Arg Phe Thr
            35                  40                  45

Ile Ser Arg Asp Asn Ser Lys Asn Thr Leu Tyr Leu Gln Met Asn Ser
        50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 125
<211> LENGTH: 89
<212> TYPE: PRT
<213> ORGANISM: Artificial Sequence
<220> FEATURE:
<223> OTHER INFORMATION: MG4-17; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 125

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Phe Xaa Trp Val
            20                  25                  30

Arg Leu Ala Pro Gly Lys Gly Arg Glu Trp Val Ser Xaa Arg Phe Thr
            35                  40                  45

Ile Ser Arg Asp Asn Ser Lys Asn Thr Leu Tyr Leu Gln Met Asn Ser
            50                  55                  60

Leu Arg Ala Glu Asp Thr Ala Val Tyr Tyr Cys Ala Ser Xaa Trp Gly
65                      70                  75                  80

Gln Gly Thr Leu Val Thr Val Ser Ser
                85

<210> SEQ ID NO 126
<211> LENGTH: 89
<212> TYPE: PRT
<213> ORGANISM: Artificial Sequence
<220> FEATURE:
<223> OTHER INFORMATION: MG4-18; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Tyr Ala Pro Gly Lys Gly Val Glu Phe Val Ser Xaa Arg Phe Thr
            35                  40                  45

Ile Ser Arg Asp Asn Ser Lys Asn Thr Leu Tyr Leu Gln Met Asn Ser
            50                  55                  60

Leu Arg Ala Glu Asp Thr Ala Val Tyr Tyr Cys Ala Ser Xaa Trp Gly
65                      70                  75                  80

Gln Gly Thr Leu Val Thr Val Ser Ser
                85

<210> SEQ ID NO 127
<211> LENGTH: 89
<212> TYPE: PRT
<213> ORGANISM: Artificial Sequence
<220> FEATURE:
<223> OTHER INFORMATION: MG4-20; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 127
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Phe Ala Pro Gly Lys Gly Leu Glu Met Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85
```

<210> SEQ ID NO 128
<211> LENGTH: 89
<212> TYPE: PRT
<213> ORGANISM: Artificial Sequence
<220> FEATURE:
<223> OTHER INFORMATION: MG4-28; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Val Ala Pro Gly Lys Gly Thr Glu Arg Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85
```

<210> SEQ ID NO 129
<211> LENGTH: 89
<212> TYPE: PRT
<213> ORGANISM: Artificial Sequence
<220> FEATURE:
<223> OTHER INFORMATION: MG4-2; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 129

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Ile Ala Pro Gly Lys Gly Met Glu Met Val Ser Xaa Arg Phe Thr
            35                  40                  45

Ile Ser Arg Asp Asn Ser Lys Asn Thr Leu Tyr Leu Gln Met Asn Ser
        50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85
```

<210> SEQ ID NO 130
<211> LENGTH: 89
<212> TYPE: PRT
<213> ORGANISM: Artificial Sequence
<220> FEATURE:
<223> OTHER INFORMATION: MG4-32; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 130

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Ala Ala Pro Gly Lys Gly Pro Glu Leu Val Ser Xaa Arg Phe Thr
            35                  40                  45

Ile Ser Arg Asp Asn Ser Lys Asn Thr Leu Tyr Leu Gln Met Asn Ser
        50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85
```

<210> SEQ ID NO 131
<211> LENGTH: 89
<212> TYPE: PRT
<213> ORGANISM: Artificial Sequence
<220> FEATURE:
<223> OTHER INFORMATION: MG4-33; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Val Ala Pro Gly Lys Gly Tyr Glu His Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 132
<211> LENGTH: 89
<212> TYPE: PRT
<213> ORGANISM: Artificial Sequence
<220> FEATURE:
<223> OTHER INFORMATION: MG4-34; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Val Ala Pro Gly Lys Gly Leu Glu Cys Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 133
<211> LENGTH: 89
<212> TYPE: PRT
<213> ORGANISM: Artificial Sequence
<220> FEATURE:
<223> OTHER INFORMATION: MG4-5; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Val Ala Pro Gly Lys Gly Pro Glu Thr Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 134
<211> LENGTH: 89
<212> TYPE: PRT
<213> ORGANISM: Artificial Sequence
<220> FEATURE:
<223> OTHER INFORMATION: MG4-6; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Met Ala Pro Gly Lys Gly Ser Glu Val Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 135
<211> LENGTH: 89
<212> TYPE: PRT
<213> ORGANISM: Artificial Sequence
<220> FEATURE:
<223> OTHER INFORMATION: MG4-7; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)

<223> OTHER INFORMATION: Xaa can be any naturally occurring amino acid

<400> SEQUENCE: 135

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Xaa | Trp | Val |
|---|---|---|---|---|---|---|---|---|---|---|---|---|---|---|---|
| | | | 20 | | | | | 25 | | | | | 30 | | |

| Arg | Leu | Ala | Pro | Gly | Lys | Gly | Thr | Glu | Met | Val | Ser | Xaa | Arg | Phe | Thr |
|---|---|---|---|---|---|---|---|---|---|---|---|---|---|---|---|
| | | 35 | | | | | 40 | | | | | 45 | | | |

| Ile | Ser | Arg | Asp | Asn | Ser | Lys | Asn | Thr | Leu | Tyr | Leu | Gln | Met | Asn | Ser |
|---|---|---|---|---|---|---|---|---|---|---|---|---|---|---|---|
| 50 | | | | | 55 | | | | | 60 | | | | | |

| Leu | Arg | Ala | Glu | Asp | Thr | Ala | Val | Tyr | Tyr | Cys | Ala | Ser | Xaa | Trp | Gly |
|---|---|---|---|---|---|---|---|---|---|---|---|---|---|---|---|
| 65 | | | | | 70 | | | | | 75 | | | | | 80 |

| Gln | Gly | Thr | Leu | Val | Thr | Val | Ser | Ser |
|---|---|---|---|---|---|---|---|---|
| | | | | 85 | | | | |

<210> SEQ ID NO 136
<211> LENGTH: 89
<212> TYPE: PRT
<213> ORGANISM: Artificial Sequence
<220> FEATURE:
<223> OTHER INFORMATION: MG8-11; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 136

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Xaa | Trp | Val |
|---|---|---|---|---|---|---|---|---|---|---|---|---|---|---|---|
| | | | 20 | | | | | 25 | | | | | 30 | | |

| Arg | Thr | Ala | Pro | Gly | Lys | Gly | Ala | Glu | Trp | Val | Ser | Xaa | Arg | Phe | Thr |
|---|---|---|---|---|---|---|---|---|---|---|---|---|---|---|---|
| | | 35 | | | | | 40 | | | | | 45 | | | |

| Ile | Ser | Arg | Asp | Asn | Ser | Lys | Asn | Thr | Leu | Tyr | Leu | Gln | Met | Asn | Ser |
|---|---|---|---|---|---|---|---|---|---|---|---|---|---|---|---|
| | 50 | | | | | 55 | | | | | 60 | | | | |

| Leu | Arg | Ala | Glu | Asp | Thr | Ala | Val | Tyr | Tyr | Cys | Ala | Ser | Xaa | Trp | Gly |
|---|---|---|---|---|---|---|---|---|---|---|---|---|---|---|---|
| 65 | | | | | 70 | | | | | 75 | | | | | 80 |

| Gln | Gly | Thr | Leu | Val | Thr | Val | Ser | Ser |
|---|---|---|---|---|---|---|---|---|
| | | | | 85 | | | | |

<210> SEQ ID NO 137
<211> LENGTH: 89
<212> TYPE: PRT
<213> ORGANISM: Artificial Sequence
<220> FEATURE:
<223> OTHER INFORMATION: MG8-12; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature

```
<222> LOCATION: (78)..(78)
<223> OTHER INFORMATION: Xaa can be any naturally occurring amino acid

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Trp Ala Pro Gly Lys Gly Lys Glu Val Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 138
<211> LENGTH: 89
<212> TYPE: PRT
<213> ORGANISM: Artificial Sequence
<220> FEATURE:
<223> OTHER INFORMATION: MG8-13; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Ile Glu Pro Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 139
<211> LENGTH: 89
<212> TYPE: PRT
<213> ORGANISM: Artificial Sequence
<220> FEATURE:
<223> OTHER INFORMATION: MG8-14; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
```

```
<221> NAME/KEY: misc_feature
<222> LOCATION: (78)..(78)
<223> OTHER INFORMATION: Xaa can be any naturally occurring amino acid

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Pro Glu Trp Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 140
<211> LENGTH: 89
<212> TYPE: PRT
<213> ORGANISM: Artificial Sequence
<220> FEATURE:
<223> OTHER INFORMATION: MG8-4; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Gln Ala Pro Gly Lys Gly Pro Glu Val Val Ser Xaa Arg Phe Thr
        35                  40                  45

Ile Ser Arg Asp Asn Ser Lys Asn Thr Leu Tyr Leu Gln Met Asn Ser
50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 141
<211> LENGTH: 89
<212> TYPE: PRT
<213> ORGANISM: Artificial Sequence
<220> FEATURE:
<223> OTHER INFORMATION: MG8-5; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
```

<220> FEATURE:
<221> NAME/KEY: misc_feature
<222> LOCATION: (78)..(78)
<223> OTHER INFORMATION: Xaa can be any naturally occurring amino acid

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Thr Ala Pro Gly Lys Gly Ile Glu Ile Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 142
<211> LENGTH: 89
<212> TYPE: PRT
<213> ORGANISM: Artificial Sequence
<220> FEATURE:
<223> OTHER INFORMATION: MG8-6; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Ile Ala Pro Gly Lys Gly Val Glu Ile Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 143
<211> LENGTH: 89
<212> TYPE: PRT
<213> ORGANISM: Artificial Sequence
<220> FEATURE:
<223> OTHER INFORMATION: MG8-8; Synthetic
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)

```
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Trp Val
            20                  25                  30

Arg Ala Ala Pro Gly Lys Gly Leu Glu Val Val Ser Xaa Arg Phe Thr
        35                  40                  45

Ile Ser Arg Asp Asn Ser Lys Asn Thr Leu Tyr Leu Gln Met Asn Ser
    50                  55                  60

Leu Arg Ala Glu Asp Thr Ala Val Tyr Tyr Cys Ala Ser Xaa Trp Gly
65                  70                  75                  80

Gln Gly Thr Leu Val Thr Val Ser Ser
                85

<210> SEQ ID NO 144
<211> LENGTH: 29
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)..(1)
<223> OTHER INFORMATION: Xaa is Glu or Gln
<220> FEATURE:
<221> NAME/KEY: VARIANT
<222> LOCATION: (5)..(5)
<223> OTHER INFORMATION: Xaa is Val or Leu
<220> FEATURE:
<221> NAME/KEY: VARIANT
<222> LOCATION: (6)..(6)
<223> OTHER INFORMATION: Xaa is Glu or Gln
<220> FEATURE:
<221> NAME/KEY: VARIANT
<222> LOCATION: (7)..(7)
<223> OTHER INFORMATION: Xaa is Ser or Ala
<220> FEATURE:
<221> NAME/KEY: VARIANT
<222> LOCATION: (9)..(9)
<223> OTHER INFORMATION: Xaa is Glu or Ala
<220> FEATURE:
<221> NAME/KEY: VARIANT
<222> LOCATION: (10)..(10)
<223> OTHER INFORMATION: Xaa is Gly, Met, Asn, Val or Glu
<220> FEATURE:
<221> NAME/KEY: VARIANT
<222> LOCATION: (11)..(11)
<223> OTHER INFORMATION: Xaa is Leu, Val or Trp
<220> FEATURE:
<221> NAME/KEY: VARIANT
<222> LOCATION: (12)..(12)
<223> OTHER INFORMATION: Xaa is Val, Lys, Ala or Ile
<220> FEATURE:
<221> NAME/KEY: VARIANT
<222> LOCATION: (13)..(13)
<223> OTHER INFORMATION: Xaa is Gln, Lys or His
<220> FEATURE:
<221> NAME/KEY: VARIANT
<222> LOCATION: (16)..(16)
<223> OTHER INFORMATION: Xaa is Gly, Thr, Ala, Arg, Glu, Ser or Thr
<220> FEATURE:
<221> NAME/KEY: VARIANT
<222> LOCATION: (18)..(18)
<223> OTHER INFORMATION: Xaa is Leu, Val, Arg or Met
<220> FEATURE:
<221> NAME/KEY: VARIANT
```

```
<222> LOCATION: (19)..(19)
<223> OTHER INFORMATION: Xaa is Arg or Lys
<220> FEATURE:
<221> NAME/KEY: VARIANT
<222> LOCATION: (20)..(20)
<223> OTHER INFORMATION: Xaa is Leu, Ile or Val
<220> FEATURE:
<221> NAME/KEY: VARIANT
<222> LOCATION: (21)..(21)
<223> OTHER INFORMATION: Xaa is Ser, Ala or Thr
<220> FEATURE:
<221> NAME/KEY: VARIANT
<222> LOCATION: (23)..(23)
<223> OTHER INFORMATION: Xaa is Ala, Glu, Val, Arg, Ile, Lys, Thr or Ser
<220> FEATURE:
<221> NAME/KEY: VARIANT
<222> LOCATION: (24)..(24)
<223> OTHER INFORMATION: Xaa is Ala, Gly, Pro, Val or Thr
<220> FEATURE:
<221> NAME/KEY: VARIANT
<222> LOCATION: (25)..(25)
<223> OTHER INFORMATION: Xaa is Ser, Phe or Tyr
<220> FEATURE:
<221> NAME/KEY: VARIANT
<222> LOCATION: (27)..(27)
<223> OTHER INFORMATION: Xaa is Phe, Tyr, Arg, Gly or Leu
<220> FEATURE:
<221> NAME/KEY: VARIANT
<222> LOCATION: (28)..(28)
<223> OTHER INFORMATION: Xaa is Thr, Ala, Ser, Asn, Thr, Pro, Ile, Asn,
    His or Ala
<220> FEATURE:
<221> NAME/KEY: VARIANT
<222> LOCATION: (29)..(29)
<223> OTHER INFORMATION: Xaa is Phe, Leu, Val or Cys

<400> SEQUENCE: 144

Xaa Val Gln Leu Xaa Xaa Xaa Gly Xaa Xaa Xaa Xaa Xaa Pro Gly Xaa
1               5                   10                  15

Ser Xaa Xaa Xaa Xaa Cys Xaa Xaa Xaa Gly Xaa Xaa Xaa
            20                  25

<210> SEQ ID NO 145
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: Xaa is Val, Ala or Leu
<220> FEATURE:
<221> NAME/KEY: VARIANT
<222> LOCATION: (4)..(4)
<223> OTHER INFORMATION: Xaa is Gln, Asn, Arg, Ile, Lys, Tyr, Val, Met,
    Ser, Gln, Trp, Phe, Leu, Val or Cys
<220> FEATURE:
<221> NAME/KEY: VARIANT
<222> LOCATION: (5)..(5)
<223> OTHER INFORMATION: Xaa is Ala, Gly, Lys, Ser, Val, Met or Thr
<220> FEATURE:
<221> NAME/KEY: VARIANT
<222> LOCATION: (8)..(8)
<223> OTHER INFORMATION: Xaa is Lys, Gln, Glu, Arg or Thr
<220> FEATURE:
<221> NAME/KEY: VARIANT
<222> LOCATION: (10)..(10)
<223> OTHER INFORMATION: Xaa is Leu, Asn, Ile, Pro, Tyr, Thr, Val, Trp,
    Ala, Arg, Met or Ser
<220> FEATURE:
<221> NAME/KEY: VARIANT
<222> LOCATION: (11)..(11)
<223> OTHER INFORMATION: Xaa is Val or Glu
<220> FEATURE:
<221> NAME/KEY: VARIANT
```

-continued

```
<222> LOCATION: (12)..(12)
<223> OTHER INFORMATION: Xaa is Trp, Ile, Val, Pro, Phe, His, Met, Tyr,
      Leu, Cys, or Arg
<220> FEATURE:
<221> NAME/KEY: VARIANT
<222> LOCATION: (13)..(13)
<223> OTHER INFORMATION: Xaa is Val, Met, Ile or Leu
<220> FEATURE:
<221> NAME/KEY: VARIANT
<222> LOCATION: (14)..(14)
<223> OTHER INFORMATION: Xaa is Ser, Ala or Gly

<400> SEQUENCE: 145

Trp Xaa Arg Xaa Xaa Pro Gly Xaa Gly Xaa Xaa Xaa Xaa Xaa
1               5                   10

<210> SEQ ID NO 146
<211> LENGTH: 32
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: Xaa is Arg, His, Gln or Thr
<220> FEATURE:
<221> NAME/KEY: VARIANT
<222> LOCATION: (2)..(2)
<223> OTHER INFORMATION: Xaa is Phe, Val, Leu or Ile
<220> FEATURE:
<221> NAME/KEY: VARIANT
<222> LOCATION: (3)..(3)
<223> OTHER INFORMATION: Xaa is Thr, Ser or Ile
<220> FEATURE:
<221> NAME/KEY: VARIANT
<222> LOCATION: (4)..(4)
<223> OTHER INFORMATION: Xaa is Ile, Leu, Val, Met or Arg
<220> FEATURE:
<221> NAME/KEY: VARIANT
<222> LOCATION: (5)..(5)
<223> OTHER INFORMATION: Xaa is Ser, Thr or Asp
<220> FEATURE:
<221> NAME/KEY: VARIANT
<222> LOCATION: (6)..(6)
<223> OTHER INFORMATION: Xaa is Arg, Ala, Val, Asn or Ile
<220> FEATURE:
<221> NAME/KEY: VARIANT
<222> LOCATION: (7)..(7)
<223> OTHER INFORMATION: Xaa is Asp, Asn or Ala
<220> FEATURE:
<221> NAME/KEY: VARIANT
<222> LOCATION: (8)..(8)
<223> OTHER INFORMATION: Xaa is Asn, Thr, Asp, Ile, Arg, Lys, Tyr or Glu
<220> FEATURE:
<221> NAME/KEY: VARIANT
<222> LOCATION: (9)..(9)
<223> OTHER INFORMATION: Xaa is Ala, Ser, Val or Thr
<220> FEATURE:
<221> NAME/KEY: VARIANT
<222> LOCATION: (10)..(10)
<223> OTHER INFORMATION: Xaa is Lys, Arg, Thr, Gln, Val Glu, Met, Asn or
      Ile
<220> FEATURE:
<221> NAME/KEY: VARIANT
<222> LOCATION: (11)..(11)
<223> OTHER INFORMATION: Xaa is Asn, Arg, Thr, Lys, Ser, Asp or Val
<220> FEATURE:
<221> NAME/KEY: VARIANT
<222> LOCATION: (12)..(12)
<223> OTHER INFORMATION: Xaa is Thr, Met, Ser, Val, Ile, Tyr or Ala
<220> FEATURE:
<221> NAME/KEY: VARIANT
<222> LOCATION: (13)..(13)
<223> OTHER INFORMATION: Xaa is Leu, Val, Ala or Met
<220> FEATURE:
<221> NAME/KEY: VARIANT
```

```
<222> LOCATION: (14)..(14)
<223> OTHER INFORMATION: Xaa is Phe, Tyr, Asn, Asp, His or Ser
<220> FEATURE:
<221> NAME/KEY: VARIANT
<222> LOCATION: (15)..(15)
<223> OTHER INFORMATION: Xaa is Leu or Met
<220> FEATURE:
<221> NAME/KEY: VARIANT
<222> LOCATION: (16)..(16)
<223> OTHER INFORMATION: Xaa is Gln, Glu, His or Asn
<220> FEATURE:
<221> NAME/KEY: VARIANT
<222> LOCATION: (17)..(17)
<223> OTHER INFORMATION: Xaa is Met, Leu, Val, Ile or Trp
<220> FEATURE:
<221> NAME/KEY: VARIANT
<222> LOCATION: (18)..(18)
<223> OTHER INFORMATION: Xaa is Asn, Thr, Lys, Asp, Tyr, Ile or Ser
<220> FEATURE:
<221> NAME/KEY: VARIANT
<222> LOCATION: (19)..(19)
<223> OTHER INFORMATION: Xaa is Ser or Asn
<220> FEATURE:
<221> NAME/KEY: VARIANT
<222> LOCATION: (20)..(20)
<223> OTHER INFORMATION: Xaa is Leu or Val
<220> FEATURE:
<221> NAME/KEY: VARIANT
<222> LOCATION: (21)..(21)
<223> OTHER INFORMATION: Xaa is Arg, Lys or Thr
<220> FEATURE:
<221> NAME/KEY: VARIANT
<222> LOCATION: (22)..(22)
<223> OTHER INFORMATION: Xaa is Asp, Ala, Ser, Pro, Thr, Val, Ile or Ser
<220> FEATURE:
<221> NAME/KEY: VARIANT
<222> LOCATION: (23)..(23)
<223> OTHER INFORMATION: Xaa is Glu, Ala, Asp or Ser
<220> FEATURE:
<221> NAME/KEY: VARIANT
<222> LOCATION: (25)..(25)
<223> OTHER INFORMATION: Xaa is Thr, Asn or Ser
<220> FEATURE:
<221> NAME/KEY: VARIANT
<222> LOCATION: (26)..(26)
<223> OTHER INFORMATION: Xaa is Ser, Ala or Gly
<220> FEATURE:
<221> NAME/KEY: VARIANT
<222> LOCATION: (27)..(27)
<223> OTHER INFORMATION: Xaa is Val, Ile, Leu or Met
<220> FEATURE:
<221> NAME/KEY: VARIANT
<222> LOCATION: (29)..(29)
<223> OTHER INFORMATION: Xaa is Tyr or Phe
<220> FEATURE:
<221> NAME/KEY: VARIANT
<222> LOCATION: (31)..(31)
<223> OTHER INFORMATION: Xaa is Ala, Gly, Val or Ser
<220> FEATURE:
<221> NAME/KEY: VARIANT
<222> LOCATION: (32)..(32)
<223> OTHER INFORMATION: Xaa is Arg, Ser, Lys, Thr, Leu, Asn or Phe

<400> SEQUENCE: 146

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Asp Xaa Xaa Xaa Tyr Xaa Cys Xaa Xaa
            20                  25                  30

<210> SEQ ID NO 147
<211> LENGTH: 11
<212> TYPE: PRT
<213> ORGANISM: Artificial Sequence
<220> FEATURE:
<223> OTHER INFORMATION: Consensus sequence
<220> FEATURE:
```

```
<221> NAME/KEY: VARIANT
<222> LOCATION: (1)..(1)
<223> OTHER INFORMATION: Xaa is Trp, Cys, Tyr, Gly, Ser or Ala
<220> FEATURE:
<221> NAME/KEY: VARIANT
<222> LOCATION: (3)..(3)
<223> OTHER INFORMATION: Xaa is Gln, Arg or Leu
<220> FEATURE:
<221> NAME/KEY: VARIANT
<222> LOCATION: (5)..(5)
<223> OTHER INFORMATION: Xaa is Ala, Thr, Ile or Val
<220> FEATURE:
<221> NAME/KEY: VARIANT
<222> LOCATION: (6)..(6)
<223> OTHER INFORMATION: Xaa is Leu, Met, Pro, Val or Thr

<400> SEQUENCE: 147

Xaa Gly Xaa Gly Xaa Xaa Val Thr Val Ser Ser
1               5                   10

<210> SEQ ID NO 148
<211> LENGTH: 29
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: Xaa is Glu or Gln
<220> FEATURE:
<221> NAME/KEY: VARIANT
<222> LOCATION: (5)..(5)
<223> OTHER INFORMATION: Xaa is Val or Leu
<220> FEATURE:
<221> NAME/KEY: VARIANT
<222> LOCATION: (6)..(6)
<223> OTHER INFORMATION: Xaa is Glu or Gln
<220> FEATURE:
<221> NAME/KEY: VARIANT
<222> LOCATION: (10)..(10)
<223> OTHER INFORMATION: Xaa is Gly, Asn, Val or Glu
<220> FEATURE:
<221> NAME/KEY: VARIANT
<222> LOCATION: (11)..(11)
<223> OTHER INFORMATION: Xaa is Leu or Val
<220> FEATURE:
<221> NAME/KEY: VARIANT
<222> LOCATION: (12)..(12)
<223> OTHER INFORMATION: Xaa is Val or Lys
<220> FEATURE:
<221> NAME/KEY: VARIANT
<222> LOCATION: (13)..(13)
<223> OTHER INFORMATION: Xaa is Gln, Lys or His
<220> FEATURE:
<221> NAME/KEY: VARIANT
<222> LOCATION: (16)..(16)
<223> OTHER INFORMATION: Xaa is Gly, Thr, Ala Arg, Glu or Thr
<220> FEATURE:
<221> NAME/KEY: VARIANT
<222> LOCATION: (18)..(18)
<223> OTHER INFORMATION: Xaa is Leu or Val
<220> FEATURE:
<221> NAME/KEY: VARIANT
<222> LOCATION: (20)..(20)
<223> OTHER INFORMATION: Xaa is Leu or Val
<220> FEATURE:
<221> NAME/KEY: VARIANT
<222> LOCATION: (23)..(23)
<223> OTHER INFORMATION: Xaa is Ala, Glu, Val, Ile, Lys or Ser
<220> FEATURE:
<221> NAME/KEY: VARIANT
<222> LOCATION: (24)..(24)
<223> OTHER INFORMATION: Xaa is Ala, Gly or Val
<220> FEATURE:
<221> NAME/KEY: VARIANT
<222> LOCATION: (27)..(27)
```

-continued

```
<223> OTHER INFORMATION: Xaa is Phe, Tyr, Arg, Gly or Leu
<220> FEATURE:
<221> NAME/KEY: VARIANT
<222> LOCATION: (28)..(28)
<223> OTHER INFORMATION: Xaa is Thr, Ala, Ser, Asn, Thr, Pro, Ile, Asn,
      His or Ala
<220> FEATURE:
<221> NAME/KEY: VARIANT
<222> LOCATION: (29)..(29)
<223> OTHER INFORMATION: Xaa is Phe, Leu, Val or Cys

<400> SEQUENCE: 148

Xaa Val Gln Leu Xaa Xaa Ser Gly Gly Xaa Xaa Xaa Xaa Pro Gly Xaa
1               5                   10                  15

Ser Xaa Arg Xaa Ser Cys Xaa Xaa Ser Gly Xaa Xaa Xaa
            20                  25

<210> SEQ ID NO 149
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (4)..(4)
<223> OTHER INFORMATION: Xaa is Gln, Asn, Arg, Ile, Lys, Tyr, Val, Met,
      Ser, Gln, Trp, Phe, Leu, Val or Cys
<220> FEATURE:
<221> NAME/KEY: VARIANT
<222> LOCATION: (5)..(5)
<223> OTHER INFORMATION: Xaa is Ala, Gly, Lys, Ser or Met
<220> FEATURE:
<221> NAME/KEY: VARIANT
<222> LOCATION: (8)..(8)
<223> OTHER INFORMATION: Xaa is Lys, Gln, Glu, Arg or Thr
<220> FEATURE:
<221> NAME/KEY: VARIANT
<222> LOCATION: (10)..(10)
<223> OTHER INFORMATION: Xaa is Leu, Asn, Ile, Pro, Tyr, Thr, Val, Trp,
      Ala, Arg, Met or Ser
<220> FEATURE:
<221> NAME/KEY: VARIANT
<222> LOCATION: (11)..(11)
<223> OTHER INFORMATION: Xaa is Val or Glu
<220> FEATURE:
<221> NAME/KEY: VARIANT
<222> LOCATION: (12)..(12)
<223> OTHER INFORMATION: Xaa is Trp, Ile, Val, Pro, Phe, His, Met, Tyr,
      Leu, Cys or Arg
<220> FEATURE:
<221> NAME/KEY: VARIANT
<222> LOCATION: (13)..(13)
<223> OTHER INFORMATION: Xaa is Val, Met, Ile or Leu
<220> FEATURE:
<221> NAME/KEY: VARIANT
<222> LOCATION: (14)..(14)
<223> OTHER INFORMATION: Xaa is Ser, Ala or Gly

<400> SEQUENCE: 149

Trp Val Arg Xaa Xaa Pro Gly Xaa Gly Xaa Xaa Xaa Xaa Xaa
1               5                   10

<210> SEQ ID NO 150
<211> LENGTH: 32
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: Xaa is Phe, Val, Leu or Ile
<220> FEATURE:
```

-continued

```
<221> NAME/KEY: VARIANT
<222> LOCATION: (4)..(4)
<223> OTHER INFORMATION: Xaa is Ile, Leu, Val or Met
<220> FEATURE:
<221> NAME/KEY: VARIANT
<222> LOCATION: (6)..(6)
<223> OTHER INFORMATION: Xaa is Arg, Ala, Val or Ile
<220> FEATURE:
<221> NAME/KEY: VARIANT
<222> LOCATION: (8)..(8)
<223> OTHER INFORMATION: Xaa is Asn, Thr, Asp, Ile, Arg, Lys, Tyr or Glu
<220> FEATURE:
<221> NAME/KEY: VARIANT
<222> LOCATION: (9)..(9)
<223> OTHER INFORMATION: Xaa is Ala, Ser, Val or Thr
<220> FEATURE:
<221> NAME/KEY: VARIANT
<222> LOCATION: (10)..(10)
<223> OTHER INFORMATION: Xaa is Lys, Arg, Thr, Gln, Val, Glu, Met, Asn
     or Ile
<220> FEATURE:
<221> NAME/KEY: VARIANT
<222> LOCATION: (11)..(11)
<223> OTHER INFORMATION: Xaa is Asn, Arg, Thr, Lys, Ser, Asp or Val
<220> FEATURE:
<221> NAME/KEY: VARIANT
<222> LOCATION: (12)..(12)
<223> OTHER INFORMATION: Xaa is Thr, Met, Ser, Val, Ile, Tyr or Ala
<220> FEATURE:
<221> NAME/KEY: VARIANT
<222> LOCATION: (13)..(13)
<223> OTHER INFORMATION: Xaa is Leu, Val, Ala or Met
<220> FEATURE:
<221> NAME/KEY: VARIANT
<222> LOCATION: (14)..(14)
<223> OTHER INFORMATION: Xaa is Phe, Tyr, Asn, Asp, His or Ser
<220> FEATURE:
<221> NAME/KEY: VARIANT
<222> LOCATION: (15)..(15)
<223> OTHER INFORMATION: Xaa is Leu or Met
<220> FEATURE:
<221> NAME/KEY: VARIANT
<222> LOCATION: (16)..(16)
<223> OTHER INFORMATION: Xaa is Gln, Glu, His or Asn
<220> FEATURE:
<221> NAME/KEY: VARIANT
<222> LOCATION: (17)..(17)
<223> OTHER INFORMATION: Xaa is Met, Leu, Val, Ile or Trp
<220> FEATURE:
<221> NAME/KEY: VARIANT
<222> LOCATION: (18)..(18)
<223> OTHER INFORMATION: Xaa is Asn, Thr, Lys, Asp, Tyr, Ile or Ser
<220> FEATURE:
<221> NAME/KEY: VARIANT
<222> LOCATION: (19)..(19)
<223> OTHER INFORMATION: Xaa is Ser or Asn
<220> FEATURE:
<221> NAME/KEY: VARIANT
<222> LOCATION: (20)..(20)
<223> OTHER INFORMATION: Xaa is Leu or Val
<220> FEATURE:
<221> NAME/KEY: VARIANT
<222> LOCATION: (21)..(21)
<223> OTHER INFORMATION: Xaa is Arg, Lys or Thr
<220> FEATURE:
<221> NAME/KEY: VARIANT
<222> LOCATION: (22)..(22)
<223> OTHER INFORMATION: Xaa is Asp, Ala, Ser, Pro, Thr, Val, Ile or Ser
<220> FEATURE:
<221> NAME/KEY: VARIANT
<222> LOCATION: (23)..(23)
<223> OTHER INFORMATION: Xaa is Glu, Ala, Asp or Ser
<220> FEATURE:
<221> NAME/KEY: VARIANT
<222> LOCATION: (27)..(27)
<223> OTHER INFORMATION: Xaa is Val, Ile, Leu or Met
<220> FEATURE:
<221> NAME/KEY: VARIANT
<222> LOCATION: (29)..(29)
```

```
<223> OTHER INFORMATION: Xaa is Tyr or Phe
<220> FEATURE:
<221> NAME/KEY: VARIANT
<222> LOCATION: (31)..(31)
<223> OTHER INFORMATION: Xaa is Ala, Gly, Val or Ser
<220> FEATURE:
<221> NAME/KEY: VARIANT
<222> LOCATION: (32)..(32)
<223> OTHER INFORMATION: Xaa is Arg, Ser, Lys, Thr, Leu, Asn or Phe

<400> SEQUENCE: 150

Arg Xaa Thr Xaa Ser Xaa Asp Xaa Xaa Xaa Xaa Xaa Xaa Xaa Xaa
1               5                   10                  15

Xaa Xaa Xaa Xaa Xaa Xaa Xaa Asp Thr Ala Xaa Tyr Xaa Cys Xaa Xaa
            20                  25                  30

<210> SEQ ID NO 151
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: Xaa is Trp, Cys, Tyr, Gly, Ser or Ala
<220> FEATURE:
<221> NAME/KEY: VARIANT
<222> LOCATION: (5)..(5)
<223> OTHER INFORMATION: Xaa is Ala, Thr, Ile or Val
<220> FEATURE:
<221> NAME/KEY: VARIANT
<222> LOCATION: (6)..(6)
<223> OTHER INFORMATION: Xaa is Leu, Met, Val or Thr

<400> SEQUENCE: 151

Xaa Gly Gln Gly Xaa Xaa Val Thr Val Ser Ser
1               5                   10

<210> SEQ ID NO 152
<211> LENGTH: 29
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 153
<211> LENGTH: 29
<212> TYPE: PRT
<213> ORGANISM: Artificial Sequence
<220> FEATURE:
<223> OTHER INFORMATION: Synthetic Construct

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 154
<211> LENGTH: 29
<212> TYPE: PRT
```

-continued

```
<213> ORGANISM: Artificial Sequence
<220> FEATURE:
<223> OTHER INFORMATION: Synthetic Construct

<400> SEQUENCE: 154

Gln Val Gln Leu Val Glu Ser Gly Gly Asn Val Val Gln Pro Gly Thr
1               5                   10                  15

Ser Leu Arg Leu Ser Cys Ala Ala Ser Gly Phe Thr Phe
            20                  25

<210> SEQ ID NO 155
<211> LENGTH: 29
<212> TYPE: PRT
<213> ORGANISM: Artificial Sequence
<220> FEATURE:
<223> OTHER INFORMATION: Synthetic Construct

<400> SEQUENCE: 155

Gln Val Gln Leu Val Gln Ser Gly Ala Glu Val Lys Lys Pro Gly Ala
1               5                   10                  15

Ser Val Lys Ile Ser Cys Glu Ala Ser Gly Tyr Ala Phe
            20                  25

<210> SEQ ID NO 156
<211> LENGTH: 29
<212> TYPE: PRT
<213> ORGANISM: Artificial Sequence
<220> FEATURE:
<223> OTHER INFORMATION: Synthetic Construct

<400> SEQUENCE: 156

Glu Val Gln Leu Leu Glu Ser Gly Gly Gly Val Val Gln Pro Gly Lys
1               5                   10                  15

Ser Leu Arg Leu Ser Cys Val Gly Ser Gly Phe Ser Phe
            20                  25

<210> SEQ ID NO 157
<211> LENGTH: 29
<212> TYPE: PRT
<213> ORGANISM: Artificial Sequence
<220> FEATURE:
<223> OTHER INFORMATION: Synthetic Construct

<400> SEQUENCE: 157

Gln Val Gln Leu Val Glu Ser Gly Gly Gly Val Val Gln Pro Gly Arg
1               5                   10                  15

Ser Leu Arg Leu Ser Cys Val Ala Ser Gly Phe Asn Phe
            20                  25

<210> SEQ ID NO 158
<211> LENGTH: 29
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe
            20                  25

<210> SEQ ID NO 159
<211> LENGTH: 29
```

```
<212> TYPE: PRT
<213> ORGANISM: Artificial Sequence
<220> FEATURE:
<223> OTHER INFORMATION: Synthetic Construct

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe
            20                  25

<210> SEQ ID NO 160
<211> LENGTH: 29
<212> TYPE: PRT
<213> ORGANISM: Artificial Sequence
<220> FEATURE:
<223> OTHER INFORMATION: Synthetic Construct

<400> SEQUENCE: 160

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Pro Phe
            20                  25

<210> SEQ ID NO 161
<211> LENGTH: 29
<212> TYPE: PRT
<213> ORGANISM: Artificial Sequence
<220> FEATURE:
<223> OTHER INFORMATION: Synthetic Construct

<400> SEQUENCE: 161

Glu Val Gln Leu Leu Glu Ser Gly Gly Gly Leu Val Lys Pro Gly Gly
1               5                   10                  15

Ser Leu Arg Leu Ser Cys Val Gly Ser Glu Arg Ser Phe
            20                  25

<210> SEQ ID NO 162
<211> LENGTH: 29
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Leu Glu Ser Gly Gly Gly Leu Ala Gln Ser Gly Gly
1               5                   10                  15

Ser Leu Arg Leu Ser Cys Ala Ala Ser Gly Phe Thr Phe
            20                  25

<210> SEQ ID NO 163
<211> LENGTH: 29
<212> TYPE: PRT
<213> ORGANISM: Artificial Sequence
<220> FEATURE:
<223> OTHER INFORMATION: Synthetic Construct

<400> SEQUENCE: 163

Glu Val Gln Leu Val Gln Ser Gly Ala Glu Val Lys Lys Pro Gly Glu
1               5                   10                  15

Ser Leu Arg Ile Ser Cys Arg Gly Ser Gly Tyr Arg Phe
            20                  25

<210> SEQ ID NO 164
```

```
<211> LENGTH: 29
<212> TYPE: PRT
<213> ORGANISM: Artificial Sequence
<220> FEATURE:
<223> OTHER INFORMATION: Synthetic Construct

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Val Pro Ser Gly Phe Thr Phe
            20                  25

<210> SEQ ID NO 165
<211> LENGTH: 29
<212> TYPE: PRT
<213> ORGANISM: Artificial Sequence
<220> FEATURE:
<223> OTHER INFORMATION: Synthetic Construct

<400> SEQUENCE: 165

Gln Val Gln Leu Val Glu Ser Gly Gly Gly Leu Val Gln Pro Gly Gly
1               5                   10                  15

Ser Leu Arg Leu Ser Cys Ile Ala Ser Gly Phe Ser Leu
            20                  25

<210> SEQ ID NO 166
<211> LENGTH: 29
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 167
<211> LENGTH: 29
<212> TYPE: PRT
<213> ORGANISM: Artificial Sequence
<220> FEATURE:
<223> OTHER INFORMATION: Synthetic Construct

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 168
<211> LENGTH: 29
<212> TYPE: PRT
<213> ORGANISM: Artificial Sequence
<220> FEATURE:
<223> OTHER INFORMATION: Synthetic Construct

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe
            20                  25
```

```
<210> SEQ ID NO 169
<211> LENGTH: 29
<212> TYPE: PRT
<213> ORGANISM: Artificial Sequence
<220> FEATURE:
<223> OTHER INFORMATION: Synthetic Construct

<400> SEQUENCE: 169

Glu Val Gln Leu Leu Glu Ser Gly Gly Gly Val Val Gln Pro Gly Arg
1               5                   10                  15

Ser Leu Arg Leu Ser Cys Glu Val Phe Gly Phe Thr Leu
            20                  25

<210> SEQ ID NO 170
<211> LENGTH: 29
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe
            20                  25

<210> SEQ ID NO 171
<211> LENGTH: 29
<212> TYPE: PRT
<213> ORGANISM: Artificial Sequence
<220> FEATURE:
<223> OTHER INFORMATION: Synthetic Construct

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 172
<211> LENGTH: 29
<212> TYPE: PRT
<213> ORGANISM: Artificial Sequence
<220> FEATURE:
<223> OTHER INFORMATION: Synthetic Construct

<400> SEQUENCE: 172

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 173
<211> LENGTH: 29
<212> TYPE: PRT
<213> ORGANISM: Artificial Sequence
<220> FEATURE:
<223> OTHER INFORMATION: Synthetic Construct

<400> SEQUENCE: 173

Gln Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe
            20                  25
```

<210> SEQ ID NO 174
<211> LENGTH: 29
<212> TYPE: PRT
<213> ORGANISM: Artificial Sequence
<220> FEATURE:
<223> OTHER INFORMATION: Synthetic Construct

<400> SEQUENCE: 174

Glu Val Gln Leu Leu Glu Ser Gly Gly Met Leu Val Lys Pro Gly Glu
1               5                   10                  15

Ser Leu Arg Leu Ser Cys Val Gly Ser Gly Leu Ile Phe
            20                  25

<210> SEQ ID NO 175
<211> LENGTH: 29
<212> TYPE: PRT
<213> ORGANISM: Artificial Sequence
<220> FEATURE:
<223> OTHER INFORMATION: Synthetic Construct

<400> SEQUENCE: 175

Glu Val Gln Leu Leu Glu Ser Gly Gly Gly Leu Val His Ala Gly Gly
1               5                   10                  15

Ser Val Arg Leu Ser Cys Ala Ala Ser Gly Phe Thr Phe
            20                  25

<210> SEQ ID NO 176
<211> LENGTH: 29
<212> TYPE: PRT
<213> ORGANISM: Artificial Sequence
<220> FEATURE:
<223> OTHER INFORMATION: Synthetic Construct

<400> SEQUENCE: 176

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe
            20                  25

<210> SEQ ID NO 177
<211> LENGTH: 29
<212> TYPE: PRT
<213> ORGANISM: Artificial Sequence
<220> FEATURE:
<223> OTHER INFORMATION: Synthetic Construct

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 178
<211> LENGTH: 29
<212> TYPE: PRT
<213> ORGANISM: Artificial Sequence
<220> FEATURE:
<223> OTHER INFORMATION: Synthetic Construct

<400> SEQUENCE: 178

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 179
<211> LENGTH: 29
<212> TYPE: PRT
<213> ORGANISM: Artificial Sequence
<220> FEATURE:
<223> OTHER INFORMATION: Synthetic Construct

<400> SEQUENCE: 179

Gln Val Gln Leu Val Glu Ser Gly Gly Gly Leu Val Gln Pro Gly Gly
1               5                   10                  15

Ser Leu Arg Leu Ser Cys Glu Ala Ser Gly Leu His Phe
            20                  25

<210> SEQ ID NO 180
<211> LENGTH: 29
<212> TYPE: PRT
<213> ORGANISM: Artificial Sequence
<220> FEATURE:
<223> OTHER INFORMATION: Synthetic Construct

<400> SEQUENCE: 180

Gln Val Gln Leu Val Glu Ala Gly Gly Gly Leu Val Gln Pro Gly Gly
1               5                   10                  15

Ser Leu Arg Leu Ala Cys Ala Ala Ser Gly Phe Thr Phe
            20                  25

<210> SEQ ID NO 181
<211> LENGTH: 29
<212> TYPE: PRT
<213> ORGANISM: Artificial Sequence
<220> FEATURE:
<223> OTHER INFORMATION: Synthetic Construct

<400> SEQUENCE: 181

Glu Val Gln Leu Val Gln Ser Gly Ala Glu Val Lys Lys Pro Gly Glu
1               5                   10                  15

Ser Leu Arg Lys Ser Cys Lys Gly Ser Gly Tyr Ser Phe
            20                  25

<210> SEQ ID NO 182
<211> LENGTH: 29
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 183
<211> LENGTH: 29
<212> TYPE: PRT
<213> ORGANISM: Artificial Sequence
<220> FEATURE:
<223> OTHER INFORMATION: Synthetic Construct

<400> SEQUENCE: 183

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe

<210> SEQ ID NO 184
<211> LENGTH: 29
<212> TYPE: PRT
<213> ORGANISM: Artificial Sequence
<220> FEATURE:
<223> OTHER INFORMATION: Synthetic Construct

<400> SEQUENCE: 184

Glu Val Gln Leu Val Glu Ala Gly Gly Gly Leu Val Gln Pro Gly Gly
1               5                   10                  15

Ser Leu Arg Leu Ala Cys Ala Ala Ser Gly Phe Thr Phe
            20                  25

<210> SEQ ID NO 185
<211> LENGTH: 29
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe
            20                  25

<210> SEQ ID NO 186
<211> LENGTH: 29
<212> TYPE: PRT
<213> ORGANISM: Artificial Sequence
<220> FEATURE:
<223> OTHER INFORMATION: Synthetic Construct

<400> SEQUENCE: 186

Gln Val Gln Leu Val Glu Ser Gly Gly Gly Leu Ile Gln Pro Gly Glu
1               5                   10                  15

Ser Leu Arg Leu Ser Cys Glu Ala Phe Gly Phe Thr Val
            20                  25

<210> SEQ ID NO 187
<211> LENGTH: 29
<212> TYPE: PRT
<213> ORGANISM: Artificial Sequence
<220> FEATURE:
<223> OTHER INFORMATION: Synthetic Construct

<400> SEQUENCE: 187

Glu Val Gln Leu Val Gln Ser Gly Ala Glu Leu Lys Lys Pro Gly Ser
1               5                   10                  15

Ser Val Lys Val Ser Cys Thr Ser Ser Gly Gly Ser Phe
            20                  25

<210> SEQ ID NO 188
<211> LENGTH: 29
<212> TYPE: PRT
<213> ORGANISM: Artificial Sequence
<220> FEATURE:
<223> OTHER INFORMATION: Synthetic Construct

<400> SEQUENCE: 188

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe
            20                  25

<210> SEQ ID NO 189
<211> LENGTH: 29
<212> TYPE: PRT
<213> ORGANISM: Artificial Sequence
<220> FEATURE:
<223> OTHER INFORMATION: Synthetic Construct

<400> SEQUENCE: 189

Glu Val Gln Leu Leu Glu Ser Gly Gly Gly Val Val Gln Pro Gly Arg
1               5                   10                  15

Ser Leu Arg Leu Ser Cys Val Ala Ser Gly Phe Thr Phe
            20                  25

<210> SEQ ID NO 190
<211> LENGTH: 29
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe
            20                  25

<210> SEQ ID NO 191
<211> LENGTH: 29
<212> TYPE: PRT
<213> ORGANISM: Artificial Sequence
<220> FEATURE:
<223> OTHER INFORMATION: Synthetic Construct

<400> SEQUENCE: 191

Glu Val Gln Leu Val Glu Ser Gly Gly Gly Leu Val Gln Pro Gly Arg
1               5                   10                  15

Ser Leu Arg Leu Ser Cys Thr Thr Ser Gly Phe Ser Phe
            20                  25

<210> SEQ ID NO 192
<211> LENGTH: 29
<212> TYPE: PRT
<213> ORGANISM: Artificial Sequence
<220> FEATURE:
<223> OTHER INFORMATION: Synthetic Construct

<400> SEQUENCE: 192

Glu Val Gln Leu Leu Glu Ser Gly Gly Gly Leu Val Arg Pro Gly Gly
1               5                   10                  15

Ser Leu Arg Leu Ser Cys Ser Ala Ser Gly Phe Ala Phe
            20                  25

<210> SEQ ID NO 193
<211> LENGTH: 29
<212> TYPE: PRT
<213> ORGANISM: Artificial Sequence
<220> FEATURE:
<223> OTHER INFORMATION: Synthetic Construct

<400> SEQUENCE: 193

Gln Val Gln Leu Val Glu Ser Gly Gly Asn Val Val Gln Pro Gly Thr
1               5                   10                  15

-continued

Ser Leu Arg Leu Ser Cys Ala Ala Ser Gly Phe Thr Phe
            20                  25

<210> SEQ ID NO 194
<211> LENGTH: 29
<212> TYPE: PRT
<213> ORGANISM: Artificial Sequence
<220> FEATURE:
<223> OTHER INFORMATION: Synthetic Construct

<400> SEQUENCE: 194

Glu Val Gln Leu Leu Glu Ser Gly Gly Gly Leu Val Gln Pro Gly Gly
1               5                   10                  15

Ser Leu Arg Leu Thr Cys Val Gly Tyr Gly Phe Thr Phe
            20                  25

<210> SEQ ID NO 195
<211> LENGTH: 29
<212> TYPE: PRT
<213> ORGANISM: Artificial Sequence
<220> FEATURE:
<223> OTHER INFORMATION: Synthetic construct

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Leu
            20                  25

<210> SEQ ID NO 196
<211> LENGTH: 29
<212> TYPE: PRT
<213> ORGANISM: Artificial Sequence
<220> FEATURE:
<223> OTHER INFORMATION: Synthetic construct

<400> SEQUENCE: 196

Glu Val Gln Leu Leu Glu Ser Gly Gly Gly Val Val His Pro Gly Arg
1               5                   10                  15

Ser Leu Arg Leu Ser Cys Ala Val Ser Gly Phe Ser Leu
            20                  25

<210> SEQ ID NO 197
<211> LENGTH: 29
<212> TYPE: PRT
<213> ORGANISM: Artificial Sequence
<220> FEATURE:
<223> OTHER INFORMATION: Synthetic construct

<400> SEQUENCE: 197

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe
            20                  25

<210> SEQ ID NO 198
<211> LENGTH: 29
<212> TYPE: PRT
<213> ORGANISM: Artificial Sequence
<220> FEATURE:
<223> OTHER INFORMATION: Synthetic construct

<400> SEQUENCE: 198

Gln Val Gln Leu Val Glu Ser Gly Gly Gly Val Val Gln Pro Gly Arg

```
                1               5                  10                  15
Ser Leu Arg Leu Ser Cys Val Ala Ser Gly Phe Ala Phe
            20                  25
```

<210> SEQ ID NO 199
<211> LENGTH: 29
<212> TYPE: PRT
<213> ORGANISM: Artificial Sequence
<220> FEATURE:
<223> OTHER INFORMATION: Synthetic construct

<400> SEQUENCE: 199

```
Gln Val Gln Leu Val Glu Ser Gly Gly Val Val Gln Pro Gly Gly
1               5                  10                  15

Ser Leu Arg Leu Ser Cys Ala Ala Ser Gly Phe Thr Phe
            20                  25
```

<210> SEQ ID NO 200
<211> LENGTH: 29
<212> TYPE: PRT
<213> ORGANISM: Artificial Sequence
<220> FEATURE:
<223> OTHER INFORMATION: Synthetic construct

<400> SEQUENCE: 200

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe
            20                  25
```

<210> SEQ ID NO 201
<211> LENGTH: 29
<212> TYPE: PRT
<213> ORGANISM: Artificial Sequence
<220> FEATURE:
<223> OTHER INFORMATION: Synthetic construct

<400> SEQUENCE: 201

```
Glu Val Gln Leu Leu Gln Ser Gly Gly Gly Trp Val Lys Pro Gly Gly
1               5                  10                  15

Ser Leu Arg Leu Ser Cys Ala Ala Ser Gly Phe Ile Cys
            20                  25
```

<210> SEQ ID NO 202
<211> LENGTH: 29
<212> TYPE: PRT
<213> ORGANISM: Artificial Sequence
<220> FEATURE:
<223> OTHER INFORMATION: Synthetic construct

<400> SEQUENCE: 202

```
Glu Val Gln Leu Leu Glu Ser Gly Gly Val Val Val Gln Pro Gly Arg
1               5                  10                  15

Ser Leu Arg Leu Ser Cys Ala Ala Ser Gly Phe Thr Phe
            20                  25
```

<210> SEQ ID NO 203
<211> LENGTH: 29
<212> TYPE: PRT
<213> ORGANISM: Artificial Sequence
<220> FEATURE:
<223> OTHER INFORMATION: Synthetic construct

<400> SEQUENCE: 203

```
Gln Met Gln Leu Val Gln Ser Glu Ala Glu Val Lys Lys Pro Gly Ala
1               5                   10                  15

Ser Met Lys Val Ser Cys Lys Ala Ser Gly Tyr Thr Phe
            20                  25

<210> SEQ ID NO 204
<211> LENGTH: 29
<212> TYPE: PRT
<213> ORGANISM: Artificial Sequence
<220> FEATURE:
<223> OTHER INFORMATION: Synthetic construct

<400> SEQUENCE: 204

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe
            20                  25

<210> SEQ ID NO 205
<211> LENGTH: 14
<212> TYPE: PRT
<213> ORGANISM: Artificial Sequence
<220> FEATURE:
<223> OTHER INFORMATION: Synthetic Construct

<400> SEQUENCE: 205

Trp Val Arg Gln Ala Pro Gly Lys Gly Leu Val Trp Val Ser
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Synthetic Construct

<400> SEQUENCE: 206

Trp Val Arg Gln Ala Pro Gly Lys Gly Leu Glu Trp Val Ser
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Synthetic Construct

<400> SEQUENCE: 207

Trp Val Arg Gln Ala Pro Gly Lys Gly Leu Glu Trp Val Ala
1               5                   10

<210> SEQ ID NO 208
<211> LENGTH: 14
<212> TYPE: PRT
<213> ORGANISM: Artificial Sequence
<220> FEATURE:
<223> OTHER INFORMATION: Synthetic Construct

<400> SEQUENCE: 208

Trp Val Arg Gln Ala Pro Gly Gln Gly Leu Glu Trp Met Gly
1               5                   10

<210> SEQ ID NO 209
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 209

Trp Val Arg Gln Ala Pro Gly Lys Gly Leu Glu Trp Leu Ala
1               5                   10

<210> SEQ ID NO 210
<211> LENGTH: 14
<212> TYPE: PRT
<213> ORGANISM: Artificial Sequence
<220> FEATURE:
<223> OTHER INFORMATION: Synthetic Construct

<400> SEQUENCE: 210

Trp Leu Arg Gln Ala Pro Gly Lys Gly Leu Glu Trp Val Ala
1               5                   10

<210> SEQ ID NO 211
<211> LENGTH: 14
<212> TYPE: PRT
<213> ORGANISM: Artificial Sequence
<220> FEATURE:
<223> OTHER INFORMATION: Synthetic Construct

<400> SEQUENCE: 211

Trp Val Arg Gln Ala Pro Gly Lys Gly Leu Glu Trp Val Gly
1               5                   10

<210> SEQ ID NO 212
<211> LENGTH: 14
<212> TYPE: PRT
<213> ORGANISM: Artificial Sequence
<220> FEATURE:
<223> OTHER INFORMATION: Synthetic Construct

<400> SEQUENCE: 212

Trp Val Arg Gln Gly Pro Gly Glu Gly Leu Val Trp Leu Ser
1               5                   10

<210> SEQ ID NO 213
<211> LENGTH: 14
<212> TYPE: PRT
<213> ORGANISM: Artificial Sequence
<220> FEATURE:
<223> OTHER INFORMATION: Synthetic Construct

<400> SEQUENCE: 213

Trp Val Arg Gln Ala Pro Gly Lys Gly Leu Glu Trp Val Ser
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Synthetic Construct

<400> SEQUENCE: 214

Trp Val Arg Gln Ala Pro Gly Lys Gly Leu Glu Trp Val Ala
1               5                   10

<210> SEQ ID NO 215
<211> LENGTH: 14
<212> TYPE: PRT
<213> ORGANISM: Artificial Sequence
<220> FEATURE:
```

<223> OTHER INFORMATION: Synthetic Construct

<400> SEQUENCE: 215

Trp Val Arg Gln Ala Pro Gly Lys Gly Leu Glu Trp Ile Ser
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Synthetic Construct

<400> SEQUENCE: 216

Trp Ala Arg Asp Lys Pro Gly Lys Gly Leu Glu Trp Ile Gly
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Synthetic Construct

<400> SEQUENCE: 217

Trp Val Arg Gln Ala Pro Gly Lys Gly Leu Val Trp Val Ser
1               5                   10

<210> SEQ ID NO 218
<211> LENGTH: 14
<212> TYPE: PRT
<213> ORGANISM: Artificial Sequence
<220> FEATURE:
<223> OTHER INFORMATION: Synthetic Construct

<400> SEQUENCE: 218

Trp Val Arg Arg Ser Pro Gly Lys Gly Leu Glu Trp Val Ala
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Synthetic Construct

<400> SEQUENCE: 219

Trp Val Arg Gln Ala Pro Gly Lys Gly Leu Glu Trp Val Ala
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Synthetic Construct

<400> SEQUENCE: 220

Trp Val Arg Gln Ala Pro Gly Lys Gly Leu Glu Trp Leu Ser
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Synthetic Construct

<400> SEQUENCE: 221

Trp Val Arg Gln Gly Pro Gly Lys Gly Leu Glu Trp Val Ala
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Synthetic Construct

<400> SEQUENCE: 222

Trp Val Arg Gln Ala Pro Gly Arg Arg Leu Glu Trp Val Ala
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Synthetic Construct

<400> SEQUENCE: 223

Trp Val Arg Gln Ala Pro Gly Lys Gly Leu Glu Trp Val Ser
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Synthetic Construct

<400> SEQUENCE: 224

Trp Val Arg Gln Ala Pro Gly Lys Gly Leu Glu Trp Val Ser
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Synthetic Construct

<400> SEQUENCE: 225

Trp Val Arg Gln Val Pro Gly Lys Gly Leu Glu Trp Val Ala
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Synthetic Construct

<400> SEQUENCE: 226

Trp Val Arg Gln Ala Pro Gly Thr Gly Leu Leu Trp Leu Ser
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Synthetic Construct

<400> SEQUENCE: 227

Trp Val Arg His Ala Pro Gly Lys Gly Leu Glu Trp Val Gly
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Synthetic Construct

<400> SEQUENCE: 228

Trp Val Arg Gln Ala Pro Gly Lys Gly Leu Glu Trp Val Ala
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Synthetic Construct

<400> SEQUENCE: 229

Trp Leu Arg Gln Ala Pro Gly Lys Gly Pro Glu Tyr Val Ala
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Synthetic Construct

<400> SEQUENCE: 230

Trp Val Arg Gln Ala Pro Gly Lys Gly Leu Glu Trp Val Ser
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Synthetic Construct

<400> SEQUENCE: 231

Trp Val Arg Gln Ala Pro Gly Lys Gly Leu Glu Trp Val Ser
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Synthetic Construct

<400> SEQUENCE: 232

Trp Val Arg Gln Ala Pro Gly Lys Gly Leu Glu Trp Val Ala
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Synthetic Construct

<400> SEQUENCE: 233

Trp Val Arg Gln Ala Pro Gly Lys Gly Leu Glu Trp Ile Ser
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Synthetic Construct

<400> SEQUENCE: 234

Trp Val Arg Gln Met Pro Gly Lys Gly Leu Glu Trp Met Gly
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Synthetic Construct

<400> SEQUENCE: 235

Trp Val Arg Gln Ala Pro Gly Lys Gly Leu Glu Trp Val Ala
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Synthetic Construct

<400> SEQUENCE: 236

Trp Val Arg Gln Ala Pro Gly Gln Gly Leu Glu Trp Met Gly
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Synthetic Construct

<400> SEQUENCE: 237

Trp Val Arg Gln Ala Pro Gly Lys Gly Leu Glu Trp Ile Ser
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Synthetic Construct

<400> SEQUENCE: 238

Trp Val Arg Gln Met Pro Gly Arg Gly Leu Glu Trp Leu Gly
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Synthetic Construct

<400> SEQUENCE: 239

Trp Val Arg Gln Ala Pro Gly Lys Gly Leu Glu Trp Val Ser
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Synthetic Construct

<400> SEQUENCE: 240

Trp Val Arg Gln Ala Pro Gly Gln Gly Leu Glu Trp Met Gly
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Synthetic Construct

<400> SEQUENCE: 241

Trp Val Arg Gln Ala Pro Gly Lys Gly Leu Glu Trp Val Ser
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Synthetic Construct

<400> SEQUENCE: 242

Trp Val Arg Gln Ala Pro Gly Lys Gly Leu Glu Trp Val Ser
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Synthetic Construct

<400> SEQUENCE: 243

Trp Val Arg Gln Ala Pro Gly Lys Gly Leu Glu Cys Val Ala
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Synthetic Construct

<400> SEQUENCE: 244

Trp Val Arg Gln Ala Pro Gly Lys Gly Leu Glu Trp Val Ser
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Synthetic Construct

<400> SEQUENCE: 245

Trp Val Arg Gln Ala Pro Gly Lys Gly Leu Glu Trp Val Ser

```
<210> SEQ ID NO 246
<211> LENGTH: 14
<212> TYPE: PRT
<213> ORGANISM: Artificial Sequence
<220> FEATURE:
<223> OTHER INFORMATION: Synthetic Construct

<400> SEQUENCE: 246

Trp Val Arg Gln Ala Pro Gly Lys Gly Leu Glu Trp Val Ala
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Synthetic Construct

<400> SEQUENCE: 247

Trp Val Arg Gln Ala Pro Gly Lys Gly Pro Glu Trp Val Ala
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Synthetic construct

<400> SEQUENCE: 248

Trp Val Arg Gln Ala Pro Gly Lys Gly Leu Val Trp Val Ser
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Synthetic construct

<400> SEQUENCE: 249

Trp Val Arg Gln Ala Pro Asp Lys Gly Leu Glu Trp Val Ala
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Synthetic construct

<400> SEQUENCE: 250

Trp Phe Arg Gln Gly Pro Gly Lys Gly Leu Glu Trp Val Ala
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Synthetic construct

<400> SEQUENCE: 251

Trp Val Arg Gln Thr Pro Gly Arg Gly Leu Glu Trp Leu Ala
1               5                   10
```

```
<210> SEQ ID NO 252
<211> LENGTH: 14
<212> TYPE: PRT
<213> ORGANISM: Artificial Sequence
<220> FEATURE:
<223> OTHER INFORMATION: Synthetic construct

<400> SEQUENCE: 252

Trp Val Arg Gln Ala Pro Gly Lys Gly Leu Glu Trp Val Ser
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Synthetic construct

<400> SEQUENCE: 253

Trp Val Arg Gln Ala Pro Gly Lys Gly Leu Glu Trp Val Ser
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Synthetic construct

<400> SEQUENCE: 254

Trp Val Arg Gln Ala Pro Gly Lys Gly Leu Glu Trp Val Gly
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Synthetic construct

<400> SEQUENCE: 255

Trp Val Arg Gln Ala Pro Gly Lys Gly Leu Glu Trp Val Gly
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Synthetic construct

<400> SEQUENCE: 256

Trp Val Arg Gln Ala Thr Gly Gln Gly Leu Glu Trp Met Gly
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Synthetic construct

<400> SEQUENCE: 257

Trp Val Arg Gln Met Pro Gly Lys Gly Leu Glu Trp Met Gly
1               5                   10
```

<210> SEQ ID NO 258
<211> LENGTH: 32
<212> TYPE: PRT
<213> ORGANISM: Artificial Sequence
<220> FEATURE:
<223> OTHER INFORMATION: Synthetic Construct

<400> SEQUENCE: 258

Arg Phe Thr Ile Ser Arg Asp Asn Ala Lys Asn Thr Leu Phe Leu Gln
1               5                   10                  15

Met Asn Ser Leu Arg Asp Glu Asp Thr Ser Val Tyr Tyr Cys Ala Arg
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: Synthetic Construct

<400> SEQUENCE: 259

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 260
<211> LENGTH: 32
<212> TYPE: PRT
<213> ORGANISM: Artificial Sequence
<220> FEATURE:
<223> OTHER INFORMATION: Synthetic Construct

<400> SEQUENCE: 260

Arg Phe Thr Ile Ser Arg Asp Asn Ser Arg Asn Thr Val Phe Leu Gln
1               5                   10                  15

Met Thr Ser Leu Arg Ala Glu Asp Thr Ala Val Tyr Tyr Cys Gly Arg
            20                  25                  30

<210> SEQ ID NO 261
<211> LENGTH: 32
<212> TYPE: PRT
<213> ORGANISM: Artificial Sequence
<220> FEATURE:
<223> OTHER INFORMATION: Synthetic Construct

<400> SEQUENCE: 261

Arg Val Thr Leu Thr Arg Asp Thr Ser Thr Arg Thr Val Tyr Met Glu
1               5                   10                  15

Leu Lys Asn Leu Arg Ser Ala Asp Thr Gly Val Tyr Tyr Cys Ala Arg
            20                  25                  30

<210> SEQ ID NO 262
<211> LENGTH: 32
<212> TYPE: PRT
<213> ORGANISM: Artificial Sequence
<220> FEATURE:
<223> OTHER INFORMATION: Synthetic Construct

<400> SEQUENCE: 262

Arg Phe Thr Ile Ser Arg Asp Asn Ser Lys Thr Met Val Asn Leu Gln
1               5                   10                  15

Met Asn Ser Leu Arg Pro Asp Asp Thr Ala Val Tyr Phe Cys Ala Arg
            20                  25                  30

<210> SEQ ID NO 263
<211> LENGTH: 32
<212> TYPE: PRT
<213> ORGANISM: Artificial Sequence
<220> FEATURE:
<223> OTHER INFORMATION: Synthetic Construct

<400> SEQUENCE: 263

Arg Phe Thr Ile Ser Arg Asp Asn Ser Lys Asn Thr Leu Tyr Leu Glu
1               5                   10                  15

Met Asn Ser Leu Arg Pro Glu Asp Thr Ala Val Tyr Tyr Cys Ala Lys
            20                  25                  30

<210> SEQ ID NO 264
<211> LENGTH: 32
<212> TYPE: PRT
<213> ORGANISM: Artificial Sequence
<220> FEATURE:
<223> OTHER INFORMATION: Synthetic Construct

<400> SEQUENCE: 264

Arg Phe Thr Ile Ser Arg Asp Asp Ser Lys Asn Met Val Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 265
<211> LENGTH: 32
<212> TYPE: PRT
<213> ORGANISM: Artificial Sequence
<220> FEATURE:
<223> OTHER INFORMATION: Synthetic Construct

<400> SEQUENCE: 265

Arg Phe Thr Ile Ser Arg Asp Asn Ala Lys Asn Thr Val Tyr Leu Glu
1               5                   10                  15

Met Asn Ser Val Arg Val Asp Asp Thr Ala Val Tyr Tyr Cys Val Ser
            20                  25                  30

<210> SEQ ID NO 266
<211> LENGTH: 32
<212> TYPE: PRT
<213> ORGANISM: Artificial Sequence
<220> FEATURE:
<223> OTHER INFORMATION: Synthetic Construct

<400> SEQUENCE: 266

Arg Phe Thr Ile Ser Arg Asp Asp Ser Thr Asn Thr Leu Tyr Leu Gln
1               5                   10                  15

Val Asn Ser Leu Arg Ala Glu Asp Thr Ala Val Tyr Tyr Cys Ala Lys
            20                  25                  30

<210> SEQ ID NO 267
<211> LENGTH: 32
<212> TYPE: PRT
<213> ORGANISM: Artificial Sequence
<220> FEATURE:
<223> OTHER INFORMATION: Synthetic Construct

<400> SEQUENCE: 267

Arg Phe Thr Val Ser Arg Asp Asn Val Gln Lys Ser Leu Asp Leu Gln
1               5                   10                  15

Met Asp Ser Leu Arg Ala Glu Asp Thr Ala Val Tyr Phe Cys Ala Arg 20                  25                  30

<210> SEQ ID NO 268
<211> LENGTH: 32
<212> TYPE: PRT
<213> ORGANISM: Artificial Sequence
<220> FEATURE:
<223> OTHER INFORMATION: Synthetic Construct

<400> SEQUENCE: 268

Arg Phe Thr Ile Ser Arg Asp Ile Ala Lys Asn Ser Leu Tyr Leu Gln
1               5                   10                  15

Met Asn Ser Leu Arg Asp Glu Asp Thr Ala Val Tyr Tyr Cys Ala Lys
            20                  25                  30

<210> SEQ ID NO 269
<211> LENGTH: 32
<212> TYPE: PRT
<213> ORGANISM: Artificial Sequence
<220> FEATURE:
<223> OTHER INFORMATION: Synthetic Construct

<400> SEQUENCE: 269

His Val Thr Ile Ser Ser Asp Arg Ser Val Ser Val Ala Tyr Leu Gln
1               5                   10                  15

Trp Asp Ser Leu Lys Ala Ser Asp Asn Gly Ile Tyr Tyr Cys Ala Leu
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Synthetic Construct

<400> SEQUENCE: 270

Arg Phe Thr Ile Ser Arg Asp Asn Ala Glu Asp Thr Leu Phe Leu Gln
1               5                   10                  15

Met Asn Ser Leu Arg Val Asp Asp Thr Ala Val Tyr Tyr Cys Val Arg
            20                  25                  30

<210> SEQ ID NO 271
<211> LENGTH: 32
<212> TYPE: PRT
<213> ORGANISM: Artificial Sequence
<220> FEATURE:
<223> OTHER INFORMATION: Synthetic Construct

<400> SEQUENCE: 271

Arg Phe Thr Val Ser Arg Asp Asn Ala Lys Asn Ser Leu Phe Leu Gln
1               5                   10                  15

Met Asn Asn Val Arg Pro Glu Asp Thr Ala Leu Tyr Phe Cys Ala Arg
            20                  25                  30

<210> SEQ ID NO 272
<211> LENGTH: 32
<212> TYPE: PRT
<213> ORGANISM: Artificial Sequence
<220> FEATURE:
<223> OTHER INFORMATION: Synthetic Construct

<400> SEQUENCE: 272

Arg Phe Thr Ile Ser Arg Asp Asn Ala Lys Asn Ser Leu Tyr Leu Gln
1               5                   10                  15

```
Met Asn Ser Leu Arg Ala Glu Asp Thr Ala Leu Tyr Tyr Cys Ala Arg
            20                  25                  30
```

<210> SEQ ID NO 273
<211> LENGTH: 32
<212> TYPE: PRT
<213> ORGANISM: Artificial Sequence
<220> FEATURE:
<223> OTHER INFORMATION: Synthetic Construct

<400> SEQUENCE: 273

```
Arg Phe Thr Ile Ser Arg Asn Asn Ala Lys Asn Ser Leu Tyr Leu Gln
1               5                   10                  15

Met Asn Ser Leu Arg Val Asp Asp Thr Ala Val Tyr Tyr Cys Ala Arg
            20                  25                  30
```

<210> SEQ ID NO 274
<211> LENGTH: 32
<212> TYPE: PRT
<213> ORGANISM: Artificial Sequence
<220> FEATURE:
<223> OTHER INFORMATION: Synthetic Construct

<400> SEQUENCE: 274

```
Arg Phe Thr Ile Ser Arg Asp Asn Ala Glu Asn Ser Leu Tyr Leu Gln
1               5                   10                  15

Val Asn Ser Leu Arg Ala Glu Asp Thr Ala Ile Tyr Tyr Cys Ala Lys
            20                  25                  30
```

<210> SEQ ID NO 275
<211> LENGTH: 32
<212> TYPE: PRT
<213> ORGANISM: Artificial Sequence
<220> FEATURE:
<223> OTHER INFORMATION: Synthetic Construct

<400> SEQUENCE: 275

```
Arg Phe Thr Ile Ser Arg Asp Ile Ala Thr Asn Arg Leu Tyr Leu Gln
1               5                   10                  15

Met Arg Ser Leu Arg Ala Glu Asp Thr Ala Leu Tyr Tyr Cys Ala Arg
            20                  25                  30
```

<210> SEQ ID NO 276
<211> LENGTH: 32
<212> TYPE: PRT
<213> ORGANISM: Artificial Sequence
<220> FEATURE:
<223> OTHER INFORMATION: Synthetic Construct

<400> SEQUENCE: 276

```
Arg Phe Thr Ile Ser Arg Asp Asn Ser Lys Asn Thr Leu Tyr Leu Gln
1               5                   10                  15

Met Asn Ser Leu Arg Val Glu Asp Thr Ala Val Tyr Tyr Cys Ala Val
            20                  25                  30
```

<210> SEQ ID NO 277
<211> LENGTH: 32
<212> TYPE: PRT
<213> ORGANISM: Artificial Sequence
<220> FEATURE:
<223> OTHER INFORMATION: Synthetic Construct

<400> SEQUENCE: 277

```
Arg Phe Thr Ile Ser Arg Asp Asn Ser Asn Asn Thr Leu Tyr Leu Gln
1               5                   10                  15
```

Met Asn Ser Leu Arg Ala Asp Asp Thr Ala Val Tyr Phe Cys Ala Lys
            20                  25                  30

<210> SEQ ID NO 278
<211> LENGTH: 32
<212> TYPE: PRT
<213> ORGANISM: Artificial Sequence
<220> FEATURE:
<223> OTHER INFORMATION: Synthetic Construct

<400> SEQUENCE: 278

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Asn
            20                  25                  30

<210> SEQ ID NO 279
<211> LENGTH: 32
<212> TYPE: PRT
<213> ORGANISM: Artificial Sequence
<220> FEATURE:
<223> OTHER INFORMATION: Synthetic Construct

<400> SEQUENCE: 279

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 280
<211> LENGTH: 32
<212> TYPE: PRT
<213> ORGANISM: Artificial Sequence
<220> FEATURE:
<223> OTHER INFORMATION: Synthetic Construct

<400> SEQUENCE: 280

Arg Leu Ser Ile Ser Arg Asp Asp Ser Met Asn Thr Val Tyr Leu Asp
1               5                   10                  15

Ile Tyr Asn Leu Lys Ile Asp Asp Thr Gly Val Tyr Tyr Cys Thr Phe
            20                  25                  30

<210> SEQ ID NO 281
<211> LENGTH: 32
<212> TYPE: PRT
<213> ORGANISM: Artificial Sequence
<220> FEATURE:
<223> OTHER INFORMATION: Synthetic Construct

<400> SEQUENCE: 281

Arg Phe Thr Ile Ser Arg Asp Asn Ser Lys Asn Ser Met Tyr Leu Gln
1               5                   10                  15

Met Asn Ser Leu Arg Val Glu Asp Thr Ala Val Tyr Tyr Cys Ala Arg
            20                  25                  30

<210> SEQ ID NO 282
<211> LENGTH: 32
<212> TYPE: PRT
<213> ORGANISM: Artificial Sequence
<220> FEATURE:
<223> OTHER INFORMATION: Synthetic Construct

<400> SEQUENCE: 282

Arg Phe Ile Ile Ser Arg Asp Asp Ser Asn Asp Met Leu Tyr Leu Glu

```
1               5                   10                  15
Met Ile Ser Leu Lys Ser Glu Asp Thr Ala Val Tyr Tyr Cys Ser Asp
            20                  25                  30
```

<210> SEQ ID NO 283
<211> LENGTH: 32
<212> TYPE: PRT
<213> ORGANISM: Artificial Sequence
<220> FEATURE:
<223> OTHER INFORMATION: Synthetic Construct

<400> SEQUENCE: 283

```
Arg Phe Thr Ile Ser Arg Asp Asn Ser Lys Asn Thr Leu Tyr Leu His
1               5                   10                  15
Met Asn Ser Leu Arg Ala Glu Asp Thr Ala Val Tyr Tyr Cys Val Lys
            20                  25                  30
```

<210> SEQ ID NO 284
<211> LENGTH: 32
<212> TYPE: PRT
<213> ORGANISM: Artificial Sequence
<220> FEATURE:
<223> OTHER INFORMATION: Synthetic Construct

<400> SEQUENCE: 284

```
Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Lys
            20                  25                  30
```

<210> SEQ ID NO 285
<211> LENGTH: 32
<212> TYPE: PRT
<213> ORGANISM: Artificial Sequence
<220> FEATURE:
<223> OTHER INFORMATION: Synthetic Construct

<400> SEQUENCE: 285

```
Arg Phe Thr Val Ser Arg Asp Asn Ser Arg Asn Thr Leu Tyr Leu Gln
1               5                   10                  15
Met Lys Ser Leu Ser Ala Glu Asp Thr Ala Val Tyr Tyr Cys Ala Lys
            20                  25                  30
```

<210> SEQ ID NO 286
<211> LENGTH: 32
<212> TYPE: PRT
<213> ORGANISM: Artificial Sequence
<220> FEATURE:
<223> OTHER INFORMATION: Synthetic Construct

<400> SEQUENCE: 286

```
Arg Phe Thr Ile Ser Arg Asp Asn Ser Gln Asn Ser Leu Phe Leu Gln
1               5                   10                  15
Met Asn Ser Leu Arg Ala Glu Asp Thr Ala Val Tyr Tyr Cys Ala Thr
            20                  25                  30
```

<210> SEQ ID NO 287
<211> LENGTH: 31
<212> TYPE: PRT
<213> ORGANISM: Artificial Sequence
<220> FEATURE:
<223> OTHER INFORMATION: Synthetic Construct

<400> SEQUENCE: 287

His Val Thr Ile Ser Val Asp Lys Ser Ile Ser Thr Ala Tyr Leu Gln
1               5                   10                  15

Trp Ser Ser Leu Lys Ala Ser Asp Ser Ala Met Tyr Tyr Phe Leu
            20                  25                  30

<210> SEQ ID NO 288
<211> LENGTH: 32
<212> TYPE: PRT
<213> ORGANISM: Artificial Sequence
<220> FEATURE:
<223> OTHER INFORMATION: Synthetic Construct

<400> SEQUENCE: 288

Arg Phe Thr Ile Ser Arg Asp Asn Ala Lys Asn Ser Leu Tyr Leu Gln
1               5                   10                  15

Met Asn Ser Leu Arg Asp Glu Asp Thr Ala Val Tyr Tyr Cys Ala Arg
            20                  25                  30

<210> SEQ ID NO 289
<211> LENGTH: 32
<212> TYPE: PRT
<213> ORGANISM: Artificial Sequence
<220> FEATURE:
<223> OTHER INFORMATION: Synthetic Construct

<400> SEQUENCE: 289

Arg Val Thr Met Thr Arg Asp Thr Ser Ser Thr Ala Tyr Met Glu
1               5                   10                  15

Leu Asn Arg Leu Thr Ser Asp Asp Thr Ala Val Tyr Phe Cys Ala Arg
            20                  25                  30

<210> SEQ ID NO 290
<211> LENGTH: 32
<212> TYPE: PRT
<213> ORGANISM: Artificial Sequence
<220> FEATURE:
<223> OTHER INFORMATION: Synthetic Construct

<400> SEQUENCE: 290

Arg Phe Thr Ile Ser Arg Asp Asn Ala Gln Asn Ser Leu Phe Leu Gln
1               5                   10                  15

Met Asn Ser Leu Arg Ala Glu Asp Thr Ala Val Tyr Tyr Cys Ala Thr
            20                  25                  30

<210> SEQ ID NO 291
<211> LENGTH: 32
<212> TYPE: PRT
<213> ORGANISM: Artificial Sequence
<220> FEATURE:
<223> OTHER INFORMATION: Synthetic Construct

<400> SEQUENCE: 291

Gln Val Thr Met Ser Ala Asn Arg Ser Ile Ser Thr Ala Tyr Leu Gln
1               5                   10                  15

Trp Ser Ser Leu Lys Ala Ser Asp Thr Gly Ile Tyr Tyr Cys Ala Thr
            20                  25                  30

<210> SEQ ID NO 292
<211> LENGTH: 32
<212> TYPE: PRT
<213> ORGANISM: Artificial Sequence
<220> FEATURE:
<223> OTHER INFORMATION: Synthetic Construct

<400> SEQUENCE: 292

Arg Phe Thr Ile Ser Arg Asp Ser Thr Gln Asn Thr Val His Leu Gln
1               5                   10                  15

Met Asn Ser Leu Thr Ala Glu Asp Thr Ala Val Tyr Tyr Cys Ala Arg
            20                  25                  30

<210> SEQ ID NO 293
<211> LENGTH: 32
<212> TYPE: PRT
<213> ORGANISM: Artificial Sequence
<220> FEATURE:
<223> OTHER INFORMATION: Synthetic Construct

<400> SEQUENCE: 293

Arg Leu Ile Leu Ser Val Asp Glu Pro Thr Arg Thr Val Tyr Met Glu
1               5                   10                  15

Leu Thr Ser Leu Arg Ser Asp Asp Thr Ala Met Tyr Tyr Cys Ala Arg
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Synthetic Construct

<400> SEQUENCE: 294

Arg Phe Thr Ile Ser Arg Asp Asn Ala Lys Asp Ser Leu Tyr Leu Gln
1               5                   10                  15

Met Asn Ser Leu Arg Pro Glu Asp Thr Ala Leu Tyr Tyr Cys Ala Arg
            20                  25                  30

<210> SEQ ID NO 295
<211> LENGTH: 32
<212> TYPE: PRT
<213> ORGANISM: Artificial Sequence
<220> FEATURE:
<223> OTHER INFORMATION: Synthetic Construct

<400> SEQUENCE: 295

Arg Phe Thr Ile Ser Arg Asp Tyr Ser Asn Lys Ile Val His Leu Glu
1               5                   10                  15

Met Asp Ser Leu Arg Ala Glu Asp Thr Ala Val Tyr Phe Cys Val Arg
            20                  25                  30

<210> SEQ ID NO 296
<211> LENGTH: 32
<212> TYPE: PRT
<213> ORGANISM: Artificial Sequence
<220> FEATURE:
<223> OTHER INFORMATION: Synthetic Construct

<400> SEQUENCE: 296

Arg Phe Thr Ile Ser Arg Asp Asp Ser Arg Asp Met Leu Tyr Leu Gln
1               5                   10                  15

Met Asn Asn Leu Lys Thr Glu Asp Thr Ala Val Tyr Tyr Cys Ser Asp
            20                  25                  30

<210> SEQ ID NO 297
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 297

Arg Phe Thr Ile Ser Arg Asp Asp Ser Lys Ser Ile Val Tyr Leu Gln
1               5                   10                  15

Met Ser Ser Leu Gln Thr Glu Asp Thr Ala Val Tyr Tyr Cys Ser Arg
                20                  25                  30

<210> SEQ ID NO 298
<211> LENGTH: 30
<212> TYPE: PRT
<213> ORGANISM: Artificial Sequence
<220> FEATURE:
<223> OTHER INFORMATION: Synthetic Construct

<400> SEQUENCE: 298

Thr Ile Ser Arg Asp Asn Ala Lys Asn Ser Val Tyr Leu Gln Met Asn
1               5                   10                  15

Ser Leu Arg Ala Glu Asp Ser Ala Val Tyr Phe Cys Ala Arg
                20                  25                  30

<210> SEQ ID NO 299
<211> LENGTH: 32
<212> TYPE: PRT
<213> ORGANISM: Artificial Sequence
<220> FEATURE:
<223> OTHER INFORMATION: Synthetic Construct

<400> SEQUENCE: 299

Arg Phe Thr Ile Ser Arg Asp Asn Ser Arg Asn Thr Val Phe Leu Gln
1               5                   10                  15

Met Thr Ser Leu Arg Ala Glu Asp Thr Ala Val Tyr Tyr Cys Gly Arg
                20                  25                  30

<210> SEQ ID NO 300
<211> LENGTH: 32
<212> TYPE: PRT
<213> ORGANISM: Artificial Sequence
<220> FEATURE:
<223> OTHER INFORMATION: Synthetic Construct

<400> SEQUENCE: 300

Arg Phe Thr Ile Ser Arg Asp Asn Ala Lys Asp Ser Leu Tyr Leu Gln
1               5                   10                  15

Met Asp Ser Leu Arg Pro Glu Asp Thr Ala Val Tyr Tyr Cys Ala Arg
                20                  25                  30

<210> SEQ ID NO 301
<211> LENGTH: 32
<212> TYPE: PRT
<213> ORGANISM: Artificial Sequence
<220> FEATURE:
<223> OTHER INFORMATION: Synthetic construct

<400> SEQUENCE: 301

Gln Phe Thr Ile Ser Arg Asp Asn Ala Lys Asn Thr Leu Tyr Leu Gln
1               5                   10                  15

Met Asn Ser Leu Arg Val Glu Asp Thr Ala Val Tyr Tyr Cys Ala Arg
                20                  25                  30

<210> SEQ ID NO 302
<211> LENGTH: 32
<212> TYPE: PRT
<213> ORGANISM: Artificial Sequence
<220> FEATURE:
<223> OTHER INFORMATION: Synthetic construct
```

```
<400> SEQUENCE: 302

Arg Phe Thr Val Ser Arg Asp Ile Ser Lys Asn Thr Val Tyr Leu Gln
1               5                   10                  15

Met Asn Ser Leu Arg Ala Glu Asp Thr Ala Leu Tyr Tyr Cys Ala Arg
            20                  25                  30

<210> SEQ ID NO 303
<211> LENGTH: 32
<212> TYPE: PRT
<213> ORGANISM: Artificial Sequence
<220> FEATURE:
<223> OTHER INFORMATION: Synthetic construct

<400> SEQUENCE: 303

Arg Phe Thr Ile Ser Arg Asp Asp Ser Lys Asn Ser Leu Ser Leu Gln
1               5                   10                  15

Met Asp Ser Leu Arg Thr Glu Asp Thr Ala Val Tyr Tyr Cys Val Arg
            20                  25                  30

<210> SEQ ID NO 304
<211> LENGTH: 32
<212> TYPE: PRT
<213> ORGANISM: Artificial Sequence
<220> FEATURE:
<223> OTHER INFORMATION: Synthetic construct

<400> SEQUENCE: 304

Arg Phe Thr Ile Ser Arg Asp Asn Ser Asn Asn Thr Val Tyr Leu Glu
1               5                   10                  15

Met Asn Ser Leu Arg Pro Glu Asp Ser Ala Ile Tyr Tyr Cys Ala Lys
            20                  25                  30

<210> SEQ ID NO 305
<211> LENGTH: 31
<212> TYPE: PRT
<213> ORGANISM: Artificial Sequence
<220> FEATURE:
<223> OTHER INFORMATION: Synthetic construct

<400> SEQUENCE: 305

Arg Phe Thr Ile Ser Arg Asp Asn Ser Lys Asn Ser Leu Tyr Leu Gln
1               5                   10                  15

Met Asn Ser Leu Arg Thr Asp Glu Thr Ala Leu Tyr Tyr Cys Val
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: Synthetic construct

<400> SEQUENCE: 306

Arg Phe Thr Ile Ser Arg Asp Asn Ala Lys Asn Ser Leu Tyr Leu Gln
1               5                   10                  15

Met Asn Ser Leu Arg Thr Asp Glu Thr Ala Val Tyr Tyr Cys Ala Arg
            20                  25                  30

<210> SEQ ID NO 307
<211> LENGTH: 32
<212> TYPE: PRT
<213> ORGANISM: Artificial Sequence
<220> FEATURE:
```

<223> OTHER INFORMATION: Synthetic construct

<400> SEQUENCE: 307

Arg Phe Thr Ile Ser Ile Asp Glu Ser Arg Asn Ala Leu Phe Leu His
1               5                   10                  15
Met Asn Ser Leu Thr Thr Asp Asp Thr Ala Val Tyr Tyr Cys Ser Thr
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Synthetic construct

<400> SEQUENCE: 308

Arg Phe Thr Val Ser Arg Asp Thr Ser Thr Asn Thr Leu Tyr Leu Gln
1               5                   10                  15
Met Asn Ser Leu Arg Val Glu Asp Thr Ala Val Tyr Tyr Cys Ala Arg
            20                  25                  30

<210> SEQ ID NO 309
<211> LENGTH: 32
<212> TYPE: PRT
<213> ORGANISM: Artificial Sequence
<220> FEATURE:
<223> OTHER INFORMATION: Synthetic construct

<400> SEQUENCE: 309

Arg Val Thr Met Thr Arg Asn Thr Ser Ile Ser Thr Ala Tyr Met Glu
1               5                   10                  15
Leu Ser Ser Leu Thr Ser Ala Asp Thr Ala Val Tyr Tyr Cys Ala Arg
            20                  25                  30

<210> SEQ ID NO 310
<211> LENGTH: 32
<212> TYPE: PRT
<213> ORGANISM: Artificial Sequence
<220> FEATURE:
<223> OTHER INFORMATION: Synthetic construct

<400> SEQUENCE: 310

Gln Val Thr Ile Ser Ala Asp Lys Ser Ile Ser Thr Ala Phe Leu Gln
1               5                   10                  15
Trp Asn Ser Leu Lys Ala Ser Asp Thr Ala Met Tyr Tyr Cys Ala Arg
            20                  25                  30

<210> SEQ ID NO 311
<211> LENGTH: 11
<212> TYPE: PRT
<213> ORGANISM: Artificial Sequence
<220> FEATURE:
<223> OTHER INFORMATION: Synthetic Construct

<400> SEQUENCE: 311

Trp Gly Gln Gly Ala Leu Val Thr Val Ser Ser
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Synthetic Construct

<400> SEQUENCE: 312

Trp Gly Gln Gly Thr Leu Val Thr Val Ser Ser
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic Construct

<400> SEQUENCE: 313

Trp Gly Gln Gly Ile Leu Val Thr Val Ser Ser
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic Construct

<400> SEQUENCE: 314

Trp Gly Gln Gly Thr Leu Val Thr Val Ser Ser
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Synthetic Construct

<400> SEQUENCE: 315

Trp Gly Gln Gly Thr Leu Val Thr Val Ser Ser
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Synthetic Construct

<400> SEQUENCE: 316

Cys Gly Gln Gly Thr Leu Val Thr Val Ser Ser
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Synthetic Construct

<400> SEQUENCE: 317

Tyr Gly Gln Gly Thr Leu Val Thr Val Ser Ser
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Synthetic Construct

<400> SEQUENCE: 318

```
Trp Gly Gln Gly Ala Leu Val Thr Val Ser Ser
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Synthetic Construct

<400> SEQUENCE: 319

Trp Gly Arg Gly Thr Leu Val Thr Val Ser Ser
1               5                   10

<210> SEQ ID NO 320
<211> LENGTH: 11
<212> TYPE: PRT
<213> ORGANISM: Artificial Sequence
<220> FEATURE:
<223> OTHER INFORMATION: Synthetic Construct

<400> SEQUENCE: 320

Trp Gly Gln Gly Thr Thr Val Thr Val Ser Ser
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Synthetic Construct

<400> SEQUENCE: 321

Trp Gly Gln Gly Ala Leu Val Thr Val Ser Ser
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthetic Construct

<400> SEQUENCE: 322

Trp Gly Gln Gly Thr Leu Val Thr Val Ser Ser
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Synthetic Construct

<400> SEQUENCE: 323

Trp Gly Gln Gly Val Leu Val Thr Val Ser Ser
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Synthetic Construct

<400> SEQUENCE: 324
```

Trp Gly Gln Gly Thr Met Val Thr Val Ser Ser
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic Construct

<400> SEQUENCE: 325

Trp Gly Gln Gly Thr Leu Val Thr Val Ser Ser
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Synthetic Construct

<400> SEQUENCE: 326

Trp Gly Gln Gly Thr Leu Val Thr Val Ser Ser
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Synthetic Construct

<400> SEQUENCE: 327

Trp Gly Gln Gly Ala Leu Val Thr Val Ser Ser
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Synthetic Construct

<400> SEQUENCE: 328

Trp Gly Gln Gly Thr Leu Val Thr Val Ser Ser
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Synthetic Construct

<400> SEQUENCE: 329

Trp Gly Gln Gly Thr Thr Val Thr Val Ser Ser
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Synthetic Construct

<400> SEQUENCE: 330

Trp Gly Gln Gly Thr Leu Val Thr Val Ser Ser

<210> SEQ ID NO 331
<211> LENGTH: 11
<212> TYPE: PRT
<213> ORGANISM: Artificial Sequence
<220> FEATURE:
<223> OTHER INFORMATION: Synthetic Construct

<400> SEQUENCE: 331

Trp Gly Gln Gly Thr Leu Val Thr Val Ser Ser
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 332

Trp Gly Xaa Gly Thr Met Val Thr Val Ser Xaa
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Synthetic Construct

<400> SEQUENCE: 333

Trp Gly Gln Gly Thr Pro Val Thr Val Ser Ser
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Synthetic Construct

<400> SEQUENCE: 334

Trp Gly Gln Gly Thr Val Val Thr Val Ser Ser
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Synthetic Construct

<400> SEQUENCE: 335

Gly Ser Gln Gly Thr Leu Val Thr Val Ser Ser
1               5                   10

<210> SEQ ID NO 336
<211> LENGTH: 11
<212> TYPE: PRT

<213> ORGANISM: Artificial Sequence
<220> FEATURE:
<223> OTHER INFORMATION: Synthetic Construct

<400> SEQUENCE: 336

Trp Gly Gln Gly Thr Leu Val Thr Val Ser Ser
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Synthetic Construct

<400> SEQUENCE: 337

Trp Gly Gln Gly Thr Leu Val Thr Val Ser Ser
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Synthetic Construct

<400> SEQUENCE: 338

Trp Gly Gln Gly Thr Met Val Thr Val Ser Ser
1               5                   10

<210> SEQ ID NO 339
<211> LENGTH: 11
<212> TYPE: PRT
<213> ORGANISM: Artificial Sequence
<220> FEATURE:
<223> OTHER INFORMATION: Synthetic Construct

<400> SEQUENCE: 339

Trp Gly Gln Gly Thr Met Val Thr Val Ser Ser
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Synthetic Construct

<400> SEQUENCE: 340

Trp Gly Gln Gly Thr Leu Val Thr Val Ser Ser
1               5                   10

<210> SEQ ID NO 341
<211> LENGTH: 11
<212> TYPE: PRT
<213> ORGANISM: Artificial Sequence
<220> FEATURE:
<223> OTHER INFORMATION: Synthetic Construct

<400> SEQUENCE: 341

Trp Gly Gln Gly Thr Leu Val Thr Val Ser Ser
1               5                   10

<210> SEQ ID NO 342
<211> LENGTH: 11
<212> TYPE: PRT
<213> ORGANISM: Artificial Sequence

```
<220> FEATURE:
<223> OTHER INFORMATION: Synthetic Construct

<400> SEQUENCE: 342

Trp Gly Gln Gly Thr Leu Val Thr Val Ser Ser
1               5                   10

<210> SEQ ID NO 343
<211> LENGTH: 11
<212> TYPE: PRT
<213> ORGANISM: Artificial Sequence
<220> FEATURE:
<223> OTHER INFORMATION: Synthetic Construct

<400> SEQUENCE: 343

Trp Gly Gln Gly Thr Met Val Thr Val Ser Ser
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Synthetic Construct

<400> SEQUENCE: 344

Trp Gly Gln Gly Thr Thr Val Thr Val Ser Ser
1               5                   10

<210> SEQ ID NO 345
<211> LENGTH: 11
<212> TYPE: PRT
<213> ORGANISM: Artificial Sequence
<220> FEATURE:
<223> OTHER INFORMATION: Synthetic Construct

<400> SEQUENCE: 345

Trp Gly Gln Gly Thr Leu Val Thr Val Ser Ser
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Synthetic Construct

<400> SEQUENCE: 346

Trp Gly Gln Gly Thr Thr Val Thr Val Ser Ser
1               5                   10

<210> SEQ ID NO 347
<211> LENGTH: 11
<212> TYPE: PRT
<213> ORGANISM: Artificial Sequence
<220> FEATURE:
<223> OTHER INFORMATION: Synthetic Construct

<400> SEQUENCE: 347

Trp Gly Gln Gly Thr Met Val Thr Val Ser Ser
1               5                   10

<210> SEQ ID NO 348
<211> LENGTH: 11
<212> TYPE: PRT
<213> ORGANISM: Artificial Sequence
<220> FEATURE:
```

```
<223> OTHER INFORMATION: Synthetic Construct

<400> SEQUENCE: 348

Trp Gly Gln Gly Thr Leu Val Thr Val Ser Ser
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Synthetic Construct

<400> SEQUENCE: 349

Ser Ser Gln Gly Thr Leu Val Thr Val Ser Ser
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Synthetic Construct

<400> SEQUENCE: 350

Trp Gly Arg Gly Thr Leu Val Thr Val Ser Ser
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Synthetic Construct

<400> SEQUENCE: 351

Trp Gly Gln Gly Thr Leu Val Thr Val Ser Ser
1               5                   10

<210> SEQ ID NO 352
<211> LENGTH: 11
<212> TYPE: PRT
<213> ORGANISM: Artificial Sequence
<220> FEATURE:
<223> OTHER INFORMATION: Synthetic Construct

<400> SEQUENCE: 352

Trp Gly Gln Gly Ile Leu Val Thr Val Ser Ser
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Synthetic Construct

<400> SEQUENCE: 353

Ala Pro Gln Gly Thr Leu Val Thr Val Ser Ser
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Synthetic construct
```

<400> SEQUENCE: 354

Trp Gly Gln Gly Thr Met Val Thr Val Ser Ser
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Synthetic construct

<400> SEQUENCE: 355

Trp Gly Gln Gly Thr Met Val Thr Val Ser Ser
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Synthetic construct

<400> SEQUENCE: 356

Trp Gly Gln Gly Thr Val Val Thr Val Ser Ser
1               5                   10

<210> SEQ ID NO 357
<211> LENGTH: 11
<212> TYPE: PRT
<213> ORGANISM: Artificial Sequence
<220> FEATURE:
<223> OTHER INFORMATION: Synthetic construct

<400> SEQUENCE: 357

Trp Gly Leu Gly Thr Val Val Thr Val Ser Ser
1               5                   10

<210> SEQ ID NO 358
<211> LENGTH: 11
<212> TYPE: PRT
<213> ORGANISM: Artificial Sequence
<220> FEATURE:
<223> OTHER INFORMATION: Synthetic construct

<400> SEQUENCE: 358

Trp Gly Gln Gly Thr Leu Val Thr Val Ser Ser
1               5                   10

<210> SEQ ID NO 359
<211> LENGTH: 11
<212> TYPE: PRT
<213> ORGANISM: Artificial Sequence
<220> FEATURE:
<223> OTHER INFORMATION: Synthetic construct

<400> SEQUENCE: 359

Trp Gly Gln Gly Thr Thr Val Thr Val Ser Ser
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Synthetic construct

<400> SEQUENCE: 360

Trp Gly Gln Gly Thr Leu Val Thr Val Ser Ser
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Synthetic construct

<400> SEQUENCE: 361

Trp Gly Gln Gly Thr Leu Val Thr Val Ser Ser
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Synthetic construct

<400> SEQUENCE: 362

Trp Gly Gln Gly Thr Leu Val Thr Val Ser Ser
1               5                   10

<210> SEQ ID NO 363
<211> LENGTH: 11
<212> TYPE: PRT
<213> ORGANISM: Artificial Sequence
<220> FEATURE:
<223> OTHER INFORMATION: Synthetic construct

<400> SEQUENCE: 363

Trp Gly Leu Gly Thr Leu Val Thr Val Ser Ser
1               5                   10

<210> SEQ ID NO 364
<211> LENGTH: 29
<212> TYPE: PRT
<213> ORGANISM: Artificial Sequence
<220> FEATURE:
<223> OTHER INFORMATION: Synthetic Construct

<400> SEQUENCE: 364

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 365
<211> LENGTH: 29
<212> TYPE: PRT
<213> ORGANISM: Artificial Sequence
<220> FEATURE:
<223> OTHER INFORMATION: Synthetic Construct

<400> SEQUENCE: 365

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 366
<211> LENGTH: 29

<212> TYPE: PRT
<213> ORGANISM: Artificial Sequence
<220> FEATURE:
<223> OTHER INFORMATION: Synthetic Construct

<400> SEQUENCE: 366

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 367
<211> LENGTH: 29
<212> TYPE: PRT
<213> ORGANISM: Artificial Sequence
<220> FEATURE:
<223> OTHER INFORMATION: Synthetic Construct

<400> SEQUENCE: 367

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 368
<211> LENGTH: 29
<212> TYPE: PRT
<213> ORGANISM: Artificial Sequence
<220> FEATURE:
<223> OTHER INFORMATION: Synthetic Construct

<400> SEQUENCE: 368

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 369
<211> LENGTH: 29
<212> TYPE: PRT
<213> ORGANISM: Artificial Sequence
<220> FEATURE:
<223> OTHER INFORMATION: Synthetic Construct

<400> SEQUENCE: 369

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 370
<211> LENGTH: 29
<212> TYPE: PRT
<213> ORGANISM: Artificial Sequence
<220> FEATURE:
<223> OTHER INFORMATION: Synthetic Construct

<400> SEQUENCE: 370

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 371

<211> LENGTH: 29
<212> TYPE: PRT
<213> ORGANISM: Artificial Sequence
<220> FEATURE:
<223> OTHER INFORMATION: Synthetic Construct

<400> SEQUENCE: 371

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 372
<211> LENGTH: 29
<212> TYPE: PRT
<213> ORGANISM: Artificial Sequence
<220> FEATURE:
<223> OTHER INFORMATION: Synthetic Construct

<400> SEQUENCE: 372

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 373
<211> LENGTH: 29
<212> TYPE: PRT
<213> ORGANISM: Artificial Sequence
<220> FEATURE:
<223> OTHER INFORMATION: Synthetic Construct

<400> SEQUENCE: 373

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 374
<211> LENGTH: 29
<212> TYPE: PRT
<213> ORGANISM: Artificial Sequence
<220> FEATURE:
<223> OTHER INFORMATION: Synthetic Construct

<400> SEQUENCE: 374

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 375
<211> LENGTH: 29
<212> TYPE: PRT
<213> ORGANISM: Artificial Sequence
<220> FEATURE:
<223> OTHER INFORMATION: Synthetic Construct

<400> SEQUENCE: 375

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

```
<210> SEQ ID NO 376
<211> LENGTH: 29
<212> TYPE: PRT
<213> ORGANISM: Artificial Sequence
<220> FEATURE:
<223> OTHER INFORMATION: Synthetic Construct

<400> SEQUENCE: 376

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 377
<211> LENGTH: 29
<212> TYPE: PRT
<213> ORGANISM: Artificial Sequence
<220> FEATURE:
<223> OTHER INFORMATION: Synthetic Construct

<400> SEQUENCE: 377

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 378
<211> LENGTH: 29
<212> TYPE: PRT
<213> ORGANISM: Artificial Sequence
<220> FEATURE:
<223> OTHER INFORMATION: Synthetic Construct

<400> SEQUENCE: 378

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 379
<211> LENGTH: 29
<212> TYPE: PRT
<213> ORGANISM: Artificial Sequence
<220> FEATURE:
<223> OTHER INFORMATION: Synthetic Construct

<400> SEQUENCE: 379

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 380
<211> LENGTH: 29
<212> TYPE: PRT
<213> ORGANISM: Artificial Sequence
<220> FEATURE:
<223> OTHER INFORMATION: Synthetic Construct

<400> SEQUENCE: 380

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25
```

```
<210> SEQ ID NO 381
<211> LENGTH: 29
<212> TYPE: PRT
<213> ORGANISM: Artificial Sequence
<220> FEATURE:
<223> OTHER INFORMATION: Synthetic Construct

<400> SEQUENCE: 381

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 382
<211> LENGTH: 29
<212> TYPE: PRT
<213> ORGANISM: Artificial Sequence
<220> FEATURE:
<223> OTHER INFORMATION: Synthetic Construct

<400> SEQUENCE: 382

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 383
<211> LENGTH: 29
<212> TYPE: PRT
<213> ORGANISM: Artificial Sequence
<220> FEATURE:
<223> OTHER INFORMATION: Synthetic Construct

<400> SEQUENCE: 383

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 384
<211> LENGTH: 29
<212> TYPE: PRT
<213> ORGANISM: Artificial Sequence
<220> FEATURE:
<223> OTHER INFORMATION: Synthetic Construct

<400> SEQUENCE: 384

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 385
<211> LENGTH: 29
<212> TYPE: PRT
<213> ORGANISM: Artificial Sequence
<220> FEATURE:
<223> OTHER INFORMATION: Synthetic Construct

<400> SEQUENCE: 385

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25
```

<210> SEQ ID NO 386
<211> LENGTH: 29
<212> TYPE: PRT
<213> ORGANISM: Artificial Sequence
<220> FEATURE:
<223> OTHER INFORMATION: Synthetic Construct

<400> SEQUENCE: 386

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 387
<211> LENGTH: 29
<212> TYPE: PRT
<213> ORGANISM: Artificial Sequence
<220> FEATURE:
<223> OTHER INFORMATION: Synthetic Construct

<400> SEQUENCE: 387

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 388
<211> LENGTH: 29
<212> TYPE: PRT
<213> ORGANISM: Artificial Sequence
<220> FEATURE:
<223> OTHER INFORMATION: Synthetic Construct

<400> SEQUENCE: 388

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 389
<211> LENGTH: 29
<212> TYPE: PRT
<213> ORGANISM: Artificial Sequence
<220> FEATURE:
<223> OTHER INFORMATION: Synthetic Construct

<400> SEQUENCE: 389

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 390
<211> LENGTH: 29
<212> TYPE: PRT
<213> ORGANISM: Artificial Sequence
<220> FEATURE:
<223> OTHER INFORMATION: Synthetic Construct

<400> SEQUENCE: 390

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe

<210> SEQ ID NO 391
<211> LENGTH: 29
<212> TYPE: PRT
<213> ORGANISM: Artificial Sequence
<220> FEATURE:
<223> OTHER INFORMATION: Synthetic Construct

<400> SEQUENCE: 391

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 392
<211> LENGTH: 29
<212> TYPE: PRT
<213> ORGANISM: Artificial Sequence
<220> FEATURE:
<223> OTHER INFORMATION: Synthetic Construct

<400> SEQUENCE: 392

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 393
<211> LENGTH: 29
<212> TYPE: PRT
<213> ORGANISM: Artificial Sequence
<220> FEATURE:
<223> OTHER INFORMATION: Synthetic Construct

<400> SEQUENCE: 393

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 394
<211> LENGTH: 29
<212> TYPE: PRT
<213> ORGANISM: Artificial Sequence
<220> FEATURE:
<223> OTHER INFORMATION: Synthetic Construct

<400> SEQUENCE: 394

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 395
<211> LENGTH: 29
<212> TYPE: PRT
<213> ORGANISM: Artificial Sequence
<220> FEATURE:
<223> OTHER INFORMATION: Synthetic Construct

<400> SEQUENCE: 395

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 396
<211> LENGTH: 29
<212> TYPE: PRT
<213> ORGANISM: Artificial Sequence
<220> FEATURE:
<223> OTHER INFORMATION: Synthetic Construct

<400> SEQUENCE: 396

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 397
<211> LENGTH: 29
<212> TYPE: PRT
<213> ORGANISM: Artificial Sequence
<220> FEATURE:
<223> OTHER INFORMATION: Synthetic Construct

<400> SEQUENCE: 397

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 398
<211> LENGTH: 29
<212> TYPE: PRT
<213> ORGANISM: Artificial Sequence
<220> FEATURE:
<223> OTHER INFORMATION: Synthetic Construct

<400> SEQUENCE: 398

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 399
<211> LENGTH: 29
<212> TYPE: PRT
<213> ORGANISM: Artificial Sequence
<220> FEATURE:
<223> OTHER INFORMATION: Synthetic Construct

<400> SEQUENCE: 399

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 400
<211> LENGTH: 29
<212> TYPE: PRT
<213> ORGANISM: Artificial Sequence
<220> FEATURE:
<223> OTHER INFORMATION: Synthetic Construct

<400> SEQUENCE: 400

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 401
<211> LENGTH: 29
<212> TYPE: PRT
<213> ORGANISM: Artificial Sequence
<220> FEATURE:
<223> OTHER INFORMATION: Synthetic Construct

<400> SEQUENCE: 401

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 402
<211> LENGTH: 29
<212> TYPE: PRT
<213> ORGANISM: Artificial Sequence
<220> FEATURE:
<223> OTHER INFORMATION: Synthetic Construct

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 403
<211> LENGTH: 29
<212> TYPE: PRT
<213> ORGANISM: Artificial Sequence
<220> FEATURE:
<223> OTHER INFORMATION: Synthetic Construct

<400> SEQUENCE: 403

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 404
<211> LENGTH: 29
<212> TYPE: PRT
<213> ORGANISM: Artificial Sequence
<220> FEATURE:
<223> OTHER INFORMATION: Synthetic Construct

<400> SEQUENCE: 404

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe
            20                  25

<210> SEQ ID NO 405
<211> LENGTH: 29
<212> TYPE: PRT
<213> ORGANISM: Artificial Sequence
<220> FEATURE:
<223> OTHER INFORMATION: Synthetic Construct

<400> SEQUENCE: 405

Glu Val Gln Leu Val Glu Ser Gly Gly Gly Leu Val Gln Pro Gly Gly

```
            1               5                  10                  15
Ser Leu Arg Leu Ser Cys Ala Ala Ser Gly Phe Thr Phe
            20                  25
```

<210> SEQ ID NO 406
<211> LENGTH: 14
<212> TYPE: PRT
<213> ORGANISM: Artificial Sequence
<220> FEATURE:
<223> OTHER INFORMATION: Synthetic Construct

<400> SEQUENCE: 406

```
Trp Val Arg Asn Ala Pro Gly Lys Gly Asn Glu Ile Val Ser
1               5                  10
```

<210> SEQ ID NO 407
<211> LENGTH: 14
<212> TYPE: PRT
<213> ORGANISM: Artificial Sequence
<220> FEATURE:
<223> OTHER INFORMATION: Synthetic Construct

<400> SEQUENCE: 407

```
Trp Val Arg Arg Ala Pro Gly Lys Gly Ile Glu Val Val Ser
1               5                  10
```

<210> SEQ ID NO 408
<211> LENGTH: 14
<212> TYPE: PRT
<213> ORGANISM: Artificial Sequence
<220> FEATURE:
<223> OTHER INFORMATION: Synthetic Construct

<400> SEQUENCE: 408

```
Trp Val Arg Ile Ala Pro Gly Lys Gly Pro Glu Pro Val Ser
1               5                  10
```

<210> SEQ ID NO 409
<211> LENGTH: 14
<212> TYPE: PRT
<213> ORGANISM: Artificial Sequence
<220> FEATURE:
<223> OTHER INFORMATION: Synthetic Construct

<400> SEQUENCE: 409

```
Trp Val Arg Lys Ala Pro Gly Lys Gly Tyr Glu Pro Val Ser
1               5                  10
```

<210> SEQ ID NO 410
<211> LENGTH: 14
<212> TYPE: PRT
<213> ORGANISM: Artificial Sequence
<220> FEATURE:
<223> OTHER INFORMATION: Synthetic Construct

<400> SEQUENCE: 410

```
Trp Val Arg Asn Ala Pro Gly Lys Gly Tyr Glu Ile Val Ser
1               5                  10
```

<210> SEQ ID NO 411
<211> LENGTH: 14
<212> TYPE: PRT
<213> ORGANISM: Artificial Sequence
<220> FEATURE:
<223> OTHER INFORMATION: Synthetic Construct

<400> SEQUENCE: 411

Trp Val Arg Tyr Ala Pro Gly Lys Gly Tyr Glu Phe Val Ser
1               5                   10

<210> SEQ ID NO 412
<211> LENGTH: 14
<212> TYPE: PRT
<213> ORGANISM: Artificial Sequence
<220> FEATURE:
<223> OTHER INFORMATION: Synthetic Construct

<400> SEQUENCE: 412

Trp Val Arg Val Ala Pro Gly Lys Gly Ile Glu Pro Val Ser
1               5                   10

<210> SEQ ID NO 413
<211> LENGTH: 14
<212> TYPE: PRT
<213> ORGANISM: Artificial Sequence
<220> FEATURE:
<223> OTHER INFORMATION: Synthetic Construct

<400> SEQUENCE: 413

Trp Val Arg Met Ala Pro Gly Lys Gly Pro Glu His Val Ser
1               5                   10

<210> SEQ ID NO 414
<211> LENGTH: 14
<212> TYPE: PRT
<213> ORGANISM: Artificial Sequence
<220> FEATURE:
<223> OTHER INFORMATION: Synthetic Construct

<400> SEQUENCE: 414

Trp Val Arg Ser Ala Pro Gly Lys Gly Val Glu Met Val Ser
1               5                   10

<210> SEQ ID NO 415
<211> LENGTH: 14
<212> TYPE: PRT
<213> ORGANISM: Artificial Sequence
<220> FEATURE:
<223> OTHER INFORMATION: Synthetic Construct

<400> SEQUENCE: 415

Trp Val Arg Thr Ala Pro Gly Lys Gly Thr Glu Met Val Ser
1               5                   10

<210> SEQ ID NO 416
<211> LENGTH: 14
<212> TYPE: PRT
<213> ORGANISM: Artificial Sequence
<220> FEATURE:
<223> OTHER INFORMATION: Synthetic Construct

<400> SEQUENCE: 416

Trp Val Arg Cys Ala Pro Gly Lys Gly Tyr Glu Phe Val Ser
1               5                   10

<210> SEQ ID NO 417
<211> LENGTH: 14
<212> TYPE: PRT
<213> ORGANISM: Artificial Sequence
<220> FEATURE:
<223> OTHER INFORMATION: Synthetic Construct

<400> SEQUENCE: 417

```
Trp Val Arg Ile Ala Pro Gly Lys Gly Leu Glu Met Val Ser
1               5                   10
```

<210> SEQ ID NO 418
<211> LENGTH: 14
<212> TYPE: PRT
<213> ORGANISM: Artificial Sequence
<220> FEATURE:
<223> OTHER INFORMATION: Synthetic Construct

<400> SEQUENCE: 418

```
Trp Val Arg Met Ala Pro Gly Lys Gly Leu Glu Tyr Val Ser
1               5                   10
```

<210> SEQ ID NO 419
<211> LENGTH: 14
<212> TYPE: PRT
<213> ORGANISM: Artificial Sequence
<220> FEATURE:
<223> OTHER INFORMATION: Synthetic Construct

<400> SEQUENCE: 419

```
Trp Val Arg Tyr Ala Pro Gly Lys Gly Thr Glu Phe Val Ser
1               5                   10
```

<210> SEQ ID NO 420
<211> LENGTH: 14
<212> TYPE: PRT
<213> ORGANISM: Artificial Sequence
<220> FEATURE:
<223> OTHER INFORMATION: Synthetic Construct

<400> SEQUENCE: 420

```
Trp Val Arg Gln Ala Pro Gly Lys Gly Val Glu Trp Val Ser
1               5                   10
```

<210> SEQ ID NO 421
<211> LENGTH: 14
<212> TYPE: PRT
<213> ORGANISM: Artificial Sequence
<220> FEATURE:
<223> OTHER INFORMATION: Synthetic Construct

<400> SEQUENCE: 421

```
Trp Val Arg Trp Ala Pro Gly Lys Gly Pro Glu Phe Val Ser
1               5                   10
```

<210> SEQ ID NO 422
<211> LENGTH: 14
<212> TYPE: PRT
<213> ORGANISM: Artificial Sequence
<220> FEATURE:
<223> OTHER INFORMATION: Synthetic Construct

<400> SEQUENCE: 422

```
Trp Val Arg Phe Ala Pro Gly Lys Gly Arg Glu Trp Val Ser
1               5                   10
```

<210> SEQ ID NO 423
<211> LENGTH: 14
<212> TYPE: PRT
<213> ORGANISM: Artificial Sequence
<220> FEATURE:
<223> OTHER INFORMATION: Synthetic Construct

<400> SEQUENCE: 423

```
Trp Val Arg Phe Ala Pro Gly Lys Gly Cys Glu Leu Val Ser
```

```
1               5                   10

<210> SEQ ID NO 424
<211> LENGTH: 14
<212> TYPE: PRT
<213> ORGANISM: Artificial Sequence
<220> FEATURE:
<223> OTHER INFORMATION: Synthetic Construct

<400> SEQUENCE: 424

Trp Val Arg Lys Ala Pro Gly Lys Gly Leu Glu Thr Val Ser
1               5                   10

<210> SEQ ID NO 425
<211> LENGTH: 14
<212> TYPE: PRT
<213> ORGANISM: Artificial Sequence
<220> FEATURE:
<223> OTHER INFORMATION: Synthetic Construct

<400> SEQUENCE: 425

Trp Val Arg Asn Ala Pro Gly Lys Gly Leu Glu Cys Val Ser
1               5                   10

<210> SEQ ID NO 426
<211> LENGTH: 14
<212> TYPE: PRT
<213> ORGANISM: Artificial Sequence
<220> FEATURE:
<223> OTHER INFORMATION: Synthetic Construct

<400> SEQUENCE: 426

Trp Val Arg Cys Ala Pro Gly Lys Gly Trp Glu Val Val Ser
1               5                   10

<210> SEQ ID NO 427
<211> LENGTH: 14
<212> TYPE: PRT
<213> ORGANISM: Artificial Sequence
<220> FEATURE:
<223> OTHER INFORMATION: Synthetic Construct

<400> SEQUENCE: 427

Trp Val Arg Leu Ala Pro Gly Lys Gly Val Glu Leu Val Ser
1               5                   10

<210> SEQ ID NO 428
<211> LENGTH: 14
<212> TYPE: PRT
<213> ORGANISM: Artificial Sequence
<220> FEATURE:
<223> OTHER INFORMATION: Synthetic Construct

<400> SEQUENCE: 428

Trp Val Arg Phe Ala Pro Gly Lys Gly Ala Glu Trp Val Ser
1               5                   10

<210> SEQ ID NO 429
<211> LENGTH: 14
<212> TYPE: PRT
<213> ORGANISM: Artificial Sequence
<220> FEATURE:
<223> OTHER INFORMATION: Synthetic Construct

<400> SEQUENCE: 429

Trp Val Arg Leu Ala Pro Gly Lys Gly Arg Glu Trp Val Ser
1               5                   10
```

```
<210> SEQ ID NO 430
<211> LENGTH: 14
<212> TYPE: PRT
<213> ORGANISM: Artificial Sequence
<220> FEATURE:
<223> OTHER INFORMATION: Synthetic Construct

<400> SEQUENCE: 430

Trp Val Arg Tyr Ala Pro Gly Lys Gly Val Glu Phe Val Ser
1               5                   10

<210> SEQ ID NO 431
<211> LENGTH: 14
<212> TYPE: PRT
<213> ORGANISM: Artificial Sequence
<220> FEATURE:
<223> OTHER INFORMATION: Synthetic Construct

<400> SEQUENCE: 431

Trp Val Arg Phe Ala Pro Gly Lys Gly Leu Glu Met Val Ser
1               5                   10

<210> SEQ ID NO 432
<211> LENGTH: 14
<212> TYPE: PRT
<213> ORGANISM: Artificial Sequence
<220> FEATURE:
<223> OTHER INFORMATION: Synthetic Construct

<400> SEQUENCE: 432

Trp Val Arg Val Ala Pro Gly Lys Gly Thr Glu Arg Val Ser
1               5                   10

<210> SEQ ID NO 433
<211> LENGTH: 14
<212> TYPE: PRT
<213> ORGANISM: Artificial Sequence
<220> FEATURE:
<223> OTHER INFORMATION: Synthetic Construct

<400> SEQUENCE: 433

Trp Val Arg Ile Ala Pro Gly Lys Gly Met Glu Met Val Ser
1               5                   10

<210> SEQ ID NO 434
<211> LENGTH: 14
<212> TYPE: PRT
<213> ORGANISM: Artificial Sequence
<220> FEATURE:
<223> OTHER INFORMATION: Synthetic Construct

<400> SEQUENCE: 434

Trp Val Arg Ala Ala Pro Gly Lys Gly Pro Glu Leu Val Ser
1               5                   10

<210> SEQ ID NO 435
<211> LENGTH: 14
<212> TYPE: PRT
<213> ORGANISM: Artificial Sequence
<220> FEATURE:
<223> OTHER INFORMATION: Synthetic Construct

<400> SEQUENCE: 435

Trp Val Arg Val Ala Pro Gly Lys Gly Tyr Glu His Val Ser
1               5                   10
```

<210> SEQ ID NO 436
<211> LENGTH: 14
<212> TYPE: PRT
<213> ORGANISM: Artificial Sequence
<220> FEATURE:
<223> OTHER INFORMATION: Synthetic Construct

<400> SEQUENCE: 436

Trp Val Arg Val Ala Pro Gly Lys Gly Leu Glu Cys Val Ser
1               5                   10

<210> SEQ ID NO 437
<211> LENGTH: 14
<212> TYPE: PRT
<213> ORGANISM: Artificial Sequence
<220> FEATURE:
<223> OTHER INFORMATION: Synthetic Construct

<400> SEQUENCE: 437

Trp Val Arg Val Ala Pro Gly Lys Gly Pro Glu Thr Val Ser
1               5                   10

<210> SEQ ID NO 438
<211> LENGTH: 14
<212> TYPE: PRT
<213> ORGANISM: Artificial Sequence
<220> FEATURE:
<223> OTHER INFORMATION: Synthetic Construct

<400> SEQUENCE: 438

Trp Val Arg Met Ala Pro Gly Lys Gly Ser Glu Val Val Ser
1               5                   10

<210> SEQ ID NO 439
<211> LENGTH: 14
<212> TYPE: PRT
<213> ORGANISM: Artificial Sequence
<220> FEATURE:
<223> OTHER INFORMATION: Synthetic Construct

<400> SEQUENCE: 439

Trp Val Arg Leu Ala Pro Gly Lys Gly Thr Glu Met Val Ser
1               5                   10

<210> SEQ ID NO 440
<211> LENGTH: 14
<212> TYPE: PRT
<213> ORGANISM: Artificial Sequence
<220> FEATURE:
<223> OTHER INFORMATION: Synthetic Construct

<400> SEQUENCE: 440

Trp Val Arg Thr Ala Pro Gly Lys Gly Ala Glu Trp Val Ser
1               5                   10

<210> SEQ ID NO 441
<211> LENGTH: 14
<212> TYPE: PRT
<213> ORGANISM: Artificial Sequence
<220> FEATURE:
<223> OTHER INFORMATION: Synthetic Construct

<400> SEQUENCE: 441

Trp Val Arg Trp Ala Pro Gly Lys Gly Lys Glu Val Val Ser
1               5                   10

```
<210> SEQ ID NO 442
<211> LENGTH: 14
<212> TYPE: PRT
<213> ORGANISM: Artificial Sequence
<220> FEATURE:
<223> OTHER INFORMATION: Synthetic Construct

<400> SEQUENCE: 442

Trp Val Arg Gln Ala Pro Gly Lys Gly Ile Glu Pro Val Ser
1               5                   10

<210> SEQ ID NO 443
<211> LENGTH: 14
<212> TYPE: PRT
<213> ORGANISM: Artificial Sequence
<220> FEATURE:
<223> OTHER INFORMATION: Synthetic Construct

<400> SEQUENCE: 443

Trp Val Arg Gln Ala Pro Gly Lys Gly Pro Glu Trp Val Ser
1               5                   10

<210> SEQ ID NO 444
<211> LENGTH: 14
<212> TYPE: PRT
<213> ORGANISM: Artificial Sequence
<220> FEATURE:
<223> OTHER INFORMATION: Synthetic Construct

<400> SEQUENCE: 444

Trp Val Arg Gln Ala Pro Gly Lys Gly Pro Glu Val Val Ser
1               5                   10

<210> SEQ ID NO 445
<211> LENGTH: 14
<212> TYPE: PRT
<213> ORGANISM: Artificial Sequence
<220> FEATURE:
<223> OTHER INFORMATION: Synthetic Construct

<400> SEQUENCE: 445

Trp Val Arg Thr Ala Pro Gly Lys Gly Ile Glu Ile Val Ser
1               5                   10

<210> SEQ ID NO 446
<211> LENGTH: 14
<212> TYPE: PRT
<213> ORGANISM: Artificial Sequence
<220> FEATURE:
<223> OTHER INFORMATION: Synthetic Construct

<400> SEQUENCE: 446

Trp Val Arg Ile Ala Pro Gly Lys Gly Val Glu Ile Val Ser
1               5                   10

<210> SEQ ID NO 447
<211> LENGTH: 14
<212> TYPE: PRT
<213> ORGANISM: Artificial Sequence
<220> FEATURE:
<223> OTHER INFORMATION: Synthetic Construct

<400> SEQUENCE: 447

Trp Val Arg Ala Ala Pro Gly Lys Gly Leu Glu Val Val Ser
1               5                   10

<210> SEQ ID NO 448
```

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 448

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 449
<211> LENGTH: 32
<212> TYPE: PRT
<213> ORGANISM: Artificial Sequence
<220> FEATURE:
<223> OTHER INFORMATION: Synthetic Construct

<400> SEQUENCE: 449

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 450
<211> LENGTH: 32
<212> TYPE: PRT
<213> ORGANISM: Artificial Sequence
<220> FEATURE:
<223> OTHER INFORMATION: Synthetic Construct

<400> SEQUENCE: 450

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 451
<211> LENGTH: 32
<212> TYPE: PRT
<213> ORGANISM: Artificial Sequence
<220> FEATURE:
<223> OTHER INFORMATION: Synthetic Construct

<400> SEQUENCE: 451

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 452
<211> LENGTH: 32
<212> TYPE: PRT
<213> ORGANISM: Artificial Sequence
<220> FEATURE:
<223> OTHER INFORMATION: Synthetic Construct

<400> SEQUENCE: 452

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30
```

-continued

<210> SEQ ID NO 453
<211> LENGTH: 32
<212> TYPE: PRT
<213> ORGANISM: Artificial Sequence
<220> FEATURE:
<223> OTHER INFORMATION: Synthetic Construct

<400> SEQUENCE: 453

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 454
<211> LENGTH: 32
<212> TYPE: PRT
<213> ORGANISM: Artificial Sequence
<220> FEATURE:
<223> OTHER INFORMATION: Synthetic Construct

<400> SEQUENCE: 454

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 455
<211> LENGTH: 32
<212> TYPE: PRT
<213> ORGANISM: Artificial Sequence
<220> FEATURE:
<223> OTHER INFORMATION: Synthetic Construct

<400> SEQUENCE: 455

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 456
<211> LENGTH: 32
<212> TYPE: PRT
<213> ORGANISM: Artificial Sequence
<220> FEATURE:
<223> OTHER INFORMATION: Synthetic Construct

<400> SEQUENCE: 456

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 457
<211> LENGTH: 32
<212> TYPE: PRT
<213> ORGANISM: Artificial Sequence
<220> FEATURE:
<223> OTHER INFORMATION: Synthetic Construct

<400> SEQUENCE: 457

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

```
<210> SEQ ID NO 458
<211> LENGTH: 32
<212> TYPE: PRT
<213> ORGANISM: Artificial Sequence
<220> FEATURE:
<223> OTHER INFORMATION: Synthetic Construct

<400> SEQUENCE: 458

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 459
<211> LENGTH: 32
<212> TYPE: PRT
<213> ORGANISM: Artificial Sequence
<220> FEATURE:
<223> OTHER INFORMATION: Synthetic Construct

<400> SEQUENCE: 459

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 460
<211> LENGTH: 32
<212> TYPE: PRT
<213> ORGANISM: Artificial Sequence
<220> FEATURE:
<223> OTHER INFORMATION: Synthetic Construct

<400> SEQUENCE: 460

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 461
<211> LENGTH: 32
<212> TYPE: PRT
<213> ORGANISM: Artificial Sequence
<220> FEATURE:
<223> OTHER INFORMATION: Synthetic Construct

<400> SEQUENCE: 461

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 462
<211> LENGTH: 32
<212> TYPE: PRT
<213> ORGANISM: Artificial Sequence
<220> FEATURE:
<223> OTHER INFORMATION: Synthetic Construct

<400> SEQUENCE: 462

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30
```

<210> SEQ ID NO 463
<211> LENGTH: 32
<212> TYPE: PRT
<213> ORGANISM: Artificial Sequence
<220> FEATURE:
<223> OTHER INFORMATION: Synthetic Construct

<400> SEQUENCE: 463

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 464
<211> LENGTH: 32
<212> TYPE: PRT
<213> ORGANISM: Artificial Sequence
<220> FEATURE:
<223> OTHER INFORMATION: Synthetic Construct

<400> SEQUENCE: 464

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 465
<211> LENGTH: 32
<212> TYPE: PRT
<213> ORGANISM: Artificial Sequence
<220> FEATURE:
<223> OTHER INFORMATION: Synthetic Construct

<400> SEQUENCE: 465

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 466
<211> LENGTH: 32
<212> TYPE: PRT
<213> ORGANISM: Artificial Sequence
<220> FEATURE:
<223> OTHER INFORMATION: Synthetic Construct

<400> SEQUENCE: 466

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 467
<211> LENGTH: 32
<212> TYPE: PRT
<213> ORGANISM: Artificial Sequence
<220> FEATURE:
<223> OTHER INFORMATION: Synthetic Construct

<400> SEQUENCE: 467

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser

-continued

```
                 20                  25                  30

<210> SEQ ID NO 468
<211> LENGTH: 32
<212> TYPE: PRT
<213> ORGANISM: Artificial Sequence
<220> FEATURE:
<223> OTHER INFORMATION: Synthetic Construct

<400> SEQUENCE: 468

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 469
<211> LENGTH: 32
<212> TYPE: PRT
<213> ORGANISM: Artificial Sequence
<220> FEATURE:
<223> OTHER INFORMATION: Synthetic Construct

<400> SEQUENCE: 469

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 470
<211> LENGTH: 32
<212> TYPE: PRT
<213> ORGANISM: Artificial Sequence
<220> FEATURE:
<223> OTHER INFORMATION: Synthetic Construct

<400> SEQUENCE: 470

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 471
<211> LENGTH: 32
<212> TYPE: PRT
<213> ORGANISM: Artificial Sequence
<220> FEATURE:
<223> OTHER INFORMATION: Synthetic Construct

<400> SEQUENCE: 471

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 472
<211> LENGTH: 32
<212> TYPE: PRT
<213> ORGANISM: Artificial Sequence
<220> FEATURE:
<223> OTHER INFORMATION: Synthetic Construct

<400> SEQUENCE: 472

Arg Phe Thr Ile Ser Arg Asp Asn Ser Lys Asn Thr Leu Tyr Leu Gln
1               5                  10                  15
```

Met Asn Ser Leu Arg Ala Glu Asp Thr Ala Val Tyr Tyr Cys Ala Ser
            20                  25                  30

<210> SEQ ID NO 473
<211> LENGTH: 32
<212> TYPE: PRT
<213> ORGANISM: Artificial Sequence
<220> FEATURE:
<223> OTHER INFORMATION: Synthetic Construct

<400> SEQUENCE: 473

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 474
<211> LENGTH: 32
<212> TYPE: PRT
<213> ORGANISM: Artificial Sequence
<220> FEATURE:
<223> OTHER INFORMATION: Synthetic Construct

<400> SEQUENCE: 474

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 475
<211> LENGTH: 32
<212> TYPE: PRT
<213> ORGANISM: Artificial Sequence
<220> FEATURE:
<223> OTHER INFORMATION: Synthetic Construct

<400> SEQUENCE: 475

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 476
<211> LENGTH: 32
<212> TYPE: PRT
<213> ORGANISM: Artificial Sequence
<220> FEATURE:
<223> OTHER INFORMATION: Synthetic Construct

<400> SEQUENCE: 476

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 477
<211> LENGTH: 32
<212> TYPE: PRT
<213> ORGANISM: Artificial Sequence
<220> FEATURE:
<223> OTHER INFORMATION: Synthetic Construct

<400> SEQUENCE: 477

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 478
<211> LENGTH: 32
<212> TYPE: PRT
<213> ORGANISM: Artificial Sequence
<220> FEATURE:
<223> OTHER INFORMATION: Synthetic Construct

<400> SEQUENCE: 478

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 479
<211> LENGTH: 32
<212> TYPE: PRT
<213> ORGANISM: Artificial Sequence
<220> FEATURE:
<223> OTHER INFORMATION: Synthetic Construct

<400> SEQUENCE: 479

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 480
<211> LENGTH: 32
<212> TYPE: PRT
<213> ORGANISM: Artificial Sequence
<220> FEATURE:
<223> OTHER INFORMATION: Synthetic Construct

<400> SEQUENCE: 480

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 481
<211> LENGTH: 32
<212> TYPE: PRT
<213> ORGANISM: Artificial Sequence
<220> FEATURE:
<223> OTHER INFORMATION: Synthetic Construct

<400> SEQUENCE: 481

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 482
<211> LENGTH: 32
<212> TYPE: PRT
<213> ORGANISM: Artificial Sequence
<220> FEATURE:
<223> OTHER INFORMATION: Synthetic Construct

<400> SEQUENCE: 482

Arg Phe Thr Ile Ser Arg Asp Asn Ser Lys Asn Thr Leu Tyr Leu Gln

```
                1               5                  10                  15
Met Asn Ser Leu Arg Ala Glu Asp Thr Ala Val Tyr Tyr Cys Ala Ser
                20                  25                  30

<210> SEQ ID NO 483
<211> LENGTH: 32
<212> TYPE: PRT
<213> ORGANISM: Artificial Sequence
<220> FEATURE:
<223> OTHER INFORMATION: Synthetic Construct

<400> SEQUENCE: 483

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 484
<211> LENGTH: 32
<212> TYPE: PRT
<213> ORGANISM: Artificial Sequence
<220> FEATURE:
<223> OTHER INFORMATION: Synthetic Construct

<400> SEQUENCE: 484

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 485
<211> LENGTH: 32
<212> TYPE: PRT
<213> ORGANISM: Artificial Sequence
<220> FEATURE:
<223> OTHER INFORMATION: Synthetic Construct

<400> SEQUENCE: 485

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 486
<211> LENGTH: 32
<212> TYPE: PRT
<213> ORGANISM: Artificial Sequence
<220> FEATURE:
<223> OTHER INFORMATION: Synthetic Construct

<400> SEQUENCE: 486

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ser
                20                  25                  30

<210> SEQ ID NO 487
<211> LENGTH: 32
<212> TYPE: PRT
<213> ORGANISM: Artificial Sequence
<220> FEATURE:
<223> OTHER INFORMATION: Synthetic Construct

<400> SEQUENCE: 487
```

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 488
<211> LENGTH: 32
<212> TYPE: PRT
<213> ORGANISM: Artificial Sequence
<220> FEATURE:
<223> OTHER INFORMATION: Synthetic Construct

<400> SEQUENCE: 488

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 489
<211> LENGTH: 32
<212> TYPE: PRT
<213> ORGANISM: Artificial Sequence
<220> FEATURE:
<223> OTHER INFORMATION: Synthetic Construct

<400> SEQUENCE: 489

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 490
<211> LENGTH: 11
<212> TYPE: PRT
<213> ORGANISM: Artificial Sequence
<220> FEATURE:
<223> OTHER INFORMATION: Synthetic Construct

<400> SEQUENCE: 490

Trp Gly Gln Gly Thr Leu Val Thr Val Ser Ser
1               5                   10

<210> SEQ ID NO 491
<211> LENGTH: 11
<212> TYPE: PRT
<213> ORGANISM: Artificial Sequence
<220> FEATURE:
<223> OTHER INFORMATION: Synthetic Construct

<400> SEQUENCE: 491

Trp Gly Gln Gly Thr Leu Val Thr Val Ser Ser
1               5                   10

<210> SEQ ID NO 492
<211> LENGTH: 11
<212> TYPE: PRT
<213> ORGANISM: Artificial Sequence
<220> FEATURE:
<223> OTHER INFORMATION: Synthetic Construct

<400> SEQUENCE: 492

Trp Gly Gln Gly Thr Leu Val Thr Val Ser Ser
1               5                   10

<210> SEQ ID NO 493

<211> LENGTH: 11
<212> TYPE: PRT
<213> ORGANISM: Artificial Sequence
<220> FEATURE:
<223> OTHER INFORMATION: Synthetic Construct

<400> SEQUENCE: 493

Trp Gly Gln Gly Thr Leu Val Thr Val Ser Ser
1               5                   10

<210> SEQ ID NO 494
<211> LENGTH: 11
<212> TYPE: PRT
<213> ORGANISM: Artificial Sequence
<220> FEATURE:
<223> OTHER INFORMATION: Synthetic Construct

<400> SEQUENCE: 494

Trp Gly Gln Gly Thr Leu Val Thr Val Ser Ser
1               5                   10

<210> SEQ ID NO 495
<211> LENGTH: 11
<212> TYPE: PRT
<213> ORGANISM: Artificial Sequence
<220> FEATURE:
<223> OTHER INFORMATION: Synthetic Construct

<400> SEQUENCE: 495

Trp Gly Gln Gly Thr Leu Val Thr Val Ser Ser
1               5                   10

<210> SEQ ID NO 496
<211> LENGTH: 11
<212> TYPE: PRT
<213> ORGANISM: Artificial Sequence
<220> FEATURE:
<223> OTHER INFORMATION: Synthetic Construct

<400> SEQUENCE: 496

Trp Gly Gln Gly Thr Leu Val Thr Val Ser Ser
1               5                   10

<210> SEQ ID NO 497
<211> LENGTH: 11
<212> TYPE: PRT
<213> ORGANISM: Artificial Sequence
<220> FEATURE:
<223> OTHER INFORMATION: Synthetic Construct

<400> SEQUENCE: 497

Trp Gly Gln Gly Thr Leu Val Thr Val Ser Ser
1               5                   10

<210> SEQ ID NO 498
<211> LENGTH: 11
<212> TYPE: PRT
<213> ORGANISM: Artificial Sequence
<220> FEATURE:
<223> OTHER INFORMATION: Synthetic Construct

<400> SEQUENCE: 498

Trp Gly Gln Gly Thr Leu Val Thr Val Ser Ser
1               5                   10

<210> SEQ ID NO 499
<211> LENGTH: 11

```
<212> TYPE: PRT
<213> ORGANISM: Artificial Sequence
<220> FEATURE:
<223> OTHER INFORMATION: Synthetic Construct

<400> SEQUENCE: 499

Trp Gly Gln Gly Thr Leu Val Thr Val Ser Ser
1               5                   10

<210> SEQ ID NO 500
<211> LENGTH: 11
<212> TYPE: PRT
<213> ORGANISM: Artificial Sequence
<220> FEATURE:
<223> OTHER INFORMATION: Synthetic Construct

<400> SEQUENCE: 500

Trp Gly Gln Gly Thr Leu Val Thr Val Ser Ser
1               5                   10

<210> SEQ ID NO 501
<211> LENGTH: 11
<212> TYPE: PRT
<213> ORGANISM: Artificial Sequence
<220> FEATURE:
<223> OTHER INFORMATION: Synthetic Construct

<400> SEQUENCE: 501

Trp Gly Gln Gly Thr Leu Val Thr Val Ser Ser
1               5                   10

<210> SEQ ID NO 502
<211> LENGTH: 11
<212> TYPE: PRT
<213> ORGANISM: Artificial Sequence
<220> FEATURE:
<223> OTHER INFORMATION: Synthetic Construct

<400> SEQUENCE: 502

Trp Gly Gln Gly Thr Leu Val Thr Val Ser Ser
1               5                   10

<210> SEQ ID NO 503
<211> LENGTH: 11
<212> TYPE: PRT
<213> ORGANISM: Artificial Sequence
<220> FEATURE:
<223> OTHER INFORMATION: Synthetic Construct

<400> SEQUENCE: 503

Trp Gly Gln Gly Thr Leu Val Thr Val Ser Ser
1               5                   10

<210> SEQ ID NO 504
<211> LENGTH: 11
<212> TYPE: PRT
<213> ORGANISM: Artificial Sequence
<220> FEATURE:
<223> OTHER INFORMATION: Synthetic Construct

<400> SEQUENCE: 504

Trp Gly Gln Gly Thr Leu Val Thr Val Ser Ser
1               5                   10

<210> SEQ ID NO 505
<211> LENGTH: 11
<212> TYPE: PRT
```

-continued

<213> ORGANISM: Artificial Sequence
<220> FEATURE:
<223> OTHER INFORMATION: Synthetic Construct

<400> SEQUENCE: 505

Trp Gly Gln Gly Thr Leu Val Thr Val Ser Ser
1               5                   10

<210> SEQ ID NO 506
<211> LENGTH: 11
<212> TYPE: PRT
<213> ORGANISM: Artificial Sequence
<220> FEATURE:
<223> OTHER INFORMATION: Synthetic Construct

<400> SEQUENCE: 506

Trp Gly Gln Gly Thr Leu Val Thr Val Ser Ser
1               5                   10

<210> SEQ ID NO 507
<211> LENGTH: 11
<212> TYPE: PRT
<213> ORGANISM: Artificial Sequence
<220> FEATURE:
<223> OTHER INFORMATION: Synthetic Construct

<400> SEQUENCE: 507

Trp Gly Gln Gly Thr Leu Val Thr Val Ser Ser
1               5                   10

<210> SEQ ID NO 508
<211> LENGTH: 11
<212> TYPE: PRT
<213> ORGANISM: Artificial Sequence
<220> FEATURE:
<223> OTHER INFORMATION: Synthetic Construct

<400> SEQUENCE: 508

Trp Gly Gln Gly Thr Leu Val Thr Val Ser Ser
1               5                   10

<210> SEQ ID NO 509
<211> LENGTH: 11
<212> TYPE: PRT
<213> ORGANISM: Artificial Sequence
<220> FEATURE:
<223> OTHER INFORMATION: Synthetic Construct

<400> SEQUENCE: 509

Trp Gly Gln Gly Thr Leu Val Thr Val Ser Ser
1               5                   10

<210> SEQ ID NO 510
<211> LENGTH: 11
<212> TYPE: PRT
<213> ORGANISM: Artificial Sequence
<220> FEATURE:
<223> OTHER INFORMATION: Synthetic Construct

<400> SEQUENCE: 510

Trp Gly Gln Gly Thr Leu Val Thr Val Ser Ser
1               5                   10

<210> SEQ ID NO 511
<211> LENGTH: 11
<212> TYPE: PRT
<213> ORGANISM: Artificial Sequence
<220> FEATURE:
<223> OTHER INFORMATION: Synthetic Construct

<400> SEQUENCE: 511

Trp Gly Gln Gly Thr Leu Val Thr Val Ser Ser
1               5                   10

<210> SEQ ID NO 512
<211> LENGTH: 11
<212> TYPE: PRT
<213> ORGANISM: Artificial Sequence
<220> FEATURE:
<223> OTHER INFORMATION: Synthetic Construct

<400> SEQUENCE: 512

Trp Gly Gln Gly Thr Leu Val Thr Val Ser Ser
1               5                   10

<210> SEQ ID NO 513
<211> LENGTH: 11
<212> TYPE: PRT
<213> ORGANISM: Artificial Sequence
<220> FEATURE:
<223> OTHER INFORMATION: Synthetic Construct

<400> SEQUENCE: 513

Trp Gly Gln Gly Thr Leu Val Thr Val Ser Ser
1               5                   10

<210> SEQ ID NO 514
<211> LENGTH: 11
<212> TYPE: PRT
<213> ORGANISM: Artificial Sequence
<220> FEATURE:
<223> OTHER INFORMATION: Synthetic Construct

<400> SEQUENCE: 514

Trp Gly Gln Gly Thr Leu Val Thr Val Ser Ser
1               5                   10

<210> SEQ ID NO 515
<211> LENGTH: 11
<212> TYPE: PRT
<213> ORGANISM: Artificial Sequence
<220> FEATURE:
<223> OTHER INFORMATION: Synthetic Construct

<400> SEQUENCE: 515

Trp Gly Gln Gly Thr Leu Val Thr Val Ser Ser
1               5                   10

<210> SEQ ID NO 516
<211> LENGTH: 11
<212> TYPE: PRT
<213> ORGANISM: Artificial Sequence
<220> FEATURE:
<223> OTHER INFORMATION: Synthetic Construct

<400> SEQUENCE: 516

Trp Gly Gln Gly Thr Leu Val Thr Val Ser Ser
1               5                   10

<210> SEQ ID NO 517
<211> LENGTH: 11
<212> TYPE: PRT
<213> ORGANISM: Artificial Sequence
<220> FEATURE:

<223> OTHER INFORMATION: Synthetic Construct

<400> SEQUENCE: 517

Trp Gly Gln Gly Thr Leu Val Thr Val Ser Ser
1               5                   10

<210> SEQ ID NO 518
<211> LENGTH: 11
<212> TYPE: PRT
<213> ORGANISM: Artificial Sequence
<220> FEATURE:
<223> OTHER INFORMATION: Synthetic Construct

<400> SEQUENCE: 518

Trp Gly Gln Gly Thr Leu Val Thr Val Ser Ser
1               5                   10

<210> SEQ ID NO 519
<211> LENGTH: 11
<212> TYPE: PRT
<213> ORGANISM: Artificial Sequence
<220> FEATURE:
<223> OTHER INFORMATION: Synthetic Construct

<400> SEQUENCE: 519

Trp Gly Gln Gly Thr Leu Val Thr Val Ser Ser
1               5                   10

<210> SEQ ID NO 520
<211> LENGTH: 11
<212> TYPE: PRT
<213> ORGANISM: Artificial Sequence
<220> FEATURE:
<223> OTHER INFORMATION: Synthetic Construct

<400> SEQUENCE: 520

Trp Gly Gln Gly Thr Leu Val Thr Val Ser Ser
1               5                   10

<210> SEQ ID NO 521
<211> LENGTH: 11
<212> TYPE: PRT
<213> ORGANISM: Artificial Sequence
<220> FEATURE:
<223> OTHER INFORMATION: Synthetic Construct

<400> SEQUENCE: 521

Trp Gly Gln Gly Thr Leu Val Thr Val Ser Ser
1               5                   10

<210> SEQ ID NO 522
<211> LENGTH: 11
<212> TYPE: PRT
<213> ORGANISM: Artificial Sequence
<220> FEATURE:
<223> OTHER INFORMATION: Synthetic Construct

<400> SEQUENCE: 522

Trp Gly Gln Gly Thr Leu Val Thr Val Ser Ser
1               5                   10

<210> SEQ ID NO 523
<211> LENGTH: 11
<212> TYPE: PRT
<213> ORGANISM: Artificial Sequence
<220> FEATURE:
<223> OTHER INFORMATION: Synthetic Construct

<400> SEQUENCE: 523

Trp Gly Gln Gly Thr Leu Val Thr Val Ser Ser
1               5                   10

<210> SEQ ID NO 524
<211> LENGTH: 11
<212> TYPE: PRT
<213> ORGANISM: Artificial Sequence
<220> FEATURE:
<223> OTHER INFORMATION: Synthetic Construct

<400> SEQUENCE: 524

Trp Gly Gln Gly Thr Leu Val Thr Val Ser Ser
1               5                   10

<210> SEQ ID NO 525
<211> LENGTH: 11
<212> TYPE: PRT
<213> ORGANISM: Artificial Sequence
<220> FEATURE:
<223> OTHER INFORMATION: Synthetic Construct

<400> SEQUENCE: 525

Trp Gly Gln Gly Thr Leu Val Thr Val Ser Ser
1               5                   10

<210> SEQ ID NO 526
<211> LENGTH: 11
<212> TYPE: PRT
<213> ORGANISM: Artificial Sequence
<220> FEATURE:
<223> OTHER INFORMATION: Synthetic Construct

<400> SEQUENCE: 526

Trp Gly Gln Gly Thr Leu Val Thr Val Ser Ser
1               5                   10

<210> SEQ ID NO 527
<211> LENGTH: 11
<212> TYPE: PRT
<213> ORGANISM: Artificial Sequence
<220> FEATURE:
<223> OTHER INFORMATION: Synthetic Construct

<400> SEQUENCE: 527

Trp Gly Gln Gly Thr Leu Val Thr Val Ser Ser
1               5                   10

<210> SEQ ID NO 528
<211> LENGTH: 11
<212> TYPE: PRT
<213> ORGANISM: Artificial Sequence
<220> FEATURE:
<223> OTHER INFORMATION: Synthetic Construct

<400> SEQUENCE: 528

Trp Gly Gln Gly Thr Leu Val Thr Val Ser Ser
1               5                   10

<210> SEQ ID NO 529
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 529

Trp Gly Gln Gly Thr Leu Val Thr Val Ser Ser
1               5                   10

<210> SEQ ID NO 530
<211> LENGTH: 11
<212> TYPE: PRT
<213> ORGANISM: Artificial Sequence
<220> FEATURE:
<223> OTHER INFORMATION: Synthetic Construct

<400> SEQUENCE: 530

Trp Gly Gln Gly Thr Leu Val Thr Val Ser Ser
1               5                   10

<210> SEQ ID NO 531
<211> LENGTH: 11
<212> TYPE: PRT
<213> ORGANISM: Artificial Sequence
<220> FEATURE:
<223> OTHER INFORMATION: Synthetic Construct

<400> SEQUENCE: 531

Trp Gly Gln Gly Thr Leu Val Thr Val Ser Ser
1               5                   10

<210> SEQ ID NO 532
<211> LENGTH: 116
<212> TYPE: PRT
<213> ORGANISM: Artificial Sequence
<220> FEATURE:
<223> OTHER INFORMATION: Synthetic Construct

<400> SEQUENCE: 532

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Gln Trp Ser Arg Gln Gln Trp Gly Gln Gly Thr Leu Val
            100                 105                 110

Thr Val Ser Ser
        115

<210> SEQ ID NO 533
<211> LENGTH: 116
<212> TYPE: PRT
<213> ORGANISM: Artificial Sequence
<220> FEATURE:
<223> OTHER INFORMATION: Synthetic Construct

<400> SEQUENCE: 533

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Lys Phe Arg Asn Leu Lys Trp Gly Gln Gly Thr Leu Val
            100                 105                 110

Thr Val Ser Ser
        115

<210> SEQ ID NO 534
<211> LENGTH: 116
<212> TYPE: PRT
<213> ORGANISM: Artificial Sequence
<220> FEATURE:
<223> OTHER INFORMATION: Synthetic Construct

<400> SEQUENCE: 534

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Gln Phe Thr Thr Thr Gln Trp Gly Gln Gly Thr Leu Val
            100                 105                 110

Thr Val Ser Ser
        115

<210> SEQ ID NO 535
<211> LENGTH: 116
<212> TYPE: PRT
<213> ORGANISM: Artificial Sequence
<220> FEATURE:
<223> OTHER INFORMATION: Synthetic Construct

<400> SEQUENCE: 535

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
            35                  40                  45

Ser Leu Ile Ser Gly Ser Gly Gly Ser Thr Trp Tyr Asp Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Ser His Pro Pro Arg Val Asp Thr Trp Gly Gln Gly Thr Leu Val
            100                 105                 110

Thr Val Ser Ser
        115

<210> SEQ ID NO 536
<211> LENGTH: 116
<212> TYPE: PRT
<213> ORGANISM: Artificial Sequence
<220> FEATURE:
<223> OTHER INFORMATION: Synthetic Construct

<400> SEQUENCE: 536

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Tyr Asn Tyr
            20                  25                  30

Pro Met Gly Trp Val Arg Gln Ala Pro Gly Lys Gly Pro Glu Val Val
        35                  40                  45

Ser Leu Ile Ser Gly Ser Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asn Thr Ala Val Tyr Tyr Cys
                85                  90                  95

Ala Ser His Pro Val Ser Leu Leu Phe Trp Gly Gln Gly Thr Leu Val
            100                 105                 110

Thr Val Ser Ser
        115

<210> SEQ ID NO 537
<211> LENGTH: 116
<212> TYPE: PRT
<213> ORGANISM: Artificial Sequence
<220> FEATURE:
<223> OTHER INFORMATION: Synthetic Construct

<400> SEQUENCE: 537

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Leu
            20                  25                  30

Met Met Gly Trp Val Arg Gln Ala Pro Gly Lys Gly Pro Glu Val Val
        35                  40                  45

Ser Leu Ile Ser Gly Ser Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Arg His Pro Pro Gly Leu Met Trp Gly Gln Gly Thr Leu Val
            100                 105                 110

Thr Val Ser Ser
        115

<210> SEQ ID NO 538
```

```
<211> LENGTH: 118
<212> TYPE: PRT
<213> ORGANISM: Artificial Sequence
<220> FEATURE:
<223> OTHER INFORMATION: Synthetic Construct

<400> SEQUENCE: 538

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser His
            20                  25                  30

Trp Met Tyr Trp Val Arg Gln Ala Pro Gly Lys Gly Leu Val Trp Val
        35                  40                  45

Ser Thr Ile Asn Asn Asp Gly Thr Gly Thr Thr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Arg Asp Glu Asp Thr Ser Val Tyr Tyr Cys
                85                  90                  95

Ala Arg Gly Gly Phe Asn His Ala Asn Asp Cys Trp Gly Gln Gly Ala
            100                 105                 110

Leu Val Thr Val Ser Ser
        115

<210> SEQ ID NO 539
<211> LENGTH: 119
<212> TYPE: PRT
<213> ORGANISM: Artificial Sequence
<220> FEATURE:
<223> OTHER INFORMATION: Synthetic Construct

<400> SEQUENCE: 539

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 540
<211> LENGTH: 124
<212> TYPE: PRT
<213> ORGANISM: Artificial Sequence
<220> FEATURE:
<223> OTHER INFORMATION: Synthetic Construct

<400> SEQUENCE: 540

Gln Val Gln Leu Val Glu Ser Gly Gly Asn Val Val Gln Pro Gly Thr
1               5                   10                  15
```

```
Ser Leu Arg Leu Ser Cys Ala Ala Ser Gly Phe Thr Phe Ser Asp His
            20                  25                  30

Ala Met His Trp Val Arg Gln Ala Pro Gly Lys Gly Leu Glu Trp Val
        35                  40                  45

Ala Leu Ile Ser Ile Asp Ala Ser Asn His Tyr Tyr Ala Asp Ser Val
    50                  55                  60

Lys Gly Arg Phe Thr Ile Ser Arg Asp Asn Ser Arg Asn Thr Val Phe
65                  70                  75                  80

Leu Gln Met Thr Ser Leu Arg Ala Glu Asp Thr Ala Val Tyr Tyr Cys
                85                  90                  95

Gly Arg Asp Arg Leu Gly Val Thr Arg Gly Pro Ser Asn Trp Phe Asp
            100                 105                 110

Ser Trp Gly Gln Gly Ile Leu Val Thr Val Ser Ser
        115                 120

<210> SEQ ID NO 541
<211> LENGTH: 122
<212> TYPE: PRT
<213> ORGANISM: Artificial Sequence
<220> FEATURE:
<223> OTHER INFORMATION: Synthetic Construct

<400> SEQUENCE: 541

Gln Val Gln Leu Val Gln Ser Gly Ala Glu Val Lys Lys Pro Gly Ala
1               5                   10                  15

Ser Val Lys Ile Ser Cys Glu Ala Ser Gly Tyr Ala Phe Thr Thr Tyr
            20                  25                  30

Phe Leu His Trp Val Arg Gln Ala Pro Gly Gln Gly Leu Glu Trp Met
        35                  40                  45

Gly Ile Ile Asn Pro Ser Ala Gly Ser Thr Thr Tyr Ala His Lys Phe
    50                  55                  60

Gln Gly Arg Val Thr Leu Thr Arg Asp Thr Ser Thr Arg Thr Val Tyr
65                  70                  75                  80

Met Glu Leu Lys Asn Leu Arg Ser Ala Asp Thr Gly Val Tyr Tyr Cys
                85                  90                  95

Ala Arg Ala Ala Ala Ser Phe Thr Ser Gly Phe Asn Val Asp His Trp
            100                 105                 110

Gly Gln Gly Thr Leu Val Thr Val Ser Ser
        115                 120

<210> SEQ ID NO 542
<211> LENGTH: 128
<212> TYPE: PRT
<213> ORGANISM: Artificial Sequence
<220> FEATURE:
<223> OTHER INFORMATION: Synthetic Construct

<400> SEQUENCE: 542

Glu Val Gln Leu Leu Glu Ser Gly Gly Gly Val Val Gln Pro Gly Lys
1               5                   10                  15

Ser Leu Arg Leu Ser Cys Val Gly Ser Gly Phe Ser Phe Ala Thr Tyr
            20                  25                  30

Pro Met His Trp Val Arg Gln Ala Pro Gly Lys Gly Leu Glu Trp Leu
        35                  40                  45

Ala Ala Leu Pro Ala Asp Gly Ser Asn Ala His Tyr Ser Asp Ser Val
    50                  55                  60

Arg Gly Arg Phe Thr Ile Ser Arg Asp Asn Ser Lys Thr Met Val Asn
65                  70                  75                  80
```

```
Leu Gln Met Asn Ser Leu Arg Pro Asp Asp Thr Ala Val Tyr Phe Cys
                85                  90                  95

Ala Arg Asp Arg Ile Gln Val Asn Gly Ala Tyr Tyr Gln Val Gly
            100                 105                 110

Tyr Tyr Phe Asp Phe Trp Gly Gln Gly Thr Leu Val Thr Val Ser Ser
        115                 120                 125
```

<210> SEQ ID NO 543
<211> LENGTH: 121
<212> TYPE: PRT
<213> ORGANISM: Artificial Sequence
<220> FEATURE:
<223> OTHER INFORMATION: Synthetic Construct

<400> SEQUENCE: 543

```
Gln Val Gln Leu Val Glu Ser Gly Gly Val Val Gln Pro Gly Arg
1               5                   10                  15

Ser Leu Arg Leu Ser Cys Val Ala Ser Gly Phe Asn Phe Arg Asp Tyr
            20                  25                  30

Gly Met His Trp Leu Arg Gln Ala Pro Gly Lys Gly Leu Glu Trp Val
        35                  40                  45

Ala Gly Met Ala Tyr Asp Glu Ile Thr Lys Trp Tyr Ala Asp Ser Val
    50                  55                  60

Asn Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Lys Asp Pro Ser Ile Arg Lys Asn Ser Gly Ala Val Tyr Cys Gly
            100                 105                 110

Gln Gly Thr Leu Val Thr Val Ser Ser
        115                 120
```

<210> SEQ ID NO 544
<211> LENGTH: 118
<212> TYPE: PRT
<213> ORGANISM: Artificial Sequence
<220> FEATURE:
<223> OTHER INFORMATION: Synthetic Construct

<400> SEQUENCE: 544

```
Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ile Asn Ala
            20                  25                  30

Trp Met Ser Trp Val Arg Gln Ala Pro Gly Lys Gly Leu Glu Trp Val
        35                  40                  45

Gly Arg Ile Gln Ser Lys Ser Asp Gly Gly Thr Asp Tyr Ala Ala
    50                  55                  60

Pro Val Lys Asp Arg Phe Thr Ile Ser Arg Asp Ser Lys Asn Met
65                  70                  75                  80

Val Tyr Leu Gln Met Asn Ser Leu Lys Thr Glu Asp Thr Ala Val Tyr
                85                  90                  95

Tyr Cys Thr Thr Gly Thr Tyr Gly Ser Val Ser Tyr Gly Gln Gly Thr
            100                 105                 110

Leu Val Thr Val Ser Ser
        115
```

-continued

```
<210> SEQ ID NO 545
<211> LENGTH: 117
<212> TYPE: PRT
<213> ORGANISM: Artificial Sequence
<220> FEATURE:
<223> OTHER INFORMATION: Synthetic Construct

<400> SEQUENCE: 545

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Tyr Phe
            20                  25                  30

Trp Met His Trp Val Arg Gln Gly Pro Gly Glu Gly Leu Val Trp Leu
        35                  40                  45

Ser Gln Ile Ser Gly Asp Gly Thr Thr Thr Tyr Ala Asp Ser Val
    50                  55                  60

Glu Gly Arg Phe Thr Ile Ser Arg Asp Asn Ala Lys Asn Thr Val Tyr
65                  70                  75                  80

Leu Glu Met Asn Ser Val Arg Val Asp Asp Thr Ala Val Tyr Tyr Cys
                85                  90                  95

Val Ser Asp Leu Leu Ser Gly Thr Asn Tyr Trp Gly Gln Gly Ala Leu
            100                 105                 110

Val Thr Val Ser Ser
        115

<210> SEQ ID NO 546
<211> LENGTH: 123
<212> TYPE: PRT
<213> ORGANISM: Artificial Sequence
<220> FEATURE:
<223> OTHER INFORMATION: Synthetic Construct

<400> SEQUENCE: 546

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Pro Phe Ser Ser Tyr
            20                  25                  30

Ala Met Asn Trp Val Arg Gln Ala Pro Gly Lys Gly Leu Glu Trp Val
        35                  40                  45

Ser Gly Ile Asn Phe Arg Gly Gly Leu Thr Tyr Tyr Ala Asp Ser Val
    50                  55                  60

Lys Gly Arg Phe Thr Ile Ser Arg Asp Asp Ser Thr Asn Thr Leu Tyr
65                  70                  75                  80

Leu Gln Val Asn Ser Leu Arg Ala Glu Asp Thr Ala Val Tyr Tyr Cys
                85                  90                  95

Ala Lys Asp Gly Ser Gly Thr His Tyr Leu Asn Trp Tyr Phe Asp Val
            100                 105                 110

Trp Gly Arg Gly Thr Leu Val Thr Val Ser Ser
        115                 120

<210> SEQ ID NO 547
<211> LENGTH: 131
<212> TYPE: PRT
<213> ORGANISM: Artificial Sequence
<220> FEATURE:
<223> OTHER INFORMATION: Synthetic Construct

<400> SEQUENCE: 547

Glu Val Gln Leu Leu Glu Ser Gly Gly Gly Leu Val Lys Pro Gly Gly
1               5                   10                  15
```

```
Ser Leu Arg Leu Ser Cys Val Gly Ser Glu Arg Ser Phe Pro Ser Tyr
            20                  25                  30

Gly Met Ser Trp Val Arg Gln Ala Pro Gly Lys Gly Leu Glu Trp Val
            35                  40                  45

Ala Ser Ile Ser Ser Ser Ser Val Tyr Ile Tyr Ala Asp Ser Val
 50                      55                  60

Lys Gly Arg Phe Thr Val Ser Arg Asp Asn Val Gln Lys Ser Leu Asp
 65                  70                  75                  80

Leu Gln Met Asp Ser Leu Arg Ala Glu Asp Thr Ala Val Tyr Phe Cys
                85                  90                  95

Ala Arg Asp Arg Val Pro Ser Tyr Thr Ser Gly Tyr Phe Phe Gln Lys
            100                 105                 110

Tyr Tyr Tyr Tyr Pro Met Asp Val Trp Gly Gln Gly Thr Thr Val Thr
            115                 120                 125

Val Ser Ser
    130

<210> SEQ ID NO 548
<211> LENGTH: 123
<212> TYPE: PRT
<213> ORGANISM: Artificial Sequence
<220> FEATURE:
<223> OTHER INFORMATION: Synthetic Construct

<400> SEQUENCE: 548

Glu Val Gln Leu Leu Glu Ser Gly Gly Gly Leu Ala Gln Ser Gly Gly
 1               5                  10                  15

Ser Leu Arg Leu Ser Cys Ala Ala Ser Gly Phe Thr Phe Asp Ser Tyr
            20                  25                  30

Ser Met Ser Trp Val Arg Gln Ala Pro Gly Lys Gly Leu Glu Trp Ile
            35                  40                  45

Ser Tyr Ile Ser Ser Ser Gly Thr Thr Ile Tyr Ala Asp Ser Val
            50                  55                  60

Arg Gly Arg Phe Thr Ile Ser Arg Asp Ile Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Arg Pro Phe Pro Leu Ala Ala Ala Tyr Tyr Phe Asp Tyr
            100                 105                 110

Trp Gly Gln Gly Ala Leu Val Thr Val Ser Ser
            115                 120

<210> SEQ ID NO 549
<211> LENGTH: 120
<212> TYPE: PRT
<213> ORGANISM: Artificial Sequence
<220> FEATURE:
<223> OTHER INFORMATION: Synthetic Construct

<400> SEQUENCE: 549

Glu Val Gln Leu Val Gln Ser Gly Ala Glu Val Lys Lys Pro Gly Glu
 1               5                  10                  15

Ser Leu Arg Ile Ser Cys Arg Gly Ser Gly Tyr Arg Phe Asn Ala Tyr
            20                  25                  30

Trp Ile Gly Trp Ala Arg Asp Lys Pro Gly Lys Gly Leu Glu Trp Ile
            35                  40                  45

Gly Thr Ile Tyr Pro Gly Asp Ser Asp Gly Thr Tyr Ser Pro Ser Phe
```

```
                    50                  55                  60
Gln Gly His Val Thr Ile Ser Ala Asp Arg Ser Val Ser Val Ala Tyr
 65                  70                  75                  80

Leu Gln Trp Asp Ser Leu Lys Ala Ser Asp Asn Gly Ile Tyr Tyr Cys
                     85                  90                  95

Ala Leu Phe Arg Gly Gly Ser His Pro Pro Phe Gly Pro Trp Gly Gln
                100                 105                 110

Gly Thr Leu Val Thr Val Ser Ser
            115                 120

<210> SEQ ID NO 550
<211> LENGTH: 121
<212> TYPE: PRT
<213> ORGANISM: Artificial Sequence
<220> FEATURE:
<223> OTHER INFORMATION: Synthetic Construct

<400> SEQUENCE: 550

Glu Val Gln Leu Val Glu Ser Gly Gly Gly Leu Val Gln Pro Gly Gly
 1               5                  10                  15

Ser Leu Arg Leu Ser Cys Val Pro Ser Gly Phe Thr Phe Ser Asn His
                 20                  25                  30

Trp Met His Trp Val Arg Gln Ala Pro Gly Lys Gly Leu Val Trp Val
             35                  40                  45

Ser Arg Ile Arg Gly Asp Glu Asn Glu Ile Asn Tyr Ala Glu Ser Val
         50                  55                  60

Lys Gly Arg Phe Thr Ile Ser Arg Asp Asn Ala Glu Asp Thr Leu Phe
 65                  70                  75                  80

Leu Gln Met Asn Ser Leu Arg Val Asp Thr Ala Val Tyr Tyr Cys
                     85                  90                  95

Val Arg Gly His Val Val Gly Ser Ile Lys His Phe Asp Tyr Trp Gly
                100                 105                 110

Gln Gly Val Leu Val Thr Val Ser Ser
            115                 120

<210> SEQ ID NO 551
<211> LENGTH: 125
<212> TYPE: PRT
<213> ORGANISM: Artificial Sequence
<220> FEATURE:
<223> OTHER INFORMATION: Synthetic Construct

<400> SEQUENCE: 551

Gln Val Gln Leu Val Glu Ser Gly Gly Gly Leu Val Gln Pro Gly Gly
 1               5                  10                  15

Ser Leu Arg Leu Ser Cys Ile Ala Ser Gly Phe Ser Leu Gly Ser Tyr
                 20                  25                  30

Trp Met Thr Trp Val Arg Arg Ser Pro Gly Lys Gly Leu Glu Trp Val
             35                  40                  45

Ala Asn Ile Asn Arg Asp Gly Ser Val Val His Tyr Val Asp Ser Val
         50                  55                  60

Glu Gly Arg Phe Thr Val Ser Arg Asp Asn Ala Lys Asn Ser Leu Phe
 65                  70                  75                  80

Leu Gln Met Asn Asn Val Arg Pro Glu Asp Thr Ala Leu Tyr Phe Cys
                     85                  90                  95

Ala Arg Asp Asp Thr Arg Gly Thr Arg Gly Ser Tyr Phe Asp Ala Leu
                100                 105                 110
```

Asp Met Trp Gly Gln Gly Thr Met Val Thr Val Ser Ser
            115                 120                 125

<210> SEQ ID NO 552
<211> LENGTH: 119
<212> TYPE: PRT
<213> ORGANISM: Artificial Sequence
<220> FEATURE:
<223> OTHER INFORMATION: Synthetic Construct

<400> SEQUENCE: 552

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Asn Arg Val Lys Asp Phe His Asp Tyr Trp Gly Gln Gly
            100                 105                 110

Thr Leu Val Thr Val Ser Ser
            115

<210> SEQ ID NO 553
<211> LENGTH: 124
<212> TYPE: PRT
<213> ORGANISM: Artificial Sequence
<220> FEATURE:
<223> OTHER INFORMATION: Synthetic Construct

<400> SEQUENCE: 553

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Asn Trp Val Arg Gln Ala Pro Gly Lys Gly Leu Glu Trp Leu
        35                  40                  45

Ser Tyr Ile Ser Ser Ser Ala Gly Thr Ile Tyr Tyr Ala Asp Ser Val
    50                  55                  60

Lys Gly Arg Phe Thr Ile Ser Arg Asn Asn Ala Lys Asn Ser Leu Tyr
65                  70                  75                  80

Leu Gln Met Asn Ser Leu Arg Val Asp Asp Thr Ala Val Tyr Tyr Cys
                85                  90                  95

Ala Arg Asp Trp Arg Gly Arg Val Asp Ile Ala Thr Thr Pro Asp
            100                 105                 110

Phe Trp Gly Gln Gly Thr Leu Val Thr Val Ser Ser
        115                 120

<210> SEQ ID NO 554
<211> LENGTH: 120
<212> TYPE: PRT
<213> ORGANISM: Artificial Sequence
<220> FEATURE:
<223> OTHER INFORMATION: Synthetic Construct

<400> SEQUENCE: 554

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Ser Trp Val Arg Gln Gly Pro Gly Lys Gly Leu Glu Trp Val
        35                  40                  45

Ala Asn Ile Asn Gln Asp Gly Ser Ser Lys Tyr Tyr Val Asp Ser Val
    50                  55                  60

Lys Gly Arg Phe Thr Ile Ser Arg Asp Asn Ala Glu Asn Ser Leu Tyr
65                  70                  75                  80

Leu Gln Val Asn Ser Leu Arg Ala Glu Asp Thr Ala Ile Tyr Tyr Cys
                85                  90                  95

Ala Lys Asp Ala Gly Asp Tyr Gly Gly Asn Phe Asp Tyr Trp Gly Gln
            100                 105                 110

Gly Ala Leu Val Thr Val Ser Ser
        115                 120

<210> SEQ ID NO 555
<211> LENGTH: 120
<212> TYPE: PRT
<213> ORGANISM: Artificial Sequence
<220> FEATURE:
<223> OTHER INFORMATION: Synthetic Construct

<400> SEQUENCE: 555

Glu Val Gln Leu Leu Glu Ser Gly Gly Gly Val Val Gln Pro Gly Arg
1               5                   10                  15

Ser Leu Arg Leu Ser Cys Glu Val Phe Gly Phe Thr Leu Ser Thr Asn
            20                  25                  30

Gly Met His Trp Val Arg Gln Ala Pro Gly Arg Arg Leu Glu Trp Val
        35                  40                  45

Ala Gly Val Leu Ser Ser Gly Asn Asn Glu Phe Tyr Ala Asp Ser Val
    50                  55                  60

Lys Gly Arg Phe Thr Ile Ser Arg Asp Ile Ala Thr Asn Arg Leu Tyr
65                  70                  75                  80

Leu Gln Met Arg Ser Leu Arg Ala Glu Asp Thr Ala Leu Tyr Tyr Cys
                85                  90                  95

Ala Arg Glu Val Leu Glu Arg Arg Gly Tyr Phe Asp Tyr Trp Gly Gln
            100                 105                 110

Gly Thr Leu Val Thr Val Ser Ser
        115                 120

<210> SEQ ID NO 556
<211> LENGTH: 126
<212> TYPE: PRT
<213> ORGANISM: Artificial Sequence
<220> FEATURE:
<223> OTHER INFORMATION: Synthetic Construct

<400> SEQUENCE: 556

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

```
Ser Ser Val Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Val Pro Tyr Gly Gly Ser Gly Ser His Tyr Phe Tyr Phe His Gly
            100                 105                 110

Met Asp Val Trp Gly Gln Gly Thr Thr Val Thr Val Ser Ser
            115                 120                 125
```

<210> SEQ ID NO 557
<211> LENGTH: 121
<212> TYPE: PRT
<213> ORGANISM: Artificial Sequence
<220> FEATURE:
<223> OTHER INFORMATION: Synthetic Construct

<400> SEQUENCE: 557

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Ser Tyr
                 20                  25                  30

Val Met Ser Trp Val Arg Gln Ala Pro Gly Lys Gly Leu Glu Trp Val
             35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Asn Thr Leu Tyr
 65                  70                  75                  80

Leu Gln Met Asn Ser Leu Arg Ala Asp Asp Thr Ala Val Tyr Phe Cys
                 85                  90                  95

Ala Lys Asp Tyr Ser Asp Leu Glu Pro Gln Val Gly Cys Tyr Trp Gly
            100                 105                 110

Gln Gly Thr Leu Val Thr Val Ser Ser
            115                 120
```

<210> SEQ ID NO 558
<211> LENGTH: 120
<212> TYPE: PRT
<213> ORGANISM: Artificial Sequence
<220> FEATURE:
<223> OTHER INFORMATION: Synthetic Construct

<400> SEQUENCE: 558

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Val Pro Gly Lys Gly Leu Glu Trp Val
             35                  40                  45

Ala Asn Ile Asn Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Asn Trp Val Val Ala Gly Arg Asn Tyr Phe Asp Cys Trp Gly Gln
            100                 105                 110
```

Gly Thr Leu Val Thr Val Ser Ser
        115                 120

<210> SEQ ID NO 559
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid

<400> SEQUENCE: 559

Gln Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Ser Asn Tyr
            20                  25                  30

Trp Met His Trp Val Arg Gln Ala Pro Gly Thr Gly Leu Leu Trp Leu
        35                  40                  45

Ser Arg Ile Ser Ser Asp Gly Ser Thr Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Xaa Asn Ser Val Arg Ala Phe Asp Ile Trp Gly Xaa Gly
            100                 105                 110

Thr Met Val Thr Val Ser Xaa
        115

<210> SEQ ID NO 560
<211> LENGTH: 124
<212> TYPE: PRT
<213> ORGANISM: Artificial Sequence
<220> FEATURE:
<223> OTHER INFORMATION: Synthetic Construct

<400> SEQUENCE: 560

Glu Val Gln Leu Leu Glu Ser Gly Gly Met Leu Val Lys Pro Gly Glu
1               5                   10                  15

Ser Leu Arg Leu Ser Cys Val Gly Ser Gly Leu Ile Phe Ser Asn Ala
            20                  25                  30

Trp Met Asn Trp Val Arg His Ala Pro Gly Lys Gly Leu Glu Trp Val
        35                  40                  45

Gly Arg Ile Lys Ala Leu Ser Asp Ser Gly Thr Ala Glu Tyr Asn Glu
    50                  55                  60

Ala Leu Lys Asp Arg Leu Ser Ile Ser Arg Asp Asp Ser Met Asn Thr
65                  70                  75                  80

Val Tyr Leu Asp Ile Tyr Asn Leu Lys Ile Asp Asp Thr Gly Val Tyr
                85                  90                  95

Tyr Cys Thr Phe Trp Ser Arg Val Gly Gly Leu Val Arg Ala Leu Asp

His Trp Gly Gln Gly Thr Pro Val Thr Val Ser Ser
            115                 120

<210> SEQ ID NO 561
<211> LENGTH: 125
<212> TYPE: PRT
<213> ORGANISM: Artificial Sequence
<220> FEATURE:
<223> OTHER INFORMATION: Synthetic Construct

<400> SEQUENCE: 561

Glu Val Gln Leu Leu Glu Ser Gly Gly Leu Val His Ala Gly Gly
1               5                   10                  15

Ser Val Arg Leu Ser Cys Ala Ala Ser Gly Phe Thr Phe Asn Asp Tyr
            20                  25                  30

Trp Met Thr Trp Val Arg Gln Ala Pro Gly Lys Gly Leu Glu Trp Val
        35                  40                  45

Ala Asn Ile Gln Glu Tyr Gly Ser Glu Glu Asn Tyr Val Asp Ser Val
    50                  55                  60

Lys Gly Arg Phe Thr Ile Ser Arg Asp Asn Ser Lys Asn Ser Met Tyr
65                  70                  75                  80

Leu Gln Met Asn Ser Leu Arg Val Glu Asp Thr Ala Val Tyr Tyr Cys
                85                  90                  95

Ala Arg Asp Leu Asn Tyr His Asp Thr Val Ser Tyr Tyr Asp Val Leu
            100                 105                 110

Asp Val Trp Gly Gln Gly Thr Val Val Thr Val Ser Ser
        115                 120                 125

<210> SEQ ID NO 562
<211> LENGTH: 115
<212> TYPE: PRT
<213> ORGANISM: Artificial Sequence
<220> FEATURE:
<223> OTHER INFORMATION: Synthetic Construct

<400> SEQUENCE: 562

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Trp Met Thr Trp Leu Arg Gln Ala Pro Gly Lys Gly Pro Glu Tyr Val
        35                  40                  45

Ala Arg Ile Lys Ser Lys Ala Asp Gly Ala Thr Lys Asp Tyr Ala Gly
    50                  55                  60

Pro Val Glu Gly Arg Phe Ile Ile Ser Arg Asp Asp Ser Asn Asp Met
65                  70                  75                  80

Leu Tyr Leu Glu Met Ile Ser Leu Lys Ser Glu Asp Thr Ala Val Tyr
                85                  90                  95

Tyr Cys Ser Asp Gln Ile Tyr Val Gly Ser Gln Gly Thr Leu Val Thr
            100                 105                 110

Val Ser Ser
        115

<210> SEQ ID NO 563
<211> LENGTH: 127
<212> TYPE: PRT
<213> ORGANISM: Artificial Sequence
<220> FEATURE:

<223> OTHER INFORMATION: Synthetic Construct

<400> SEQUENCE: 563

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Val Lys Glu Ile Gly Asp Gly Tyr Asn Ser Gly Val Asp Lys Lys Val
            100                 105                 110

Ala Phe Asp Tyr Trp Gly Gln Gly Thr Leu Val Thr Val Ser Ser
        115                 120                 125

<210> SEQ ID NO 564
<211> LENGTH: 121
<212> TYPE: PRT
<213> ORGANISM: Artificial Sequence
<220> FEATURE:
<223> OTHER INFORMATION: Synthetic Construct

<400> SEQUENCE: 564

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Trp Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Arg Asp Tyr Ser Asn Tyr Pro Phe Asp Tyr Trp Gly
            100                 105                 110

Gln Gly Thr Leu Val Thr Val Ser Ser
        115                 120

<210> SEQ ID NO 565
<211> LENGTH: 121
<212> TYPE: PRT
<213> ORGANISM: Artificial Sequence
<220> FEATURE:
<223> OTHER INFORMATION: Synthetic Construct

<400> SEQUENCE: 565

Gln Val Gln Leu Val Glu Ser Gly Gly Gly Val Val Gln Pro Gly Arg
1               5                   10                  15

Ser Leu Arg Leu Ser Cys Val Ala Ser Gly Phe Asn Phe Arg Asp Tyr
            20                  25                  30

Gly Met His Trp Leu Arg Gln Ala Pro Gly Lys Gly Leu Glu Trp Val

```
                35                  40                  45
Ala Gly Met Ala Tyr Asp Glu Ile Thr Lys Trp Tyr Ala Asp Ser Val
        50                  55                  60
Asn Gly Arg Phe Thr Ile Ser Arg Asp Asn Ser Lys Asn Thr Leu Tyr
65                  70                  75                  80
Leu Glu Met Asn Ser Leu Arg Pro Glu Asp Thr Ala Val Tyr Tyr Cys
                85                  90                  95
Ala Lys Asp Pro Ser Ile Arg Lys Asn Ser Gly Ala Val Tyr Cys Gly
                100                 105                 110
Gln Gly Thr Leu Val Thr Val Ser Ser
            115                 120
```

<210> SEQ ID NO 566
<211> LENGTH: 124
<212> TYPE: PRT
<213> ORGANISM: Artificial Sequence
<220> FEATURE:
<223> OTHER INFORMATION: Synthetic Construct

<400> SEQUENCE: 566

```
Gln Val Gln Leu Val Glu Ser Gly Gly Gly Leu Val Gln Pro Gly Gly
1               5                   10                  15
Ser Leu Arg Leu Ser Cys Glu Ala Ser Gly Leu His Phe Arg Asn Tyr
                20                  25                  30
Ala Met Asn Trp Val Arg Gln Ala Pro Gly Lys Gly Leu Glu Trp Val
                35                  40                  45
Ala Phe Ile Ser Gly Ser Gly Glu Thr Pro Leu Tyr Ala Asp Ser Val
        50                  55                  60
Lys Gly Arg Phe Thr Val Ser Arg Asp Asn Ser Arg Asn Thr Leu Tyr
65                  70                  75                  80
Leu Gln Met Lys Ser Leu Ser Ala Glu Asp Thr Ala Val Tyr Tyr Cys
                85                  90                  95
Ala Lys Met Tyr Gly Asp Glu Asn Ser Ser Gly Leu Asp Ala Phe Asp
                100                 105                 110
Val Trp Gly Gln Gly Thr Met Val Thr Val Ser Ser
            115                 120
```

<210> SEQ ID NO 567
<211> LENGTH: 121
<212> TYPE: PRT
<213> ORGANISM: Artificial Sequence
<220> FEATURE:
<223> OTHER INFORMATION: Synthetic Construct

<400> SEQUENCE: 567

```
Gln Val Gln Leu Val Glu Ala Gly Gly Gly Leu Val Gln Pro Gly Gly
1               5                   10                  15
Ser Leu Arg Leu Ala Cys Ala Ala Ser Gly Phe Thr Phe Thr Thr Ser
                20                  25                  30
Glu Met Ser Trp Val Arg Gln Ala Pro Gly Lys Gly Leu Glu Trp Ile
                35                  40                  45
Ser Phe Ile Asn Arg Ser Gly Ser Met Ile Tyr Tyr Ala Asp Ser Val
        50                  55                  60
Lys Gly Arg Phe Thr Ile Ser Arg Asp Asn Ala Gln Asn Ser Leu Phe
65                  70                  75                  80
Leu Gln Met Asn Ser Leu Arg Ala Glu Asp Thr Ala Val Tyr Tyr Cys
                85                  90                  95
```

Ala Thr Ser Ser Gly Asp Asn Thr Tyr Ser Ala Phe Asp Ile Trp Gly
            100                 105                 110

Gln Gly Thr Met Val Thr Val Ser Ser
        115                 120

<210> SEQ ID NO 568
<211> LENGTH: 120
<212> TYPE: PRT
<213> ORGANISM: Artificial Sequence
<220> FEATURE:
<223> OTHER INFORMATION: Synthetic Construct

<400> SEQUENCE: 568

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Arg Pro Ser Phe
    50                  55                  60

Gln Gly His Val Thr Ile Ser Val Asp Lys Ser Ile Ser Thr Ala Tyr
65                  70                  75                  80

Leu Gln Trp Ser Ser Leu Lys Ala Ser Asp Ser Ala Met Tyr Tyr Phe
                85                  90                  95

Leu His Pro Leu Arg Asn Leu Arg Asp Phe Asp Cys Ser Trp Gly Gln
            100                 105                 110

Gly Thr Leu Val Thr Val Ser Ser
        115                 120

<210> SEQ ID NO 569
<211> LENGTH: 122
<212> TYPE: PRT
<213> ORGANISM: Artificial Sequence
<220> FEATURE:
<223> OTHER INFORMATION: Synthetic Construct

<400> SEQUENCE: 569

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Phe
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Arg Ser Ala Ile Asn Ser Val Trp Glu Phe Asp Tyr Trp
            100                 105                 110

Gly Gln Gly Thr Leu Val Thr Val Ser Ser
        115                 120

<210> SEQ ID NO 570
<211> LENGTH: 125
<212> TYPE: PRT
<213> ORGANISM: Artificial Sequence
<220> FEATURE:
<223> OTHER INFORMATION: Synthetic Construct

<400> SEQUENCE: 570

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Trp
            20                  25                  30

Tyr Met His Trp Val Arg Gln Ala Pro Gly Gln Gly Leu Glu Trp Met
        35                  40                  45

Gly Trp Ile Ser Pro Arg Ser Gly Asp Thr Asp Ser Ala Gln Lys Phe
    50                  55                  60

Gln Gly Arg Val Thr Met Thr Arg Asp Thr Ser Thr Thr Ala Tyr
65                  70                  75                  80

Met Glu Leu Asn Arg Leu Thr Ser Asp Asp Thr Ala Val Tyr Phe Cys
                85                  90                  95

Ala Arg Gly His Asp Ile Leu Thr Ser Asp Phe Arg Leu Tyr Tyr Phe
            100                 105                 110

Asp Ser Trp Gly Gln Gly Thr Leu Val Thr Val Ser Ser
        115                 120                 125

<210> SEQ ID NO 571
<211> LENGTH: 121
<212> TYPE: PRT
<213> ORGANISM: Artificial Sequence
<220> FEATURE:
<223> OTHER INFORMATION: Synthetic Construct

<400> SEQUENCE: 571

Glu Val Gln Leu Val Glu Ala Gly Gly Gly Leu Val Gln Pro Gly Gly
1               5                   10                  15

Ser Leu Arg Leu Ala Cys Ala Ala Ser Gly Phe Thr Phe Thr Thr Ser
            20                  25                  30

Glu Met Ser Trp Val Arg Gln Ala Pro Gly Lys Gly Leu Glu Trp Ile
        35                  40                  45

Ser Phe Ile Asn Arg Ser Gly Ser Met Ile Tyr Tyr Ala Asp Ser Val
    50                  55                  60

Lys Gly Arg Phe Thr Ile Ser Arg Asp Asn Ala Gln Asn Ser Leu Phe
65                  70                  75                  80

Leu Gln Met Asn Ser Leu Arg Ala Glu Asp Thr Ala Val Tyr Tyr Cys
                85                  90                  95

Ala Thr Ser Ser Gly Asp Asn Thr Tyr Ser Ala Phe Asp Ile Trp Gly
            100                 105                 110

Gln Gly Thr Met Val Thr Val Ser Ser
        115                 120

<210> SEQ ID NO 572
<211> LENGTH: 122
<212> TYPE: PRT
<213> ORGANISM: Artificial Sequence
<220> FEATURE:
<223> OTHER INFORMATION: Synthetic Construct

<400> SEQUENCE: 572

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Arg Gly Leu Glu Trp Leu
            35                  40                  45

Gly Arg Ile Asp Pro Thr Asp Ser Tyr Ile Asn Asn Ser Pro Ser Phe
        50                  55                  60

Gln Gly Gln Val Thr Met Ser Ala Asn Arg Ser Ile Ser Thr Ala Tyr
65                  70                  75                  80

Leu Gln Trp Ser Ser Leu Lys Ala Ser Asp Thr Gly Ile Tyr Tyr Cys
                85                  90                  95

Ala Thr Cys Leu Asp Ala Val Ser Ser Gly Gly Ala Met Asp Val Trp
            100                 105                 110

Gly Gln Gly Thr Thr Val Thr Val Ser Ser
        115                 120

<210> SEQ ID NO 573
<211> LENGTH: 118
<212> TYPE: PRT
<213> ORGANISM: Artificial Sequence
<220> FEATURE:
<223> OTHER INFORMATION: Synthetic Construct

<400> SEQUENCE: 573

Gln Val Gln Leu Val Glu Ser Gly Gly Gly Leu Ile Gln Pro Gly Glu
1               5                   10                  15

Ser Leu Arg Leu Ser Cys Glu Ala Phe Gly Phe Thr Val Ser Ser Asn
            20                  25                  30

His Met Ser Trp Val Arg Gln Ala Pro Gly Lys Gly Leu Glu Trp Val
            35                  40                  45

Ser Val Val Gln Tyr Gly Gly Arg Thr Tyr Tyr Ala Asp Ser Val Lys
        50                  55                  60

Gly Arg Phe Thr Ile Ser Arg Asp Ser Thr Gln Asn Thr Val His Leu
65                  70                  75                  80

Gln Met Asn Ser Leu Thr Ala Glu Asp Thr Ala Val Tyr Tyr Cys Ala
                85                  90                  95

Arg Asp Tyr Gly Tyr Asn Phe Tyr Phe Val Asp Trp Gly Gln Gly Thr
            100                 105                 110

Leu Val Thr Val Ser Ser
        115

<210> SEQ ID NO 574
<211> LENGTH: 124
<212> TYPE: PRT
<213> ORGANISM: Artificial Sequence
<220> FEATURE:
<223> OTHER INFORMATION: Synthetic Construct

<400> SEQUENCE: 574

Glu Val Gln Leu Val Gln Ser Gly Ala Glu Leu Lys Lys Pro Gly Ser
1               5                   10                  15

Ser Val Lys Val Ser Cys Thr Ser Ser Gly Gly Ser Phe Thr Pro Tyr
            20                  25                  30

Ala Ile Ser Trp Val Arg Gln Ala Pro Gly Gln Gly Leu Glu Trp Met
            35                  40                  45

Gly Gly Val Val Pro Ile Phe Gly Thr Pro His Tyr Ala Gln Lys Phe
        50                  55                  60

Gln Asp Arg Leu Ile Leu Ser Val Asp Glu Pro Thr Arg Thr Val Tyr
65                  70                  75                  80

Met Glu Leu Thr Ser Leu Arg Ser Asp Asp Thr Ala Met Tyr Tyr Cys
                85                  90                  95

-continued

Ala Arg Gly Gly Val Gly Ala Thr Asp Tyr Asp Leu Gly Met Asp
            100                 105                 110

Ala Trp Gly Gln Gly Thr Thr Val Thr Val Ser Ser
        115                 120

<210> SEQ ID NO 575
<211> LENGTH: 122
<212> TYPE: PRT
<213> ORGANISM: Artificial Sequence
<220> FEATURE:
<223> OTHER INFORMATION: Synthetic Construct

<400> SEQUENCE: 575

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Gly Trp Ser Ser Gly Thr Ile Gly Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Pro Glu Asp Thr Ala Leu Tyr Tyr Cys
                85                  90                  95

Ala Arg Ala Thr Gly Pro Ser Pro Thr Tyr His Ala Phe Asp Ile Trp
            100                 105                 110

Gly Gln Gly Thr Met Val Thr Val Ser Ser
        115                 120

<210> SEQ ID NO 576
<211> LENGTH: 126
<212> TYPE: PRT
<213> ORGANISM: Artificial Sequence
<220> FEATURE:
<223> OTHER INFORMATION: Synthetic Construct

<400> SEQUENCE: 576

Glu Val Gln Leu Leu Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Ala Met Ile Trp Val Arg Gln Ala Pro Gly Lys Gly Leu Glu Trp Val
        35                  40                  45

Ser Gly Ile Ser Gly Ser Gly Gly Asp Thr Tyr Tyr Ala Asp Ser Val
    50                  55                  60

Lys Gly Arg Phe Thr Ile Ser Arg Asp Tyr Ser Asn Lys Ile Val His
65                  70                  75                  80

Leu Glu Met Asp Ser Leu Arg Ala Glu Asp Thr Ala Val Tyr Phe Cys
                85                  90                  95

Val Arg Val Ala Ile Asp Thr Ile Asn Ser Pro Ser Pro Trp Cys Tyr
            100                 105                 110

Phe Asp Tyr Trp Gly Gln Gly Thr Leu Val Thr Val Ser Ser
        115                 120                 125

<210> SEQ ID NO 577
<211> LENGTH: 115
<212> TYPE: PRT

<213> ORGANISM: Artificial Sequence
<220> FEATURE:
<223> OTHER INFORMATION: Synthetic Construct

<400> SEQUENCE: 577

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ser
            20                  25                  30

Trp Met Thr Trp Val Arg Gln Ala Pro Gly Lys Gly Leu Glu Cys Val
        35                  40                  45

Ala Arg Ile Lys Ser Lys Ala Asp Gly Gly Thr Thr Asp Tyr Ser Ala
    50                  55                  60

Pro Val Glu Gly Arg Phe Thr Ile Ser Arg Asp Asp Ser Arg Asp Met
65                  70                  75                  80

Leu Tyr Leu Gln Met Asn Asn Leu Lys Thr Glu Asp Thr Ala Val Tyr
                85                  90                  95

Tyr Cys Ser Asp Gln Ile Tyr Leu Ser Ser Gly Thr Leu Val Thr
            100                 105                 110

Val Ser Ser
        115

<210> SEQ ID NO 578
<211> LENGTH: 122
<212> TYPE: PRT
<213> ORGANISM: Artificial Sequence
<220> FEATURE:
<223> OTHER INFORMATION: Synthetic Construct

<400> SEQUENCE: 578

Glu Val Gln Leu Val Glu Ser Gly Gly Gly Leu Val Gln Pro Gly Arg
1               5                   10                  15

Ser Leu Arg Leu Ser Cys Thr Thr Ser Gly Phe Ser Phe Gly Asp Ser
            20                  25                  30

Val Met Ser Trp Val Arg Gln Ala Pro Gly Lys Gly Leu Glu Trp Val
        35                  40                  45

Ser Leu Ile Arg Ala Arg Thr Phe Gly Glu Thr Lys Asp Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Gln Thr Glu Asp Thr Ala Val Tyr
                85                  90                  95

Tyr Cys Ser Arg Met Ala Thr Thr Tyr Asp Trp Tyr Phe Asp Leu Trp
            100                 105                 110

Gly Arg Gly Thr Leu Val Thr Val Ser Ser
        115                 120

<210> SEQ ID NO 579
<211> LENGTH: 126
<212> TYPE: PRT
<213> ORGANISM: Artificial Sequence
<220> FEATURE:
<223> OTHER INFORMATION: Synthetic Construct

<400> SEQUENCE: 579

Glu Val Gln Leu Leu Glu Ser Gly Gly Gly Leu Val Arg Pro Gly Gly
1               5                   10                  15

Ser Leu Arg Leu Ser Cys Ser Ala Ser Gly Phe Ala Phe Ser Ser Tyr
            20                  25                  30

```
Thr Met His Trp Val Arg Gln Ala Pro Gly Lys Gly Leu Glu Trp Val
        35                  40                  45

Ser Ser Met Ser Ser Ser Ile Arg Tyr Tyr Ala Asp Ser Val Lys Gly
 50                  55                  60

Arg Phe Thr Ile Ser Arg Asp Asn Ala Lys Asn Ser Val Tyr Leu Gln
 65                  70                  75                  80

Met Asn Ser Leu Arg Ala Glu Asp Ser Ala Val Tyr Phe Cys Ala Arg
                85                  90                  95

Asp Ser Pro Ser Phe Cys Gly Asp Asp Cys Tyr Arg Ser Gly Val Arg
               100                 105                 110

Val Asp Ser Trp Gly Gln Gly Thr Leu Val Thr Val Ser Ser
            115                 120                 125

<210> SEQ ID NO 580
<211> LENGTH: 124
<212> TYPE: PRT
<213> ORGANISM: Artificial Sequence
<220> FEATURE:
<223> OTHER INFORMATION: Synthetic Construct

<400> SEQUENCE: 580

Gln Val Gln Leu Val Glu Ser Gly Gly Asn Val Val Gln Pro Gly Thr
 1               5                  10                  15

Ser Leu Arg Leu Ser Cys Ala Ala Ser Gly Phe Thr Phe Ser Asp His
                20                  25                  30

Ala Met His Trp Val Arg Gln Ala Pro Gly Lys Gly Leu Glu Trp Val
            35                  40                  45

Ala Leu Ile Ser Ile Asp Ala Ser Asn His Tyr Tyr Ala Asp Ser Val
 50                  55                  60

Lys Gly Arg Phe Thr Ile Ser Arg Asp Asn Ser Arg Asn Thr Val Phe
 65                  70                  75                  80

Leu Gln Met Thr Ser Leu Arg Ala Glu Asp Thr Ala Val Tyr Tyr Cys
                85                  90                  95

Gly Arg Asp Arg Leu Gly Val Thr Arg Gly Pro Ser Asn Trp Phe Asp
               100                 105                 110

Ser Trp Gly Gln Gly Ile Leu Val Thr Val Ser Ser
            115                 120

<210> SEQ ID NO 581
<211> LENGTH: 115
<212> TYPE: PRT
<213> ORGANISM: Artificial Sequence
<220> FEATURE:
<223> OTHER INFORMATION: Synthetic Construct

<400> SEQUENCE: 581

Glu Val Gln Leu Leu Glu Ser Gly Gly Gly Leu Val Gln Pro Gly Gly
 1               5                  10                  15

Ser Leu Arg Leu Thr Cys Val Gly Tyr Gly Phe Thr Phe Ser Arg Asp
                20                  25                  30

Trp Met Asn Trp Val Arg Gln Ala Pro Gly Lys Gly Pro Glu Trp Val
            35                  40                  45

Ala Ile Met Asn Gln Asp Gly Ser Glu Glu Tyr Tyr Val Asp Ser Val
 50                  55                  60

Lys Gly Arg Phe Thr Ile Ser Arg Asp Asn Ala Lys Asp Ser Leu Tyr
 65                  70                  75                  80

Leu Gln Met Asp Ser Leu Arg Pro Glu Asp Thr Ala Val Tyr Tyr Cys
```

85                  90                  95

Ala Arg Asp Leu Ile Leu Ala Pro Ala Pro Gln Gly Thr Leu Val Thr
                100                 105                 110

Val Ser Ser
        115

<210> SEQ ID NO 582
<211> LENGTH: 120
<212> TYPE: PRT
<213> ORGANISM: Artificial Sequence
<220> FEATURE:
<223> OTHER INFORMATION: Synthetic Construct

<400> SEQUENCE: 582

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Leu Ser Asn Tyr
            20                  25                  30

Trp Met His Trp Val Arg Gln Ala Pro Gly Lys Gly Leu Val Trp Val
        35                  40                  45

Ser Arg Ile Asn Ser Glu Gly Ser Ser Thr Arg Tyr Ala Asp Ser Val
    50                  55                  60

Lys Gly Gln Phe Thr Ile Ser Arg Asp Asn Ala Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Ser Asn Asn Trp Tyr Asn Ala Phe Asp Ile Trp Gly Gln
                100                 105                 110

Gly Thr Met Val Thr Val Ser Ser
        115                 120

<210> SEQ ID NO 583
<211> LENGTH: 117
<212> TYPE: PRT
<213> ORGANISM: Artificial Sequence
<220> FEATURE:
<223> OTHER INFORMATION: Synthetic Construct

<400> SEQUENCE: 583

Glu Val Gln Leu Leu Glu Ser Gly Gly Gly Val Val His Pro Gly Arg
1               5                   10                  15

Ser Leu Arg Leu Ser Cys Ala Val Ser Gly Phe Ser Leu Thr Thr Tyr
            20                  25                  30

Gly Met His Trp Val Arg Gln Ala Pro Asp Lys Gly Leu Glu Trp Val
        35                  40                  45

Ala Val Ile Trp Phe Asp Gly Asp Tyr Lys Asn Tyr Ala Asp Ser Val
    50                  55                  60

Lys Gly Arg Phe Thr Val Ser Arg Asp Ile Ser Lys Asn Thr Val Tyr
65                  70                  75                  80

Leu Gln Met Asn Ser Leu Arg Ala Glu Asp Thr Ala Leu Tyr Tyr Cys
                85                  90                  95

Ala Arg Asp Tyr Ser Asn Tyr Pro Asp Ile Trp Gly Gln Gly Thr Met
                100                 105                 110

Val Thr Val Ser Ser
        115

<210> SEQ ID NO 584
<211> LENGTH: 120

```
<212> TYPE: PRT
<213> ORGANISM: Artificial Sequence
<220> FEATURE:
<223> OTHER INFORMATION: Synthetic Construct

<400> SEQUENCE: 584
```

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Ser Asp His
            20                  25                  30

Asn Met Asp Trp Phe Arg Gln Gly Pro Gly Lys Gly Leu Glu Trp Val
        35                  40                  45

Ala Arg Ile Arg Ser Lys Arg Asp Ser Tyr Arg Thr Glu Tyr Ala Ala
50                  55                  60

Ser Ala Lys Gly Arg Phe Thr Ile Ser Arg Asp Asp Ser Lys Asn Ser
65                  70                  75                  80

Leu Ser Leu Gln Met Asp Ser Leu Arg Thr Glu Asp Thr Ala Val Tyr
                85                  90                  95

Tyr Cys Val Arg Asp Ser Lys Ala Phe Ala Phe Asp Ile Trp Gly Gln
            100                 105                 110

Gly Thr Val Val Thr Val Ser Ser
        115                 120

```
<210> SEQ ID NO 585
<211> LENGTH: 121
<212> TYPE: PRT
<213> ORGANISM: Artificial Sequence
<220> FEATURE:
<223> OTHER INFORMATION: Synthetic Construct

<400> SEQUENCE: 585
```

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ala Phe Gly Thr Tyr
            20                  25                  30

Gly Met His Trp Val Arg Gln Thr Pro Gly Arg Gly Leu Glu Trp Leu
        35                  40                  45

Ala Val Leu Ala Tyr Asp Gly Ser Asp Thr Asn Tyr Val Asp Ser Val
50                  55                  60

Lys Gly Arg Phe Thr Ile Ser Arg Asp Asn Ser Asn Thr Val Tyr
65                  70                  75                  80

Leu Glu Met Asn Ser Leu Arg Pro Glu Asp Ser Ala Ile Tyr Tyr Cys
                85                  90                  95

Ala Lys Asp Arg Tyr Gly Arg Asn Ser Gly Phe Leu Gln Tyr Trp Gly
            100                 105                 110

Leu Gly Thr Val Val Thr Val Ser Ser
        115                 120

```
<210> SEQ ID NO 586
<211> LENGTH: 119
<212> TYPE: PRT
<213> ORGANISM: Artificial Sequence
<220> FEATURE:
<223> OTHER INFORMATION: Synthetic Construct

<400> SEQUENCE: 586
```

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr

```
                20                  25                  30
Thr Met His Trp Val Arg Gln Ala Pro Gly Lys Gly Leu Glu Trp Val
            35                  40                  45
Ser Phe Ile Ser Trp Asp Gly Arg Ser Thr Lys Tyr Ala Asp Ser Val
        50                  55                  60
Lys Gly Arg Phe Thr Ile Ser Arg Asp Asn Ser Lys Asn Ser Leu Tyr
65                  70                  75                  80
Leu Gln Met Asn Ser Leu Arg Thr Glu Asp Thr Ala Leu Tyr Tyr Cys
                85                  90                  95
Val Glu Asp Gly Ser Gly Asn Tyr Tyr Phe Asp Tyr Trp Gly Gln Gly
            100                 105                 110
Thr Leu Val Thr Val Ser Ser
            115

<210> SEQ ID NO 587
<211> LENGTH: 121
<212> TYPE: PRT
<213> ORGANISM: Artificial Sequence
<220> FEATURE:
<223> OTHER INFORMATION: Synthetic Construct

<400> SEQUENCE: 587

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Glu Met Asn Trp Val Arg Gln Ala Pro Gly Lys Gly Leu Glu Trp Val
            35                  40                  45
Ser Tyr Ile Ser Gly Ser Gly Asn Thr Ile His Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Thr Glu Asp Thr Ala Val Tyr Tyr Cys
                85                  90                  95
Ala Arg Arg Asp Thr Thr Ser Ser Arg Tyr Gly Leu Asp Val Trp Gly
            100                 105                 110
Gln Gly Thr Thr Val Thr Val Ser Ser
            115                 120

<210> SEQ ID NO 588
<211> LENGTH: 128
<212> TYPE: PRT
<213> ORGANISM: Artificial Sequence
<220> FEATURE:
<223> OTHER INFORMATION: Synthetic Construct

<400> SEQUENCE: 588

Glu Val Gln Leu Val Gln Ser Gly Gly Gly Trp Val Lys Pro Gly Gly
1               5                   10                  15
Ser Leu Arg Leu Ser Cys Ala Ala Ser Gly Phe Ile Cys Ser Gln Ala
                20                  25                  30
Trp Met Thr Trp Val Arg Gln Ala Pro Gly Lys Gly Leu Glu Trp Val
            35                  40                  45
Gly Arg Ile Arg Ser Ile Thr Asp Gly Gly Thr Thr Asp Phe Ala Ala
        50                  55                  60
Pro Val Lys Gly Arg Phe Ile Ile Ser Ile Asp Glu Ser Arg Asn Ala
65                  70                  75                  80
```

```
Leu Phe Leu His Met Asn Ser Leu Thr Thr Asp Asp Thr Ala Val Tyr
                85                  90                  95

Tyr Cys Ser Thr Ser Pro Leu Ser Gly Asn Cys Asn Glu Thr Ser Cys
            100                 105                 110

Tyr Pro Phe Asp Ser Trp Gly Gln Gly Thr Leu Val Thr Val Ser Ser
            115                 120                 125

<210> SEQ ID NO 589
<211> LENGTH: 122
<212> TYPE: PRT
<213> ORGANISM: Artificial Sequence
<220> FEATURE:
<223> OTHER INFORMATION: Synthetic Construct

<400> SEQUENCE: 589

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ile Arg Lys Tyr Tyr Ala Asp Ser Val
        50                  55                  60

Lys Gly Arg Phe Thr Val Ser Arg Asp Thr Ser Thr Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Val Asp Thr Ser Ser Arg Tyr Gly Trp Phe Asp Pro Trp
            100                 105                 110

Gly Gln Gly Thr Leu Val Thr Val Ser Ser
        115                 120

<210> SEQ ID NO 590
<211> LENGTH: 128
<212> TYPE: PRT
<213> ORGANISM: Artificial Sequence
<220> FEATURE:
<223> OTHER INFORMATION: Synthetic Construct

<400> SEQUENCE: 590

Gln Met Gln Leu Val Gln Ser Glu Ala Glu Val Lys Lys Pro Gly Ala
1               5                   10                  15

Ser Met Lys Val Ser Cys Lys Ala Ser Gly Tyr Thr Phe Ala Asn Phe
                20                  25                  30

Glu Ile Asn Trp Val Arg Gln Ala Thr Gly Gln Gly Leu Glu Trp Met
            35                  40                  45

Gly Trp Met Asn Pro Asn Asn Gly Asn Thr Gly Tyr Ala Gln Lys Phe
        50                  55                  60

Gln Ala Arg Val Thr Met Thr Arg Asn Thr Ser Ile Ser Thr Ala Tyr
65                  70                  75                  80

Met Glu Leu Ser Ser Leu Thr Ser Ala Asp Thr Ala Val Tyr Tyr Cys
                85                  90                  95

Ala Arg Val Pro Lys Lys Pro Arg Ser Ala Ser Pro Pro Pro Asp
            100                 105                 110

Asn Trp Phe Asp Pro Trp Gly Gln Gly Thr Leu Val Thr Val Ser Ser
            115                 120                 125

<210> SEQ ID NO 591
```

```
<211> LENGTH: 123
<212> TYPE: PRT
<213> ORGANISM: Artificial Sequence
<220> FEATURE:
<223> OTHER INFORMATION: Synthetic Construct

<400> SEQUENCE: 591

Gln Val Gln Leu Val Gln Ser Gly Ala Glu Val Lys Pro Gly Glu
1               5                  10                  15

Ser Leu Lys Ile Ser Cys Lys Gly Ser Gly Tyr Ser Phe Ser Ser Tyr
            20                  25                  30

Trp Ile Gly Trp Val Arg Gln Met Pro Gly Lys Gly Leu Glu Trp Met
        35                  40                  45

Gly Ile Thr Tyr Pro Gly Asp Phe Asp Thr Arg Tyr Ser Pro Ser Phe
    50                  55                  60

Gln Gly Gln Val Thr Ile Ser Ala Asp Lys Ser Ile Ser Thr Ala Phe
65                  70                  75                  80

Leu Gln Trp Asn Ser Leu Lys Ala Ser Asp Thr Ala Met Tyr Tyr Cys
                85                  90                  95

Ala Arg Gly Lys Ala Val Ala Ala Trp Ala Met Ser Pro Ile Asp Asp
            100                 105                 110

Trp Gly Leu Gly Thr Leu Val Thr Val Ser Ser
        115                 120

<210> SEQ ID NO 592
<211> LENGTH: 119
<212> TYPE: PRT
<213> ORGANISM: Artificial Sequence
<220> FEATURE:
<223> OTHER INFORMATION: Synthetic Construct

<400> SEQUENCE: 592

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 593
<211> LENGTH: 119
<212> TYPE: PRT
<213> ORGANISM: Artificial Sequence
<220> FEATURE:
<223> OTHER INFORMATION: Synthetic Construct

<400> SEQUENCE: 593

Glu Val Gln Leu Val Glu Ser Gly Gly Gly Leu Val Gln Pro Gly Gly
1               5                  10                  15
```

Ser Leu Arg Leu Ser Cys Ala Ala Ser Gly Phe Thr Phe Ser Ser Tyr
            20                  25                  30

Ala Met Gly Trp Val Arg Asn Ala Pro Gly Lys Gly Asn Glu Ile Val
        35                  40                  45

Ser Ile Ile Ser Gly Ser Gly Gly Ser Thr Trp Tyr Asn Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 594
<211> LENGTH: 119
<212> TYPE: PRT
<213> ORGANISM: Artificial Sequence
<220> FEATURE:
<223> OTHER INFORMATION: Synthetic Construct

<400> SEQUENCE: 594

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Arg Ala Pro Gly Lys Gly Ile Glu Val Val
        35                  40                  45

Ser Ile Ile Ser Gly Ser Gly Gly Ser Thr Trp Tyr Ser Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 595
<211> LENGTH: 119
<212> TYPE: PRT
<213> ORGANISM: Artificial Sequence
<220> FEATURE:
<223> OTHER INFORMATION: Synthetic Construct

<400> SEQUENCE: 595

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ile Ala Pro Gly Lys Gly Pro Glu Pro Val
        35                  40                  45

Ser Trp Ile Ser Gly Ser Gly Gly Ser Thr Tyr Ala Asp Ser Val
50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 596
<211> LENGTH: 119
<212> TYPE: PRT
<213> ORGANISM: Artificial Sequence
<220> FEATURE:
<223> OTHER INFORMATION: Synthetic Construct

<400> SEQUENCE: 596

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Lys Ala Pro Gly Lys Gly Tyr Glu Pro Val
        35                  40                  45

Ser Ile Ile Ser Gly Ser Gly Gly Ser Thr Trp Tyr Cys Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 597
<211> LENGTH: 119
<212> TYPE: PRT
<213> ORGANISM: Artificial Sequence
<220> FEATURE:
<223> OTHER INFORMATION: Synthetic Construct

<400> SEQUENCE: 597

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Asn Ala Pro Gly Lys Gly Tyr Glu Ile Val
        35                  40                  45

Ser Met Ile Ser Gly Ser Gly Gly Ser Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115
```

-continued

```
<210> SEQ ID NO 598
<211> LENGTH: 119
<212> TYPE: PRT
<213> ORGANISM: Artificial Sequence
<220> FEATURE:
<223> OTHER INFORMATION: Synthetic Construct

<400> SEQUENCE: 598

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Tyr Ala Pro Gly Lys Gly Tyr Glu Phe Val
        35                  40                  45

Ser Ala Ile Ser Gly Ser Gly Gly Ser Thr Trp Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 599
<211> LENGTH: 119
<212> TYPE: PRT
<213> ORGANISM: Artificial Sequence
<220> FEATURE:
<223> OTHER INFORMATION: Synthetic Construct

<400> SEQUENCE: 599

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Val Ala Pro Gly Lys Gly Ile Glu Pro Val
        35                  40                  45

Ser Trp Ile Ser Gly Ser Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 600
<211> LENGTH: 119
<212> TYPE: PRT
<213> ORGANISM: Artificial Sequence
<220> FEATURE:
<223> OTHER INFORMATION: Synthetic Construct

<400> SEQUENCE: 600

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Gly Trp Val Arg Met Ala Pro Gly Lys Gly Pro Glu His Val
        35                  40                  45

Ser Trp Ile Ser Gly Ser Gly Gly Ser Thr Thr Tyr Cys Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
            115
```

<210> SEQ ID NO 601
<211> LENGTH: 119
<212> TYPE: PRT
<213> ORGANISM: Artificial Sequence
<220> FEATURE:
<223> OTHER INFORMATION: Synthetic Construct

<400> SEQUENCE: 601

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ser Ala Pro Gly Lys Gly Val Glu Met Val
        35                  40                  45

Ser Phe Ile Ser Gly Ser Gly Ser Thr Trp Tyr Met Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
            115
```

<210> SEQ ID NO 602
<211> LENGTH: 119
<212> TYPE: PRT
<213> ORGANISM: Artificial Sequence
<220> FEATURE:
<223> OTHER INFORMATION: Synthetic Construct

<400> SEQUENCE: 602

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Thr Ala Pro Gly Lys Gly Thr Glu Met Val
        35                  40                  45

Ser Trp Ile Ser Gly Ser Gly Gly Ser Thr Tyr Tyr Cys Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 603
<211> LENGTH: 119
<212> TYPE: PRT
<213> ORGANISM: Artificial Sequence
<220> FEATURE:
<223> OTHER INFORMATION: Synthetic Construct

<400> SEQUENCE: 603

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Cys Ala Pro Gly Lys Gly Tyr Glu Phe Val
        35                  40                  45

Ser Ala Ile Ser Gly Ser Gly Gly Ser Thr Trp Tyr His Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 604
<211> LENGTH: 119
<212> TYPE: PRT
<213> ORGANISM: Artificial Sequence
<220> FEATURE:
<223> OTHER INFORMATION: Synthetic Construct

<400> SEQUENCE: 604

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ile Ala Pro Gly Lys Gly Leu Glu Met Val
        35                  40                  45

Ser Met Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115
```

<210> SEQ ID NO 605
<211> LENGTH: 119
<212> TYPE: PRT
<213> ORGANISM: Artificial Sequence
<220> FEATURE:
<223> OTHER INFORMATION: Synthetic Construct

<400> SEQUENCE: 605

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Met Ala Pro Gly Lys Gly Leu Glu Tyr Val
        35                  40                  45

Ser Ile Ile Ser Gly Ser Gly Gly Ser Thr Tyr Tyr Cys Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 606
<211> LENGTH: 119
<212> TYPE: PRT
<213> ORGANISM: Artificial Sequence
<220> FEATURE:
<223> OTHER INFORMATION: Synthetic Construct

<400> SEQUENCE: 606

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Tyr Ala Pro Gly Lys Gly Thr Glu Phe Val
        35                  40                  45

Ser Trp Ile Ser Gly Ser Gly Gly Ser Thr Phe Tyr Cys Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 607
<211> LENGTH: 119
<212> TYPE: PRT
<213> ORGANISM: Artificial Sequence
<220> FEATURE:
<223> OTHER INFORMATION: Synthetic Construct

<400> SEQUENCE: 607

Glu Val Gln Leu Val Glu Ser Gly Gly Gly Leu Val Gln Pro Gly Gly

```
1               5                   10                  15
Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Val Glu Trp Val
            35                  40                  45

Ser Trp Ile Ser Gly Ser Gly Ser Thr Phe Tyr Asp Asp Ser Val
            50                  55                  60

Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
            85                  90                  95

Ala Arg His Ala Pro Ser Thr Glu Ala Pro Asp Tyr Trp Gly Gln Gly
            100                 105                 110

Thr Leu Val Thr Val Ser Ser
            115
```

<210> SEQ ID NO 608
<211> LENGTH: 119
<212> TYPE: PRT
<213> ORGANISM: Artificial Sequence
<220> FEATURE:
<223> OTHER INFORMATION: Synthetic Construct

<400> SEQUENCE: 608

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Gly Trp Val Arg Trp Ala Pro Gly Lys Gly Pro Glu Phe Val
            35                  40                  45

Ser Val Ile Ser Gly Ser Gly Gly Ser Thr Leu Tyr Thr Asp Ser Val
            50                  55                  60

Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
            85                  90                  95

Ala Arg His Ala Pro Ser Thr Glu Ala Pro Asp Tyr Trp Gly Gln Gly
            100                 105                 110

Thr Leu Val Thr Val Ser Ser
            115
```

<210> SEQ ID NO 609
<211> LENGTH: 119
<212> TYPE: PRT
<213> ORGANISM: Artificial Sequence
<220> FEATURE:
<223> OTHER INFORMATION: Synthetic Construct

<400> SEQUENCE: 609

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Gly Trp Val Arg Phe Ala Pro Gly Lys Gly Arg Glu Trp Val
            35                  40                  45

Ser Trp Ile Ser Gly Ser Gly Gly Ser Thr Trp Tyr Gly Asp Ser Val
            50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 610
<211> LENGTH: 119
<212> TYPE: PRT
<213> ORGANISM: Artificial Sequence
<220> FEATURE:
<223> OTHER INFORMATION: Synthetic Construct

<400> SEQUENCE: 610

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Phe Ala Pro Gly Lys Gly Cys Glu Leu Val
        35                  40                  45

Ser Ala Ile Ser Gly Ser Gly Gly Ser Thr Trp Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 611
<211> LENGTH: 119
<212> TYPE: PRT
<213> ORGANISM: Artificial Sequence
<220> FEATURE:
<223> OTHER INFORMATION: Synthetic Construct

<400> SEQUENCE: 611

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Lys Ala Pro Gly Lys Gly Leu Glu Thr Val
        35                  40                  45

Ser Phe Ile Ser Gly Ser Gly Gly Ser Thr Phe Tyr His Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 612
<211> LENGTH: 119
<212> TYPE: PRT
<213> ORGANISM: Artificial Sequence
<220> FEATURE:
<223> OTHER INFORMATION: Synthetic Construct

<400> SEQUENCE: 612

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Asn Ala Pro Gly Lys Gly Leu Glu Cys Val
        35                  40                  45

Ser Tyr Ile Ser Gly Ser Gly Ser Thr Trp Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 613
<211> LENGTH: 119
<212> TYPE: PRT
<213> ORGANISM: Artificial Sequence
<220> FEATURE:
<223> OTHER INFORMATION: Synthetic Construct

<400> SEQUENCE: 613

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Cys Ala Pro Gly Lys Gly Trp Glu Val Val
        35                  40                  45

Ser Leu Ile Ser Gly Ser Gly Gly Ser Thr Trp Tyr Cys Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 614
<211> LENGTH: 119
<212> TYPE: PRT
<213> ORGANISM: Artificial Sequence
<220> FEATURE:
<223> OTHER INFORMATION: Synthetic Construct

<400> SEQUENCE: 614

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Leu Ala Pro Gly Lys Gly Val Glu Leu Val
        35                  40                  45

Ser Trp Ile Ser Gly Ser Gly Gly Ser Thr Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
            115

<210> SEQ ID NO 615
<211> LENGTH: 119
<212> TYPE: PRT
<213> ORGANISM: Artificial Sequence
<220> FEATURE:
<223> OTHER INFORMATION: Synthetic Construct

<400> SEQUENCE: 615

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Phe Ala Pro Gly Lys Gly Ala Glu Trp Val
        35                  40                  45

Ser Trp Ile Ser Gly Ser Gly Gly Ser Thr Val Tyr Arg Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
            115

<210> SEQ ID NO 616
<211> LENGTH: 119
<212> TYPE: PRT
<213> ORGANISM: Artificial Sequence
<220> FEATURE:
<223> OTHER INFORMATION: Synthetic Construct

<400> SEQUENCE: 616

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Leu Ala Pro Gly Lys Gly Arg Glu Trp Val
        35                  40                  45

Ser Trp Ile Ser Gly Ser Gly Gly Ser Thr Trp Tyr Arg Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 617
<211> LENGTH: 119
<212> TYPE: PRT
<213> ORGANISM: Artificial Sequence
<220> FEATURE:
<223> OTHER INFORMATION: Synthetic Construct

<400> SEQUENCE: 617

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Tyr Ala Pro Gly Lys Gly Val Glu Phe Val
            35                  40                  45

Ser Ile Ile Ser Gly Ser Gly Gly Ser Thr Trp Tyr Cys Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 618
<211> LENGTH: 119
<212> TYPE: PRT
<213> ORGANISM: Artificial Sequence
<220> FEATURE:
<223> OTHER INFORMATION: Synthetic Construct

<400> SEQUENCE: 618

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Phe Ala Pro Gly Lys Gly Leu Glu Met Val
            35                  40                  45

Ser Ser Ile Ser Gly Ser Gly Ser Thr Trp Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110

Thr Leu Val Thr Val Ser Ser
```

-continued

```
                115

<210> SEQ ID NO 619
<211> LENGTH: 119
<212> TYPE: PRT
<213> ORGANISM: Artificial Sequence
<220> FEATURE:
<223> OTHER INFORMATION: Synthetic Construct

<400> SEQUENCE: 619

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Val Ala Pro Gly Lys Gly Thr Glu Arg Val
        35                  40                  45

Ser Trp Ile Ser Gly Ser Gly Gly Ser Thr Trp Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
            115

<210> SEQ ID NO 620
<211> LENGTH: 119
<212> TYPE: PRT
<213> ORGANISM: Artificial Sequence
<220> FEATURE:
<223> OTHER INFORMATION: Synthetic Construct

<400> SEQUENCE: 620

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ile Ala Pro Gly Lys Gly Met Glu Met Val
        35                  40                  45

Ser Trp Ile Ser Gly Ser Gly Gly Ser Thr Arg Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
            115

<210> SEQ ID NO 621
<211> LENGTH: 119
<212> TYPE: PRT
<213> ORGANISM: Artificial Sequence
<220> FEATURE:
<223> OTHER INFORMATION: Synthetic Construct

<400> SEQUENCE: 621
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ala Pro Gly Lys Gly Pro Glu Leu Val
            35                  40                  45

Ser Leu Ile Ser Gly Ser Gly Gly Ser Thr Leu Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
                100                 105                 110

Thr Leu Val Thr Val Ser Ser
            115
```

<210> SEQ ID NO 622
<211> LENGTH: 119
<212> TYPE: PRT
<213> ORGANISM: Artificial Sequence
<220> FEATURE:
<223> OTHER INFORMATION: Synthetic Construct

<400> SEQUENCE: 622

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Val Ala Pro Gly Lys Gly Tyr Glu His Val
            35                  40                  45

Ser Trp Ile Ser Gly Ser Gly Gly Ser Thr Ala Tyr Asp Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
                100                 105                 110

Thr Leu Val Thr Val Ser Ser
            115
```

<210> SEQ ID NO 623
<211> LENGTH: 119
<212> TYPE: PRT
<213> ORGANISM: Artificial Sequence
<220> FEATURE:
<223> OTHER INFORMATION: Synthetic Construct

<400> SEQUENCE: 623

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Val Ala Pro Gly Lys Gly Leu Glu Cys Val
            35                  40                  45

Ser Val Ile Ser Gly Ser Gly Gly Ser Thr Trp Tyr Ser Asp Ser Val
```

```
                   50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg His Ala Pro Ser Thr Glu Ala Pro Asp Tyr Trp Gly Gln Gly
                    100                 105                 110

Thr Leu Val Thr Val Ser Ser
                115

<210> SEQ ID NO 624
<211> LENGTH: 119
<212> TYPE: PRT
<213> ORGANISM: Artificial Sequence
<220> FEATURE:
<223> OTHER INFORMATION: Synthetic Construct

<400> SEQUENCE: 624

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Gly Trp Val Arg Val Ala Pro Gly Lys Gly Pro Glu Thr Val
             35                  40                  45

Ser Leu Ile Ser Gly Ser Gly Gly Ser Thr Arg Tyr Ser Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg His Ala Pro Ser Thr Glu Ala Pro Asp Tyr Trp Gly Gln Gly
                    100                 105                 110

Thr Leu Val Thr Val Ser Ser
                115

<210> SEQ ID NO 625
<211> LENGTH: 119
<212> TYPE: PRT
<213> ORGANISM: Artificial Sequence
<220> FEATURE:
<223> OTHER INFORMATION: Synthetic Construct

<400> SEQUENCE: 625

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Gly Trp Val Arg Met Ala Pro Gly Lys Gly Ser Glu Val Val
             35                  40                  45

Ser Tyr Ile Ser Gly Ser Gly Gly Ser Thr Trp Tyr Arg Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg His Ala Pro Ser Thr Glu Ala Pro Asp Tyr Trp Gly Gln Gly
                    100                 105                 110
```

```
Thr Leu Val Thr Val Ser Ser
        115

<210> SEQ ID NO 626
<211> LENGTH: 119
<212> TYPE: PRT
<213> ORGANISM: Artificial Sequence
<220> FEATURE:
<223> OTHER INFORMATION: Synthetic Construct

<400> SEQUENCE: 626

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Leu Ala Pro Gly Lys Gly Thr Glu Met Val
        35                  40                  45

Ser Trp Ile Ser Gly Ser Gly Gly Ser Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 627
<211> LENGTH: 119
<212> TYPE: PRT
<213> ORGANISM: Artificial Sequence
<220> FEATURE:
<223> OTHER INFORMATION: Synthetic Construct

<400> SEQUENCE: 627

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Thr Ala Pro Gly Lys Gly Ala Glu Trp Val
        35                  40                  45

Ser Phe Ile Ser Gly Ser Gly Gly Ser Thr Trp Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 628
<211> LENGTH: 119
<212> TYPE: PRT
<213> ORGANISM: Artificial Sequence
<220> FEATURE:
<223> OTHER INFORMATION: Synthetic Construct
```

<400> SEQUENCE: 628

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Trp Ala Pro Gly Lys Gly Lys Glu Val Val
        35                  40                  45

Ser Leu Ile Ser Gly Ser Gly Gly Ser Thr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 629
<211> LENGTH: 119
<212> TYPE: PRT
<213> ORGANISM: Artificial Sequence
<220> FEATURE:
<223> OTHER INFORMATION: Synthetic Construct

<400> SEQUENCE: 629

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Ile Glu Pro Val
        35                  40                  45

Ser Val Ile Ser Gly Ser Gly Gly Ser Thr Trp Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 630
<211> LENGTH: 119
<212> TYPE: PRT
<213> ORGANISM: Artificial Sequence
<220> FEATURE:
<223> OTHER INFORMATION: Synthetic Construct

<400> SEQUENCE: 630

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Trp Val
        35                  40                  45

```
Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110

Thr Leu Val Thr Val Ser Ser
            115
```

<210> SEQ ID NO 631
<211> LENGTH: 119
<212> TYPE: PRT
<213> ORGANISM: Artificial Sequence
<220> FEATURE:
<223> OTHER INFORMATION: Synthetic Construct

<400> SEQUENCE: 631

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Gln Ala Pro Gly Lys Gly Pro Glu Val Val
         35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110

Thr Leu Val Thr Val Ser Ser
            115
```

<210> SEQ ID NO 632
<211> LENGTH: 119
<212> TYPE: PRT
<213> ORGANISM: Artificial Sequence
<220> FEATURE:
<223> OTHER INFORMATION: Synthetic Construct

<400> SEQUENCE: 632

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Thr Ala Pro Gly Lys Gly Ile Glu Ile Val
         35                  40                  45

Ser Trp Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110
```

Thr Leu Val Thr Val Ser Ser
        115

<210> SEQ ID NO 633
<211> LENGTH: 119
<212> TYPE: PRT
<213> ORGANISM: Artificial Sequence
<220> FEATURE:
<223> OTHER INFORMATION: Synthetic Construct

<400> SEQUENCE: 633

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ile Ala Pro Gly Lys Gly Val Glu Ile Val
        35                  40                  45

Ser Trp Ile Ser Gly Ser Gly Gly Ser Thr Trp Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 634
<211> LENGTH: 119
<212> TYPE: PRT
<213> ORGANISM: Artificial Sequence
<220> FEATURE:
<223> OTHER INFORMATION: Synthetic Construct

<400> SEQUENCE: 634

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Ala Ala Pro Gly Lys Gly Leu Glu Val Val
        35                  40                  45

Ser Leu Ile Ser Gly Ser Gly Gly Ser Thr Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 635
<211> LENGTH: 119
<212> TYPE: PRT
<213> ORGANISM: Artificial Sequence
<220> FEATURE:
<223> OTHER INFORMATION: Synthetic Construct

<400> SEQUENCE: 635

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 636
<211> LENGTH: 119
<212> TYPE: PRT
<213> ORGANISM: Artificial Sequence
<220> FEATURE:
<223> OTHER INFORMATION: Synthetic Construct

<400> SEQUENCE: 636

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Val Val
        35                  40                  45

Ser Leu Ile Ser Gly Ser Gly Gly Ser Thr Trp Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Ser Thr Glu Ala Pro Asp Tyr Trp Gly Gln Gly
            100                 105                 110

Thr Leu Val Thr Val Ser Ser
        115

<210> SEQ ID NO 637
<211> LENGTH: 119
<212> TYPE: PRT
<213> ORGANISM: Artificial Sequence
<220> FEATURE:
<223> OTHER INFORMATION: Synthetic Construct

<400> SEQUENCE: 637

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Pro Glu Trp Val
        35                  40                  45

```
Ser Leu Ile Ser Gly Ser Gly Gly Ser Thr Trp Tyr Asp Asp Ser Val
    50              55                  60

Lys Gly Arg Phe Thr Ile Ser Arg Asp Asn Ser Lys Asn Thr Leu Tyr
65              70                  75                      80

Leu Gln Met Asn Ser Leu Arg Ala Glu Asp Thr Ala Val Tyr Tyr Cys
            85                  90                      95

Ala Arg His Ala Pro Ser Thr Glu Ala Pro Asp Tyr Trp Gly Gln Gly
            100                 105                 110

Thr Leu Val Thr Val Ser Ser
            115
```

SCREENING AND ENGINEERING METHOD OF SUPER-STABLE IMMUNOGLOBULIN VARIABLE DOMAINS AND THEIR USES

CROSS-REFERENCE TO RELATED APPLICATIONS

This application is the U.S. National Phase under U.S.C. § 371 of International Application PCT/KR2012/006680, filed Aug. 22, 2012.

REFERENCE TO SEQUENCE LISTING

This application incorporates by reference the sequence listing submitted as ASCII text filed via EFS-Web on Apr. 28, 2017. The Sequence Listing is provided as a file entitled "258109893_1.txt," created on Apr. 28, 2017, and which is approximately 373 kilobytes in size.

TECHNICAL FIELD OF THE INVENTION

The following disclosure relates to a method named Tat-associated protein engineering (TAPE), of screening a target protein having a higher solubility and excellent thermostability, in particular, an immunoglobulin variable domain (VH or VL) derived from human germ-line, by fusing the target protein and an antibiotic-resistant protein to a Tat signal sequence and expressing this within E. coli. This invention also relates to human heavy chain variable domain antibody (hereinafter "VH domain antibody") and light chain variable domain antibody (hereinafter "VL domain antibody") and human, or engineered VH and VL domain antibody scaffolds having excellent solubility and thermostability, which are screened by the TAPE method. Also, the following disclosure relates to amino acid sequences of the VH and VL domain antibodies and the antibody scaffolds, and polynucleotides encoding the amino acid sequences.

In the case where the VH or VL domain antibody containing the human, or engineered VH or VL scaffold screened according to the present invention has a corresponding human, or engineered VH or VL domain antibody scaffold regardless of CDR sequences, it still retains solubility and thermostability.

Further, the following disclosure relates to a library including random CDR sequences in the human, or engineered VH or VL domain antibody scaffold screened by the TAPE method, and a preparing method thereof.

Further, the following disclosure relates to a VH or VL domain antibody having binding ability toward the target protein screened by using the library, an amino acid sequence of the domain antibody, and a polynucleotide encoding the amino acid sequence.

BACKGROUND OF THE INVENTION

A fragmented small-size antibody is a promising antibody capable of overcoming the limitations of the existing antibody therapeutics because of its physicochemical properties different from the full-length monoclonal antibody (mAb). There are a single chain antibody (scFv), a Fab (fragment antibody-binding) antibody, an immunoglobulin variable domain antibody such as VH or VL, and the like in general antibody fragments, and a tandem scFv, a diabody, a minibody, and the like in their modification forms (Better et al., Science 1988 240(4855):1041-3; Huston et al., Proc. Natl. Acad. Sci. USA. 1988 85(16):5879-83; Bird et al., Science 1988 242(4877):423-6; Pei et al., Proc. Natl. Acad. Sci. USA. 1997 94(18):9637-42; Iliades et al., FEBS Lett. 1997 409(3):437-41; Ward et al., Nature 1989 341(6242):544-6).

A antibody fragment or a small-size antibody mainly loses functions of Fc (crystallizable fragment) as compared with the full-length monoclonal antibody, and thus, there are no anticipated effects due to the existence of Fc, such as, an increased circulating half-life, an effector function, and the like.

However, the small-size fragmented antibody is being magnified as a next generation antibody capable of overcoming the limitations, such as limitations on accessibility to epitope structurally hidden, drug penetration and biodistribution, format flexibility, high production costs, and the like, which result from a large size of the existing whole antibody (Zhao et al., Blood 2007 110(7):2569-77; Holliger et al., Nat. Biotechnol. 2005 23(9):1126-36; Hudson et al., Med. Microbiol. Immunol. 2009 198(3):157-74; Enever et al., Curr. Opin. Biotechnol. 2009 20(4):405-11).

Furthermore, various kinds of antibody fragments and small-size antibodies have an advantage in that dual or multiple-specificity can be realized by connection in a chemical method or a recombinant protein fusion method.

Recently, this advantage has been utilized to introduce the multiple-specificity such that the Fc function is modularized, and thereby, supplementing the effector function and a short circulating half-life, which has been pointed out as disadvantages. For example, a fragment or a small-size antibody having binding specificity toward human serum albumin is introduced into a module to realize a dual-specificity antibody, thereby increasing the circulating half-life, or a small-size antibody having specific affinity to an immune cell, such as a natural killer or a T cell, is introduced into a module, thereby conferring a cell killing function thereto (Els et al., J Biol Chem. 2001 9; 276(10):7346-50; Bargou et al., Science 2008 321(5891):974-7; et al., Mol. Cancer Ther. 2008 7(8):2288-97). Also, since a single antibody can be designed to confer specificity to two or more molecules targets anticipating different action modes, the possibility that efficacy and economic feasibility of the antibody are significantly improved is opened.

A smallest unit of human antibody structure that has an antigen-specific binding function is a heavy chain variable domain (VH) or a light chain variable domain (VL), which is a variable domain positioned at the N-terminal of a light chain or a heavy chain. Since respective two N-terminals have been evolved to have a complementary structure, VH and VL constitute a non-covalent binding type complex in the procedure of assembling the heavy chain and the light chain when a monoclonal antibody is produced from a plasma B cell, and thereby maintain structural stability thereof. Human antibody variable domain VH segments are classified into 7 families (VH1, VH2, VH3, VH4, VH5, VH6, VH7) depending on the homology of amino acid sequences in a frame portion, excluding CDRs (complementarity determining regions) binding to epitope, and each family contains three to twenty-two kinds of distinct amino acid sequences. VLs of the light chain are divided into V kappa and V lamda, and V kappa is classified into six families and V lamda is classified into ten families (Chothia et al., 1992 J. Mol. Biol. 227, 799-917; Tomlinson et al., 1995 EMBO J. 14, 4628-4638; Williams et al., J. Mol. Biol. 264, 220-232). It has been known that a number of VH and VL have preferred VH/VL pairing combinations depending on the degree of mutual affinity, and thus, it has been known that this combinatorial rearrangement of genes has an important role in enlarging diversity of antibody repertoire (Ruud et al., J. Mol. Biol. 1999, 285, 895-901).

A bound type of VH/VL confers complementary binding specificity to a particular antigen according to combinations of 6 CDRs. CDR1 CDR2, and CDR3 of the light chain and CDR1 CDR2, and CDR3 of the heavy chain, which are a total of 6 CDRs, participate in binding to the antigen. According to analyses of human germ-line sequence, it was found that a variety of the respective CDRs mostly depend on CDR3 of the heavy chain variable domain. Therefore, this analysis implies that the binding specificity of an antibody mostly depends on variability of the heavy chain CDR3 (J. Mol. Recogni. 2000, 13, 167-187).

Unlike this, animals such as a camel and a llama and fish having a cartilage backbone such as a shark have antibodies of a single heavy chain structure without a light chain structure. Therefore, a variable domain of theses antibodies include only a single heavy chain variable domain ($V_{HH}$ and $V_{NAR}$ for camel and shark, respectively), and it is known that this antibody is no less competent than the human antibody where VH and VL simultaneously participate in binding to antigens, in view of binding to antigens and a neutralizing function. VH or VL alone is rarely present, except in human patients having heavy chain diseases (Hendershot et al., J. Cell. Biol. 1987 104(3):761-7; Prelli et al., J. Immunol. 1992 148(3): 949-52). The reason is that VH or VL is not structurally stable at the time of separation of VH or VL alone due to structural complementarity thereof, and thus, protein aggregation may easily occur. It is known that this protein aggregation partially results from hydrophobic interaction caused by distribution of hydrophobic amino acid residues mainly at an interface of VH and VL. In the case of camel antibody, amino acid residues having hydrophilicity may be specifically positioned on the surface of VH/VL border region, unlike human antibody. Particularly, amino acids at four sites of the camel antibody, which are specifically different from those of a human VH3 family, are called a tetrad. These amino acids are positioned at 37, 44, 45, and 47 in a Kabat numbering system (Kabat et al., 1991 J. Immunol. 147(5), 1709-1719). This difference in the amino acid sequence may explain stability of a single variable domain antibody (VHH). There was an attempt to produce improved, camelid antibodies by replacing amino acids at tetrad positions with hydrophilic amino acids of the camel antibody (G44E/L45R/W47G) in the human variable domain antibody.

As a result, solubility thereof may be somewhat improved in view of physical and chemical properties (Coppieters et al., Arthritis Rheum. 2006 54(6):1856-66; Dolk et al., Proteins. 2005 59(3):555-64; Ewert et al., Biochem. 2002 41(11):3628-36; Kortt et al., J. Protein Chem. 1995 14(3): 167-78; Martin et al., Protein Eng. 1997 10(5):607-14). However, stability thereof is difficult to obtain as compared with the camel antibody, for example, decreased protein expression yield and thermostability (Davies et al., FEBS Lett. 1994 Feb. 21; 339(3):285-90; Aires et al., J. Mol. Biol. 2004 340(3):525-42). It has been found that the reason therefor was that modification of amino acids at the VH/VL border region causes modification in a beta-sheet structure of the corresponding region (Riechmann et al., J. Mol. Biol. 1996 259(5):957-69). The CDR3 of the camel single domain antibody has an abnormally long loop structure as compared with the human antibody. According to structural analysis, it was found that this loop structure folds into the VH/VL border region of the human antibody, and it has been suggested that this distinct structure partially shields a hydrophobic patch positioned at the border region, thereby helping stabilization of the camel single domain antibody (Joost et al., 2010 Drug Discovery Today: Technologies 7(2), 139-146).

This shielding effect is hardly anticipated in the human antibody due to a relatively short loop structure of CDR3. In conclusion, the human single variable domain itself has deficient physical and chemical properties as compared with the camel single domain antibody, and thereby is not sufficient to be utilized as a scaffold of a binding ligand to a particular antigen. As the method for overcoming this, mere replacement of tetrad amino acids which are structural signatures of the camel antibody is not sufficient, and protein structure design and directed evolution of VH or VL are further needed.

A human immunoglobulin variable domain (VH or VL) that exists in nature is a minimum-size antibody (1/12 the size of monoclonal antibody) capable of maintaining an antigen binding characteristic, and thus, is anticipated to be different from the conventional monoclonal antibody in view of physical properties and therapeutic effects as a therapeutic protein. Hence, a demand for developing human antibodies having only one variable domain has increased. Nevertheless, aggregation and unstable tendency of protein when VH or VL alone exists still remain as major obstacles that should be overcome in developing a binding scaffold with respect to a specific antigen.

Accordingly, in order that an antibody fragment and a small-size antibody provide advantages that cannot be achieved by general monoclonal antibodies and stay competitive themselves, it is important to secure robust pharmaceutical and physicochemical properties of a substance itself.

Some molecular directed evolution methods have been attempted also in the prior art so as to stabilize human heavy chain or light chain variable domains (Barthelemy et al., J. Biol. Chem. 2008 283(6):3639-54). They constructed a phage display system with a CDR-engineered library of VH, and then screened VHs having binding activity toward the protein A after applying thermal stress. There was a report that CDR engineered human VH having increased solubility, and allowing reversible folding after protein thermal denaturation was screened by this method (Jespers et al., Nat. Biotechnol. 2004 22(9):1161-5). Also, there was a report that various libraries where mutations were induced at a CDR3 portion and a frame portion without thermal denaturation treatment were prepared, and VH exhibiting high binding activity toward protein A after phage display was screened by the same method, and thus, an engineered VH that is thermodynamically stable and has increased soluble expression as compared with a wild type VH can be obtained (Barthelemy et al., J Biol Chem. 2008 283(6):3639-54). In the phage display system, the target protein is induced to a Sec pathway by a Sec signal sequence of pelB protein fused to N-terminal of the target protein. However, in this case, the protein, which is previously folded within the cytoplasm of E. coli cannot pass through the pathway due to the limitation of an inherent translocation pathway of a protein. The reason is that a general phage display uses a Sec pathway, which is a representative protein translocation pathway of E. coli, and, due to the nature of this pathway, target protein has a linear structure not a three-dimensional structure with the help of chaperon within the cytoplasm when passing through a cell membrane. Sec pathway-specific proteins that naturally exist, distinctively in a linear form, without being folded, with the help of a chaperon called SecB within the cytoplasm, directly after protein transcription. The Sec pathway target protein, which is moved to a translocase complex, consisting of Sec A, SecYEG, and SecDFYajC existing on an intracellular membrane by Sec B, passes through the membrane in a linear form, without being in a three-dimensional structure, and the passed amino acid chain forms a complete three-dimensional structure, including a disulfide linkage, by oxidation and reduction of DsbA and DsbB until it arrives at the periplasm (Baneyx and Mujacic Nature Biotech. 2004, 22, 1399~1408). Therefore, if folding and three-dimensional structure formation of certain a protein quickly occurs in the cytoplasm due to the nature of the protein itself, this protein does not have compatibility with a phage display screening system designed to the Sec pathway.

In addition, it was reported that the wild type VH having improved physiochemical properties could be selected when clones are directly screened from a plate spread with bacterial lawn based on the size of a plaque size (To et al., J. Biol. Chem. 2005 280(50):41395-403). However, large-scale treatment is impossible by plate-based screening, and thus, in order to reduce the size of the library, an initial library for only the VH3 family subjected to a protein A screening procedure in vitro was manufactured.

Meanwhile, in order to improve folding characteristics of the recombinant protein, a genetic selection method was attempted (Maxwell et al., Protein Sci. 1999 8(9):1908-11; Wigley et al., Nat. Biotechnol. 2001 19(2):131-6; Cabantous et al., Nat Biotechnol. 2005 23(1):102-7; Waldo G S. Curr. Opin. Chem. Biol. 2003 7(1):33-8). One of the representative methods for improving folding characteristics of the recombinant protein is that the folding degree of a protein of interest is indirectly determined by measuring activity of a reporter protein fused to the protein of interest in a recombinant DNA technology. However, the folding cannot be accurately reflected when the protein of interest exists alone.

In addition, in order to increase solubility of the protein, there has been developed a molecular directed evolution method where a Tat (twin-arginine translocation) pathway, which is a protein tranlocation pathway having a function of proof-reading folding quality of proteins, is utilized as a biological filter of determining whether or not the protein is folded. Specifically, the protein of interest is fused to a reporter gene and a Tat signal sequence and expressed by the Tat pathway within *Escherichia coli*, and then is subjected to a protein folding proof-reading by a Tat ABC translocase complex according to folding degrees and solubility of the protein. If the target protein has sufficient solubility, a fusion protein consisting of the target protein and the reporter protein passes through an inner membrane of *Escherichia coli* and reaches the periplasm. The fusion protein reaching the periplasm is detected by a method such as antibiotic resistance measurement or the like, thereby screening proteins having a desired degree of solubility (Fisher et al., Protein Sci. 2006 15(3):449-58). It can be seen that, when the recombinant protein, not only a Tat pathway substrate protein in a natural system, is applied to the Tat pathway, but it also significantly passes through the Tat pathway in proportional to solubility and stability of recombinant proteins (Lim et al., Protein Sci. 2009 18(12):2537-49). In addition, it has been reported that a single chain antibody (scFv) allowing protein folding within the cytoplasm of *E. coli* is effectively screened by using the Tat pathway (Fisher A C and DeLisa M P. J Mol Biol. 2009 385(1): 299-311). According to the above document, molecular directed evolution was completely achieved in vitro by using scFv13 that is insoluble in and expressed in *E. coli* as a template base sequence. A disulfide bond presents within scFv has a level of about 4 to 6 kcal/mol, and contributes to stabilization of protein molecules. This bond is formed in an oxidizing environment such as the periplasm of bacteria or the endoplasmic recticulum (ER) of eukaryote. The periplasm of bacteria usually maintains oxidation conditions through the flow of electrons between DsbA and DsbB present on an inner membrane. Therefore, in the case of scFv13 protein selected from the scFv-engineered library by artificially passing through the Tat pathway, intrabodies, which are autonomously self-folded without forming a disulfide bond within reduction conditional cytoplasm but not oxidation conditional cytoplasm, are preferentially selected. Specifically, when a gene where a signal sequence leading the protein to the Tat pathway is fused to N-terminal of the target protein and TEM-1 beta-lactamase is fused to a C-terminal of the target protein, for functioning as a reporter gene, is expressed within *E. coli*, a triple-function fusion protein (tripartite) is expressed.

The expressed fusion protein heads for the Tat pathway, and is subjected to a protein folding inspection by machinery of a Tat ABC translocase complex existing on the inner cell membrane. Several studies found that, among many recombinant proteins, only those having solubility keeps compatibility with specific machineries of the Tat pathway (Sanders et al., Mol. Microbiol. 2001 41(1):241-6; DeLisa et al., Proc. Natl. Acad. Sci. USA. 2003 100(10):6115-20; Matos et al., EMBO J. 2008 27(15):2055-63; Fisher A C and DeLisa M P. J. Mol. Biol. 2009 385(1): 299-311; Lim et al., Protein Sci. 2009 18(12): 2537-49).

However, the above method for improving the folding characteristics of protein has been never applied in selecting domain antibodies, particularly, VH or VL domain antibodies or the like.

In conclusion, presently, engineered modification and screening of human VH domain antibody were unexceptionally conducted based on phage display and binding activity to protein A (Kristensen P and Winter G. Fold. Des. 1998 3(5):321-8; Sieber et al., Nat. Biotechnol. 1998 16(10): 955-60; Jung et al., J. Mol. Biol. 1999 294(1):163-80; Wörn A and Plückthun A. J. Mol. Biol. 2001 305(5): 989-1010).

Therefore, methods of selecting VH domain antibodies having more efficient solubility and high thermostability are desperately in need of development, and further, the smallest unit next generation antibodies having improved efficacy by utilizing the selected domain antibodies are promptly in need of development.

SUMMARY OF THE INVENTION

An embodiment of the present invention is directed to providing a method named Tat-associated protein engineering (TAPE), capable of efficiently screening a VH or VL domain antibody having solubility and high thermostability.

Further, an embodiment of the present invention is directed to providing human VH and VL domain antibodies and human or engineered VH and VL domain antibody scaffolds, that have solubility and excellent thermostability, which are screened by the TAPE method, and providing amino acid sequences of the VH and VL domain antibodies and the antibody scaffolds, and polynucleotides encoding the same.

In the case where the VH or VL domain antibody containing the human or engineered VH or VL scaffold screened according to the present invention has a corresponding human or engineered VH or VL domain antibody scaffold regardless of CDR sequences, it still retains solubility and thermostability.

Further, an embodiment of the present invention is directed to providing a library including random CDR sequences in the human VH or VL domain antibody scaffold screened by the TAPE method, and a preparing method thereof.

Further, an embodiment of the present invention is directed to providing a VH or VL domain antibody having binding ability to the target protein screened by using the library, an amino acid sequence of the domain antibody, and a polynucleotide encoding the same.

DETAILED DESCRIPTION OF THE INVENTION

In one general aspect, the present invention provides a method named Tat-associated protein engineering (TAPE), capable of efficiently screening ligands, particularly, VH and VL domain antibodies having high solubility and high thermostability from human immunoglobulin variable domain libraries or combinatorial libraries.

Also, the present invention provides a system, a vector, and a host cell for screening the ligands, and provides the ligands screened by the TAPE method, particularly VH and VL domain antibodies.

Surprisingly, it was found that the VH domain antibody screened by the TAPE method according to the present invention has high solubility and thermostability, as well as maintains high solubility and thermostability regardless of sequences of CDRs that are inserted, that is, sequences of CDR1 to CDR3, as long as a VH domain antibody scaffold, that is, FR1 to FR4 frames are maintained.

From this point of view, the present invention provides a VH domain antibody library where randomized human-derived or combinatorial CDR sequences, that is, sequences of CDR1 to CDR3, are inserted in the VH domain antibody scaffold, that is, FR1 to FR4 frames, screened by the TAPE method of the present invention, and a method of constructing the same.

In addition, the present invention provides a method of screening VH domain antibodies having binding ability to target proteins from the constructed library.

The VH domain antibody scaffold, that is, FR1 to FR4 frames, having high solubility and thermostability provided in the present invention have amino acid sequences below:

Amino Acid Sequence of FR1:

$$X_0VQLX_1X_2X_3GX_4X_5X_6X_7X_8PGX_9SX_{10}X_{11}X_{12}X_{13}CX_{14}X_{15}X_{16}GX_{17}X_{18}X_{19}$$ (SEQ ID NO: 144)

wherein,
$X_0$ is E or Q,
$X_1$ is V or L,
$X_2$ is E or Q,
$X_3$ is S or A,
$X_4$ is G or A,
$X_5$ is G, M, N, V, or E,
$X_6$ is L, V, or W,
$X_7$ is V, K, A, or I,
$X_8$ is Q, K, or H,
$X_9$ is G, T, A, R, E, S, or T,
$X_{10}$ is L, V, R, or M,
$X_{11}$ is R or K,
$X_{12}$ is L, I, or V,
$X_{13}$ is S, A, or T,
$X_{14}$ is A, E, V, R, I, K, T, or S,
$X_{15}$ is A, G, P, V, or T,
$X_{16}$ is S, F, or Y,
$X_{17}$ is F, Y, R, G, or L,
$X_{18}$ is T, A, S, N, T, P, I, N, H, or A, and
$X_{19}$ is F, L, V, or C;

Amino Acid Sequence of FR2:

$$WX_{20}RX_{21}X_{22}PGX_{23}GX_{24}X_{25}X_{26}X_{27}X_{28}$$ (SEQ ID NO: 145)

wherein,
$X_{20}$ is V, A, or L,
$X_{21}$ is Q, N, R, I, K, Y, V, M, S, Q, W, F, L, V, or C,
$X_{22}$ is A, G, K, S, V, M, or T,
$X_{23}$ is K, Q, E, R, or T,
$X_{24}$ is L, N, I, P, Y, T, V, W, A, R, M, or S,
$X_{25}$ is V or E,
$X_{26}$ is W, I, V, P, F, H, M, Y, L, C, or R,
$X_{27}$ is V, M, I, or L, and
$X_{28}$ is S, A, or G;

Amino Acid Sequence of FR3:

$$X_{29}X_{30}X_{31}X_{32}X_{33}X_{34}X_{35}X_{36}X_{37}X_{38}X_{39}X_{40}X_{41}X_{42}X_{43}X_{44}X_4X_{46}X_{47}X_{48}X_{49}X_{50}X_{51}DX_{52}X_{53}X_{54}YX_{55}CX_{56}X_{57}$$ (SEQ ID NO: 146)

wherein,
$X_{29}$ is R, H, Q, or T,
$X_{30}$ is F, V, L, or I,
$X_{31}$ is T, S, or I,
$X_{32}$ is I, L, V, M, or R,
$X_{33}$ is S, T, or D,
$X_{34}$ is R, A, V, N, or I,
$X_{35}$ is D, N, or A,
$X_{36}$ is N, T, D, I, R, K, Y, or E,
$X_{37}$ is A, S, V, or T,
$X_{38}$ is K, R, T, Q, V, E, M, N, or I,
$X_{39}$ is N, R, T, K, S, D, or V,
$X_{40}$ is T, M, S, V, I, Y, or A,
$X_{41}$ is L, V, A, or M,
$X_{42}$ is F, Y, N, D, H, or S,
$X_{43}$ is L or M,
$X_{44}$ is Q, E, H, or N,
$X_{45}$ is M, L, V, I, or W,
$X_{46}$ is N, T, K, D, Y, I, or S,
$X_{47}$ is S or N,
$X_{48}$ is L or V,
$X_{49}$ is R, K, or T,
$X_{50}$ is D, A, S, P, T, V, I, or S,
$X_{51}$ is E, A, D, or S,
$X_{52}$ is T, N, or S,
$X_{53}$ is S, A, or G,
$X_{54}$ is V, I, L, or M,
$X_{55}$ is Y or F,
$X_{56}$ is A, G, V, or S, and
$X_{57}$ is R, S, K, T, L, N, or F; and Amino Acid Sequence of FR4:

$$X_{58}GX_{59}GX_{60}X_{61}VTVSS$$ (SEQ ID NO: 147)

wherein,
$X_{58}$ is W, C, Y, G, S, or A,
$X_{59}$ is Q, R, or L,
$X_{60}$ is A, T, I, or V, and
$X_{61}$ is L, M, P, V, or T.

Also, the present invention provides a polynucleotide encoding an amino acid sequence of the VH domain antibody scaffold, that is, amino acid sequences of FR1 to FR4 frames.

More preferably, the VH domain antibody scaffold, that is, FR1 to FR4 frames, having high solubility and thermostability provided in the present invention have amino acid sequences below:

Amino Acid Sequence of FR1:

$$X_0VQLX_1X_2SGGX_5X_6X_7X_8PGX_9SX_{10}RX_{12}SCX_{14}X_{15}SGX_{17}X_{18}X_{19}$$ (SEQ ID NO: 148)

wherein,
X₀ is E or Q,
X₁ is V or L,
X₂ is E or Q,
X₅ is G, N, V, or E,
X₆ is L or V,
X₇ is V or K,
X₈ is Q, K, or H,
X₉ is G, T, A, R, E, or T,
X₁₀ is L or V,
X₁₂ is L or V,
X₁₄ is A, E, V, I, K, or S,
X₁₅ is A, G, or V,
X₁₇ is F, Y, R, G, or L,
X₁₈ is T, A, S, N, T, P, I, N, H, or A, and
X₁₉ is F, L, V, or C;
Amino Acid Sequence of FR2:

$$WVRX_{21}X_{22}PGX_{23}GX_{24}X_{25}X_{26}X_{27}X_{28} \quad (SEQ\ ID\ NO:\ 149)$$

wherein,
X₂₁ is Q, N, R, I, K, Y, V, M, S, Q, W, F, L, V, or C,
X₂₂ is A, G, K, S, or M,
X₂₃ is K, Q, E, R, or T,
X₂₄ is L, N, I, P, Y, T, V, W, A, R, M, or S,
X₂₅ is V or E,
X₂₆ is W, I, V, P, F, H, M, Y, L, C, or R,
X₂₇ is V, M, I, or L, and
X₂₈ is S, A, or G;
Amino Acid Sequence of FR3:

$$RX_{30}TX_{32}SX_{34}DX_{36}X_{37}X_{38}X_{39}X_{40}X_{41}X_{42}X_{43}$$
$$X_{44}X_{45}X_{46}X_{47}X_{48}X_{49}X_{50}X_{51}DTAX_{54}$$
$$YX_{55}CX_{56}X_{57} \quad (SEQ\ ID\ NO:\ 150)$$

wherein,
X₃₀ is F, V, L, or I,
X₃₂ is I, L, V, or M,
X₃₄ is R, A, V, or I,
X₃₆ is N, T, D, I, R, K, Y, or E,
X₃₇ is A, S, V, or T,
X₃₈ is K, R, T, Q, V, E, M, N, or I,
X₃₉ is N, R, T, K, S, D, or V,
X₄₀ is T, M, S, V, I, Y, or A,
X₄₁ is L, V, A, or M,
X₄₂ is F, Y, N, D, H, or S
X₄₃ is L or M,
X₄₄ is Q, E, H, or N,
X₄₅ is M, L, V, I, or W,
X₄₆ is N, T, K, D, Y, I, or S,
X₄₇ is S or N,
X₄₈ is L or V,
X₄₉ is R, K, or T,
X₅₀ is D, A, S, P, T, V, I, or S,
X₅₁ is E, A, D, or S,
X₅₄ is V, I, L, or M,
X₅₅ is Y or F,
X₅₆ is A, G, V, or S, and
X₅₇ is R, S, K, T, L, N, or F; and
Amino Acid Sequence of FR4:

$$X_{58}GQGX_{60}X_{61}VTVSS \quad (SEQ\ ID\ NO:\ 151)$$

wherein,
X₅₈ is W, C, Y, G, S, or A,
X₆₀ is A, T, I, or V, and
X₆₁ is L, M, V, or T.

Also, the present invention provides a polynucleotide encoding an amino acid sequence of the heavy chain variable domain (VH) antibody scaffold, that is, amino acid sequences of FR1 to FR4 frames.

More preferably, the VH domain antibody scaffold, that is, FR1 to FR4 frames, having high solubility and thermostability provided in the present invention have amino acid sequences described in Table 1.

TABLE 1

Amino acid sequences of FR1 to FR4 frames of VH antibody scaffold screened by TAPE (derived from human germline)

| Scaffold name | FR1 | FR2 | FR3 | FR4 |
|---|---|---|---|---|
| MG1X8 | QVQLVESGGGLVQPGGSL RLSCAASGFTF (SEQ ID NO: 152) | WVRQAPGKGLVWVS (SEQ ID NO: 205) | RFTISRDNAKNTLFLQMN SLRDEDTSVYYCAR (SEQ ID NO: 258) | WGQGALVTVSS (SEQ ID NO: 311) |
| MG2X1 | EVQLVESGGGLVQPGGSL RLSCAASGFTF (SEQ ID NO: 153) | WVRQAPGKGLEWVS (SEQ ID NO: 206) | RFTISRDNSKNTLYLQMN SLRAEDTAVYYCAS (SEQ ID NO: 259) | WGQGTLVTVSS (SEQ ID NO: 312) |
| MG2X1-34 | QVQLVESGGNVVQPGTSL RLSCAASGFTF (SEQ ID NO: 154) | WVRQAPGKGLEWLA (SEQ ID NO: 207) | RFTISRDNSRNTVFLQMT SLRAEDTAVYYCGR (SEQ ID NO: 260) | WGQGILVTVSS (SEQ ID NO: 313) |
| MG2X2-12 | QVQLVQSGAEVKKPGASV KISCEASGYAF (SEQ ID NO: 155) | WVRQAPGQGLEWMG (SEQ ID NO: 208) | RVTLTRDTSTRTVYMELK NLRSADTGVYYCAR (SEQ ID NO: 261) | WGQGTLVTVSS (SEQ ID NO: 314) |
| MG2X2-13 | EVQLLESGGGVVQPGKSL RLSCVGSGFSF (SEQ ID NO: 156) | WVRQAPGKGLEWLA (SEQ ID NO: 209) | RFTISRDNSKTMVNLQMN SLRPDDTAVYFCAR (SEQ ID NO: 262) | WGQGTLVTVSS (SEQ ID NO: 315) |
| MG3X1 | QVQLVESGGGVVQPGRSL RLSCVASGFNF (SEQ ID NO: 157) | WLRQAPGKGLEWLA (SEQ ID NO: 210) | RFTISRDNSKNTLYLEMN SLRPEDTAVYYCAK (SEQ ID NO: 263) | CGQGTLVTVSS (SEQ ID NO: 316) |
| MG3X10 | EVQLVESGGGLVKPGGSL RVSCAASGFTF (SEQ ID NO: 158) | WVRQAPGKGLEWMG (SEQ ID NO: 211) | RFTISRDDSKNMVYLQMN SLKTEDTAVYYCTT (SEQ ID NO: 264) | YGQGTLVTVSS (SEQ ID NO: 317) |

TABLE 1-continued

Amino acid sequences of FR1 to FR4 frames of VH antibody
scaffold screened by TAPE (derived from human germline)

| Scaffold name | FR1 | FR2 | FR3 | FR4 |
|---|---|---|---|---|
| MG4X1-8 | EVQLVESGGGLVQPGGSL RLSCAASGFSF (SEQ ID NO: 159) | WVRQGPGEGLVWLS (SEQ ID NO: 212) | RFTISRDNAKNTVYLEMN SVRVDDTAVYYCVS (SEQ ID NO: 265) | WGQGALVTVSS (SEQ ID NO: 318) |
| MG4X1-33 | QVQLVESGGGLVQPGGSL RLSCEASGFPF (SEQ ID NO: 160) | WVRQAPGKGLEWIS (SEQ ID NO: 213) | RFTISRDDSTNTLYLQVN SLRAEDTAVYYCAK (SEQ ID NO: 266) | WGRGTLVTVSS (SEQ ID NO: 319) |
| MG4X1-35 | EVQLLESGGGLVKPGGSL RLSCVGSERSF (SEQ ID NO: 161) | WVRQAPGKGLEWVA (SEQ ID NO: 214) | RFTVSRDNVQKSLDLQMD SLRAEDTAVYFCAR (SEQ ID NO: 267) | WGQGTTVTVSS (SEQ ID NO: 320) |
| MG4X3-27 | EVQLLESGGGLAQSGGSL RLSCAASGFTF (SEQ ID NO: 162) | WVRQAPGKGLEWIS (SEQ ID NO: 215) | RFTISRDIAKNSLYLQMN SLRDEDTAVYYCAK (SEQ ID NO: 268) | WGQGALVTVSS (SEQ ID NO: 321) |
| MG4X4-2 | EVQLVQSGAEVKKPGESL RISCRGSGYRF (SEQ ID NO: 163) | WARDKPGKGLEWIG (SEQ ID NO: 216) | HVTISSDRSVSVAYLQWD SLKASDNGIYYCAL (SEQ ID NO: 269) | WGQGTLVTVSS (SEQ ID NO: 322) |
| MG4X4-4 | EVQLVESGGGLVQPGGSL RLSCVPSGFTF (SEQ ID NO: 164) | WVRQAPGKGLVWLS (SEQ ID NO: 217) | RFTISRDNAEDTLFLQMN SLRVDDTAVYYCVR (SEQ ID NO: 270) | WGQGVLVTVSS (SEQ ID NO: 323) |
| MG4X4-25 | QVQLVESGGGLVQPGGSL RLSCIASGFSL (SEQ ID NO: 165) | WVRRSPGKGLEWVA (SEQ ID NO: 218) | RFTVSRDNAKNSLFLQMN NVRPEDTALYFCAR (SEQ ID NO: 271) | WGQGTMVTVSS (SEQ ID NO: 324) |
| MG4X4-44 | EVQLVESGGGLVQPGGSL RLSCAASGFTF (SEQ ID NO: 166) | WVRQAPGKGLEWVA (SEQ ID NO: 219) | RFTISRDNAKNSLYLQMN SLRAEDTALYYCAR (SEQ ID NO: 272) | WGQGTLVTVSS (SEQ ID NO: 325) |
| MG4X5-30 | EVQLLESGGGLVQPGGSL RLSCAASGFTF (SEQ ID NO: 167) | WVRQAPGKGLEWLS (SEQ ID NO: 220) | RFTISRNNAKNSLYLQMN SLRVDDTAVYYCAR (SEQ ID NO: 273) | WGQGTLVTVSSS (SEQ ID NO: 326) |
| MG4X6-27 | EVQLLESGGGLVQPGGSL RLSCAASGFTF (SEQ ID NO: 168) | WVRQGPGKGLEWVA (SEQ ID NO: 221) | RFTISRDNAENSLYLQVN SLRAEDTAIYYCAK (SEQ ID NO: 274) | WGQGALVTVSS (SEQ ID NO: 327) |
| MG4X6-48 | EVQLLESGGGVVQPGRSL RLSCEVFGFTL (SEQ ID NO: 169) | WVRQAPGRRLEWVA (SEQ ID NO: 222) | RFTISRDIATNRLYLQMR SLRAEDTALYYCAR (SEQ ID NO: 275) | WGQGTLVTVSS (SEQ ID NO: 328) |
| MG4X7-15 | EVQLLESGGGLVQPGGSL RLSCAASGFSF (SEQ ID NO: 170) | WVRQAPGKGLEWIS (SEQ ID NO: 223) | RFTISRDNSKNTLYLQMN SLRVEDTAVYYCAV (SEQ ID NO: 276) | WGQGTTVTVSS (SEQ ID NO: 329) |
| MG4X8-24 | EVQLLESGGGLVQPGGSL RLSCAASGFTF (SEQ ID NO: 171) | WVRQAPGKGLEWIS (SEQ ID NO: 224) | RFTISRDNSNNTLYLQMN SLRADDTAVYFCAK (SEQ ID NO: 277) | WGQGTLVTVSS (SEQ ID NO: 330) |
| MG0.5X-1 | QVQLVESGGGLVQPGGSL RLSCAASGFTF (SEQ ID NO: 172) | WVRQVPGKGLEWVA (SEQ ID NO: 225) | RFTISRDNAKNSLYLQMN SLRAEDTAVYYCAN (SEQ ID NO: 278) | WGQGTLVTVSS (SEQ ID NO: 331) |
| MG0.5X-3 | QVQLVESGGGLVQPGGSL TLSCAASGFTF (SEQ ID NO: 173) | WVRQAPGTGLLWLS (SEQ ID NO: 226) | RFTISRDNSKNTLYLQMN SLRAEDTAVYYCAR (SEQ ID NO: 279) | WGXGTMVTVSX (SEQ ID NO: 332) |
| MG0.5X-4 | EVQLLESGGMLVKPGESL RLSCVGSGLIF (SEQ ID NO: 174) | WVRHAPGKGLEWMG (SEQ ID NO: 227) | RLSISRDDSMNTVYLDIY NLKIDDTGVYYCTF (SEQ ID NO: 280) | WGQGTPVTVSS (SEQ ID NO: 333) |
| MG0.5X-14 | EVQLLESGGGLVHAGGSV RLSCAASGFTF (SEQ ID NO: 175) | WVRQAPGKGLEWVA (SEQ ID NO: 228) | RFTISRDNSKNSMYLQMN SLRVEDTAVYYCAR (SEQ ID NO: 281) | WGQGTVVTVSS (SEQ ID NO: 334) |
| MG0.75X-4 | QVQLVESGGGLVKPGGSL RLSCAASGFTF (SEQ ID NO: 176) | WLRQAPGKGPEYVA (SEQ ID NO: 229) | RFIISRDDSNDMLYLEMI SLKSEDTAVYYCSD (SEQ ID NO: 282) | GSQGTLVTVSS (SEQ ID NO: 335) |

TABLE 1-continued

Amino acid sequences of FR1 to FR4 frames of VH antibody scaffold screened by TAPE (derived from human germline)

| Scaffold name | FR1 | FR2 | FR3 | FR4 |
|---|---|---|---|---|
| MG2X-5 | EVQLLESGGGLVQPGGSL RLSCAASGFTF (SEQ ID NO: 177) | WVRQAPGKGLEWVS (SEQ ID NO: 230) | RFTISRDNSKNTLYLHMN SLRAEDTAVYYCVK (SEQ ID NO: 283) | WGQGTLVTVSS (SEQ ID NO: 336) |
| MG2X-15 | QVQLVESGGGLVQPGGSL RLSCAASGFTF (SEQ ID NO: 178) | WVRQAPGKGLEWVS (SEQ ID NO: 231) | RFTISRDNSKNTLYLQMN SLRAEDTAVYYCAK (SEQ ID NO: 284) | WGQGTLVTVSS (SEQ ID NO: 337) |
| MG4X-5 | QVQLVESGGGLVQPGGSL RLSCEASGLHF (SEQ ID NO: 179) | WVRQAPGKGLEWVA (SEQ ID NO: 232) | RFTVSRDNSRNTLYLQMK SLSAEDTAVYYCAK (SEQ ID NO: 285) | WGQGTMVTVSS (SEQ ID NO: 338) |
| MG1-4 | QVQLVEAGGGLVQPGGSL RLACAASGFTF (SEQ ID NO: 180) | WVRQAPGKGLEWIS (SEQ ID NO: 233) | RFTISRDNSQNSLFLQMN SLRAEDTAVYYCAT (SEQ ID NO: 286) | WGQGTMVTVSS (SEQ ID NO: 339) |
| MG1-6 | EVQLVQSGAEVKKPGESL RKSCKGSGYSF (SEQ ID NO: 181) | WVRQMPGKGLEWMG (SEQ ID NO: 234) | HVTISVDKSISTAYLQWS SLKASDSAMYYFL (SEQ ID NO: 287) | WGQGTLVTVSS (SEQ ID NO: 340) |
| MG1-7 | QVQLVESGGGLVQPGGSL RLSCAASGFTF (SEQ ID NO: 182) | WVRQAPGKGLEWVA (SEQ ID NO: 235) | RFTISRDNAKNSLYLQMN SLRDEDTAVYYCAR (SEQ ID NO: 288) | WGQGTLVTVSS (SEQ ID NO: 341) |
| MG1-8 | EVQLVQSGAEVKKPGASV KVSCKASGYTF (SEQ ID NO: 183) | WVRQAPGQGLEWMG (SEQ ID NO: 236) | RVTMTRDTSSTAYMELN RLTSDDTAVYFCAR (SEQ ID NO: 289) | WGQGTLVTVSS (SEQ ID NO: 342) |
| MG1-9 | EVQLVEAGGGLVQPGGSL RLSCAASGFTF (SEQ ID NO: 184) | WVRQAPGKGLEWIS (SEQ ID NO: 237) | RFTISRDNAQNSLFLQMN SLRAEDTAVYYCAT (SEQ ID NO: 290) | WGQGTMVTVSS (SEQ ID NO: 343) |
| MG1-10 | EVQLVQSGAEVKKPGESL KISCKGSGYSF (SEQ ID NO: 185) | WVRQMPGRGLEWLG (SEQ ID NO: 238) | QVTMSANRSISTAYLQWS SLKASDTGIYYCAT (SEQ ID NO: 291) | WGQGTTVTVSS (SEQ ID NO: 344) |
| MG5-1 | QVQLVESGGGLIQPGESL RLSCEAFGFTV (SEQ ID NO: 186) | WVRQAPGKGLEWVS (SEQ ID NO: 239) | RFTISRDSTQNTVHLQMN SLTAEDTAVYYCAR (SEQ ID NO: 292) | WGQGTLVTVSS (SEQ ID NO: 345) |
| MG5-2 | EVQLVQSGAELKKPGSSV KVSCTSSGGSF (SEQ ID NO: 187) | WVRQAPGQGLEWMG (SEQ ID NO: 240) | RLILSVDEPTRTVYMELT SLRSDDTAMYYCAR (SEQ ID NO: 293) | WGQGTTVTVSS (SEQ ID NO: 346) |
| MG5-4 | EVQLLESGGGLVQPGRSL RLSCAASGFTF (SEQ ID NO: 188) | WVRQAPGKGLEWVS (SEQ ID NO: 241) | RFTISRDNAKDSLYLQMN SLRPEDTALYYCAR (SEQ ID NO: 294) | WGQGTMVTVSS (SEQ ID NO: 347) |
| MG5-5 | EVQLLESGGGVVQPGRSL RLSCVASGFTF (SEQ ID NO: 189) | WVRQAPGKGLEWVS (SEQ ID NO: 242) | RFTISRDYSNKIVHLEMD SLRAEDTAVYFCVR (SEQ ID NO: 295) | WGQGTLVTVSS (SEQ ID NO: 348) |
| MG5-6 | EVQLLESGGGLVKPGGSL RLSCAASGFTF (SEQ ID NO: 190) | WVRQAPGKGLECVA (SEQ ID NO: 243) | RFTISRDDSRDMLYLQMN NLKTEDTAVYYCSD (SEQ ID NO: 296) | SSQGTLVTVSS (SEQ ID NO: 349) |
| MG5-7 | EVQLVESGGGLVQPGRSL RLSCTTSGFSF (SEQ ID NO: 191) | WVRQAPGKGLEWVS (SEQ ID NO: 244) | RFTISRDDSKSIVYLQMS SLQTEDTAVYYCSR (SEQ ID NO: 297) | WGRGTLVTVSS (SEQ ID NO: 350) |
| MG5-9 | EVQLLESGGGLVRPGGSL RLSCSASGFAF (SEQ ID NO: 192) | WVRQAPGKGLEWVS (SEQ ID NO: 245) | TISRDNAKNSVYLQMNSL RAEDSAVYFCAR (SEQ ID NO: 298) | WGQGTLVTVSS (SEQ ID NO: 351) |
| MG10-1 | QVQLVESGGNVVQPGTSL RLSCAASGFTF (SEQ ID NO: 193) | WVRQAPGKGLEWVA (SEQ ID NO: 246) | RFTISRDNSRNTVFLQMT SLRAEDTAVYYCGR (SEQ ID NO: 299) | WGQGILVTVSS (SEQ ID NO: 352) |
| MG10-2 | EVQLLESGGGLVQPGGSL RLTCVGYGFTF (SEQ ID NO: 194) | WVRQAPGKGPEWVA (SEQ ID NO: 247) | RFTISRDNAKDSLYLQMD SLRPEDTAVYYCAR (SEQ ID NO: 300) | APQGTLVTVSS (SEQ ID NO: 353) |

TABLE 1-continued

Amino acid sequences of FR1 to FR4 frames of VH antibody
scaffold screened by TAPE (derived from human germline)

| Scaffold name | FR1 | FR2 | FR3 | FR4 |
|---|---|---|---|---|
| MG10-4 | EVQLLESGGGLVQPGGSL RLSCAASGFIL (SEQ ID NO: 195) | WVRQAPGKGLVWVS (SEQ ID NO: 248) | QFTISRDNAKNTLYLQMN SLRVEDTAVYYCAR (SEQ ID NO: 301) | WGQGTMVTVSS (SEQ ID NO: 354) |
| MG10-5 | EVQLLESGGGVVHPGRSL RLSCAVSGFSL (SEQ ID NO: 196) | WVRQAPDKGLEWLA (SEQ ID NO: 249) | RFTVSRDISKNTVYLQMN SLRAEDTALYYCAR (SEQ ID NO: 302) | WGQGTMVTVSS (SEQ ID NO: 355) |
| MG10-6 | EVQLLESGGGLVQPGGSR RLSCAASGFTF (SEQ ID NO: 197) | WFRQGPGKGLEWLA (SEQ ID NO: 250) | RFTISRDDSKNSLSLQMD SLRTEDTAVYYCVR (SEQ ID NO: 303) | WGQGTVVTVSS (SEQ ID NO: 356) |
| MG10-8 | QVQLVESGGGVVQPGRSL RLSCVASGPAF (SEQ ID NO: 198) | WVRQTPGRGLEWLA (SEQ ID NO: 251) | RFTISRDNSNNTVYLEMN SLRPEDSAIYYCAK (SEQ ID NO: 304) | WGLGTVVTVSS (SEQ ID NO: 357) |
| MG10-10 | QVQLVESGGVVVQPGGSL RLSCAASGFTF (SEQ ID NO: 199) | WVRQAPGKGLEWVS (SEQ ID NO: 252) | RFTISRDNSKNSLYLQMN SLRTDETALYYCV (SEQ ID NO: 305) | WGQGTLVTVSS (SEQ ID NO: 358) |
| MG2 | EVQLLESGGGLVQPGGSL RLSCAASGFTF (SEQ ID NO: 200) | WVRQAPGKGLEWVS (SEQ ID NO: 253) | RFTISRDNAKNSLYLQMN SLRTDETAVYYCAR (SEQ ID NO: 306) | WGQGTTVTVSS (SEQ ID NO: 359) |
| M5G | EVQLLQSGGGWVKPGGSL RLSCAASGFIC (SEQ ID NO: 201) | WVRQAPGKGLEWMG (SEQ ID NO: 254) | RFTISIDESRNALFLHMN SLTTDDTAVYYCST (SEQ ID NO: 307) | WGQGTLVTVSS (SEQ ID NO: 360) |
| MG6 | EVQLLESGGGVVVQPGRSL RLSCAASGFTF (SEQ ID NO: 202) | WVRQAPGKGLEWLA (SEQ ID NO: 255) | RFTVSRDTSTNTLYLQMN SLRVEDTAVYYCAR (SEQ ID NO: 308) | WGQGTLVTVSS (SEQ ID NO: 361) |
| MG7 | QMQLVQSEAEVKKPGASM KVSCKASGYTF (SEQ ID NO: 203) | WVRQATGQGLEWMG (SEQ ID NO: 256) | RVTMTRNTSISTAYMELS SLTSADTAVYYCAR (SEQ ID NO: 309) | WGQGTLVTVSS (SEQ ID NO: 362) |
| MG10 | QVQLVQSGAEVKKPGESL KISCKGSGYSF (SEQ ID NO: 204) | WVRQMPGKLEWMGG (SEQ ID NO: 257) | QVTISADKSISTAFLQWN SLKASDTAMYYCAR (SEQ ID NO: 310) | WGLGTLVTVSS (SEQ ID NO: 363) |

Also, the present invention provides a polynucleotide encoding an amino acid sequence of the VH domain antibody scaffold, that is, amino acid sequences of FR1 to FR4 frames.

In particular, a VH domain antibody scaffold, that is, FR1 to FR4 frames, which are improved through modification of a part of the amino acid sequence of the frame, have amino acid sequences described in Table 2.

TABLE 2

Amino acid sequences of FR1 to FR4 frames of amino acid-
modified VH domain antibody scaffold

| Scaffold name | FR1 | FR2 | FR3 | FR4 |
|---|---|---|---|---|
| MG8-21 | EVQLVESGGGLVQPGG SLRLSCAASGFTF (SEQ ID NO: 364) | WVRNAPGKGNEIVS (SEQ ID NO: 406) | RFTISRDNSKNTLYLQMN SLRAEDTAVYYCAS (SEQ ID NO: 448) | WGQGTLVTVSS (SEQ ID NO: 490) |
| MG2-12L | EVQLVESGGGLVQPGG SLRLSCAASGFTF (SEQ ID NO: 365) | WVRRAPGKGIEVVS (SEQ ID NO: 407) | RFTISRDNSKNTLYLQMN SLRAEDTAVYYCAS (SEQ ID NO: 449) | WGQGTLVTVSS (SEQ ID NO: 491) |
| MG2-7I | EVQLVESGGGLVQPGG SLRLSCAASGFTF (SEQ ID NO: 366) | WVRIAPGKGPEPVS (SEQ ID NO: 408) | RFTISRDNSKNTLYLQMN SLRAEDTAVYYCAS (SEQ ID NO: 450) | WGQGTLVTVSS (SEQ ID NO: 492) |
| MG2-9I | EVQLVESGGGLVQPGG SLRLSCAASGFTF (SEQ ID NO: 367) | WVRKAPGKGYEPVS (SEQ ID NO: 409) | RFTISRDNSKNTLYLQMN SLRAEDTAVYYCAS (SEQ ID NO: 451) | WGQGTLVTVSS (SEQ ID NO: 493) |

TABLE 2-continued

Amino acid sequences of FR1 to FR4 frames of amino acid-modified VH domain antibody scaffold

| Scaffold name | FR1 | FR2 | FR3 | FR4 |
|---|---|---|---|---|
| MG2-10I | EVQLVESGGGLVQPGG SLRLSCAASGFTF (SEQ ID NO: 368) | WVRNAPGKGYEIVS (SEQ ID NO: 410) | RFTISRDNSKNTLYLQMN SLRAEDTAVYYCAS (SEQ ID NO: 452) | WGQGTLVTVSS (SEQ ID NO: 494) |
| MG2-11I | EVQLVESGGGLVQPGG SLRLSCAASGFTF (SEQ ID NO: 369) | WVRYAPGKGYEFVS (SEQ ID NO: 411) | RFTISRDNSKNTLYLQMN SLRAEDTAVYYCAS (SEQ ID NO: 453) | WGQGTLVTVSS (SEQ ID NO: 495) |
| MG2-12I | EVQLVESGGGLVQPGG SLRLSCAASGFTF (SEQ ID NO: 370) | WVRVAPGKGIEPVS (SEQ ID NO: 412) | RFTISRDNSKNTLYLQMN SLRAEDTAVYYCAS (SEQ ID NO: 454) | WGQGTLVTVSS (SEQ ID NO: 496) |
| MG2-32 | EVQLVESGGGLVQPGG SLRLSCAASGFTF (SEQ ID NO: 371) | WVRMAPGKGPEHVS (SEQ ID NO: 413) | RFTISRDNSKNTLYLQMN SLRAEDTAVYYCAS (SEQ ID NO: 455) | WGQGTLVTVSS (SEQ ID NO: 497) |
| MG2-34 | EVQLVESGGGLVQPGG SLRLSCAASGFTF (SEQ ID NO: 372) | WVRSAPGKGVEMVS (SEQ ID NO: 414) | RFTISRDNSKNTLYLQMN SLRAEDTAVYYCAS (SEQ ID NO: 456) | WGQGTLVTVSS (SEQ ID NO: 498) |
| MG2-40 | EVQLVESGGGLVQPGG SLRLSCAASGFTF (SEQ ID NO: 373) | WVRTAPGKGTEMVS (SEQ ID NO: 415) | RFTISRDNSKNTLYLQMN SLRAEDTAVYYCAS (SEQ ID NO: 457) | WGQGTLVTVSS (SEQ ID NO: 499) |
| MG2-46 | EVQLVESGGGLVQPGG SLRLSCAASGFTF (SEQ ID NO: 374) | WVRCAPGKGYEFVS (SEQ ID NO: 416) | RFTISRDNSKNTLYLQMN SLRAEDTAVYYCAS (SEQ ID NO: 458) | WGQGTLVTVSS (SEQ ID NO: 500) |
| MG2-47 | EVQLVESGGGLVQPGG SLRLSCAASGFTF (SEQ ID NO: 375) | WVRIAPGKGLEMVS (SEQ ID NO: 417) | RFTISRDNSKNTLYLQMN SLRAEDTAVYYCAS (SEQ ID NO: 459) | WGQGTLVTVSS (SEQ ID NO: 501) |
| MG2-48 | EVQLVESGGGLVQPGG SLRLSCAASGFTF (SEQ ID NO: 376) | WVRMAPGKGLEYVS (SEQ ID NO: 418) | RFTISRDNSKNTLYLQMN SLRAEDTAVYYCAS (SEQ ID NO: 460) | WGQGTLVTVSS (SEQ ID NO: 502) |
| MG2-51 | EVQLVESGGGLVQPGG SLRLSCAASGFTF (SEQ ID NO: 377) | WVRYAPGKGTEFVS (SEQ ID NO: 419) | RFTISRDNSKNTLYLQMN SLRAEDTAVYYCAS (SEQ ID NO: 461) | WGQGTLVTVSS (SEQ ID NO: 503) |
| MG2-53 | EVQLVESGGGLVQPGG SLRLSCAASGFTF (SEQ ID NO: 378) | WVRQAPGKGVEWVS (SEQ ID NO: 420) | RFTISRDNSKNTLYLQMN SLRAEDTAVYYCAS (SEQ ID NO: 462) | WGQGTLVTVSS (SEQ ID NO: 504) |
| MG2-55 | EVQLVESGGGLVQPGG SLRLSCAASGFTF (SEQ ID NO: 379) | WVRWAPGKGPEFVS (SEQ ID NO: 421) | RFTISRDNSKNTLYLQMN SLRAEDTAVYYCAS (SEQ ID NO: 463) | WGQGTLVTVSS (SEQ ID NO: 505) |
| MG2-57 | EVQLVESGGGLVQPGG SLRLSCAASGFTF (SEQ ID NO: 380) | WVRFAPGKGREWVS (SEQ ID NO: 422) | RFTISRDNSKNTLYLQMN SLRAEDTAVYYCAS (SEQ ID NO: 464) | WGQGTLVTVSS (SEQ ID NO: 506) |
| MG2-58 | EVQLVESGGGLVQPGG SLRLSCAASGFTF (SEQ ID NO: 381) | WVRFAPGKGCELVS (SEQ ID NO: 423) | RFTISRDNSKNTLYLQMN SLRAEDTAVYYCAS (SEQ ID NO: 465) | WGQGTLVTVSS (SEQ ID NO: 507) |
| MG2-59 | EVQLVESGGGLVQPGG SLRLSCAASGFTF (SEQ ID NO: 382) | WVRKAPGKGLETVS (SEQ ID NO: 424) | RFTISRDNSKNTLYLQMN SLRAEDTAVYYCAS (SEQ ID NO: 466) | WGQGTLVTVSS (SEQ ID NO: 508) |
| MG2-60 | EVQLVESGGGLVQPGG SLRLSCAASGFTF (SEQ ID NO: 383) | WVRNAPGKGLECVS (SEQ ID NO: 425) | RFTISRDNSKNTLYLQMN SLRAEDTAVYYCAS (SEQ ID NO: 467) | WGQGTLVTVSS (SEQ ID NO: 509) |
| MG2-64 | EVQLVESGGGLVQPGG SLRLSCAASGFTF (SEQ ID NO: 384) | WVRCAPGKGWEVVS (SEQ ID NO: 426) | RFTISRDNSKNTLYLQMN SLRAEDTAVYYCAS (SEQ ID NO: 468) | WGQGTLVTVSS (SEQ ID NO: 510) |
| MG4-12 | EVQLVESGGGLVQPGG SLRLSCAASGFTF (SEQ ID NO: 385) | WVRLAPGKGVELVS (SEQ ID NO: 427) | RFTISRDNSKNTLYLQMN SLRAEDTAVYYCAS (SEQ ID NO: 469) | WGQGTLVTVSS (SEQ ID NO: 511) |

TABLE 2-continued

Amino acid sequences of FR1 to FR4 frames of amino acid-modified VH domain antibody scaffold

| Scaffold name | FR1 | FR2 | FR3 | FR4 |
| --- | --- | --- | --- | --- |
| MG4-13 | EVQLVESGGGLVQPGGSLRLSCAASGFTF (SEQ ID NO: 386) | WVRFAPGKGAEWVS (SEQ ID NO: 428) | RFTISRDNSKNTLYLQMNSLRAEDTAVYYCAS (SEQ ID NO: 470) | WGQGTLVTVSS (SEQ ID NO: 512) |
| MG4-17 | EVQLVESGGGLVQPGGSLRLSCAASGFTF (SEQ ID NO: 387) | WVRLAPGKGREWVS (SEQ ID NO: 429) | RFTISRDNSKNTLYLQMNSLRAEDTAVYYCAS (SEQ ID NO: 471) | WGQGTLVTVSS (SEQ ID NO: 513) |
| MG4-18 | EVQLVESGGGLVQPGGSLRLSCAASGFTF (SEQ ID NO: 388) | WVRYAPGKGVEFVS (SEQ ID NO: 430) | RFTISRDNSKNTLYLQMNSLRAEDTAVYYCAS (SEQ ID NO: 472) | WGQGTLVTVSS (SEQ ID NO: 514) |
| MG4-20 | EVQLVESGGGLVQPGGSLRLSCAASGFTF (SEQ ID NO: 389) | WVRFAPGKGLEMVS (SEQ ID NO: 431) | RFTISRDNSKNTLYLQMNSLRAEDTAVYYCAS (SEQ ID NO: 473) | WGQGTLVTVSS (SEQ ID NO: 515) |
| MG4-28 | EVQLVESGGGLVQPGGSLRLSCAASGFTF (SEQ ID NO: 390) | WVRVAPGKGTERVS (SEQ ID NO: 432) | RFTISRDNSKNTLYLQMNSLRAEDTAVYYCAS (SEQ ID NO: 474) | WGQGTLVTVSS (SEQ ID NO: 516) |
| MG4-2 | EVQLVESGGGLVQPGGSLRLSCAASGFTF (SEQ ID NO: 391) | WVRIAPGKGMEMVS (SEQ ID NO: 433) | RFTISRDNSKNTLYLQMNSLRAEDTAVYYCAS (SEQ ID NO: 475) | WGQGTLVTVSS (SEQ ID NO: 517) |
| MG4-32 | EVQLVESGGGLVQPGGSLRLSCAASGFTF (SEQ ID NO: 392) | WVRAAPGKGPELVS (SEQ ID NO: 434) | RFTISRDNSKNTLYLQMNSLRAEDTAVYYCAS (SEQ ID NO: 476) | WGQGTLVTVSS (SEQ ID NO: 518) |
| MG4-33 | EVQLVESGGGLVQPGGSLRLSCAASGFTF (SEQ ID NO: 393) | WVRVAPGKGYEHVS (SEQ ID NO: 435) | RFTISRDNSKNTLYLQMNSLRAEDTAVYYCAS (SEQ ID NO: 477) | WGQGTLVTVSS (SEQ ID NO: 519) |
| MG4-34 | EVQLVESGGGLVQPGGSLRLSCAASGFTF (SEQ ID NO: 394) | WVRVAPGKGLECVS (SEQ ID NO: 436) | RFTISRDNSKNTLYLQMNSLRAEDTAVYYCAS (SEQ ID NO: 478) | WGQGTLVTVSS (SEQ ID NO: 520) |
| MG4-5 | EVQLVESGGGLVQPGGSLRLSCAASGFTF (SEQ ID NO: 395) | WVRVAPGKGPETVS (SEQ ID NO: 437) | RFTISRDNSKNTLYLQMNSLRAEDTAVYYCAS (SEQ ID NO: 479) | WGQGTLVTVSS (SEQ ID NO: 521) |
| MG4-6 | EVQLVESGGGLVQPGGSLRLSCAASGFTF (SEQ ID NO: 396) | WVRMAPGKGSEVVS (SEQ ID NO: 438) | RFTISRDNSKNTLYLQMNSLRAEDTAVYYCAS (SEQ ID NO: 480) | WGQGTLVTVSS (SEQ ID NO: 522) |
| MG4-7 | EVQLVESGGGLVQPGGSLRLSCAASGFTF (SEQ ID NO: 397) | WVRLAPGKGTEMVS (SEQ ID NO: 439) | RFTISRDNSKNTLYLQMNSLRAEDTAVYYCAS (SEQ ID NO: 481) | WGQGTLVTVSS (SEQ ID NO: 523) |
| MG8-11 | EVQLVESGGGLVQPGGSLRLSCAASGFTF (SEQ ID NO: 398) | WVRTAPGKGAEWVS (SEQ ID NO: 440) | RFTISRDNSKNTLYLQMNSLRAEDTAVYYCAS (SEQ ID NO: 482) | WGQGTLVTVSS (SEQ ID NO: 524) |
| MG8-12 | EVQLVESGGGLVQPGGSLRLSCAASGFTF (SEQ ID NO: 399) | WVRWAPGKGKEVVS (SEQ ID NO: 441) | RFTISRDNSKNTLYLQMNSLRAEDTAVYYCAS (SEQ ID NO: 483) | WGQGTLVTVSS (SEQ ID NO: 525) |
| MG8-13 | EVQLVESGGGLVQPGGSLRLSCAASGFTF (SEQ ID NO: 400) | WVRQAPGKGIEPVS (SEQ ID NO: 442) | RFTISRDNSKNTLYLQMNSLRAEDTAVYYCAS (SEQ ID NO: 484) | WGQGTLVTVSS (SEQ ID NO: 526) |
| MG8-14 | EVQLVESGGGLVQPGGSLRLSCAASGFTF (SEQ ID NO: 401) | WVRQAPGKGPEWVS (SEQ ID NO: 443) | RFTISRDNSKNTLYLQMNSLRAEDTAVYYCAS (SEQ ID NO: 485) | WGQGTLVTVSS (SEQ ID NO: 527) |
| MG8-4 | EVQLVESGGGLVQPGGSLRLSCAASGFTF (SEQ ID NO: 402) | WVRQAPGKGPEVVS (SEQ ID NO: 444) | RFTISRDNSKNTLYLQMNSLRAEDTAVYYCAS (SEQ ID NO: 486) | WGQGTLVTVSS (SEQ ID NO: 528) |
| MG8-5 | EVQLVESGGGLVQPGGSLRLSCAASGFTF (SEQ ID NO: 403) | WVRTAPGKGIEIVS (SEQ ID NO: 445) | RFTISRDNSKNTLYLQMNSLRAEDTAVYYCAS (SEQ ID NO: 487) | WGQGTLVTVSS (SEQ ID NO: 529) |

TABLE 2-continued

Amino acid sequences of FR1 to FR4 frames of amino acid-modified VH domain antibody scaffold

| Scaffold name | FR1 | FR2 | FR3 | FR4 |
|---|---|---|---|---|
| MG8-6 | EVQLVESGGGLVQPGG SLRLSCAASGFTF (SEQ ID NO: 404) | WVRIAPGKGVEIVS (SEQ ID NO: 446) | RFTISRDNSKNTLYLQMN SLRAEDTAVYYCAS (SEQ ID NO: 488) | WGQGTLVTVSS (SEQ ID NO: 530) |
| MG8-8 | EVQLVESGGGLVQPGG SLRLSCAASGFTF (SEQ ID NO: 405) | WVRAAPGKGLEVVS (SEQ ID NO: 447) | RFTISRDNSKNTLYLQMN SLRAEDTAVYYCAS (SEQ ID NO: 489) | WGQGTLVTVSS (SEQ ID NO: 531) |

The VH domain including the amino acid sequence of the VH antibody scaffold, that is, the amino acid sequences of FR1 to FR4 frames, according to the present invention has an amino acid sequence represented by FR1-X-FR2-X-FR3-X-FR4            Formula 9), in Formula 9), X means CDR1, CDR2, and CDR3, in order from the left side.

Specifically, the VH domain including the amino acid sequences of FR1 to FR4 frames according to the present invention has one selected from amino acid sequences of SEQ ID NOs: 37 to 89, and SEQ ID NOs: 90 to 131 as shown in Tables 3 and 4.

TABLE 3

Amino acid sequences of VH domain including FR1 to FR4 frames of the VH domain antibody scaffold screened by TAPE (derived from human germline)

| Scaffold name | SEQ ID NO | Amino acid sequence of VH region (X means CDR1, CDR2, and CDR3, in order from the left side) |
|---|---|---|
| MG1X8 | 49 | QVQLVESGGGLVQPGGSLRLSCAASGFTF-X-WVRQAPGKGLVWVS-X-RFTISRDNAKNTLFLQMNSLRDEDTSVYYCAR-X-WGQGALVTVSS |
| MG2X1 | 50 | EVQLVESGGGLVQPGGSLRLSCAASGFTF-X-WVRQAPGKGLEWVS-X-RFTISRDNSKNTLYLQMNSLRAEDTAVYYCAS-X-WGQGTLVTVSS |
| MG2X1-34 | 51 | QVQLVESGGNVVQPGTSLRLSCAASGFTF-X-WVRQAPGKGLEWVA-X-RFTISRDNSRNIVFLQMTSLRAEDTAVYYCGR-X-WGQGILVTVSS |
| MG2X2-12 | 52 | QVQLVQSGAEVKKPGASVKISCEASGYAF-X-WVRQAPGQGLEWMG-X-RVTLTRDTSTRTVYMELKNLRSADTGVYYCAR-X-WGQGTLVTVSS |
| MG2X2-13 | 53 | EVQLLESGGGVVQPGKSLRLSCVGSGFSF-X-WVRQAPGKGLEWLA-X-RFTISRDNSKTMVNLQMNSLRPDDTAVYFCAR-X-WGQGTLVTVSS |
| MG3X1 | 54 | QVQLVESGGGVVQPGRSLRLSCVASGFNF-X-WLRQAPGKGLEWVA-X-RFTISRDNSKNTLYLEMNSLRPEDTAVYYCAK-X-CGQGTLVTVSS |
| MG3X10 | 55 | EVQLVESGGGLVKPGGSLRVSCAASGFTF-X-WVRQAPGKGLEWVG-X-RFTISRDDSKNMVYLQMNSLKTEDTAVYYCTT-X-YGQGTLVTVSS |
| MG4X1-8 | 56 | EVQLVESGGGLVQPGGSLRLSCAASGFSF-X-WVRQGPGEGLVWLS-X-RFTISRDNAKNTVYLEMNSVRVDDTAVYYCVS-X-WGQGALVTVSS |
| MG4X1-33 | 57 | QVQLVESGGGLVQPGGSLRLSCEASGFPF-X-WVRQAPGKGLEWVS-X-RFTISRDDSTNTLYLQVNSLRAEDTAVYYCAK-X-WGRGTLVTVSS |
| MG4X1-35 | 58 | EVQLLESGGGLVKPGGSLRLSCVGSERSF-X-WVRQAPGKGLEWVA-X-RFTVSRDNVQKSLDLQMDSLRAEDTAVYFCAR-X-WGQGTTVTVSS |
| MG4X3-27 | 59 | EVQLLESGGGLAQSGGSLRLSCAASGFTF-X-WVRQAPGKGLEWIS-X-RFTISRDIAKNSLYLQMNSLRDEDTAVYYCAK-X-WGQGALVTVSS |
| MG4X4-2 | 60 | EVQLVQSGAEVKKPGESLRISCRGSGYRF-X-WARDKPGKGLEWIG-X-HVTISSDRSVSVAYLQWDSLKASDNGIYYCAL-X-WGQGTLVTVSS |
| MG4X4-4 | 61 | EVQLVESGGGLVQPGGSLRLSCVPSGFTF-X-WVRQAPGKGLVWVS-X-RFTISRDNAEDTLFLQMNSLRVDDTAVYYCVR-X-WGQGVLVTVSS |
| MG4X4-25 | 62 | QVQLVESGGGLVQPGGSLRLSCIASGFSL-X-WVRRSPGKGLEWVA-X-RFTVSRDNAKNSLFLQMNNVRPEDTALYFCAR-X-WGQGTMVTVSS |

TABLE 3-continued

Amino acid sequences of VH domain including FR1 to FR4 frames of the VH domain antibody scaffold screened by TAPE (derived from human germline)

| Scaffold name | SEQ ID NO | Amino acid sequence of VH region (X means CDR1, CDR2, and CDR3, in order from the left side) |
|---|---|---|
| MG4X4-44 | 63 | EVQLVESGGGLVQPGGSLRLSCAASGFTF-X-WVRQAPGKGLEWVA-X-RFTISRDNAKNSLYLQMNSLRAEDTALYYCAR-X-WGQGTLVTVSS |
| MG4X5-30 | 64 | EVQLLESGGGLVQPGGSLRLSCAASGFTF-X-WVRQAPGKGLEWLS-X-RFTISRNNAKNSLYLQMNSLRVDDTAVYYCAR-X-WGQGTLVTVSS |
| MG4X6-27 | 65 | EVQLLESGGGLVQPGGSLRLSCAASGFTF-X-WVRQGPGKGLEWVA-X-RFTISRDNAENSLYLQVNSLRAEDTAIYYCAK-X-WGQGALVTVSS |
| MG4X6-48 | 66 | EVQLLESGGGVVQPGRSLRLSCEVFGFTL-X-WVRQAPGRRLEWVA-X-RFTISRDIATNRLYLQMRSLRAEDTALYYCAR-X-WGQGTLVTVSS |
| MG4X7-15 | 67 | EVQLLESGGGLVQPGGSLRLSCAASGFSF-X-WVRQAPGKGLEWVS-X-RFTISRDNSKNTLYLQMNSLRVEDTAVYYCAV-X-WGQGTTVTVSS |
| MG4X8-24 | 68 | EVQLLESGGGLVQPGGSLRLSCAASGFTF-X-WVRQAPGKGLEWVS-X-RFTISRDNSNNTLYLQMNSLRADDTAVYFCAK-X-WGQGTLVTVSS |
| MG0.5X-1 | 69 | QVQLVESGGGLVQPGGSLRLSCAASGFTF-X-WVRQVPGKGLEWVA-X-RFTISRDNAKNSLYLQMNSLRAEDTAVYYCAN-X-WGQGTLVTVSS |
| MG0.5X-3 | 70 | QVQLVESGGGLVQPGGSLTLSCAASGFTF-X-WVRQAPGTGLLWLS-X-RFTISRDNSKNTLYLQMNSLRAEDTAVYYCAR-X-WGXGTMVTVSX |
| MG0.5X-4 | 71 | EVQLLESGGMLVKPGESLRLSCVGSGLIF-X-WVRHAPGKGLEWVG-X-RLSISRDDSMNTVYLDIYNLKIDDTGVYYCTF-X-WGQGTPVTVSS |
| MG0.5X-14 | 72 | EVQLLESGGGLVHAGGSVRLSCAASGFTF-X-WVRQAPGKGLEWVA-X-RFTISRDNSKNSMYLQMNSLRVEDTAVYYCAR-X-WGQGTVVTVSS |
| MG0.75X-4 | 73 | QVQLVESGGGLVKPGGSLRLSCAASGFTF-X-WLRQAPGKGPEYVA-X-RFIISRDDSNDMLYLEMISLKSEDTAVYYCSD-X-GSQGTLVTVSS |
| MG2X-5 | 74 | EVQLLESGGGLVQPGGSLRLSCAASGFTF-X-WVRQAPGKGLEWVS-X-RFTISRDNSKNTLYLHMNSLRAEDTAVYYCVK-X-WGQGTLVTVSS |
| MG2X-15 | 75 | QVQLVESGGGLVQPGGSLRLSCAASGFTF-X-WVRQAPGKGLEWVS-X-RFTISRDNSKNTLYLQMNSLRAEDTAVYYCAK-X-WGQGTLVTVSS |
| MG4X-5 | 76 | QVQLVESGGGLVQPGGSLRLSCEASGLHF-X-WVRQAPGKGLEWVA-X-RFTVSRDNSRNTLYLQMKSLSAEDTAVYYCAK-X-WGQGTMVTVSS |
| MG1-4 | 77 | QVQLVEAGGGLVQPGGSLRLACAASGFTF-X-WVRQAPGKGLEWIS-X-RFTISRDNSQNSLFLQMNSLRAEDTAVYYCAT-X-WGQGTMVTVSS |
| MG1-6 | 78 | EVQLVQSGAEVKKPGESLRKSCKGSGYSF-X-WVRQMPGKGLEWMG-X-HVTISVDKSISTAYLQWSSLKASDSAMYYFL-X-WGQGTLVTVSS |
| MG1-7 | 79 | QVQLVESGGGLVQPGGSLRLSCAASGFTF-X-WVRQAPGKGLEWVA-X-RFTISRDNAKNSLYLQMNSLRDEDTAVYYCAR-X-WGQGTLVTVSS |
| MG1-8 | 80 | EVQLVQSGAEVKKPGASVKVSCKASGYTF-X-WVRQAPGQGLEWMG-X-RVTMTRDTSSTTAYMELNRLTSDDTAVYFCAR-X-WGQGTLVTVSS |
| MG1-9 | 81 | EVQLVEAGGGLVQPGGSLRLACAASGFTF-X-WVRQAPGKGLEWIS-X-RFTISRDNAQNSLFLQMNSLRAEDTAVYYCAT-X-WGQGTMVTVSS |
| MG1-10 | 82 | EVQLVQSGAEVKKPGESLKISCKGSGYSF-X-WVRQMPGRGLEWLG-X-QVTMSANRSISTAYLQWSSLKASDTGIYYCAT-X-WGQGTTVTVSS |
| MG5-1 | 83 | QVQLVESGGGLIQPGESLRLSCEAFGFTV-X-WVRQAPGKGLEWVS-X-RFTISRDSTQNTVHLQMNSLTAEDTAVYYCAR-X-WGQGTLVTVSS |
| MG5-2 | 84 | EVQLVQSGAELKKPGSSVKVSCTSSGGSF-X-WVRQAPGQGLEWMG-X-RLILSVDEPTRTVYMELTSLRSDDTAMYYCAR-X-WGQGTTVTVSS |
| MG5-4 | 85 | EVQLLESGGGLVQPGRSLRLSCAASGFTF-X-WVRQAPGKGLEWVS-X-RFTISRDNAKDSLYLQMNSLRPEDTALYYCAR-X-WGQGTMVTVSS |
| MG5-5 | 86 | EVQLLESGGGVVQPGRSLRLSCVASGFTF-X-WVRQAPGKGLEWVS-X-RFTISRDYSNKIVHLEMDSLRAEDTAVYFCVR-X-WGQGTLVTVSS |

TABLE 3-continued

Amino acid sequences of VH domain including FR1 to FR4 frames of the VH domain antibody scaffold screened by TAPE (derived from human germline)

| Scaffold name | SEQ ID NO | Amino acid sequence of VH region (X means CDR1, CDR2, and CDR3, in order from the left side) |
|---|---|---|
| MG5-6 | 87 | EVQLLESGGGLVKPGGSLRLSCAASGFTF-X-WVRQAPGKGLECVA-X-RFTISRDDSRDMLYLQMNNLKTEDTAVYYCSD-X-SSQGTLVTVSS |
| MG5-7 | 88 | EVQLVESGGGLVQPGRSLRLSCTTSGFSF-X-WVRQAPGKGLEWVS-X-RFTISRDDSKSIVYLQMSSLQTEDTAVYYCSR-X-WGRGTLVTVSS |
| MG5-9 | 89 | EVQLLESGGGLVRPGGSLRLSCSASGFAF-X-WVRQAPGKGLEWVS-X-TISRDNAKNSVYLQMNSLRAEDSAVYFCAR-X-WGQGTLVTVSS |
| MG10-1 | 90 | QVQLVESGGNVVQPGTSLRLSCAASGFTF-X-WVRQAPGKGLEWVA-X-RFTISRDNSRNTVFLQMTSLRAEDTAVYYCGR-X-WGQGILVTVSS |
| MG10-2 | 91 | EVQLLESGGGLVQPGGSLRLTCVGYGFTF-X-WVRQAPGKGPEWVA-X-RFTISRDNAKDSLYLQMDSLRPEDTAVYYCAR-X-APQGTLVTVSS |
| MG10-4 | 92 | EVQLLESGGGLVQPGGSLRLSCAASGFIL-X-WVRQAPGKGLVWVS-X-QFTISRDNAKNTLYLQMNSLRVEDTAVYYCAR-X-WGQGTMVTVSS |
| MG10-5 | 93 | EVQLLESGGGVVHPGRSLRLSCAVSGFSL-X-WVRQAPDKGLEWVA-X-RFTVSRDISKNTVYLQMNSLRAEDTALYYCAR-X-WGQGTMVTVSS |
| MG10-6 | 94 | EVQLLESGGGLVQPGGSRRLSCAASGFTF-X-WFRQGPGKGLEWVA-X-RFTISRDDSKNSLSLQMDSLRTEDTAVYYCVR-X-WGQGTVVTVSS |
| MG10-8 | 95 | QVQLVESGGGVVQPGRSLRLSCVASGFAF-X-WVRQTPGRGLEWLA-X-RFTISRDNSNNTVYLEMNSLRPEDSAIYYCAK-X-WGLGTVVTVSS |
| MG10-10 | 96 | QVQLVESGGVVVQPGGSLRLSCAASGFTF-X-WVRQAPGKGLEWVS-X-RFTISRDNSKNSLYLQMNSLRTDETALYYCV-X-WGQGTLVTVSS |
| MG2 | 97 | EVQLLESGGGLVQPGGSLRLSCAASGFTF-X-WVRQAPGKGLEWVS-X-RFTISRDNAKNSLYLQMNSLRTDETAVYYCAR-X-WGQGTTVTVSS |
| MG5 | 98 | EVQLLQSGGGWVKPGGSLRLSCAASGFIC-X-WVRQAPGKGLEWVG-X-RFTISIDESRNALFLHMNSLTTDDTAVYYCST-X-WGQGTLVTVSS |
| MG6 | 99 | EVQLLESGGVVVQPGRSLRLSCAASGFTF-X-WVRQAPGKGLEWVA-X-RFTVSRDTSTNTLYLQMNSLRVEDTAVYYCAR-X-WGQGTLVTVSS |
| MG7 | 100 | QMQLVQSEAEVKKPGASMKVSCKASGYTF-X-WVRQATGQGLEWMG-X-RVTMTRNTSISTAYMELSSLTSADTAVYYCAR-X-WGQGTLVTVSS |
| MG10 | 101 | QVQLVQSGAEVKKPGESLKISCKGSGYSF-X-WVRQMPGKGLEWMG-X-QVTISADKSISTAFLQWNSLKASDTAMYYCAR-X-WGLGTLVTVSS |

TABLE 4

Amino acid sequences of VH domain including FR1 to FR4 frames of amino acid-modified VH domain antibody scaffold

| Scaffold name | SEQ ID NO | Amino acid sequence of VH region (X means CDR1, CDR2, and CDR3, in order from the left side) |
|---|---|---|
| MG8-21 | 102 | EVQLVESGGGLVQPGGSLRLSCAASGFTF-X-WVRNAPGKGNEIVS-X-RFTISRDNSKNTLYLQMNSLRAEDTAVYYCAS-X-WGQGTLVTVSS |
| MG2-12L | 103 | EVQLVESGGGLVQPGGSLRLSCAASGFTF-X-WVRRAPGKGIEVVS-X-RFTISRDNSKNTLYLQMNSLRAEDTAVYYCAS-X-WGQGTLVTVSS |
| MG2-7I | 104 | EVQLVESGGGLVQPGGSLRLSCAASGFTF-X-WVRIAPGKGPEPVS-X-RFTISRDNSKNTLYLQMNSLRAEDTAVYYCAS-X-WGQGTLVTVSS |
| MG2-9I | 105 | EVQLVESGGGLVQPGGSLRLSCAASGFTF-X-WVRKAPGKGYEPVS-X-RFTISRDNSKNTLYLQMNSLRAEDTAVYYCAS-X-WGQGTLVTVSS |
| MG2-10I | 106 | EVQLVESGGGLVQPGGSLRLSCAASGFTF-X-WVRNAPGKGYEIVS-X-RFTISRDNSKNTLYLQMNSLRAEDTAVYYCAS-X-WGQGTLVTVSS |

TABLE 4-continued

Amino acid sequences of VH domain including FR1 to FR4 frames of amino acid-modified VH domain antibody scaffold

| Scaffold name | SEQ ID NO | Amino acid sequence of VH region (X means CDR1, CDR2, and CDR3, in order from the left side) |
|---|---|---|
| MG2-11I | 107 | EVQLVESGGGLVQPGGSLRLSCAASGFTF-X-WVRYAPGKGYEFVS-X-RFTISRDNSKNTLYLQMNSLRAEDTAVYYCAS-X-WGQGTLVTVSS |
| MG2-12I | 108 | EVQLVESGGGLVQPGGSLRLSCAASGFTF-X-WVRVAPGKGIEPVS-X-RFTISRDNSKNTLYLQMNSLRAEDTAVYYCAS-X-WGQGTLVTVSS |
| MG2-32 | 109 | EVQLVESGGGLVQPGGSLRLSCAASGFTF-X-WVRMAPGKGPEHVS-X-RFTISRDNSKNTLYLQMNSLRAEDTAVYYCAS-X-WGQGTLVTVSS |
| MG2-34 | 110 | EVQLVESGGGLVQPGGSLRLSCAASGFTF-X-WVRSAPGKGVEMVS-X-RFTISRDNSKNTLYLQMNSLRAEDTAVYYCAS-X-WGQGTLVTVSS |
| MG2-40 | 111 | EVQLVESGGGLVQPGGSLRLSCAASGFTF-X-WVRTAPGKGTEMVS-X-RFTISRDNSKNTLYLQMNSLRAEDTAVYYCAS-X-WGQGTLVTVSS |
| MG2-46 | 112 | EVQLVESGGGLVQPGGSLRLSCAASGFTF-X-WVRCAPGKGYEFVS-X-RFTISRDNSKNTLYLQMNSLRAEDTAVYYCAS-X-WGQGTLVTVSS |
| MG2-47 | 113 | EVQLVESGGGLVQPGGSLRLSCAASGFTF-X-WVRIAPGKGLEMVS-X-RFTISRDNSKNTLYLQMNSLRAEDTAVYYCAS-X-WGQGTLVTVSS |
| MG2-48 | 114 | EVQLVESGGGLVQPGGSLRLSCAASGFTF-X-WVRMAPGKGLEYVS-X-RFTISRDNSKNTLYLQMNSLRAEDTAVYYCAS-X-WGQGTLVTVSS |
| MG2-51 | 115 | EVQLVESGGGLVQPGGSLRLSCAASGFTF-X-WVRYAPGKGTEFVS-X-RFTISRDNSKNTLYLQMNSLRAEDTAVYYCAS-X-WGQGTLVTVSS |
| MG2-53 | 116 | EVQLVESGGGLVQPGGSLRLSCAASGFTF-X-WVRQAPGKGVEWVS-X-RFTISRDNSKNTLYLQMNSLRAEDTAVYYCAS-X-WGQGTLVTVSS |
| MG2-55 | 117 | EVQLVESGGGLVQPGGSLRLSCAASGFTF-X-WVRWAPGKGPEFVS-X-RFTISRDNSKNTLYLQMNSLRAEDTAVYYCAS-X-WGQGTLVTVSS |
| MG2-57 | 118 | EVQLVESGGGLVQPGGSLRLSCAASGFTF-X-WVRFAPGKGREWVS-X-RFTISRDNSKNTLYLQMNSLRAEDTAVYYCAS-X-WGQGTLVTVSS |
| MG2-58 | 119 | EVQLVESGGGLVQPGGSLRLSCAASGFTF-X-WVRFAPGKGCELVS-X-RFTISRDNSKNTLYLQMNSLRAEDTAVYYCAS-X-WGQGTLVTVSS |
| MG2-59 | 120 | EVQLVESGGGLVQPGGSLRLSCAASGFTF-X-WVRKAPGKGLETVS-X-RFTISRDNSKNTLYLQMNSLRAEDTAVYYCAS-X-WGQGTLVTVSS |
| MG2-60 | 121 | EVQLVESGGGLVQPGGSLRLSCAASGFTF-X-WVRNAPGKGLECVS-X-RFTISRDNSKNTLYLQMNSLRAEDTAVYYCAS-X-WGQGTLVTVSS |
| MG2-64 | 122 | EVQLVESGGGLVQPGGSLRLSCAASGFTF-X-WVRCAPGKGWEVVS-X-RFTISRDNSKNTLYLQMNSLRAEDTAVYYCAS-X-WGQGTLVTVSS |
| MG4-12 | 123 | EVQLVESGGGLVQPGGSLRLSCAASGFTF-X-WVRLAPGKGVELVS-X-RFTISRDNSKNTLYLQMNSLRAEDTAVYYCAS-X-WGQGTLVTVSS |
| MG4-13 | 124 | EVQLVESGGGLVQPGGSLRLSCAASGFTF-X-WVRFAPGKGAEWVS-X-RFTISRDNSKNTLYLQMNSLRAEDTAVYYCAS-X-WGQGTLVTVSS |
| MG4-17 | 125 | EVQLVESGGGLVQPGGSLRLSCAASGFTF-X-WVRLAPGKGREWVS-X-RFTISRDNSKNTLYLQMNSLRAEDTAVYYCAS-X-WGQGTLVTVSS |
| MG4-18 | 126 | EVQLVESGGGLVQPGGSLRLSCAASGFTF-X-WVRYAPGKGVEFVS-X-RFTISRDNSKNTLYLQMNSLRAEDTAVYYCAS-X-WGQGTLVTVSS |
| MG4-20 | 127 | EVQLVESGGGLVQPGGSLRLSCAASGFTF-X-WVRFAPGKGLEMVS-X-RFTISRDNSKNTLYLQMNSLRAEDTAVYYCAS-X-WGQGTLVTVSS |
| MG4-28 | 128 | EVQLVESGGGLVQPGGSLRLSCAASGFTF-X-WVRVAPGKGTERVS-X-RFTISRDNSKNTLYLQMNSLRAEDTAVYYCAS-X-WGQGTLVTVSS |
| MG4-2 | 129 | EVQLVESGGGLVQPGGSLRLSCAASGFTF-X-WVRIAPGKGMEMVS-X-RFTISRDNSKNTLYLQMNSLRAEDTAVYYCAS-X-WGQGTLVTVSS |
| MG4-32 | 130 | EVQLVESGGGLVQPGGSLRLSCAASGFTF-X-WVRAAPGKGPELVS-X-RFTISRDNSKNTLYLQMNSLRAEDTAVYYCAS-X-WGQGTLVTVSS |

TABLE 4-continued

Amino acid sequences of VH domain including FR1 to FR4 frames of amino acid-modified VH domain antibody scaffold

| Scaffold name | SEQ ID NO | Amino acid sequence of VH region (X means CDR1, CDR2, and CDR3, in order from the left side) |
|---|---|---|
| MG4-33 | 131 | EVQLVESGGGLVQPGGSLRLSCAASGFTF-X-WVRVAPGKGYEHVS-X-RFTISRDNSKNTLYLQMNSLRAEDTAVYYCAS-X-WGQGTLVTVSS |
| MG4-34 | 132 | EVQLVESGGGLVQPGGSLRLSCAASGFTF-X-WVRVAPGKGLECVS-X-RFTISRDNSKNTLYLQMNSLRAEDTAVYYCAS-X-WGQGTLVTVSS |
| MG4-5 | 133 | EVQLVESGGGLVQPGGSLRLSCAASGFTF-X-WVRVAPGKGPETVS-X-RFTISRDNSKNTLYLQMNSLRAEDTAVYYCAS-X-WGQGTLVTVSS |
| MG4-6 | 134 | EVQLVESGGGLVQPGGSLRLSCAASGFTF-X-WVRMAPGKGSEVVS-X-RFTISRDNSKNTLYLQMNSLRAEDTAVYYCAS-X-WGQGTLVTVSS |
| MG4-7 | 135 | EVQLVESGGGLVQPGGSLRLSCAASGFTF-X-WVRLAPGKGTEMVS-X-RFTISRDNSKNTLYLQMNSLRAEDTAVYYCAS-X-WGQGTLVTVSS |
| MG8-11 | 136 | EVQLVESGGGLVQPGGSLRLSCAASGFTF-X-WVRTAPGKGAEWVS-X-RFTISRDNSKNTLYLQMNSLRAEDTAVYYCAS-X-WGQGTLVTVSS |
| MG8-12 | 137 | EVQLVESGGGLVQPGGSLRLSCAASGFTF-X-WVRWAPGKGKEVVS-X-RFTISRDNSKNTLYLQMNSLRAEDTAVYYCAS-X-WGQGTLVTVSS |
| MG8-13 | 138 | EVQLVESGGGLVQPGGSLRLSCAASGFTF-X-WVRQAPGKGIEPVS-X-RFTISRDNSKNTLYLQMNSLRAEDTAVYYCAS-X-WGQGTLVTVSS |
| MG8-14 | 139 | EVQLVESGGGLVQPGGSLRLSCAASGFTF-X-WVRQAPGKGPEWVS-X-RFTISRDNSKNTLYLQMNSLRAEDTAVYYCAS-X-WGQGTLVTVSS |
| MG8-4 | 140 | EVQLVESGGGLVQPGGSLRLSCAASGFTF-X-WVRQAPGKGPEVVS-X-RFTISRDNSKNTLYLQMNSLRAEDTAVYYCAS-X-WGQGTLVTVSS |
| MG8-5 | 141 | EVQLVESGGGLVQPGGSLRLSCAASGFTF-X-WVRTAPGKGIEIVS-X-RFTISRDNSKNTLYLQMNSLRAEDTAVYYCAS-X-WGQGTLVTVSS |
| MG8-6 | 142 | EVQLVESGGGLVQPGGSLRLSCAASGFTF-X-WVRIAPGKGVEIVS-X-RFTISRDNSKNTLYLQMNSLRAEDTAVYYCAS-X-WGQGTLVTVSS |
| MG8-8 | 143 | EVQLVESGGGLVQPGGSLRLSCAASGFTF-X-WVRAAPGKGLEVVS-X-RFTISRDNSKNTLYLQMNSLRAEDTAVYYCAS-X-WGQGTLVTVSS |

Also, the present invention provides a polynucleotide encoding an amino acid sequence of the VH domain antibody scaffold, that is, amino acid sequences of FR1 to FR4 frames.

In order that the present invention may be more readily understood, certain terms and abbreviations used herein are first defined before the present invention is in detail described.

Human Immunoglobulin Variable Domain:

This means heavy chain variable domains (VH) or light chain variable domains (VL), which directly participate in binding to antigen, among 12 domains (VH, CH1, CH2, CH3, VL, and CL each for one pair) constituting a structure of human immunoglobulin G. The VH or VL has a structure where nine beta-sheet strands cross each other. In the case of VH, variable regions are present between the second and the third beta-sheets, between the fourth and fifth beta-sheets, and the eighth and the ninth beta-sheets, starting from N-terminal thereof, and here, these variable regions are referred to as CDR (complementarity determining region)1, CDR2, and CDR3, respectively. When starting from the N-terminal of VH, an entire section of the first and second beta-sheet excluding CDR1 is referred to as Frame 1 (FR1), a section between CDR1 and CDR2 including the third and fourth beta-sheets is referred to as Frame 2 (FR2), a section between CDR2 and CDR3 is referred to as Frame 3 (FR3), and a section after CDR3 is referred to as Frame 4. The respective frames do not directly participate in binding to antigens even though they are the variable domains, and most amino acid sequences in these regions are consistently conserved on the human immunoglobulin. The VH segments are classified into seven families (VH1, VH2, VH3, VH4, VH5, VH6, and VH7) according to homology of amino acid sequence in the frame regions. The VL segment is divided into Vkappa and Vlamda, and the Vkappa segments are classified into six families and the Vlamda segments are classified into ten families (Chothia et al., 1992 J Mol Biol 227, 799-917; Tomlinson et al, 1995 EMBO J 14, 4628-4638; Williams et al., J Mol Biol 264, 220-232).

CDR (Complementarity Determining Region):

This may be called a hypervariable region, and it means a region which is positioned within the heavy chain or light chain variable domain in the structure of the antibody and participates in directly binding to epitope of antigen. Each variable domain has three CDR regions, and they consist of amino acid sequences with various lengths.

Antibody Scaffold:

This means the rest of the antibody structure excluding the hypervariable region, that is, CDR regions, which directly bind to antigen, and an amino acid sequence thereof is conserved when a CDR-engineered library is prepared. In other words, this means the rest of the amino acid sequence of the antibody, excluding CDR1, CDR2, and CDR3, which are hypervariable regions. In the present invention, this means a region of the entire FR1 to FR4 frames, which corresponds to the rest of the region excluding CDR1, CDR2, and CDR3 in each of the human immunoglobulin variable domains.

That is, the antibody scaffold of VH domain in the present invention means the entire region of FR1 to FR4 frames, excluding CDR1 to CDR3 regions in the VH domain antibody.

This antibody scaffold may be utilized as a scaffold for preparing a CDR-engineered library for screening a protein binding to a target, particularly, VH domain antibody.

Domain Antibody:

This means, in a broad sense, a modified protein capable of binding a specific antigen, including some of the domains constituting the structure of human immunoglobulin. This means, in a narrow sense, a modified form of human immunoglobulin variable domain (VH or VL), that can be suitably used as a therapeutic antibody.

In particular, a single domain antibody generally means a variable domain derived from a single heavy chain antibody consisting of only a heavy chain. A single domain antibody derived from dromedary is called a VHH (heavy chain variable domain from single heavy chain antibody), and a VNAR (single domain antibody derived from chondrichthyes such as sharks is called a variable new antigen receptor).

The single domain antibody in the present invention, for example, a VH domain antibody or a VL domain antibody, means an antibody consisting of only one heavy chain or light chain of human-derived variable domains, without particular limitations.

Target Protein:

This means a protein of interest which is to be selected in order to improve protein characteristics from the library, in a TAPE method. In the present invention, this means a protein which is encoded by a gene functionally linked between a Tat signal sequence and a TEM-1 beta lactamase gene of a pET-TAPE expression vector. Any protein that can require solubility may be used without limitations, and examples thereof include human-derived antibodies and fragments thereof, receptors, receptor ligands, and the like, and particularly include natural type of human immunoglobulin variable domains derived from human germline cells and artificially mutated proteins thereof.

Ligand:

This means a protein having binding ability to a specific receptor or a targeting protein among target proteins screened from the library.

Multi-Specificity:

This means property of an antibody capable of specifically binding to one or more epitopes. This may also mean property of an antibody that recognizes two or more epitopes in one target object, or property of an antibody that binds to two or more target objects.

Fusion Protein:

This means a protein where at least two proteins or peptides having different functions, which are encoded by nucleic acids, are functionally linked to each other, for example, a Tat signal sequence and a target protein are functionally linked to each other. Here, a reporter gene such as a TEM-1 beta lactamase, or a tag such as 6×His or Flag may be added thereto. Expression of the genes of proteins that are functionally linked to each other is regulated on an expression vector by one promoter (induction type, maintenance type, or the like).

Natural Type or Wild Type:

This means a gene or a product thereof (for example, protein) that can be obtained in a natural system. This is a concept contrary to mutant, polymorphism, and variant, of which products have characteristics changed due to an artificial or natural change in gene sequences.

The present invention will be described according to the above definitions of the terms and abbreviations.

As described above, a TAPE method and a TAPE system therefor according to the present invention is a method for screening target proteins such as a immunoglobulin variable domain derived from human germline cell (VH or VL), a ligand, or the like, having solubility and excellent thermostability, by preparing a gene construct where a target protein and an antibiotic resistant protein are bound to a Tat signal sequence, and then transforming a hose cell, particularly, *E. coli*, with a vector including the gene construct to express the fusion protein in *E. coli*, and a system for performing the method.

The "Tat signal sequence" is a sequence recognized by a Tat (twin-arginine translocation) pathway. It leads proteins to a pathway passing from the cytoplasm to the intracellular membrane in bacteria, and to a pathway moving from the stroma to the thylakoid in chloroplast. Generally, the Tat signal sequence is divided into the following three motifs. It is comprised of an n-region which is an N-terminal motif having positive charge, an h-region consisting of hydrophobic amino acids in the middle, and a c-region which is a C-terminal motif. As a result of analyzing several Tat signal sequences, it was found that S/T-R-R-x-F-L-K, which is a distinctive conservative sequence of the Tat signal sequence, is present throughout the n-region and the h-region. Among them, two arginines (R) are named twin-arginine because they are conserved on all the Tat signal sequences.

The Tat signal sequence may be selected from TorA, CuoO, DmsA, FdnG, FdoG, HyaA, NapA, Sufl, WcaM, TagT, YcbK, YcdB, YdhX, and YnfE, but is not limited thereto. Proteins that have a complete three dimensional structure by binding with chaperons or various cofactors in the cytoplasm move to the cell membrane through the Tat signal pathway, but are not compatible with a Sec signal which is a general cell membrane movement pathway of bacteria. In other words, since only proteins that are folded to have a complete three-dimensional structure in the cytoplasm may be recognized by a Tat ABC translocase complex, they are involved in a protein translocation pathway having different characteristics from the Sec pathway (Baneyx and Mujacic, Nat. Biotech. 2004, 22, 1399~1408).

The TAPE method according to the present invention uses the above characteristics of the Tat-signal pathway. In order that the target protein derived from a library (for example, a human VH domain library) passes through a TAPE screening system pathway, it needs to be completely folded within the cytoplasm and thus recognized by the Tat ABC translocase complex. Therefore, this complex present in the intracellular membrane may function as a fitness filter for filtering only substrates fitted to the Tat pathway. Accordingly, the present invention uses the facts that the protein generally passes through the Tat pathway only when it is completely folded in the cytoplasm, which is dependent on solubility and fast folding of the protein (DeLisa et al., 2003 PNAS 100(10): 6115-6120; Snaders et al., 2001 Mol Microbiol 41(1): 241-246; Matos et al., 2008 EMBO J 27(15): 2055-2063; Fisher et al., 2006 Protein Sci 15(3): 449-458; Lim et al., 2009 Protein Sci 18(12): 2537-2549), as found by other studies. The Tat pathway signal sequence usable in the present invention is preferably selected from signal sequences of TorA, CueO, DmsA, FdnG, FdoG, HyaA, NapA, Suf1, WcaM, YagT, TcbK, YcdB, YdhX, and YnfE proteins, but is not limited thereto.

In other words, the cytoplasm of E. coli, where protein folding occurs due to the nature of the Tat pathway, has a reducing condition not allowing a disulfide bond, and thus, VH domains, of which fast and accurate folding occurs autonomously without the help of the disulfide bond, can be filtered from the VH domain antibody library. Finding out antibodies that have functions under the reducing environment and are autonomously folded is a key point in developing specific antibodies for target antigens existing in the cytoplasm of the reducing environment, that is, intrabodies. Physicochemical properties of human VH domains or engineered VH domains of germ cells screened by the TAPE system of the present invention may be determined by analyzing characteristics of the screened VH domains. It is difficult to simply predict how the target protein autonomously folded within the cytoplasm contributes to certain physicochemical properties (for example, solubility of protein, thermostability of protein, long storage stability of protein, structural stability of protein, and the like) and further as an antibody therapeutic agent. The present invention has an object of introducing and developing the above TAPE method and applying this to protein technology, and more particularly, applying this TAPE method to screen an improved human immunoglobulin variable domain antibody (VH or VL) and applying the variable domain antibody having improved properties obtained therefrom as a scaffold for developing novel therapeutic antibodies.

The TAPE method according to the present invention has the following advantages as compared with methods of the prior art.

Through a method of performing panning by applying a predetermined stress, such as temperature, to a domain antibody library, using the phage display technology of the prior art, and then measuring binding activity to protein A (Jepsers L. et al., Nat. Biotechnol. 2004 22(9): 1161-5; Barthelemy P. A. et al., J. Biol. Chem. 2008 283(6): 3639-54), a domain named mO that is stable as a domain form was accidentally found through experiments without particular screening procedures (J. Biol. Chem. 2009 May 22; 284(21): 14203-14210).

However, according to the present invention, human immunoglobulin variable domains having high solubility and thermostability can be easily screened by employing the TAPE method using a Tat pathway of E. coli.

Also, there has been known a method of finding soluble proteins from the library including Tat signal sequences by using plate-based screening. However, this method have to follow a procedure where individual clones surviving due to antibiotic resistance thereof are obtained when an expression strain diluted with a predetermined ratio is smeared on a solid medium (plate) containing an antibiotics (Fisher A. C. et al., Protein Sci. 2006 Mar. 15(3): 449-58, Fisher A. C. et al., J. Mol. Biol. 2009 385(1): 299-311). Therefore, it is difficult to isolate individual clones of $10^5$ or more from one plate due to limitations of the plate-based screening method. Given that an antibody library for selecting general binding activities has $10^9$ to $10^{10}$, it is very physically difficult to cover the entire of a normal-size library by using the above method. As the result, it is substantially difficult to realize a high throughput form in screening. In addition, when gene sequences of plasmids of individual strains selected from the plate by antibiotic resistance is confirmed in most cases of using methods of the prior art (for example, ISELATE), a case where a target gene is cloned into a fragmented form to express a short form of protein or a case where only a reporter gene is present without the target protein (for example, TEM1-1 beta-lactamase only) is often found (Fisher A. C. et al., J. Mol. Biol. 2009 385(1): 299-311). These peptide-level (consisting of 10 to 20 amino acids) short proteins are not affected by two or three dimensional structure thereof, and thus, they themselves have very high solubility in most cases, causing false positive. In the Tat-based protein folding screening method of the prior art (for example, ISELATE, Fisher J M B 2009), this false positive ratio tends to increase with the increasing number of screenings using antibiotic resistance, and this acts as substantial hindrance so that screening of soluble protein is impossible. Therefore, most of these methods are used with the purpose of, rather than inspecting a large-scale library, studying crystalline structures by securing solubility expression through protein modification from a small-size mutant library ($10^5$ to $10^6$ size) of target proteins having difficulty in securing solubility (Pédelacq et al., Nat Biotechnol. 2002 20(9):927-32; Yang et al., Proc. Natl. Acad. Sci. 2003 100(2): 455-60).

However, according to the TAPE method according to the present invention, the entire library is inoculated on a liquid medium containing a selective antibiotics (for example, ampicillin), but not using the protein solubility screening method based on the existing solid medium (plate). Therefore, there are no limitations on the size of the library (E. coli) applicable to screening at one time in the case where the volume of medium is increased, thereby achieving high throughput screening. In addition, as described above, in the method of the prior art, it is highly like that the clone in which a self-ligated mock vector and the above-described peptide-level gene fragments are introduced is present as a false positive during a cloning procedure of a library to an expression vector (for example, pET-TAPE) after the library is screened from the liquid medium containing an antibiotics. In order to solve the false positive problem due to peptide-level gene fragments, which is caused by inherent problems of this cloning method using a ligase, total plasmids are collected from the collected E. coli, and both terminals of the previously designed gene that expresses the fusion protein of target protein and TEM-1 beta-lactamase are treated with restriction enzyme. Then, a complete size of selective gene is isolated by gel electrophoresis and gel elution methods. As the result, only all true positive VH domain genes firstly screened by the TAPE method can be collected in full. Therefore, the TAPE method according to the present invention has advantages in that only true positive clones containing only the gene construct of complete target protein can be screened depending on the degree of resistance to antibiotics, without increasing false positive in spite of the increasing number of repetitive screenings using antibiotic resistance.

Specifically, the TAPE system according to the present invention uses a gene construct coding a fusion protein where a Tat-signal sequence is functionally linked to an N-terminal of a target protein, particularly a heavy chain domain, and an antibiotic resistant protein, particularly an antibiotic resistance-conferring protein, such as matured (a Sec pathway signal sequence is self-excluded) TEM-1 beta-lactamase or the like, is functionally linked to a C-terminal thereof.

The TAPE system or the TAPE method using the same uses principles that after a host cell, particularly, E. coli, is transformed with the gene construct, only E. coli express the properly folded antibiotic-resistant protein in a soluble type by the Tat-signal sequence can survive under the culture condition containing antibiotics.

When one host cell is transformed by only one gene construct, the target protein included in the surviving host cell is assumed to be properly folded in a soluble form.

In addition, soluble target proteins can be isolated in a large-scale high throughput manner through the TAPE method according to the present invention, by using a plurality of host cell groups, particularly groups of *E. coli*, transformed with gene constructs coding different target proteins.

The TAPE method comprises:

(1) culturing a host cell group in a liquid medium containing antibiotics, the host cell group being transformed with a gene construct coding a fusion protein where a Tat-signal sequence is functionally linked to an N-terminal of a target protein, particularly a heavy chain variable domain, and an antibiotic-resistant protein is functionally linked to a C-terminal thereof;

(2) collecting plasmid DNA from the antibiotic-resistant *E. coli*;

(3) collecting a nucleic acid sequence coding the target protein from the collected plasmid DNA; and (4) confirming and screening a sequence of the target protein from the collected nucleic acid sequence.

Particularly, the method may further comprise, after the stage (3), one stage selected from:

(3') preparing a gene construct where the collected nucleic acid sequence is again functionally linked to a gene coding the Tat-signal sequence and an antibiotic resistance-conferring gene, and again transforming the host cell group with the created gene construct, or (3") directly transforming the host cell group with the plasmid containing the collected nucleic acid sequence, without preparing a separate gene construct.

The stage (3") has an advantage as compared with the stage (3') in that a next stage is more promptly performed.

The stages (1) to (3') or the stages (1) to (3") may be repeated two or more rounds, and this repetitive procedure can result in screening the target protein having solubility and high level of stability.

When the stages (1) to (3') or the stages (1) to (3") may be repeated two or more rounds, finally the target protein can be identified by performing the stage (4) of confirming and screening the sequence of the target protein, after the stage (3') or (3").

The TAPE method will be specifically described.

(1) A target protein, particularly, a human variable domain library is expressed as a fusion protein form in the cytoplasm of each host cell, particularly *E. coli*. Here, only one particular fusion protein is expressed in each host cell, particularly *E. coli*. Here, in the fusion protein, the Tat-signal sequence is functionally linked to an N-terminal of the target protein, for example, a human immunoglobulin variable domain, particularly VH and an antibiotic resistance-conferring protein, such as a matured (a Sec pathway signal sequence is self-excluded) TEM-1 beta-lactamase or the like, is functionally linked to a C-terminal thereof.

(2) The fusion protein-expressed library is inoculated in a liquid screening medium containing antibiotics, and a selection pressure is applied thereto. Here, the concentration of the antibiotics contained in the liquid screening medium may be 1×, 2×, 3×, 4×, 5×, 8×, or 10× at the initial round, based on 0.1 µg/ml (1×). The antibiotics used herein may be ampicillin, carbenicillin, or the like, but is not limited thereto. Any antibiotics that can be appropriately used depending on the antibiotic-resistant protein used in the stage (1) may be used without limitations. The expressed fusion protein passes through a Tat pathway depending on characteristics of the target protein and moves to the intracellular membrane. The fusion protein that fails to translocate due to characteristics of the target protein, that is, does not have solubility may form an inclusion body or may be degraded in the cytoplasm due to Tat proofreading mechanism. Only *E. coli* where the fusion protein moves to the periplasm can obtain resistance in the liquid screening medium containing antibiotics, by action of the antibiotic resistance-conferring protein, such as TEM-1 beta-lactamase or the like, which is functionally linked to the C-terminal of the target protein.

(3) The plasmid DNA is collected from *E. coli* that survives in the liquid screening medium, and then treated with the previously designed restriction enzyme, to collect the nucleic acid encoding only a fusion portion of the target protein and the antibiotic resistance-conferring protein such as beta-lactamase, from the entire fusion protein, by electrophoresis and gel elution methods, or, (3') The plasmid DNA is collected from *E. coli* that survives in the liquid screening medium, and then *E. coli* is directly transformed with the collected plasmid DNA, as described in Example 5, which follows the next stage.

(4) The collected nucleic acid is cloned into a mock vector in order that it is functionally linked to the Tat signal sequence again.

After that, the stages 1) to 3) may be again repeated, so as to enrich the ratio of genes expressing a protein having desired properties from the library. Here, a liquid medium for the next round may be selected to have higher concentration of antibiotic than that of the previous round.

As the target protein in the present invention, particularly the target protein that can be screened by the TAPE method, any type of protein that has the desired functions may be used. Preferably, a protein having binding ability to a specific target (scFv, intrabody, domain antibody, Fab), a receptor protein, particularly a T-cell receptor (TCR), a receptor ligand, or the like may be used, but the target protein in the present invention is not limited thereto. More preferably, a domain antibody, for example, a VH domain antibody or a VL domain antibody is suitable.

The target protein in the present invention may have mutation. For mutagenesis of the target protein, mutation methods based on amplification, such as a method of synthesizing an oligomer which is designed such that amino acids at specific sites may be randomly modified, and then employing an over-lapping polymerase chain reaction (PCR) using the oligomer, or a method of inducing random variation at random sites (error-prone PCR) in the PCR condition where the error rate of DNA polymerase is artificially increased, but the mutation methods are not limited thereto.

The fusion protein including the target protein of the present invention may include a tag consisting of a particular amino acid sequence at the C-terminal thereof, in order to facilitate separation, purification, or detection thereof. Any tag that is commonly used in the art to which the present invention pertains may be used without limitations as this tag. For example, the tag may be selected from 6×His tag, flag tag, c-myc tag, and the like, but is not limited thereto.

Any vector that is known to be capable of being expressed in *E. coli* in the art to which the present invention pertains may be used without limitations as the vector for expressing the fusion protein, and non-limited examples of this vector may include pET22b (Novagen), pAE34 (AthenaES), pET9a (Novagen), ΔpMK, or the like (Lim H K et al., Production Characteristics of Interferon-a Using an L-arabinose Promoter System in a High-cell-density Culture. Appl. Microbiol. Biotechnol. 53(2): 201-208.). As the promoter for inducing expression of the fusion protein, a lac promoter, a T7 promoter, an arabinose promoter, or the like may be used.

Only the target gene is collected from the library screened by using the TAPE method, and cloned into a new expression vector, so that only the target protein is alone expressed without the Tat signal and TEM-1 beta-lactamase that have been positioned at the N-terminal and the C-terminal, respectively, and then, a purification procedure for individual hits is performed. Here, the purification procedure may be easily performed by including a tag at the C-terminal of the target protein in order to facilitate purification and analysis. As described above, any tag that is commonly used in the art to which the present invention pertains may be used without limitations. For example, the tag may be selected from 6×His tag, flag tag, c-myc tag, and the like, but is not limited thereto. Also, the purification procedure may be performed by using protein A affinity column according to the type of variable domains, for example VH3.

A ligand having desired properties may be screened depending on the kind of library used by the TAPE method according to the present invention. Examples of this ligand may include an immunoglobulin variable domain, particularly a domain antibody, a receptor, a receptor ligand, and the like, but is not limited thereto. In particular, the ligand may be a wild type, as well as may be one having mutation by inducing mutation in the library or the like, as described above.

In addition, a gene sequence, that is, a base sequence for coding the ligand may be obtained in the common manner.

It was confirmed that the ligand obtained by the TAPE method of the present invention, for example, a wild type ligand including receptor, receptor ligands, VH and VL from a germ line base sequence or their mutated ligand screened from their combinatorial library exhibits preferable physicochemical properties. In particular, it was confirmed that the ligand was improved in solubility, long storage stability, self-folding ability in the cytoplasm of reducing environment, and thermostability.

A more preferably ligand may be, for example, a human immunoglobulin variable domain obtained from a human immune cell cDNA library and a mutant thereof. The mutant may be screened and obtained by using a library where amino acids are modified by using an NNK primer or the like at a particular position of a frame portion of a particular wild type human immunoglobulin variable domain.

When the heavy chain or light chain variable domain, that is, a VH or VL domain antibody, which is screened by the TAPE method according to the present invention, has a corresponding frame sequence of human VH or VL domain, solubility and thermostability thereof are still maintained regardless of CDR sequences.

Therefore, the VH scaffold having excellent physical properties such as high solubility, thermostability, and the like, which is screened through the present invention, may be used as a scaffold of the library for obtaining a particular ligand, that is, a domain antibody targeting a desired target, that is, an antigen. Specifically, a library is constructed by, while maintaining a scaffold of the screened mutant VH domain antibody, inserting random CDR sequences thereinto, and then an antibody having binding ability to a desired target, that is, an antigen, may be screened from the library by using common methods such as panning or the like.

Specifically, the above antibody may be screened by eluting all the VH domain antibodies that are not bound to fixed desired antigens, except VH domain antibodies that are bound thereto, similarly to the common phage display method or the like. The above procedure of eluting the VH domain antibodies that are not bound to the fixed desired antigens is repeated twice or more, thereby screening VH domain antibodies having higher binding ability to the targeting antigens.

In order to construct a CDR mutant library by using the scaffold of the VH domain antibody obtained in the present invention as described above, a corresponding variable region (for example, CDR in the case of a human immunoglobulin variable domain) may have various lengths, that is, the number of amino acid residues may be changed, or particular amino acid residues may be replaced with other random amino acids. Alternatively, only some particular sites of the hyper variable region within CDR may be randomly modified.

Accordingly, the present invention provides a library including random CDR sequences in a scaffold of a VH or VL domain antibody screened by the TAPE method and a producing method thereof, and provides a method for screening a VH or VL domain antibody having binding ability to a desired target protein by using the library, and a VH or VL domain antibody screened by the method, and also provides an amino acid sequence of the screened domain antibody and a polynucleotide encoding the same.

These methods can improve physical properties of the human single variable domain antibody, particularly the VH domain antibody, thereby obtaining a single variable domain, particularly a VH domain antibody having such excellent solubility and thermostability that cannot be found in the natural VH and VL.

BRIEF DESCRIPTION OF THE DRAWINGS

FIG. 3 is a multiple sequence alignment showing amino acid sequences of human VH domains screened from a human immunoglobulin heavy chain variable domain gene library by using TAPE method.
The following complete sequences represented by the SEQ ID NOs span both pages of FIG. 3 and include the FR1, CDRH1, FR2, CDRH2, FR3, CDRH3, and FR4 domains: MG1X8 (SEQ ID NO: 538); MG2X1 (SEQ ID NO: 539); MG2X1-34 (SEQ ID NO: 540); MG2X2-12 (SEQ ID NO: 541); MG2X2-13 (SEQ ID NO: 542); MG3X1 (SEQ ID NO: 543); MG3X10 (SEQ ID NO: 544); MG4X1-8 (SEQ ID NO: 545); MG4X1-33 (SEQ ID NO: 546); MG4X1-35 (SEQ ID NO: 547); MG4X3-27 (SEQ ID NO: 548);

MG4X4-2 (SEQ ID NO: 549); MG4X4-4 (SEQ ID NO: 550); MG4X4-25 (SEQ ID NO: 551); MG4X4-44 (SEQ ID NO: 552); MG4X5-30 (SEQ ID NO: 553); MG4X6-27 (SEQ ID NO: 554); MG4X6-48 (SEQ ID NO: 555); MG4X7-15 (SEQ ID NO: 556); MG4X8-24 (SEQ ID NO: 557); MG0.5X-1 (SEQ ID NO: 558); MG0.5X-3 (SEQ ID NO: 559); MG0.5X-4 (SEQ ID NO: 560); MG0.5X-14 (SEQ ID NO: 561); MG0.75X-4 (SEQ ID NO: 562); MG2X-5 (SEQ ID NO: 563); MG2X-15 (SEQ ID NO: 564); MG3x1 (SEQ ID NO: 565); MG4X-5 (SEQ ID NO: 566); MG1-4 (SEQ ID NO: 567); MG1-6 (SEQ ID NO: 568); MG1-7 (SEQ ID NO: 569); MG1-8 (SEQ ID NO: 570); MG1-9 (SEQ ID NO: 571); MG1-10 (SEQ ID NO: 572); MG5-1 (SEQ ID NO: 573); MG5-2 (SEQ ID NO: 574); MG5-4 (SEQ ID NO: 575); MG5-5 (SEQ ID NO: 576); MG5-6 (SEQ ID NO: 577); MG5-7 (SEQ ID NO: 578); MG5-9 (SEQ ID NO: 579); MG10-1 (SEQ ID NO: 580); MG10-2 (SEQ ID NO: 581); MG10-4 (SEQ ID NO: 582); MG10-5 (SEQ ID NO: 583); MG10-6 (SEQ ID NO: 584); MG10-8 (SEQ ID NO: 585); MG10-10 (SEQ ID NO: 586); MG2 (SEQ ID NO: 587); M5G (SEQ ID NO: 588); MG6 (SEQ ID NO: 589); MG7 (SEQ ID NO: 590); and MG10 (SEQ ID NO: 591).

Figure 4:
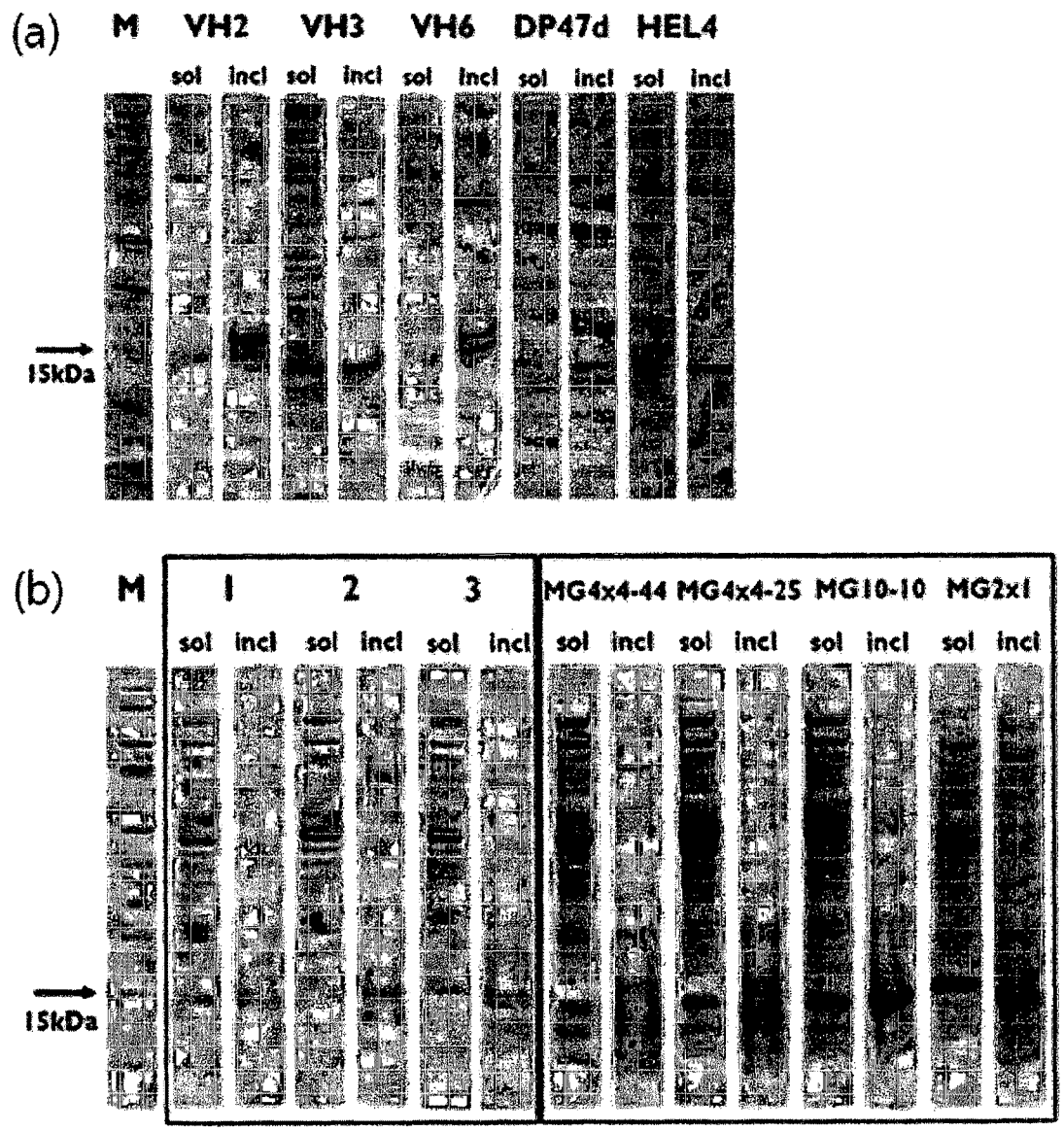

FIG. 4 shows analysis results using SDS-PAGE about expression aspects in *E. coli*, of human VH domains screened from the human immunoglobulin heavy chain variable domain gene library by using the TAPE method, wherein, sol represents a soluble fraction after cell lysis and Incl represents an insoluble fraction after cell lysis, and an arrow indicates a band at a position of the corresponding VH molecular weight:
(a) expression aspects of VH domains known to have good solubility in the prior art, and
(b) a left box showing expression aspects of VH domains randomly selected from the human immunoglobulin heavy chain variable domain derived from human germ line cells, and a right box showing expression aspects of VH domains screened by the TAPE method.

Figure 5:
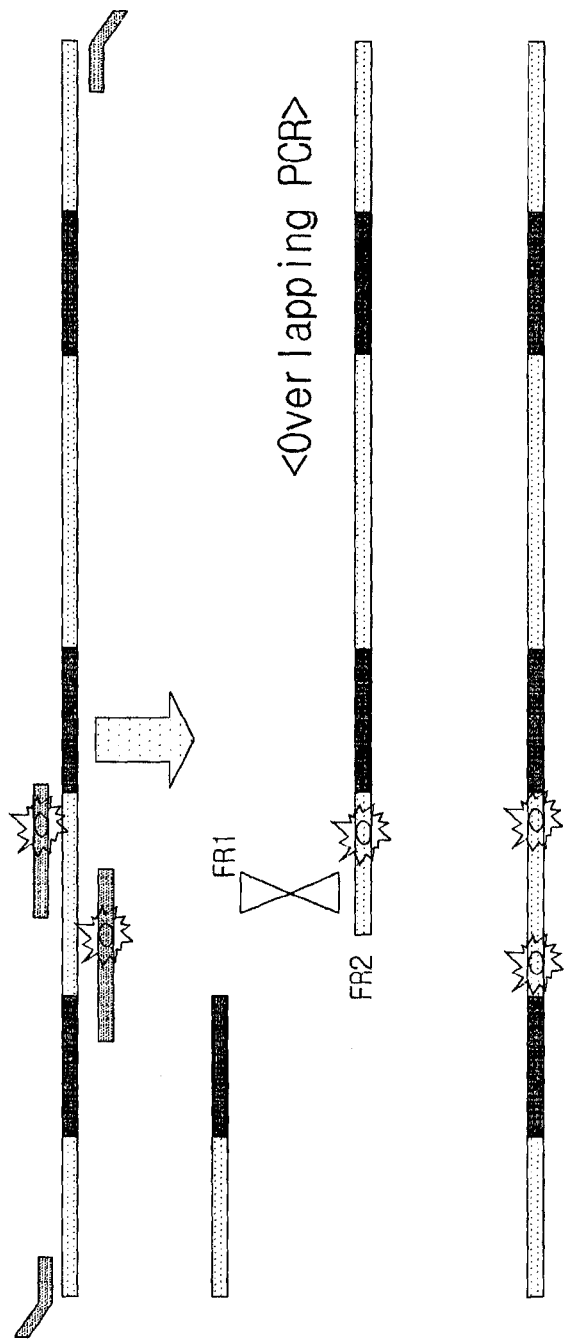

FIG. 5 is a view showing a method of preparing an engineered library of the VH domain antibody scaffolds firstly screened by the TAPE method.

Figure 6:
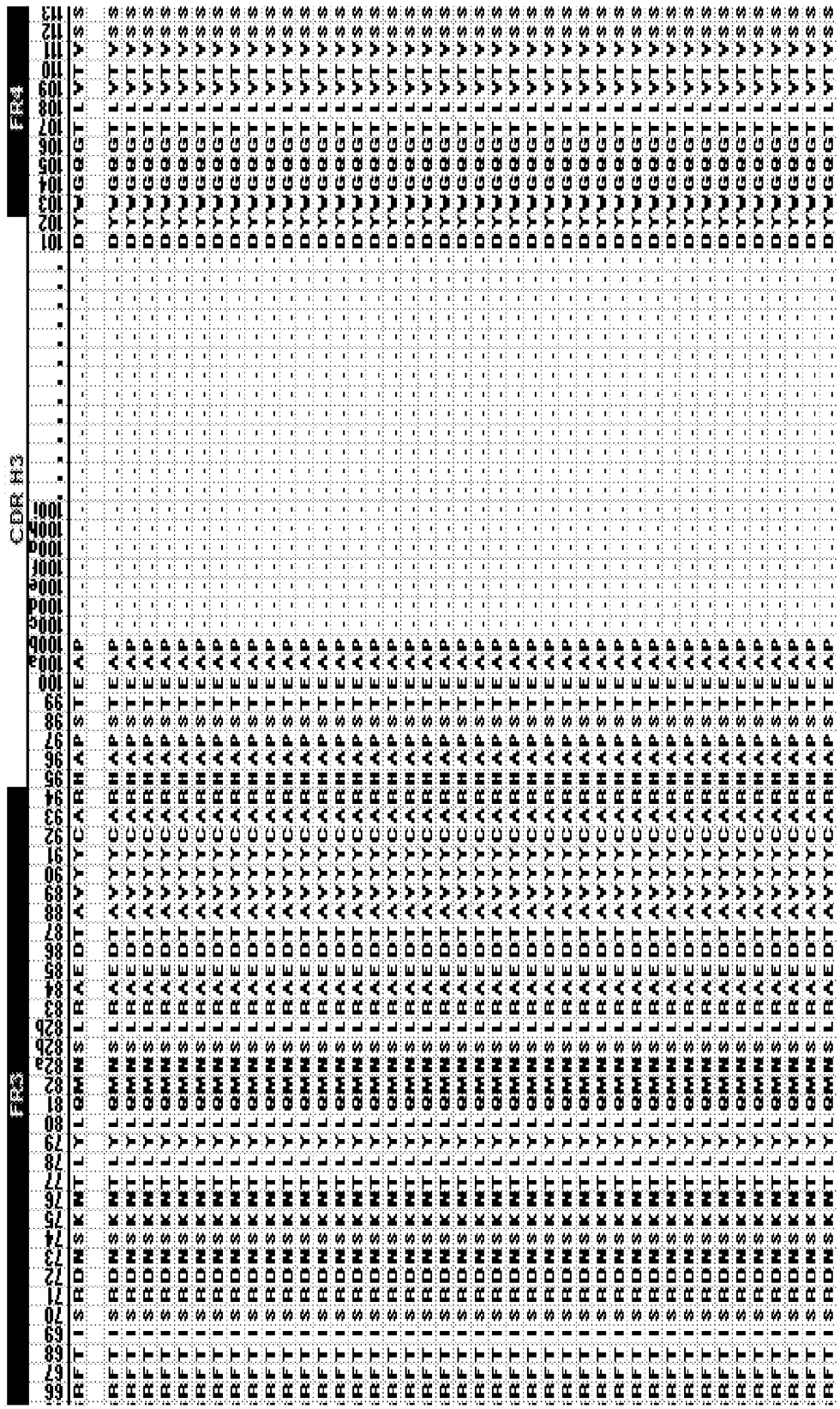

FIG. 6 is a multiple sequence alignment showing amino acid sequences of human VH domains screened by the TAPE method using the engineered library of VH domain antibody scaffolds.
The following complete sequences represented by the SEQ ID NOs span both pages of FIG. 6 and include the FR1, CDRH1, FR2, CDRH2, FR3, CDRH3, and FR4 domains:
MG2X-1 (SEQ ID NO: 592); MG8-21 (SEQ ID NO: 593); MG2-12L (SEQ ID NO: 594); MG2-7I (SEQ ID NO: 595); MG2-9 (SEQ ID NO: 596); MG2-10I (SEQ ID NO: 597); MG2-11I (SEQ ID NO: 598); MG2-12I (SEQ ID NO: 599); MG2-32 (SEQ ID NO: 600); MG2-34 (SEQ ID NO: 601); MG2-40 (SEQ ID NO: 602); MG2-46 (SEQ ID NO: 603); MG2-47 (SEQ ID NO: 604); MG2-48 (SEQ ID NO: 605); MG2-51 (SEQ ID NO: 606); MG2-53 (SEQ ID NO: 607); MG2-55 (SEQ ID NO: 608); MG2-57 (SEQ ID NO: 609); MG2-58 (SEQ ID NO: 610); MG2-59 (SEQ ID NO: 611); MG2-60 (SEQ ID NO: 612); MG2-64 (SEQ ID NO: 613); MG4-12 (SEQ ID NO: 614); MG4-13 (SEQ ID NO: 615); MG4-17 (SEQ ID NO: 616); MG4-18 (SEQ ID NO: 617); MG4-20 (SEQ ID NO: 618); MG4-28 (SEQ ID NO: 619); MG4-2 (SEQ ID NO: 620); MG4-32 (SEQ ID NO: 621); MG4-33 (SEQ ID NO: 622); MG4-34 (SEQ ID NO: 623); MG4-5 (SEQ ID NO: 624); MG4-6 (SEQ ID NO: 625); MG4-7 (SEQ ID NO: 626); MG8-11 (SEQ ID NO: 627); MG8-12 (SEQ ID NO: 628); MG8-13 (SEQ ID NO: 629); MG8-14 (SEQ ID NO: 630); MG8-4 (SEQ ID NO: 631); MG8-5 (SEQ ID NO: 632); MG8-6 (SEQ ID NO: 633); and MG8-8 (SEQ ID NO: 634).

FIG. 7 shows analysis results using SDS-PAGE about expression aspects in *E. coli*, of human VH domains screened by the TAPE method using the engineered library of VH domain antibody scaffolds,
wherein, M denotes Marker, Lane 1 represents an expression aspect of a camelid domain antibody VHH, Lane 2 a CDR synthetic human domain antibody HEL4, Lane 3 MG2X1, and Lanes 4 to 32 represent expression aspects of VH scaffolds screened from a frame-engineered library, and the frames for respective lanes are as follows: lane5:MG2-47, lane6:MG2-55, lane7:MG2-57, lane8:MG2-59, lane9:MG4-2, lane10:MG4-5, lane11:MG4-6, lane12:MG4-7, lane13: MG4-12, lane14:MG4-13, lane15:MG4-17, lane16:MG4-20, lane17:MG4-28, lane18:MG4-32, lane19:MG4-33, lane20:MG8-4, lane21:MG8-5, lane22:MG8-6, lane23: MG8-8, lane24:MG8-11, lane25:MG8-12, lane26:MG8-13, lane27:MG2-7I, lane28:MG2-9I, lane29:MG2-10I, lane30: MG2-11I, lane31:MG2-12I, lane32:MG2-12L FIG. 8 is a graph showing circular dichroism (CD) comparison results of VH domains screened by the TAPE method.

FIG. 9 is a graph showing circular dichroism (CD) comparison results of human VH domains screened by the TAPE method using the engineered library of VH domain antibody scaffolds.

FIG. 10 is a graph showing long-term storage stability of VH domains screened by the TAPE method.

FIG. 11 is a view showing a method of preparing an engineered library having a changed CDR length.

FIG. 12 is a multiple sequence alignment showing mutation positions of a rational library, for improving binding ability to antigen.
The following complete sequences include the FR1, CDRH1, FR2, CDRH2, FR3, CDRH3, and FR4 domains:
MG2X1 (SEQ ID NO: 635); MG8-4 (SEQ ID NO: 636); MG8-14 (SEQ ID NO: 637).

FIG. 13 is a view showing a method of preparing a selective CDR-engineered library.

Figure 14:
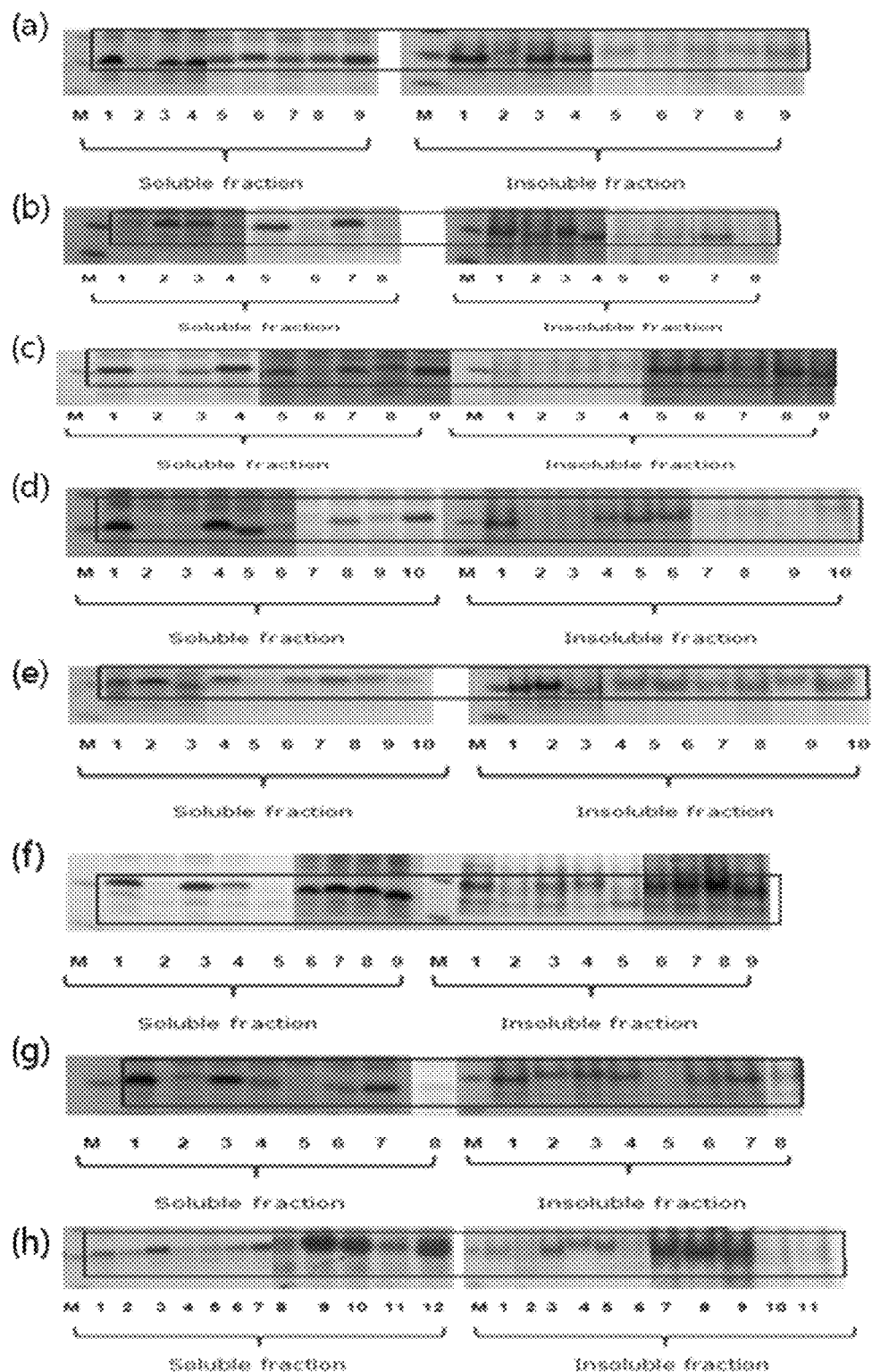

FIG. 14 shows analysis results using SDS-PAGE about expression aspects in *E. coli*, of VH scaffolds according to the number of amino acid residues of CDRH3 at the time of CDRH3 modification:
(a) a case in which the number of amino acid residues of CDRH3 is 7,
(b) a case in which the number of amino acid residues of CDRH3 is 8,
(c) a case in which the number of amino acid residues of CDRH3 is 9,
(d) a case in which the number of amino acid residues of CDRH3 is 10,
(e) a case in which the number of amino acid residues of CDRH3 is 11,
(f) a case in which the number of amino acid residues of CDRH3 is 12,
(g) a case in which the number of amino acid residues of CDRH3 is 13, and
(h) a case in which the number of amino acid residues of CDRH3 is not changed.

DETAILED DESCRIPTION OF EMBODIMENTS

Hereinafter, the present invention will be described in detail with reference to examples and the accompanying drawings. However, these are intended to explain the present invention in more detail, and the scope of the present invention is not limited by the following examples.

Example 1: Preparation of pET-TAPE for Constructing TAPE System

In order to construct a twin-arginine transport (Tat)-associated protein engineering (TAPE) system, pET-TAPE was prepared by linking a pathway signal sequence of TorA (*E. coli* trimethylamine N-oxide reductase) which is a Tat substrate protein, that is, ssTorA to an N-terminal of a target protein and linking TEM-1 beta-lactamase to a C-terminal thereof while using a pET9a vector.

However, a signal sequence that leads the protein to a Tat pathway is not limited to ssTorA, as mentioned above, and it is obvious to the ordinary skilled person that signal sequences of all Tat pathway proteins may be used. Also, it is obvious to the ordinary skilled person that, as the used vector, any vector that can meet objects of the present invention, such as pET9a (New England Biolab), ΔpMA using arabinose induction promoter (Korean Patent Laid-open Publication No. 1996-007784), pAE34 using lac promoter, or the like, may be used.

In the case of using pET9a as the vector, when expression of a fusion protein consisting of ssTorA, the target protein, and TEM-1 beta-lactamase is induced by IPTG under the optimized culturing condition, the fusion protein passes through the Tat movement pathway by guidance of the signal sequence. Here, only soluble and completely folded fusion protein passes through an intracellular membrane by Tat machinery (Tat A, B, C), and as a result, the TEM-1 beta-lactamase linked to the target protein moves to the periplasm of *E. coli*, due to folding characteristics of the target protein. Antibiotic resistance of *E. coli* is determined depending on the presence or absence of TEM-1 beta-lactamase in the periplasm.

In the present invention, for a system for screening a human immunoglobulin heavy chain variable domain, a human immunoglobulin heavy chain variable domain library, which is a target gene, was inserted between ssTorA and TEM-1 beta lactamase of the pET-TAPE vector.

An experimental procedure will be described in detail as follows. A fusion gene of ssTorA gene and a representative gene of human immunoglobulin heavy chain variable domain VH family type 2 (Stefan Ewert et al., Stability improvement of antibodies for extracellular and intracellular applications: CDR grafting to stable frameworks and structure-based framework engineering. Methods 34 (2004) 184-199) was synthesized by DNA oligomer synthesis and overlapping polymerase chain reaction (Genscript USA Inc., US). A polymerase chain reaction (PCR) was induced by using the synthesized ssTat-VH2 gene as a template while using 5' direction primer (SEQ ID NO: 1) including NdeI sequence and 3' direction primer (SEQ ID NO: 2) including NotI, 6×his, and BamHI sequences.

The PCR reaction was performed by using the two primers, 1 mM of 0.5 U I-pfu DNA polymerase (iNtRON), each 2.5 mM of four kinds of dNTPs, and 5 μl of 10× reaction buffer, and distilled was supplemented to the final volume of 50 μl. The PCR was run at 95° C. for 2 minutes, followed by 30 cycles of 94° C. for 15 seconds, 56° C. for 15 seconds, and 72° C. for 30 seconds, and finally 72° C. for 5 minutes. The amplified DNA was loaded on 1% of agarose gel to perform electrophoresis, and then, isolated by using a QIAquick gel extraction kit (QIAGEN, Valencia, Calif., USA).

The NdeI-ssTorA-VH2-NotI-6×His-BamHI gene amplified through the PCR was inserted between NdeI and BamHI cutting sites present in a multi-cloning site (MCS) of the pET9a vector, to prepare a pET9a-ssTorA-VH2 plasmid. The NotI-TEM-1 beta-lactamase-BamHI segment, which was isolated by running PCR using 5' primer (SEQ ID NO: 3) and 3' primer (SEQ ID NO: 4) while using a TEM-1 ß-lactamase (bla) gene as a template, was inserted between NotI and BamHI cutting sites of the pET9a-ssTorA-VH2 plasmid, and this was named pET-TAPE. After that, a library was constructed by removing a VH2 region from the pET-TAPE and inserting a library gene thereinto. In order to check whether or not the constructed TAPE system is dependent on solubility of the corresponding protein, representative natural type human immunoglobulin domain antibodies (Dp47d, VH2, VH3) of which the degree of soluble expression in *E. coli* was previously known, a negative control gene (VH3-Bla, no signal sequence), and a positive control gene (ssTorA-Bla, no target protein) were introduced in the pET-TAPE, and then the degree of antibiotic resistance of TEM-1 beta-lactamase was measured. It was known that soluble expression in *E. coli* of VH family type 2 was very unfavorable, and then soluble expression in *E. coli* of VH3 and DP47d was relatively favorable (Ewert et al., Stability improvement of antibodies for extracellular and intracellular applications: CDR grafting to stable frameworks and structure-based framework engineering. Methods 34 (2004) 184-199).

Specifically, control human immunoglobulin heavy chain variable domains of which protein solubility was previously known, a negative control (a construct where a representative gene of VH family type 3 is inserted into the pET-TAPE and ssTorA is removed so as to prevent TEM-1 beta-lactamase from reaching the periplasm) and a positive control (pET-TAPE itself, a construct where a VH gene is not inserted but linked to ssTorA so as to express only TEM-1 beta-lactamase) were mounted on the TAPE systems, and these were inoculated in a culture liquid containing an antibiotic agent. Then, the degree of antibiotic resistance according to solubility was measured by counting total viable cells. An LB medium containing 50 μg/ml of ampicillin was used, and expression was induced with IPTG for 3 hours, and then total viable cells were counted.

Figure 1:
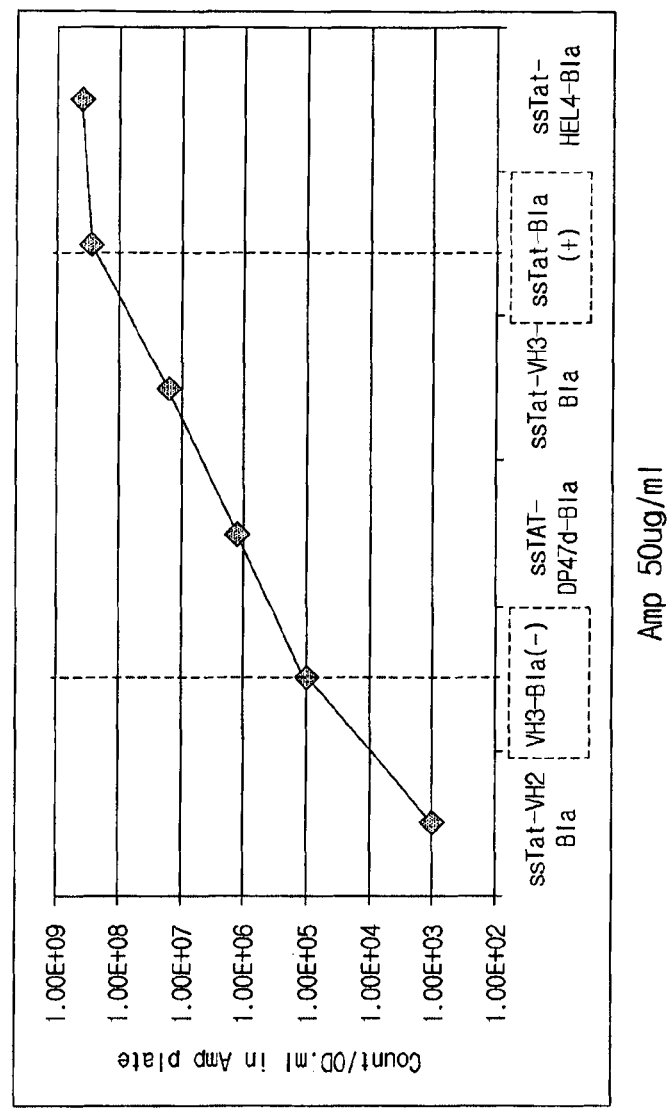
FIG. 1 is a graph showing solubility of proteins screened by a TAPE method.

Results showed that known solubility of the corresponding gene is proportional to the degree of antibiotic resistance under the pET-TAPE system (see, FIG. 1). In FIG. 1, the increasing count per unit cell concentration means stronger antibiotic resistance.

Example 2: Preparation of Immunoglobulin Heavy Chain Variable Domain (VH) Library Derived from Human Germline The cDNA libraries were secured by reverse transcription of mRNAs obtained from the liver, peripheral blood mononuclear cells (PBMC), spleen, and thyroid of human.

In order to secure DNA sequences of human immunoglobulin heavy chain variable domains from this, mixed primers depicted from SEQ ID NOs: 5 to 13 were designed to secure all human heavy chain variable domain genes usable in the human germ cell line. Each of the secured human heavy chain variable domain gene libraries was inserted between NdeI and BamHI sites of the pET-TAPE, to complete a library having a size of about $10^8$.

Specifically, cDNA was prepared from RNAs (Clontech, Madison, Wis., US) extracted from spleen, peripheral blood mononuclear cells, the liver, and thymus of human by a reverse transcription reaction. AMV reverse transcriptase and RNase inhibitor were purchased from Promega (Madison, Wis., USA). Respective RNAs were mixed to 1 μl of dNTP mixture (0.2 mM) and 1 μl an oligo dT primer, and nuclease-free water was inputted thereto to reach the total volume of 12 μl. For RNA denaturation, the mixture was cultured at 65° C. and then 4 μl of 5× strand buffer, 1 μl of RNase inhibitor, and 2 μl of 0.1M DTT were inputted thereto. The reverse transcription reaction was run at 42° C. for 15 minutes, and then left at 70° C. for 15 minutes. As the primers used in PCR, several degenerative primers were simultaneously used in order to obtain VH domains for respective family types.

Primers depicted from SEQ ID NOs: 5 to 13 (see, Table 5) and each including a forward NcoI sequence and primers depicted from SEQ ID NOs: 14 and 15 (see, Table 5) and each including a reverse NotI sequence (Integrated DNA Technologies, Inc., Coralville, Iowa, US) were used. DNA was amplified by using cDNA generated through the reverse transcription reaction as a template, the primer 10 pmolar for each case, 0.5 U of 1-pfu DNA polymerase (Interon, Korea), four kinds of dNTP each 2.5 mM, and 5 μl of 10× buffer. The PCR was run at 95° C. for 2 minutes, followed by 30 cycles of 94° C. for 20 seconds, 56° C. for 20 seconds, and 72° C. for 2 minutes, and finally 72° C. for 7 minutes. The reaction mixture after the PCR was separated by electrophoresis using 1% of agarose gel, and then purified by using a gel extraction kit (QIAGEN, Valencia, Calif., USA). The amplified PCR product and pET9a-TAPE plasmid were cut with NcoI and NotI restriction enzymes, and purified by a PCR purification kit (QIAGEN) and a gel extraction kit, respectively. The amplified VH gene was inserted between NcoI and NotI cutting sites of the pET9a-TAPE, to prepare a human germ cell-derived VH library plasmid. The prepared library was concentrated by using an ethanol precipitation method.

ElectroMAX™ DH5a-E™ (Invitrogen, Carlsbad, Calif., US), which is *E. coli*, was transformed with 1 μl of DNA through electrophoration (BTX model ECM630, Holliston, Mass., USA). In order to verify a size of the library, the transformed *E. coli* was sequentially diluted to $10^{-4}$ to $10^{-8}$, and cultured in an LB agar medium containing Kanamycin. After that, colonies were counted.

As a result, it was confirmed that the library size of VH1 family was $9.1 \times 10^6$, VH3 was $1.56 \times 10^9$, and VH5 was $6.05 \times 10^8$. The VH gene obtained by randomly selecting 50 single colonies among them, followed by culturing in an LB liquid culture containing Kanamycin, and then isolating respective plasmids, using a DNA purification kit (QIAGEN, Valencia, Calif., USA). As the result that a base sequence of the VH gene was analyzed, it was confirmed that 90% or more genes were maintained in a transcript-able form.

TABLE 5

Sequences of primers used in the present invention

| SEQ ID NO | Sequence of primer |
|---|---|
| 1 | GCCATATGAACAATAACGATCTCTTTCAGGCATCACGT |
| 2 | GCGGATCCATGGTGGTGATGGTGGTGTGCGGCCGCTGAAGAGACGGTCACCAACGTGCC |
| 3 | GCGCGGCCGCACACCCAGAAACGCTGGTG |
| 4 | GCGGATCCTTACCAATGCTTAATCAGTGAGGC |
| 5 | GCGCTAGCCAGGTKCAGCTGGTGCAG |
| 6 | GCGCTAGCCAGGTCCAGCTTGTGCAG |
| 7 | GCGCTAGCSAGGTCCAGCTGGTACAG |
| 8 | GCGCTAGCCARATGCAGCTGGTGCAG |
| 9 | GCGCTAGCCAGATCACCTTGAAGGAG |
| 10 | GCGCTAGCCAGGTCACCTTGARGGAG |
| 11 | GCGCTAGCGARGTGCAGCTGGTGGAG |
| 12 | GCGCTAGCCAGGTGCAGCTGGTGGAG |
| 13 | GCGCTAGCGAGGTGCAGCTGTTGGAG |
| 14 | GCGCGGCCGCTGAGGAGACGGTGAC |
| 15 | GCGCGGCCGCTGAAGAGACGGTGAC |
| 16 | GCGCGGCCGCTGAGGAGACAGTGAC |
| 17 | GCCCATGGGAAGTCCAACTGGTTGAATCTGGTGGCGGTTTAGTT |
| 18 | AGTTGAACCGCCAGAGCCGGAAATMNNTGAGACMNNTTCMNNACCTTTGCCTGGCGCMNNACGCACCCAGCCCATAGCATAAGAAGAAAAGGTAAAGCCACTTGCAGCACAGCT |

TABLE 5-continued

Sequences of primers used in the present invention

| SEQ ID NO | Sequence of primer |
|---|---|
| 19 | ATTTCCGGCTCTGGCGGTTCAACTNNKTACNNKGATAGCGTTAAAGGTCGTTTCACAATCTCC |
| 20 | GCGCGGCCGCACTGCTCACAGTAACCAGGGTACCCTG, | where K means G or T, S means C or G, R means A or G, M means A or C, and N means A or T or G or C An "antibody sequence numbering system" in the present invention means a system where amino acids of the immunoglobulin variable domain, VH or VL are numbered. In CDRs of the antibody, the number of amino acids in the CDR differs from antibody to antibody. Therefore, numbering needs to be performed on conservative amino acid sequences (for example, frame portions) and variable portions of an individual VH or VL of many kinds with a fixedly determined rule, starting from the N-terminal. Kabat, Chothia, and IMGT numbering systems are representative, and they differ from each other depending on in what order amino acids of the CDR portion are numbered. In the present invention, the Kabat numbering system is used. For example, the Kabat numbering system follows the following principles when numbering amino acids of the CDR1. The basic premise is that the CDR of the antibody may be divided into a hypervariable region and a canonical structure structurally supporting the hypervariable region according to degree of amino acid modification. For example, Frame 1, which is a first conservative frame, ends at a $30^{th}$ amino acid. First, a $31^{st}$ amino acid to a $35^{th}$ amino acid, which corresponds to a canonical structure of the first variable region (CDR1), is numbered 31 to 35, respectively. If amino acids after the $35^{th}$ amino acid are determined to be variable amino acids that are not identical to Frame 2, they are numbered 35a, 35b, 35c . . . , in order, until the hypervariable region ends. Therefore, according to the Kabat numbering system, Frame 2 is assured to start from amino acid no. 36. Also, numbering amino acids of CDR2 using the Kabat numbering system is the same. First, a $50^{th}$ amino acid to a $52^{nd}$ amino acid, which correspond to a canonical structure necessarily present in CDR2, were numbered, and then the next amino acids are numbered 52a, 52b, 52c . . . , in order. Then, amino acids in a canonical structure of the rear portion of CDR2 are numbered 53 to 65, in order. Therefore, Frame 3 is assured to start from amino acid no. 66. Also, numbering amino acids of CDR3 is the same. First, amino acids of a canonical structure by which CDR3 starts were numbered 95 to 100, respectively, and amino acids of the following hypervariable region are numbered 100a, 100b, 100c, . . . , in order. Then, amino acids in a canonical structure of the rear portion of CDR3 are numbered 101 to 102, in order. Therefore, the final frame connected thereto, Frame 4, surely starts from amino acid no. 103.

Example 3: Screening of VH Library Derived from Human Germline Through TAPE (Tat-Associated Protein Engineering)

(1) Construction of VH Library Derived from Human Germline

Figure 2:
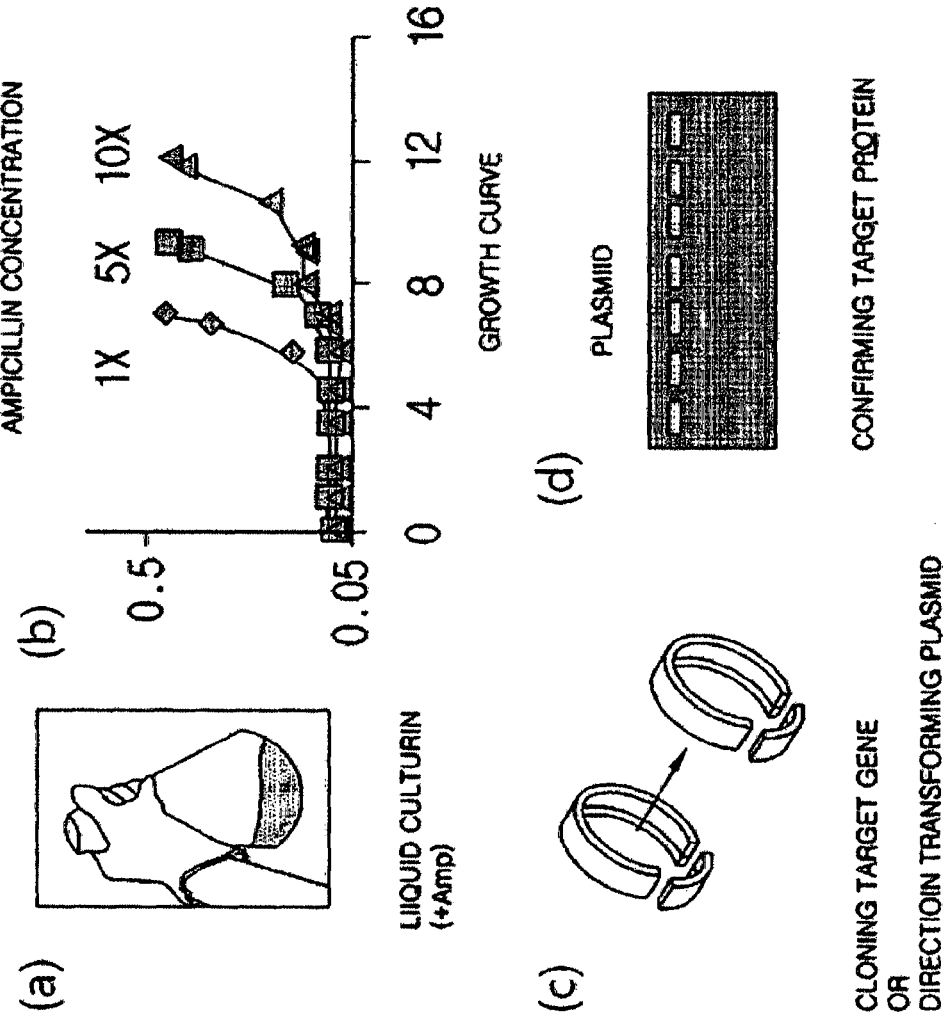
FIG. 2 is a schematic diagram showing a method of screening soluble proteins by the TAPE method, comprising:
(a) culturing a host cell group in a liquid medium containing antibiotics;
(b) confirming a growth curve of the host cell group according to concentration of antibiotics;
(c) collecting plasmids to check presence or absence of nucleic acids coding target proteins; and
(d) preparing a gene construct where the collected nucleic acid sequence is again functionally linked to a gene coding a Tat-signal sequence and an antibiotic resistance-conferring gene, and then again transforming the host cell group with the prepared gene construct.

E. coli, T7 Express LysY/I$^q$ was transformed with the pET-TAPE library by an electroporation method. Then, it was cultured in an SOC culture liquid at 370 for 1 hour, and then inoculated and cultured in an LB culture liquid containing 50 μg/ml of Carbenicillin (1×). When an OD value of E. coli was 0.6, E. coli was collected by using centrifugal separation, and then the plasmid isolated by using a plasmid DNA purification kit (QIAGEN, Valencia, Calif., USA), and followed by cutting with restriction enzymes, NcoI and BamHI. The cut gene includes the VH library and ß-lactamase genes, and this is for excluding false positive that may arise in a subsequent liquid panning procedure. The pET-TAPE plasmid also was cut with restriction enzymes, NcoI and BamHI. After cutting, respective DNAs were purified with a gel extraction kit (QIAGEN). The VH gene obtained from the pET9a-TAPE library screened in the Carbenicillin LB culture liquid was inserted between NcoI and BamHI cutting sites of the pET-TAPE, and E. coli T7 Express LysY/I$^q$ was again electro-transformed with this. After that, the above procedure was repetitively performed while the concentration of Carbenicillin in the culture liquid was increased to 250 μg/ml (5×) and 500 μg/ml (10×), for liquid panning. A schematic diagram for respective procedures is shown in FIG. 2.

Finally, after performing liquid panning for respective concentrations of Carbenicillin, 50 single colonies were selected from an LB agar plate containing ampicillin and then cultured in liquid medium containing ampicillin. Then, plasmids were collected therefrom, followed by analysis of base sequence. A culture method for analyzing characteristics of VH domains of the screened clone is as follows. E. coli, DH5a and T7 Express LysY/I$^q$ were purchased from NEB (New England BioLabs, INC., Beverly, Mass., US). In the case where E. coli includes pET-TAPE plasmid base, E. coli was cultured in an LB culture liquid containing 50 μg/ml of Kanamycin. In the case of where E. coli includes a pET22b vector, 50 μg/ml of Ampicillin or Carbenicillin was added to the culture liquid. For seed culturing, colons separated from the LB solid medium as a single colony form were inoculated in the LB liquid medium containing the above antibiotic agent, and then, cultured at 200 rpm for 12 hours or longer at 37□. The colonies were inoculated in the culture medium so that cell concentration of the seed culture liquid was diluted to 1:100.

(2) Screening Result of VH Library Derived from Human Germline

Figure 3:
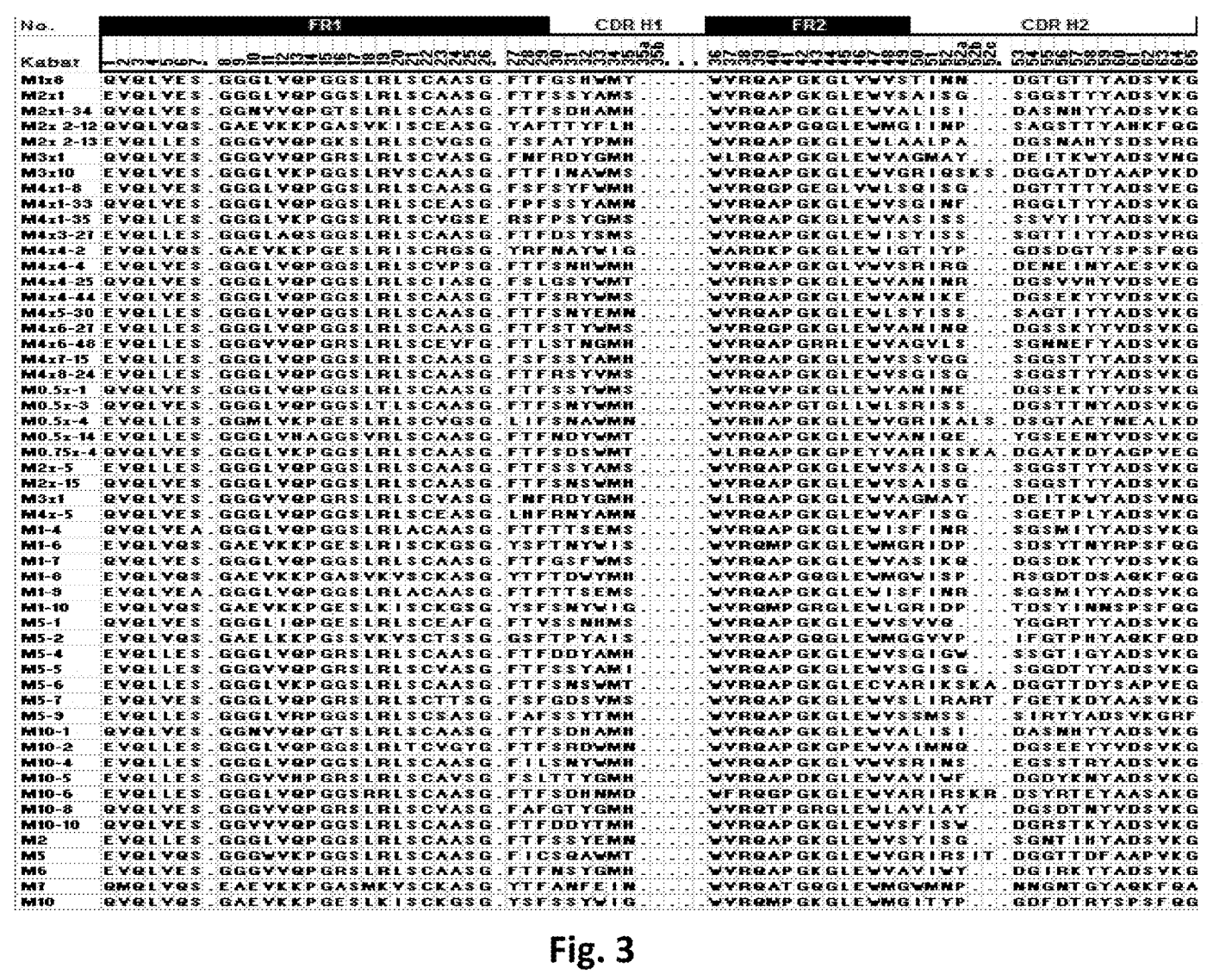
Figure 3:
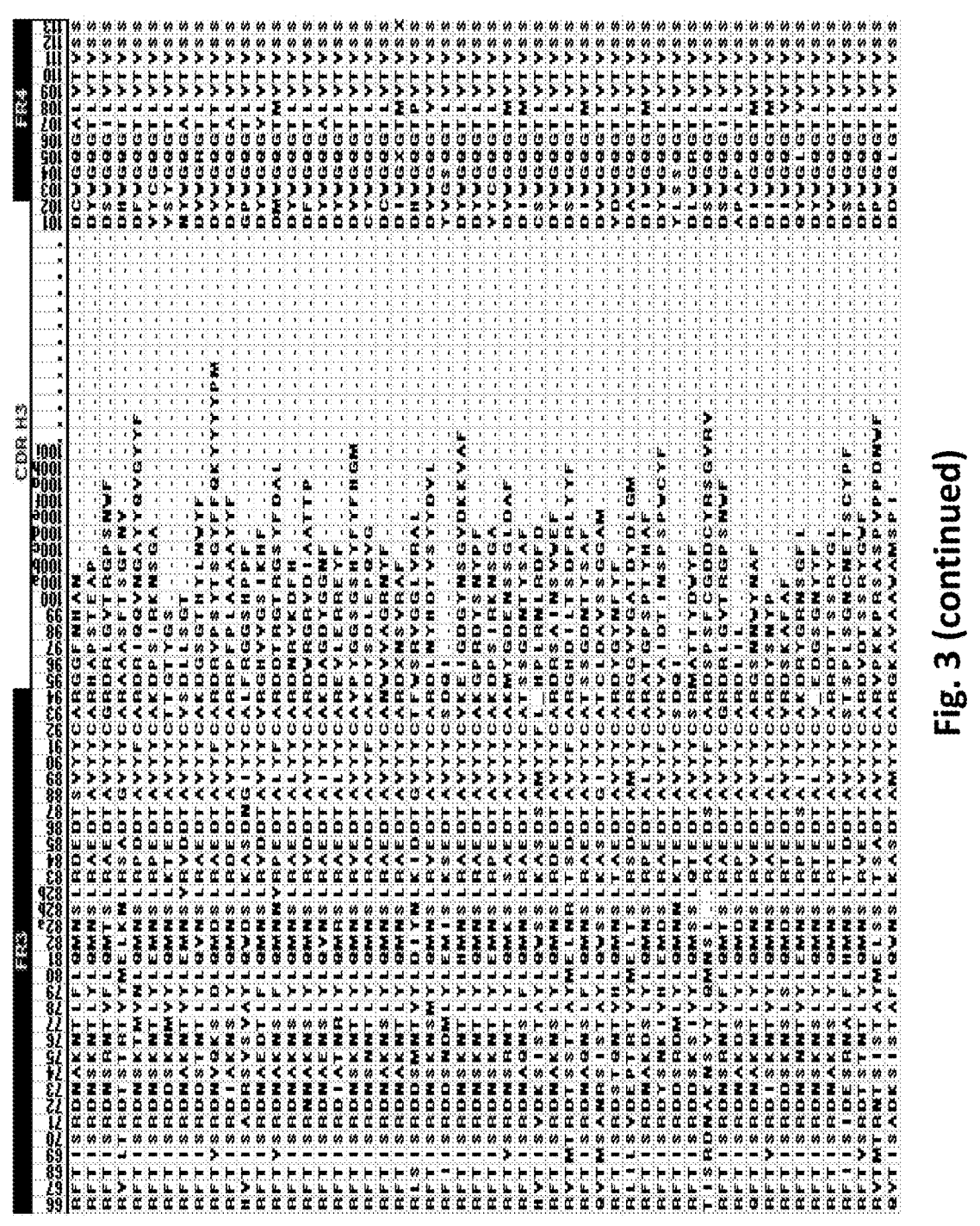

Amino acid sequences of natural type human VH domain antibodies screened by using the TAPE system from human immunoglobulin heavy chain variable domain gene libraries prepared as described above were shown in FIG. 3. For each case, the scaffold of the screened natural type human VH domain antibody, that is, the sequences of FR1 to FR4 frames, were shown in Table 1.

When the repeated, identical sequences, among a total of 154 VH sequences separated from the final third liquid panning were marked once, a total of 54 unique sequences could be obtained. Among the total of 154 sequences, 148 sequences corresponding to 96% thereof were determined to be in a VH3 family type. The VH3 family was known to be relatively highly soluble among seven families of the human immunoglobulin heavy chain domains, and thus, this proves that screening using the TAPE system of the present invention significantly shows statistically significant screening ability based on solubility.

In addition, it was found that frame sequences of 19 sequences among individual 54 sequences were unique, and among them, 13 frame sequences were classified in a VH3 family type.

In order to check the degree of soluble expression when the screened individual VH genes alone are expressed in *E. coli* without TEM-1 beta-lactamase, which is a reporter gene, the soluble fraction and the insoluble fraction were separated after induction of VH expression, and then compared with various kinds of control VH domains through SDS-PAGE (see, FIG. 4).

The corresponding genes were cloned into the pET-22b (+) expression vector, to transform *E. coli* NEBT7 as a host cell. For expression of the scaffolds, culture was performed under the conditions of 200 rpm at 37□, and then the expression was induced with 1 mM of IPTG when an OD value was 0.6 to 0.8. After the conditions of 180 rpm at 25□ for 3.5 hours, cells were collected.

A soluble fraction and an insoluble fraction of protein were separated by using B-PER Reagent (Thermo scientific) . After cell lysis, the soluble fraction (supernatant portion) could be obtained by cell down. The precipitate (pellet) was washed with PBS, and then re-suspended with solubilization buffer (pH 7.4, 50 mM NaH2PO4, 6M UREA, 0.5M NaCl, 4 mM DTT) to obtain the insoluble fraction. Expression thereof was analyzed by using SDS-PAGE.

As the result, it can be seen that, in the cases of VH domains (1, 2, 3) randomly selected from the library without the screening procedure, there was little VH domains having a corresponding size in the soluble fraction, after induction of protein expression, and it can be seen that, in the cases of VH domains screened by the TAPE procedure MG4x4-44, MG4x4-25, MG10-10, MG2x1), the soluble expression was remarkably increased (see, FIG. 4(*b*)). It can also be seen that the VH domains screened by the TAPE system had relatively higher ratio of soluble expression as compared with VH domains (VH2, VH3, VH6, DP47d, and HEL4) generally known to have excellent degree of soluble expression.

Example 4: Preparation of Frame-Engineered Synthetic Library Based on MG2x1 VH Scaffold In order to confer additive solubility and stability based on MG2X1 VH scaffold among the optimum natural type human immunoglobulin heavy chain variable domain (VH) candidate groups screened by the TAPE method, a "frame-engineered synthetic library" where mutation was introduced at particular 7 amino acid sites, which were rationally selected based on structural analysis of VH, was constructed.

Amino acid mutation sites in the MG2X1 VH scaffold are indicated by square boxes (■) in FIG. 6 based on the Kabat numbering system.

Specifically, mutation was introduced at the sequence of MG2X1 VH scaffold based on the MG2X1 scaffold firstly screened by the TAPE method. The polymerase chain reaction (PCR) for introducing mutation is described in detail as follows.

The entire gene sequence was divided into two fragments to prepare primers for polymerase chain reaction (PCR). Primers that introduce mutations at the 3' primer of the first fragment and the 5' primer of the second fragment were prepared, and respective gene fragments were generated through PCR (see, Sequences 17 and 18 of Table 5). Then, a final MG2X1 based frame-engineered synthetic library was constructed through overlapping PCR of two gene fragments (see, Sequences 18 and 19 of Table 5 and FIG. 5). The amplified DNA was separated from the agarose gel, treated with restriction enzymes NcoI and NotI, and then inserted into the pET-TAPE vector, thereby preparing a pET-TAPE frame-engineered heavy chain variable domain synthetic library.

Example 5: Screening of MG2X1 VH Scaffold Based Engineered VH Domains Through TAPE (Tat-Associated Protein Engineering) System New synthetic VH scaffolds having improved solubility and stability were screened by using the TAPE system of the present invention as described above. Respective stages for TAPE were performed by increasing concentration of Carbenicillin in the order of 50 µg/ml (hereinafter, "1× TAPE"), 100 µg/ml (hereinafter, "2× TAPE"), 200 µg/ml (hereinafter, "4× TAPE"), and 400 µg/ml (hereinafter, "8× TAPE").

As the result that base sequences of 20 single colonies after 1× TAPE were analyzed, it was confirmed that a pET-TAPE library including only TEM-1 8-lactamase gene was not found. Therefore, it was ultimately confirmed that false positive can be excluded at an initial stage of screening by the TAPE system of the present invention. Then, when 2× TAPE, 4× TAPE, and 8× TAPE were performed, a method of collecting only VH genes after NcoI and BamHI restriction enzyme reactions and then again introducing them to the TAPE system, and a method of transforming *E. coli* with the pET-TAPE VH plasmid library separated from a cell culture liquid without the cloning work were simultaneously performed. False positive colonies were not found in both of the two methods. After 8× liquid panning was finally performed, 50 single colonies were selected from an LB solid medium, and then liquid-cultured. Then, plasmids were collected therefrom, and amino acid sequence analysis was performed.

As the result, it was found that particular amino acids were biasedly selected at position Nos. 50 and 58 based on the Kabat numbering system, among seven modification positions. Specifically, it was found that alanine was modified to tryptophan at position 50 in 16 among 41 clones and tyrosine was modified to tryptophan at position 58 in 24 among 41 clones. It was not observed that the amino acids were particularly biased at the rest of the positions.

TABLE 2

Amino acid sequences of FR1 to FR4 frames of amino acid-modified VH domain antibody scaffold

| Scaffold name | FR1 | FR2 | FR3 | FR4 |
|---|---|---|---|---|
| MG8-21 | EVQLVESGGGLVQPGGSLRLSCAASGFTF (SEQ ID NO: 364) | WVRNAPGKGNEIVS (SEQ ID NO: 406) | RFTISRDNSKNTLYLQMNSLRAEDTAVYYCAS (SEQ ID NO: 448) | WGQGTLVTVSS (SEQ ID NO: 490) |
| MG2-12L | EVQLVESGGGLVQPGGSLRLSCAASGFTF (SEQ ID NO: 365) | WVRRAPGKGIEVVS (SEQ ID NO: 407) | RFTISRDNSKNTLYLQMNSLRAEDTAVYYCAS (SEQ ID NO: 449) | WGQGTLVTVSS (SEQ ID NO: 491) |
| MG2-7I | EVQLVESGGGLVQPGGSLRLSCAASGFTF (SEQ ID NO: 366) | WVRIAPGKGPEPVS (SEQ ID NO: 408) | RFTISRDNSKNTLYLQMNSLRAEDTAVYYCAS (SEQ ID NO: 450) | WGQGTLVTVSS (SEQ ID NO: 492) |
| MG2-9I | EVQLVESGGGLVQPGGSLRLSCAASGFTF (SEQ ID NO: 367) | WVRKAPGKGYEPVS (SEQ ID NO: 409) | RFTISRDNSKNTLYLQMNSLRAEDTAVYYCAS (SEQ ID NO: 451) | WGQGTLVTVSS (SEQ ID NO: 493) |
| MG2-10I | EVQLVESGGGLVQPGGSLRLSCAASGFTF (SEQ ID NO: 368) | WVRNAPGKGYEIVS (SEQ ID NO: 410) | RFTISRDNSKNTLYLQMNSLRAEDTAVYYCAS (SEQ ID NO: 452) | WGQGTLVTVSS (SEQ ID NO: 494) |
| MG2-11I | EVQLVESGGGLVQPGGSLRLSCAASGFTF (SEQ ID NO: 369) | WVRYAPGKGYEFVS (SEQ ID NO: 411) | RFTISRDNSKNTLYLQMNSLRAEDTAVYYCAS (SEQ ID NO: 453) | WGQGTLVTVSS (SEQ ID NO: 495) |
| MG2-12I | EVQLVESGGGLVQPGGSLRLSCAASGFTF (SEQ ID NO: 370) | WVRVAPGKGIEPVS (SEQ ID NO: 412) | RFTISRDNSKNTLYLQMNSLRAEDTAVYYCAS (SEQ ID NO: 454) | WGQGTLVTVSS (SEQ ID NO: 496) |
| MG2-32 | EVQLVESGGGLVQPGGSLRLSCAASGFTF (SEQ ID NO: 371) | WVRMAPGKGPEHVS (SEQ ID NO: 413) | RFTISRDNSKNTLYLQMNSLRAEDTAVYYCAS (SEQ ID NO: 455) | WGQGTLVTVSS (SEQ ID NO: 497) |
| MG2-34 | EVQLVESGGGLVQPGGSLRLSCAASGFTF (SEQ ID NO: 372) | WVRSAPGKGVEMVS (SEQ ID NO: 414) | RFTISRDNSKNTLYLQMNSLRAEDTAVYYCAS (SEQ ID NO: 456) | WGQGTLVTVSS (SEQ ID NO: 498) |
| MG2-40 | EVQLVESGGGLVQPGGSLRLSCAASGFTF (SEQ ID NO: 373) | WVRTAPGKGTEMVS (SEQ ID NO: 415) | RFTISRDNSKNTLYLQMNSLRAEDTAVYYCAS (SEQ ID NO: 457) | WGQGTLVTVSS (SEQ ID NO: 499) |
| MG2-46 | EVQLVESGGGLVQPGGSLRLSCAASGFTF (SEQ ID NO: 374) | WVRCAPGKGYEFVS (SEQ ID NO: 416) | RFTISRDNSKNTLYLQMNSLRAEDTAVYYCAS (SEQ ID NO: 458) | WGQGTLVTVSS (SEQ ID NO: 500) |
| MG2-47 | EVQLVESGGGLVQPGGSLRLSCAASGFTF (SEQ ID NO: 375) | WVRIAPGKGLEMVS (SEQ ID NO: 417) | RFTISRDNSKNTLYLQMNSLRAEDTAVYYCAS (SEQ ID NO: 459) | WGQGTLVTVSS (SEQ ID NO: 501) |
| MG2-48 | EVQLVESGGGLVQPGGSLRLSCAASGFTF (SEQ ID NO: 376) | WVRMAPGKGLEYVS (SEQ ID NO: 418) | RFTISRDNSKNTLYLQMNSLRAEDTAVYYCAS (SEQ ID NO: 460) | WGQGTLVTVSS (SEQ ID NO: 502) |
| MG2-51 | EVQLVESGGGLVQPGGSLRLSCAASGFTF (SEQ ID NO: 377) | WVRYAPGKGTEFVS (SEQ ID NO: 419) | RFTISRDNSKNTLYLQMNSLRAEDTAVYYCAS (SEQ ID NO: 461) | WGQGTLVTVSS (SEQ ID NO: 503) |
| MG2-53 | EVQLVESGGGLVQPGGSLRLSCAASGFTF (SEQ ID NO: 378) | WVRQAPGKGVEWVS (SEQ ID NO: 420) | RFTISRDNSKNTLYLQMNSLRAEDTAVYYCAS (SEQ ID NO: 462) | WGQGTLVTVSS (SEQ ID NO: 504) |
| MG2-55 | EVQLVESGGGLVQPGGSLRLSCAASGFTF (SEQ ID NO: 379) | WVRWAPGKGPEFVS (SEQ ID NO: 421) | RFTISRDNSKNTLYLQMNSLRAEDTAVYYCAS (SEQ ID NO: 463) | WGQGTLVTVSS (SEQ ID NO: 505) |
| MG2-57 | EVQLVESGGGLVQPGGSLRLSCAASGFTF (SEQ ID NO: 380) | WVRFAPGKGREWVS (SEQ ID NO: 422) | RFTISRDNSKNTLYLQMNSLRAEDTAVYYCAS (SEQ ID NO: 464) | WGQGTLVTVSS (SEQ ID NO: 506) |
| MG2-58 | EVQLVESGGGLVQPGGSLRLSCAASGFTF (SEQ ID NO: 381) | WVRFAPGKGCELVS (SEQ ID NO: 423) | RFTISRDNSKNTLYLQMNSLRAEDTAVYYCAS (SEQ ID NO: 465) | WGQGTLVTVSS (SEQ ID NO: 507) |

TABLE 2-continued

Amino acid sequences of FR1 to FR4 frames of amino acid-modified VH domain antibody scaffold

| Scaffold name | FR1 | FR2 | FR3 | FR4 |
|---|---|---|---|---|
| MG2-59 | EVQLVESGGGLVQPGGSLRLSCAASGFTF (SEQ ID NO: 382) | WVRKAPGKGLETVS (SEQ ID NO: 424) | RFTISRDNSKNTLYLQMNSLRAEDTAVYYCAS (SEQ ID NO: 466) | WGQGTLVTVSS (SEQ ID NO: 508) |
| MG2-60 | EVQLVESGGGLVQPGGSLRLSCAASGFTF (SEQ ID NO: 383) | WVRNAPGKGLECVS (SEQ ID NO: 425) | RFTISRDNSKNTLYLQMNSLRAEDTAVYYCAS (SEQ ID NO: 467) | WGQGTLVTVSS (SEQ ID NO: 509) |
| MG2-64 | EVQLVESGGGLVQPGGSLRLSCAASGFTF (SEQ ID NO: 384) | WVRCAPGKGWEVVS (SEQ ID NO: 426) | RFTISRDNSKNTLYLQMNSLRAEDTAVYYCAS (SEQ ID NO: 468) | WGQGTLVTVSS (SEQ ID NO: 510) |
| MG4-12 | EVQLVESGGGLVQPGGSLRLSCAASGFTF (SEQ ID NO: 385) | WVRLAPGKGVELVS (SEQ ID NO: 427) | RFTISRDNSKNTLYLQMNSLRAEDTAVYYCAS (SEQ ID NO: 469) | WGQGTLVTVSS (SEQ ID NO: 511) |
| MG4-13 | EVQLVESGGGLVQPGGSLRLSCAASGFTF (SEQ ID NO: 386) | WVRFAPGKGAEWVS (SEQ ID NO: 428) | RFTISRDNSKNTLYLQMNSLRAEDTAVYYCAS (SEQ ID NO: 470) | WGQGTLVTVSS (SEQ ID NO: 512) |
| MG4-17 | EVQLVESGGGLVQPGGSLRLSCAASGFTF (SEQ ID NO: 387) | WVRLAPGKGREWVS (SEQ ID NO: 429) | RFTISRDNSKNTLYLQMNSLRAEDTAVYYCAS (SEQ ID NO: 471) | WGQGTLVTVSS (SEQ ID NO: 513) |
| MG4-18 | EVQLVESGGGLVQPGGSLRLSCAASGFTF (SEQ ID NO: 388) | WVRYAPGKGVEFVS (SEQ ID NO: 430) | RFTISRDNSKNTLYLQMNSLRAEDTAVYYCAS (SEQ ID NO: 472) | WGQGTLVTVSS (SEQ ID NO: 514) |
| MG4-20 | EVQLVESGGGLVQPGGSLRLSCAASGFTF (SEQ ID NO: 389) | WVRFAPGKGLEMVS (SEQ ID NO: 431) | RFTISRDNSKNTLYLQMNSLRAEDTAVYYCAS (SEQ ID NO: 473) | WGQGTLVTVSS (SEQ ID NO: 515) |
| MG4-28 | EVQLVESGGGLVQPGGSLRLSCAASGFTF (SEQ ID NO: 390) | WVRVAPGKGTERVS (SEQ ID NO: 432) | RFTISRDNSKNTLYLQMNSLRAEDTAVYYCAS (SEQ ID NO: 474) | WGQGTLVTVSS (SEQ ID NO: 516) |
| MG4-2 | EVQLVESGGGLVQPGGSLRLSCAASGFTF (SEQ ID NO: 391) | WVRIAPGKGMEMVS (SEQ ID NO: 433) | RFTISRDNSKNTLYLQMNSLRAEDTAVYYCAS (SEQ ID NO: 475) | WGQGTLVTVSS (SEQ ID NO: 517) |
| MG4-32 | EVQLVESGGGLVQPGGSLRLSCAASGFTF (SEQ ID NO: 392) | WVRAAPGKGPELVS (SEQ ID NO: 434) | RFTISRDNSKNTLYLQMNSLRAEDTAVYYCAS (SEQ ID NO: 476) | WGQGTLVTVSS (SEQ ID NO: 518) |
| MG4-33 | EVQLVESGGGLVQPGGSLRLSCAASGFTF (SEQ ID NO: 393) | WVRVAPGKGYEHVS (SEQ ID NO: 435) | RFTISRDNSKNTLYLQMNSLRAEDTAVYYCAS (SEQ ID NO: 477) | WGQGTLVTVSS (SEQ ID NO: 519) |
| MG4-34 | EVQLVESGGGLVQPGGSLRLSCAASGFTF (SEQ ID NO: 394) | WVRVAPGKGLECVS (SEQ ID NO: 436) | RFTISRDNSKNTLYLQMNSLRAEDTAVYYCAS (SEQ ID NO: 478) | WGQGTLVTVSS (SEQ ID NO: 520) |
| MG4-5 | EVQLVESGGGLVQPGGSLRLSCAASGFTF (SEQ ID NO: 395) | WVRVAPGKGPETVS (SEQ ID NO: 437) | RFTISRDNSKNTLYLQMNSLRAEDTAVYYCAS (SEQ ID NO: 479) | WGQGTLVTVSS (SEQ ID NO: 521) |
| MG4-6 | EVQLVESGGGLVQPGGSLRLSCAASGFTF (SEQ ID NO: 396) | WVRMAPGKGSEVVS (SEQ ID NO: 438) | RFTISRDNSKNTLYLQMNSLRAEDTAVYYCAS (SEQ ID NO: 480) | WGQGTLVTVSS (SEQ ID NO: 522) |
| MG4-7 | EVQLVESGGGLVQPGGSLRLSCAASGFTF (SEQ ID NO: 397) | WVRLAPGKGTEMVS (SEQ ID NO: 439) | RFTISRDNSKNTLYLQMNSLRAEDTAVYYCAS (SEQ ID NO: 481) | WGQGTLVTVSS (SEQ ID NO: 523) |
| MG8-11 | EVQLVESGGGLVQPGGSLRLSCAASGFTF (SEQ ID NO: 398) | WVRTAPGKGAEWVS (SEQ ID NO: 440) | RFTISRDNSKNTLYLQMNSLRAEDTAVYYCAS (SEQ ID NO: 482) | WGQGTLVTVSS (SEQ ID NO: 524) |
| MG8-12 | EVQLVESGGGLVQPGGSLRLSCAASGFTF (SEQ ID NO: 399) | WVRWAPGKGKEVVS (SEQ ID NO: 441) | RFTISRDNSKNTLYLQMNSLRAEDTAVYYCAS (SEQ ID NO: 483) | WGQGTLVTVSS (SEQ ID NO: 525) |

TABLE 2-continued

Amino acid sequences of FR1 to FR4 frames of amino acid-
modified VH domain antibody scaffold

| Scaffold name | FR1 | FR2 | FR3 | FR4 |
|---|---|---|---|---|
| MG8-13 | EVQLVESGGGLVQPGG SLRLSCAASGFTF (SEQ ID NO: 400) | WVRQAPGKGIEPVS (SEQ ID NO: 442) | RFTISRDNSKNTLYLQMN SLRAEDTAVYYCAS (SEQ ID NO: 484) | WGQGTLVTVSS (SEQ ID NO: 526) |
| MG8-14 | EVQLVESGGGLVQPGG SLRLSCAASGFTF (SEQ ID NO: 401) | WVRQAPGKGPEWVS (SEQ ID NO: 443) | RFTISRDNSKNTLYLQMN SLRAEDTAVYYCAS (SEQ ID NO: 485) | WGQGTLVTVSS (SEQ ID NO: 527) |
| MG8-4 | EVQLVESGGGLVQPGG SLRLSCAASGFTF (SEQ ID NO: 402) | WVRQAPGKGPEVVS (SEQ ID NO: 444) | RFTISRDNSKNTLYLQMN SLRAEDTAVYYCAS (SEQ ID NO: 486) | WGQGTLVTVSS (SEQ ID NO: 528) |
| MG8-5 | EVQLVESGGGLVQPGG SLRLSCAASGFTF (SEQ ID NO: 403) | WVRTAPGKGIEIVS (SEQ ID NO: 445) | RFTISRDNSKNTLYLQMN SLRAEDTAVYYCAS (SEQ ID NO: 487) | WGQGTLVTVSS (SEQ ID NO: 529) |
| MG8-6 | EVQLVESGGGLVQPGG SLRLSCAASGFTF (SEQ ID NO: 404) | WVRIAPGKGVEIVS (SEQ ID NO: 446) | RFTISRDNSKNTLYLQMN SLRAEDTAVYYCAS (SEQ ID NO: 488) | WGQGTLVTVSS (SEQ ID NO: 530) |
| MG8-8 | EVQLVESGGGLVQPGG SLRLSCAASGFTF (SEQ ID NO: 405) | WVRAAPGKGLEVVS (SEQ ID NO: 447) | RFTISRDNSKNTLYLQMN SLRAEDTAVYYCAS (SEQ ID NO: 489) | WGQGTLVTVSS (SEQ ID NO: 531) |

Example 6: Separation and Purification of the Screened VH Scaffold Candidates and Analysis of Physicochemical Properties Thereof In order to determine physical-chemical properties of the screened human-derived VH scaffold candidates (see, FIG. 3) and the VH scaffold candidate group through synthetic mutation (see, FIG. 6), three analysis procedures were performed.

First, the ratio of soluble expression level of VH scaffold screened was checked in order to determine the degree of solubility of VH scaffold candidates. Second, a circular dichroism (CD) method was performed in order to determine thermostability of respective scaffold candidate groups. Third, aggregation free characteristics of protein of the purified scaffold candidates were confirmed by the ratio of monomers and long storage stability through gel filtration chromatography.

(1) Separation and Purification of the Screened VH Scaffold Candidates

The screened gene was transported to an E. coli expression vector, and exclusively expressed without the reporter protein. PCR was run by using a pET-TAPE-VH candidates plasmid as a template and using the 5' primer (SEQ ID NO: 21 of Table 6) including an NcoI restriction enzyme base sequence and the 3' primer (SEQ ID NO: 22 of Table 6) including an XhoI restriction enzyme base sequence. DNA fragments corresponding to VH candidates were amplified by PCR were treated with NcoI and XhoI restriction enzymes, and then inserted between NcoI and XhoI cutting sites of the pET22b(+) plasmid vector, thereby preparing a pET22b-VH plasmid. E. coli, T7 Express LysY/I$^q$ was transformed with the prepared plasmid. Then, single colonies were selected, and then inoculated in an SB culture liquid containing 100 µg/mL of ampicillin, 20 mM of MgCl$_2$, and 2% (w/v) of glucose. When optical density of the culture liquid was 0.6, 1 mM of IPTG was added thereto, and then culturing was performed at 25□ for 4 hours for protein expression. E. coli was collected through centrifugal separation of the culture liquid, and then re-suspended in phosphate-buffered saline (PBS). The floating E. coli was frozen and melted four times for lysing the cell wall thereof, and supernatant was collected by centrifugal separation. NaCl was added to the collected supernatant to have a concentration of 0.5M, and pH was set to 7.4 by using 5N of NaOH, followed by filtering with a 0.22 µm filter. The protein was purified by using Ni-NTA affinity chromatography that is washed by washing with 100 mM of imidazole and eluted with 300 mM of imidazole. The purified protein was confirmed by electrophoresis using NuPAGE 4-12% Bis-Tris gel purchased from Invitrogen, followed by staining with Coomassie blue dye. With respect to the eluted protein, buffer exchange to phosphate-buffered saline (PBS) was performed through PD-desalting columns (GE Healthcare Life Science, Piscataway, N.J., USA).

TABLE 6

Sequences of primers used in the present invention

| SEQ ID NO | Sequence of Primer |
|---|---|
| 21 | GCCCATGGGAAGTCCAACTGGTTGAATCTGGTGGC |
| 22 | GCCTCGAGACTGCTCACAGTAACCAGGGTACCCT |

TABLE 6-continued

Sequences of primers used in the present invention

| SEQ ID NO | Sequence of Primer |
|---|---|
| 23 | GCGCTAGCGAAGTCCAACTGGTTGAATCTGGTGGC |
| 24 | ACTGGCGCAGTAATACACTGCGGTATC |
| 25 | GCAGATCTTGAGGAGACAGTGACCAGGGTTCCCTGGCCCCAMNNMNNMNNMNNMNNMNNMNNTCTGGCGCAGTAATACACTGCGGTATCTTCAGCACGCAG |
| 26 | GCAGATCTTGAGGAGACAGTGACCAGGGTTCCCTGGCCCCAMNNMNNMNNMNNMNNMNNMNNMNNTCTGGCGCAGTAATACACTGCGGTATCTTCAGCACGCAG |
| 27 | GCAGATCTTGAGGAGACAGTGACCAGGGTTCCCTGGCCCCAMNNMNNMNNMNNMNNMNNMNNMNNMNNMNNTCTGGCGCAGTAATACACTGCGGTATCTTCAGCACGCAG |
| 28 | GCAGATCTTGAGGAGACAGTGACCAGGGTTCCCTGGCCCCAMNNMNNMNNMNNMNNMNNMNNMNNMNNMNNMNNTCTGGCGCAGTAATACACTGCGGTATCTTCAGCACGCAG |
| 29 | GCAGATCTTGAGGAGACAGTGACCAGGGTTCCCTGGCCCCAMNNMNNMNNMNNMNNMNNMNNMNNMNNMNNMNNMNNTCTGGCGCAGTAATACACTGCGGTATCTTCAGCACGCAG |
| 30 | GCAGATCTTGAGGAGACAGTGACCAGGGTTCCCTGGCCCCAMNNMNNMNNMNNMNNMNNMNNMNNMNNMNNMNNMNNMNNTCTGGCGCAGTAATACACTGCGGTATCTTCAGCACGCAG |
| 31 | GCAGATCTTGAGGAGACAGTGACCAGGGTTCCCTGGCCCCAMNNMNNMNNMNNMNNMNNMNNMNNMNNMNNMNNMNNMNNMNNTCTGGCGCAGTAATACACTGCGGTATCTTCAGCACGCAG |
| 32 | GCAGATCTTGAGGAGACAGTGACCAGGGTTCCCTGGCCCCAMNNMNNMNNMNNMNNMNNGGAGGCGCAGTAATACACTGCGGTATCTTCAGCACGCAG |
| 33 | GCAGATCTTGAGGAGACAGTGACCAGGGTTCCCTGGCCCCAMNNMNNMNNMNNMNNMNNMNNGGAGGCGCAGTAATACACTGCGGTATCTTCAGCACGCAG |
| 34 | GCAGATCTTGAGGAGACAGTGACCAGGGTTCCCTGGCCCCAMNNMNNMNNMNNMNNMNNMNNMNNGGAGGCGCAGTAATACACTGCGGTATCTTCAGCACGCAG |
| 35 | GCAGATCTTGAGGAGACAGTGACCAGGGTTCCCTGGCCCCAMNNMNNMNNMNNMNNMNNMNNMNNMNNGGAGGCGCAGTAATACACTGCGGTATCTTCAGCACGCAG |
| 36 | GCAGATCTTGAGGAGACAGTGACCAGGGTTCCCTGGCCCCAMNNMNNMNNMNNMNNMNNMNNMNNMNNMNNGGAGGCGCAGTAATACACTGCGGTATCTTCAGCACGCAG |
| 37 | GCAGATCTTGAGGAGACAGTGACCAGGGTTCCCTGGCCCCAMNNMNNMNNMNNMNNMNNMNNMNNMNNMNNMNNGGAGGCGCAGTAATACACTGCGGTATCTTCAGCACGCAG |
| 38 | GCAGATCTTGAGGAGACAGTGACCAGGGTTCCCTGGCCCCAMNNMNNMNNMNNMNNMNNMNNMNNMNNMNNMNNMNNGGAGGCGCAGTAATACACTGCGGTATCTTCAGCACGCAG |
| 39 | CTGACGCACCCAGCCCATAGCATANNNNNNAAANNNAAAGCCACTTGCAGCACAGCTTAAGCG |
| 40 | TATGCTATGGGCTGGGTGCGT |
| 41 | GCTATCATCGTACCAAGTTGAACCGCCNNNGCCGGAAATCAATGAGAC |
| 42 | GGCGGTTCAACTTGGTACGATGATAGC |
| 43 | TCCCTGGCCCCAGTAGTCAGGAGCNNNAGTNNNCGGNNNATGTCTGGCGCAGTAATACACTGCGGTATC |
| 44 | GCGGATCCTGAGGAGACAGTGACCAGGGTTCCCTGGCCCCAGTAGTCAGGAGC |
| 45 | ACGCACCCAAGACATAGCATANNNNNNAAANNNAAAGCCACTTGCAGCACAGCTTAAGCG |

TABLE 6-continued

Sequences of primers used in the present invention

| SEQ ID NO | Sequence of Primer |
|---|---|
| 46 | TATGCTATGTCTTGGGTGCGT |
| 47 | AACGCTATCAGCGTAATAAGTTGAACCGCCNNNGCCGGAAATAGCTGAGAC |
| 48 | GGCGGTTCAACTTATTACGCTGATAGCGTT, | where K means G or T, S means C or G, R means A or G, M means A or C, and N means A or T or G or C (2) Analysis on the Degree of Soluble Expression in *E. coli*, of the Screened VH Candidates In order to confirm the aspect of soluble expression in *E. coli*, of VH first screened through TAPE from a frame-engineered library based on MG2X1 VH scaffold, the corresponding VH only was expressed in the same manner as Example 3 (2), and then a soluble fraction and an insoluble fraction were separated, followed by SDS-PAGE analysis.

As the result, there can be obtained VH scaffold candidates of which soluble expression is improved as compared with natural type MG2X1 separated from the human immunoglobulin heavy chain variable domain library. As depicted in FIG. 7, most of the selected VH domains expressed in *E. coli* were soluble.

Among them, MG8-14, MG2-55, MG4-5, MG4-13, and MG8-4 scaffold candidates (arrows depicted in FIG. 7) show excellent soluble VH expression, and, as the analysis result of VH domains, it was confirmed that insoluble expression ratio of the VH domains which exhibited excellent soluble expression was decreased.

3) Analysis of Thermostability

In order to determine thermostability through analysis of the two dimensional protein structure of the VH scaffold candidate group, Tm (melting temperature; temperature at which 50% of the entire aqueous protein is thermally denatured) of the VH scaffold candidates screened by the TAPE procedure and purified was calculated by a circular dichroism (CD) method.

Folding fraction was represented by the ratio of the absorbance at a certain temperature to the absorbance before heating. The absorbance was measured at a wavelength of 235 nm according to temperature change. In a sigmoidal curve obtained therefrom, Tm means a temperature at which the folding fraction is 50%.

The scaffold candidates screened from the natural type human immunoglobulin heavy chain variable domain library and the MG2x1 VH scaffold based frame-engineered synthetic library were purified, and then diluted to a concentration of 0.2 to 0.3 mg/ml. Then CD thereof was measured by using a spectropolarimeter (Jasco J-715 model, Jascoinc, Easton, Md., USA). CD signals were recorded and measured at a wavelength of 235 nm when the temperature range of 25 to 85□ while increasing 1□ per 1 minute.

Generally, protein aggregation occurs in most of the natural type human immunoglobulin heavy chain variable domains (VH) present in the aqueous solution, and thus, CD measurement is impossible.

However, most of VHs screened by TAPE system are not aggregated when they exist alone. From the result of CD analysis of thermostability of VH screened by TAPE system, MG3-10 has a Tm value of about 45° C. (see, Table 7), and MG4x4-44, MG4x4-25, MG10-10, and MG2x1 have Tm value of about 55 to 65° C. It means that thermostability thereof was improved by about 10~20° C. as compared with average Tm of natural VH (see, FIG. 8 and Table 7).

Tm values of VH domains screened by the TAPE system from the MG2x1 VH scaffold based frame-engineered synthetic library (for example, MG2-12I, MG2-12L, MG4-13, MG8-4, MG8-14, and the like) were measured to have an average Tm of 65 to 75° C., and thus, it was confirmed that thermostability thereof was improved by average 20~30° C. (see, FIG. 9 and Table 7).

TABLE 7

Tm values of domain antibodies screened by TAPE from human immunoglobulin variable domain library

| VH domains derive from human germline | Tm value (° C.) | VH domains derived from MG2X1 based frame of engineered | Tm value (° C.) |
|---|---|---|---|
| MG4x4-44 | 55.6 | MG4-5 | 67.8 |
| MG3-10 | 46.5 | MG4-13 | 65.2 |
| MG4x4-25 | 61.8 | MG8-4 | 72.3 |
| MG10-10 | 55.4 | MG8-14 | 76.5 |
| MG2-1 | 65.2 | MG2-55 | 69.9 |
|  |  | MG2-12I | 66.6 |
|  |  | MG2-7I | 77.0 |

4) Analysis of the Degree of Aggregation of VH Screened

Stability of the protein was investigated by measuring the aggregation of candidate VH frames according to long-term storage. VH scaffold candidates purified with a concentration of 0.2 to 0.8 mg/mL were stored at 37° C. at 60% of humidity.

Samples were taken at a predetermined interval during storage for about 20 days, and then aggregated protein was removed therefrom by centrifugal separation. Then, the concentration of protein remaining aqueous was measured, and the ratio thereof was calculated.

The remaining protein was separated by electrophoresis using NuPAGE 4-12% Bis-Tris gel, and then quality thereof was confirmed through staining with Coomassie blue dye. As the result, it can be seen that most of the protein dissolved in the phosphate-buffered saline (PBS) was stably maintained without protein aggregation at the acceleration condition (37° C.) for 60 days or longer. Each data point represents a ratio of protein content remaining in the aqueous solution when the initial protein content sets as 1 (see, FIG. 10).

Example 7: Construction of Engineered Libraries According to Lengths of CDRH3 for Conferring Antigen Binding Ability to Candidate VH Scaffolds In order to confer diversity of antigen binding ability to the MG2x1 scaffold screened from the human germline derived VH library by the TAPE method, and the MG8-4 and MG8-14 scaffold screened from the frame engineered library by the TAPE method, a CDR3 synthetic library according to the length of amino acids (7 to 13 amino acids) was constructed at the CDRH3 portion of the corresponding scaffold.

This was deduced from the existing study results that the length of CDR3 of the VH domains having the most suitable stability and binding ability to the target protein corresponds to the length of 7 to 13 amino acids (Christoper J Bond. et al., J. Mol. Biol. 2005 348: 699-709). In addition, amino acids were coded by NNK nucleotide triplet, so that all 20 amino acids may be coded even while lowering the ratio of stop codon than NNN and NNS nucleotide triplets. Moreover, R94S NNK library which enhanced the flexibility of CDR3 by replacing arginine (amino acid residue preceding CDR3) to serine was constructed by the methods set forth above.

In order to minimize error from the PCR, a template DNA fragment comprising frame 1 to frame 3 was constructed by PCR. DNA amplification was performed on cDNAs of MG2x1, MG8-4 and MG8-14 respectively as a template by using 10 pmolar of 5' primer (SEQ ID NO: 23 of Table 6) and 3' primer (SEQ ID NO: 24 of Table 6), 0.5 U of I-pfu DNA polymerase, four kinds of dNTP each 2.5 mM, and 5 µL of 10× buffer. The PCR was repeated 25 cycles at the conditions of;

exposed 94° C. for 2 minutes followed by 94° C. for 20 seconds, 56° C. for 20 seconds, and 72° C. for 25 seconds for 25 times, and finally 72° C. for 5 minutes.

In order to give diversity of antigen binding ability to the template DNA, primers (SEQ ID NOs: 25 to 31) where combinatorial CDRH3 library is introduced with a length of 7 to 13 amino acids was prepared. A "CDR3 engineered library according to the length" was constructed by the PCR using the constructed DNA fragment as a template, 5' primer, and 3' primer of introducing amino acid diversity according to the length (SEQ ID NOs: 25 to 31). PCR was repeatedly performed 25 cycles under the following condition;

exposed 94° C. for 2 minutes, followed by 25 cycles of 94° C. for 20 seconds, 56° C. for 20 seconds, and 72° C. for 40 seconds for 25 times, and finally 72° C. for 5 minutes. FIG. 11 shows a schematic diagram about construction of the CDRH3 engineered library according to the length for conferring diversity of antigen binding ability.

Example 8: Construction of Rational CDR Engineered Libraries for Conferring Diversity of Antigen Binding Ability to Candidate VH Scaffolds For the same purpose as Example 7, a CDR engineered library for conferring diversity of antigen binding ability to the MG2x1 or MG8-4 or MG8-14 based scaffold VH was constructed. Unlike Example 7 where diversity was conferred according to length of CDRH3, only sequences that are expected to have antigen binding ability at the time when mutation is introduced while maintaining the length of CDR were rationally selected, and random mutation was introduced to the corresponding genes. While maintaining the lengths of three CDRs, mutation was selectively introduced to only positions to which antigens are likely to bind (SDRs: Specific Determining Residues), through structure analysis. This has an advantage in that a change in stability and immunogenicity problem due to CDR mutation can be minimized by introducing mutations at only the minimum positions of the CDR.

As for the SDR, first, SDS was selected by referring modeling data via SWISS-Model system and the canonical structures thereof, or modeling data and anticipated binding ability according to nucleotide characteristics.

In addition, amino acids were designed by introducing biased nucleotides having a relatively increased ratio of tyrosine and serine, which are known to have higher antigen binding ability than other amino acids, so that the probability of CDR binding is high even with the same library size (Akiko Koide et al., PNAS 2007 104(16):6632-6637). In order to introduce mutations at the respective CDR1, CDR2, and CDR3, the gene was divided into 3 portions and mutations were introduced thereat (see FIG. 12). The respective fragments were secured by the PCR method while the frame MG2x1 or frame MG8-4, MG8-14 cDNA was used as a template, as follows.

The first, second, and third DNA fragments of MG8-4, MG8-14 based library were synthesized through PCR by using a 5' primer (SEQ ID NO: 23) and a 3' primer (SEQ ID NO: 39), a 5' primer (SEQ ID NO: 40) and a 3' primer (SEQ ID NO: 41), and a 5' primer (SEQ ID NO: 42 and a 3' primer (SEQ ID NO: 43), respectively.

And the first, second, and third DNA fragments of MG2x1 based library were synthesized through PCR by using a 5' primer (SEQ ID NO: 23) and a 3' primer (SEQ ID NO: 45), a 5' primer (SEQ ID NO: 46) and a 3' primer (SEQ ID NO: 47), and a 5' primer (SEQ ID NO: 48) and a 3' primer (SEQ ID NO: 43), respectively.

Synthesizing of DNA fragments set forth above was carried out by PCR with 10 pmolar of each primer, 0.5 U of vent DNA polymerase, four kinds of dNTP each 10 mM, and 5 µL of 10× buffer.

The PCR was run at 94° C. for 2 minutes, followed by 25 cycles of 94° C. for 15 seconds, 56° C. for 20 seconds, and 72° C. for 25 seconds, and finally 72° C. for 5 minutes.

The entire size of rational CDR engineered library was completed by overlapping PCR using the thus obtained 3 template fragments, 5' primer (SEQ ID NO: 23), and 3' primer (SEQ ID NO: 44). The PCR was run at 94° C. for 2 minutes, followed by 25 cycles of 94° C. for 20 seconds, 56° C. for 20 seconds, and 72° C. for 40 seconds, and finally 72° C. for 5 minutes. FIG. 13 shows a schematic diagram about construction of the rational CDR engineered library for conferring diversity of antigen ability.

Example 9: Study on Effects of CDR Modification in VH Scaffold Based Libraries (Engineered Library According to CDR Length and Rational CDR Engineered Library) on Protein Stability In order to confirm effects of CDR modification on stability of VH scaffold structure, genes were randomly selected from a synthetic library of CDRH3 having 7 to 13 amino acids and a library where mutations were rationally introduced at particular positions of CDRH1, CDRH2, and CDRH3 (about 8 genes are screened per each CDR engineered library), and they were cloned into an exclusive expression vector. As the expression vector, a pET-22b(+) expression vector was used, and *E. coli* DH5a, as a host cell, was transformed. The transformed colonies were randomly selected, and sequences thereof were analyzed. Plasmids where all the genes are well maintained were isolated without a stop codon, and *E. coli* NEBT7 as a host cell was again transformed, thereby inducing expression of the corresponding genes. Culturing was performed under the expression conditions of 37° C. and 200 rpm, and then expression was induced with 1 mM of IPTG when an OD value was 0.6 to 0.8. After the conditions of 180 rpm at 25° C. for 3.5 hours, cells were harvested. A soluble protein fraction and an insoluble protein fraction were separated in the same manner as Example 3.

The VH randomly selected from each CDR engineered library was exclusively expressed, and then a soluble fraction and an insoluble fraction were separated and analyzed by SDS-PAGE. As the result, it was confirmed that, in the case of CDRH3 having seven amino acids, all samples except one were expressed as a soluble form (see, FIG. 14(a)).

It was confirmed that, in the case of CDRH3 having eight amino acids, seven of eight samples were expressed as a soluble form (see, FIG. 14(b)). It was confirmed that, in the case of CDRH3 having nine amino acids, all samples were expressed as a soluble form (see, FIG. 14(c)). It was confirmed that, in the case of CDRH3 having ten amino acids, eight of nine samples were expressed as a soluble form (see, FIG. 14(d)). It was confirmed that, in the case of CDRH3 having eleven amino acids, all nine samples were expressed as a soluble form (see, FIG. 14(e)). It was confirmed that, in the case of CDRH3 having twelve amino acids, six of eight samples were expressed as a soluble form (see, FIG. 14(f)). It was confirmed that, in the case of CDRH3 having thirteen amino acids, six of seven samples were expressed as a soluble form (see, FIG. 14(g)). It was confirmed that, in the case of the rational CDR engineered library, all samples were expressed as a soluble form. It was confirmed that soluble expression was overall stably induced regardless of CDR modification, in the CDR engineered libraries prepared based on frames of the VH domain antibodies screened by the TAPE method (see, FIG. 14 and Table 8).

TABLE 8

Frequency of soluble expression of VH after introduction of CDR modification

| Library type | CDR3 length (a/a) | Frequency of soluble expression (% out of clones tested) |
|---|---|---|
| Engineered libraries according to CDRH3 length | 7 | 88 (7/8) |
| | 8 | 87 (7/8) |
| | 9 | 100 (8/8) |
| | 10 | 89 (8/9) |
| | 11 | 100 (9/9) |
| | 12 | 75 (6/8) |
| | 13 | 86 (6/7) |
| Overall | | 89 (51/57) |
| Rational CDR engineered library | 11 | 100 (11/11) |

Example 10: Screening of VH Domain Antibody Candidates Based on Display Technology Using VH Domain Antibody Libraries Having VH Scaffolds Screened by TAPE Method In the present invention, phage display, yeast display, ribosome display, or the like, is preferable as display technology usable in order to screen VH domain antibody candidates by using VH domain antibody libraries having VH scaffolds screened by the TAPE method, but is not limited thereto.

According to the phage display technology, foreign peptides and proteins are inserted and fused to capsid protein of bacteriophage so that the foreign proteins are expressed on the phage surface (Smith et al., Science 1985 228(4705): 1315-1317). In the present invention, a domain antibody having strong binding ability was screened by binding the target antigen to the fusion protein expressed on the surface of the fixed phage.

To screen VH having binding ability to a specific antigen, a panning scheme set forth below was used (Carlos F. Barbas III et al. Phage Display—A Laboratory Manual, Cold Spring Harbor Laboratory Press);
  Cloning the VH library cloned into the phagemid vector (pComb3X) (Examples 7 and 8);
  VH domains were expressed at the end of phage;
  contacting the expressed VH domains with a target protein;
  selecting VH domains which had good binding ability to a target protein.

After contacting the target protein with VH domain expressed at the end of phage, washing out unbound phage and eluting only VH domains-target protein complex. Consequently, only phages which expressed VH domain were concentrated.

By repeating 5~6 rounds of panning process set forth above, VH domain antibody which strongly bound to a target antigen could be screened.

In addition, in the present invention, the yeast display method was also used. According to the yeast display method, after the VH library (Examples 7 and 8) was cloned into the yeast surface expression vector, VH domains were expressed on the surface of yeast, and bound to the target protein, thereby screening and eluting only domains having good binding ability (Ginger Chao. et al., Nature Protocol 2006 1(2): 755-768). A tag was attached to or biotin was labeled on the target protein, and this was reacted with the displayed VH domains. Then, a fluorescent protein targeting the bound protein and a fluorescent protein targeting the displayed VH domain were respectively labeled. Only the labeled yeast-target protein complex, which is shown in a desired region, was eluted by using fluorescence activated cell sorting (FACS), thereby collecting only yeast cells displaying VH domains specific to the target protein.

In the present invention, the ribosome display method was used in order to screen VH domains having binding ability to particular antigens. According to the ribosome display method, stop codon was removed from mRNA coding the screened VH scaffold and then synthesis of in vitro protein was performed. Then, a ribosome complex to which the protein and mRNA corresponding thereto were linked was formed (Mingyue H. et al., Nature Protocol 2007 4(3):281-288). Panning was performed on the target antigen to screen complexes having desired antibodies, and resultantly, desired complexes could be enriched. The screened mRNA was reversely transcribed to DNA, and this procedure was repeated three or four times until desired result was obtained. When screening by the above method was performed on the antigen binding libraries prepared by Examples 7 and 8, VH domain antibodies that are strongly bound to target antigens and have stable properties such as high solubility, thermostability, and long storage stability can be screened.

According to the three screening techniques set forth above, VH domains with high affinity to human serum albumin (HAS) and Human Epidermal Growth Factor Receptor-3 (HER3) were screened by using HAS or HER3 as target antigens.

The screened VH domains maintained the property of VH scaffold and showed high productivity as soluble form in *E. coli.*

Amino acid sequences and affinity of VH having high affinity to HAS or HER3 out of the screened VH domains are showed in Table 9.

TABLE 9

Amino acid sequences and affinity screened from the libraries according to lengths of CDRH3 by using HAS and HER3 as a target antigen

| Target Antigen | Clone | Amino acid sequences | Affinity (nM) |
|---|---|---|---|
| HSA | HSA9 | EVQLVESGGGLVQPGGSLRLSCAASGFTFSSYAMGWVRQAPGKG PEVVSLISGSGGSTWYDDSVKGRFTISRDNSKNTLYLQMNSLRAED TAVYYCASHQWSRQQWGQGTLVTVSS (SEQ ID NO: 532) | 1.7 |
| | HSA11 | EVQLVESGGGLVQPGGSLRLSCAASGFTFSSYAMGWVRQAPGKG PEVVSLISGSGGSTWYDDSVKGRFTISRDNSKNTLYLQMNSLRAED TAVYYCASHKFRNLKWGQGTLVTVSS (SEQ ID NO: 533) | 1.2 |
| | HSA50 | EVQLVESGGGLVQPGGSLRLSCAASGFTFSSYAMGWVRQAPGKG PEVVSLISGSGGSTWYDDSVKGRFTISRDNSKNTLYLQMNSLRAED TAVYYCASHQFTTTQWGQGTLVTVSS (SEQ ID NO: 534) | 7.8 |
| HER3 | HER3#62 | EVQLVESGGGLVQPGGSLRLSCAASGFTFSSYAMGWVRQAPGKG PEVVSLISGSGGSTWYDDSVKGRFTISRDNSKNTLYLQMNSLRAED TAVYYCASHPPRVDTWGQGTLVTVSS (SEQ ID NO: 535) | 1.8 |
| | HER3#723 | EVQLVESGGGLVQPGGSLRLSCAASGFTFYNYPMGWVRQAPGKG PEVVSLISGSGGSTWYDDSVKGRFTISRDNSKNTLYLQMNSLRAEN TAVYYCASHPVSLLFWGQGTLVTVSS (SEQ ID NO: 536) | 27.4 |
| | HER3#748 | EVQLVESGGGLVQPGGSLRLSCAASGFTFYSLMMGWVRQAPGKG PEVVSLISGSGGSTWYDDSVKGRFTISRDNSKNTLYLQMNSLRAED TAVYYCASRHPPGLMWGQGTLVTVSS (SEQ ID NO: 537) | 20.0 |

What is claimed is:

1. A soluble VH domain antibody scaffold comprising an amino acid sequence of FR2 comprising WVRQAPGKG-PEVVS (SEQ ID NO: 444).

2. The soluble VH domain antibody scaffold of claim 1, further comprising an amino acid sequence of FR1 that comprises:

$X_0VQLX_1X_2X_3GX_4X_5X_6X_7X_8PGX_9SX_{10}X_{11}X_{12}X_{13}CX_{14}X_{15}X_{16}GX_{17}X_{18}X_{19}$ (SEQ ID NO: 144), wherein:

$X_0$ is E or Q,
$X_1$ is V or L,
$X_2$ is E, or Q,
$X_3$ is S, or A,
$X_4$ is G, or A,
$X_5$ is G, M, N, V, or E,
$X_6$ is L, V, or W,
$X_7$ is V, K, A, or,
$X_8$ is Q, K, or H,
$X_9$ is G, T, A, R, E, S, or T,
$X_{10}$ is L, V, R, or M,
$X_{11}$ is R, or K,
$X_{12}$ is L, I, or V,
$X_{13}$ is S, A, or T,
$X_{14}$ is A, E, V, R, I, K, T, or S,
$X_{15}$ is A, G, P, V, or T,
$X_{16}$ is S, F, or Y,
$X_{17}$ is F, Y, R, G, or L,
$X_{18}$ is T, A, S, N, T, P, I, N, H, or A, and
$X_{19}$ is F, L, V, or C.

3. The soluble VH domain antibody scaffold of claim 1, further comprising an amino acid sequence of FR3 that comprises:

$X_{29}X_{30}X_{31}X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}X_{50}X_{51}DX_{52}X_{53}X_{54}YX_{55}CX_{56}X_{57}$ (SEQ ID NO: 146), wherein:

$X_{29}$ is R, H, Q, or T,
$X_{30}$ is F, V, L, or I,
$X_{31}$ is T, S, or I,
$X_{32}$ is I, L, V, M, or R,
$X_{33}$ is S, T, or D,
$X_{34}$ is R, A, V, N, or I,
$X_{35}$ is D, N, or A,
$X_{36}$ is N, T, D, I, R, K, Y, or E,
$X_{37}$ is A, S, V, or T,
$X_{38}$ is K, R, T, Q, V, E, M, N, or I,
$X_{39}$ is N, R, T, K, S, D, or V,
$X_{40}$ is T, M, S, V, I, Y, or A,
$X_{41}$ is L, V, A, or M,
$X_{42}$ is F, Y, N, D, H, or S,
$X_{43}$ is L, or M,
$X_{44}$ is Q, E, H, or N,
$X_{45}$ is M, L, V, I, or W,
$X_{46}$ is N, T, K, D, Y, I, or S,
$X_{47}$ is S or N,
$X_{48}$ is L or V,
$X_{49}$ is R, K, or T,
$X_{50}$ is D, A, S, P, T, V, I, or S,
$X_{51}$ is E, A, D, or S,
$X_{52}$ is T, N, or S,
$X_{53}$ is S, A, or G,
$X_{54}$ is V, I, L, or M,
$X_{55}$ is Y or F,
$X_{56}$ is A, G, V, or S, and
$X_{57}$ is R, S, K, T, L, N, or F.

4. The soluble VH domain antibody scaffold of claim 1, further comprising an amino acid sequence of FR4 that comprises:

$X_{58}GX_{59}GX_{60}X_{61}VTVSS$ (SEQ ID NO: 147), wherein:

$X_{58}$ is W, C, Y, G, S, or A,
$X_{59}$ is Q, R, or L,
$X_{60}$ is A, T, I, or V, and
$X_{61}$ is L, M, P, V, or T.

5. The soluble VH domain antibody scaffold of claim 1, further comprising amino acid sequences of FR1, FR3 and FR4 as below:

(1) FR1: $X_0VQLX_1X_2X_3GX_4X_5X_6X_7X_8PGX_9SX_{10}X_{11}X_{12}X_{13}CX_{14}X_{15}X_{16}GX_{17}X_{18}X_{19}$ (SEQ ID NO: 144), wherein:

$X_0$ is E or Q,
$X_1$ is V or L,
$X_2$ is E, or Q,
$X_3$ is S, or A,
$X_4$ is G, or A,
$X_5$ is G, M, N, V, or E,
$X_6$ is L, V, or W,
$X_7$ is V, K, A, or,
$X_8$ is Q, K, or H,
$X_9$ is G, T, A, R, E, S, or T,
$X_{10}$ is L, V, R, or M,
$X_{11}$ is R, or K,
$X_{12}$ is L, I, or V,
$X_{13}$ is S, A, or T,
$X_{14}$ is A, E, V, R, I, K, T, or S,
$X_{15}$ is A, G, P, V, or T,
$X_{16}$ is S, F, or Y,
$X_{17}$ is F, Y, R, G, or L, $X_{18}$ is T, A, S, N, T, P, I, N, H, or A, and
$X_{19}$ is F, L, V, or C;

(2) FR3: $X_{29}X_{30}X_{31}X_{32}X_{33}X_{34}X_{35}X_{36}$
$X_{37}X_{38}X_{39}X_{40}X_{41}X_{42}X_{43}X_{44}X_{45}$
$X_{46}X_{47}X_{48}X_{49}X_{50}X_{51}DX_{52}X_{53}$
$X_{54}YX_{55}C_{56}X_{57}$ (SEQ ID NO: 146), wherein:

$X_{29}$ is R, H, Q, or T,
$X_{30}$ is F, V, L, or I,
$X_{31}$ is T, S, or I,
$X_{32}$ is I, L, V, M, or R,
$X_{33}$ is S, T, or D,
$X_{34}$ is R, A, V, N, or I,
$X_{35}$ is D, N, or A,
$X_{36}$ is N, T, D, I, R, K, Y, or E,
$X_{37}$ is A, S, V, or T,
$X_{38}$ is K, R, T, Q, V, E, M, N, or I,
$X_{39}$ is N, R, T, K, S, D, or V,
$X_{40}$ is T, M, S, V, I, Y, or A,
$X_{41}$ is L, V, A, or M,
$X_{42}$ is F, Y, N, D, H, or S,
$X_{43}$ is L, or M,
$X_{44}$ is Q, E, H, or N,
$X_{45}$ is M, L, V, I, or W,
$X_{46}$ is N, T, K, D, Y, I, or S,
$X_{47}$ is S or N,
$X_{48}$ is L or V,
$X_{49}$ is R, K, or T,
$X_{50}$ is D, A, S, P, T, V, I, or S,
$X_{51}$ is E, A, D, or S,
$X_{52}$ is T, N, or S,
$X_{53}$ is S, A, or G,
$X_{54}$ is V, I, L, or M,
$X_{55}$ is Y or F,
$X_{56}$ is A, G, V, or S, and
$X_{57}$ is R, S, K, T, L, N, or F; and (3) FR4: $X_{58}GX_{59}GX_{60}X_{61}VTVSS$ (SEQ ID NO: 147), wherein:

$X_{58}$ is W, C, Y, G, S, or A,
$X_{59}$ is Q, R, or L,
$X_{60}$ is A, T, I, or V, and
$X_{61}$ is L, M, P, V, or T.

6. The soluble VH domain antibody scaffold of claim 5, further comprising amino acid sequences of FR1, FR3 and FR4 as below:

(1) FR1: $X_0VQLX_1X_2SGGX_5X_6X_7X_8$
$PGX_9SX_{10}RX_{12}SCX_{14}X_{15}$
$SGX_{17}X_{18}X_{19}$ (SEQ ID NO: 148), wherein:

$X_0$ is E or Q,
$X_1$ is V or L,
$X_2$ is E or Q,
$X_5$ is G, N, V, or E,
$X_6$ is L or V,
$X_7$ is V or K,
$X_8$ is Q, K or H,
$X_9$ is G, T, A, R, E, or T,
$X_{10}$ is L or V,
$X_{12}$ is L or V,
$X_{14}$ is A, E, V, I, K, or S,
$X_{15}$ is A, G, or V,
$X_{17}$ is F, Y, R, G, or L,
$X_{18}$ is T, A, S, N, T, P, I, N, H, or A, and
$X_{19}$ is F, L, V, or C;

(2) FR3:
$RX_{30}TX_{32}SX_{34}DX_{36}X_{37}X_{38}X_{39}X_{40}X_{41}X_{42}X_{43}X_{44}X_{45}X_{46}X_{47}$
$X_{48}X_{49}X_{50}X_{51}DT AX_{54}YX_{55}$
$CX_{56}X_{57}$ (SEQ ID NO: 150), wherein:

$X_{30}$ is F, V, L, or I,
$X_{32}$ is I, L, V, or M,
$X_{34}$ is R, A, V, or,
$X_{36}$ is N, T, D, I, R, K, Y, or E,
$X_{37}$ is A, S, V, or T,
$X_{38}$ is K, R, T, Q, V, E, M, N, or I,
$X_{39}$ is N, R, T, K, S, D, or V,
$X_{40}$ is T, M, S, V, I, Y, or A,
$X_{41}$ is L, V, A, or M,
$X_{42}$ is F, Y, N, D, H, or S,
$X_{43}$ is L or M,
$X_{44}$ is Q, E, H, or N,
$X_{45}$ is M, L, V, I, or W,
$X_{46}$ is N, T, K, D, Y, I, or S,
$X_{47}$ is S or N,
$X_{48}$ is L or V,
$X_{49}$ is R, K, or T,
$X_{50}$ is D, A, S, P, T, V, I, or S,
$X_{51}$ is E, A, D, or S,
$X_{54}$ is V, I, L, or M,
$X_{55}$ is Y or F,
$X_{56}$ is A, G, V, or S, and
$X_{57}$ is R, S, K, T, L, N, or F; and (3) FR4: $X_{58}GQGX_{60}X_{61}VTVSS$ (SEQ ID NO: 151), wherein:

$X_{58}$ is W, C, Y, G, S, or A,
$X_{60}$ is A, T, I, or V, and
$X_{61}$ is L, M, V, or T.

7. The soluble VH domain antibody scaffold of claim 1, wherein the soluble VH domain antibody scaffold comprises an amino acid sequence of SEQ ID NO. 140.

8. A VH domain antibody having the soluble VH domain antibody scaffold of claim 1.

9. A VH domain antibody library having human-derived random CDRH1, CDRH2 and CDRH3 inserted into the soluble VH domain antibody scaffold of claim 1.

10. The VH domain antibody library of claim 9, wherein the inserted CDRH3 has 5 to 15 amino acid residues.

11. The VH domain antibody library of claim 9, wherein the inserted CDRH3 has 7 to 13 amino acid residues.

12. The VH domain antibody library of claim 9, wherein the human-derived random CDRH1, CDRH2 and CDRH3 have induced mutation therein.

13. The VH domain antibody library of claim 12, wherein the mutation is induced at one or more positions selected from position nos. 30 and 31 of CDRH1, position no. 53 of CDRH2, and position nos. 97, 99, 100, and 100a of CDRH3, based on Kabat numbering system.

14. The VH domain antibody library of claim 9, wherein the library is naïve, synthetic or immune library.

\* \* \* \* \*